US012760034B2

(12) United States Patent
Garcia et al.

(10) Patent No.: US 12,760,034 B2
(45) Date of Patent: Oct. 13, 2026

(54) RIFAMYCIN ANALOGS

(71) Applicants: THE REGENTS OF THE UNIVERSITY OF MICHIGAN, Ann Arbor, MI (US); THE BOARD OF TRUSTEES OF THE UNIVERSITY OF ILLINOIS, Urbana, IL (US); THE PENN STATE RESEARCH FOUNDATION, University Park, PA (US)

(72) Inventors: George Garcia, Ann Arbor, MI (US); Hollis Showalter, Ann Arbor, MI (US); Walajapet Rajeswaran, Ann Arbor, MI (US); Pil Lee, Ann Arbor, MI (US); Scott Franzblau, Urbana, IL (US); Katsuhiko Murakami, University Park, PA (US)

(73) Assignees: THE REGENTS OF THE UNIVERSITY OF MICHIGAN, Ann Arbor, MI (US); THE BOARD OF TRUSTEES OF THE UNIVERSITY OF ILLINOIS, Urbana, IL (US); THE PENN STATE RESEARCH FOUNDATION, University Park, PA (US)

( * ) Notice: Subject to any disclaimer, the term of this patent is extended or adjusted under 35 U.S.C. 154(b) by 601 days.

(21) Appl. No.: 18/261,932

(22) PCT Filed: Jan. 19, 2022

(86) PCT No.: PCT/US2022/012980

§ 371 (c)(1),
(2) Date: Jul. 18, 2023

(87) PCT Pub. No.: WO2022/159491

PCT Pub. Date: Jul. 28, 2022

(65) Prior Publication Data

US 2025/0188092 A1 Jun. 12, 2025

Related U.S. Application Data

(60) Provisional application No. 63/139,119, filed on Jan. 19, 2021.

(51) Int. Cl.

| | |
|---|---|
| ***C07D 498/18*** | (2006.01) |
| ***A61K 31/5386*** | (2006.01) |
| ***A61K 31/541*** | (2006.01) |
| ***A61P 31/06*** | (2006.01) |
| ***C07D 519/00*** | (2006.01) |

(52) U.S. Cl.

CPC ........ *C07D 498/18* (2013.01); *A61K 31/5386* (2013.01); *A61K 31/541* (2013.01); *A61P 31/06* (2018.01); *C07D 519/00* (2013.01)

(58) Field of Classification Search

None

See application file for complete search history.

(56) References Cited

U.S. PATENT DOCUMENTS

| | | | |
|---|---|---|---|
| 4,137,914 | A | 2/1979 | Wetterlin |
| 4,174,712 | A | 11/1979 | Moren et al. |
| 4,524,769 | A | 6/1985 | Wetterlin |
| 4,667,688 | A | 5/1987 | Roig et al. |
| 5,033,252 | A | 7/1991 | Carter |
| 5,052,558 | A | 10/1991 | Carter |
| 5,323,907 | A | 6/1994 | Kalvelage |
| 5,672,581 | A | 9/1997 | Rubsamen et al. |
| 5,709,202 | A | 1/1998 | Lloyd et al. |
| 5,780,014 | A | 7/1998 | Eljamal et al. |
| 5,915,378 | A | 6/1999 | Lloyd et al. |
| 5,981,522 | A | 11/1999 | Yamashita et al. |
| 5,997,848 | A | 12/1999 | Patton et al. |
| 6,087,358 | A | 7/2000 | Baker et al. |
| 6,123,068 | A | 9/2000 | Lloyd et al. |
| 6,123,936 | A | 9/2000 | Platz et al. |
| 6,397,838 | B1 | 6/2002 | Zimlich, Jr. et al. |
| 6,566,354 | B1 | 5/2003 | Rose et al. |
| 6,991,902 | B2 | 1/2006 | Cook |
| 7,884,099 | B2 | 2/2011 | Ding et al. |
| 10,689,325 | B2 | 6/2020 | Bachmann et al. |
| 2005/0043298 | A1 | 2/2005 | Van Duzer et al. |
| 2018/0125995 | A1 | 5/2018 | Brown et al. |

FOREIGN PATENT DOCUMENTS

| | | |
|---|---|---|
| CN | 105228617 A | 1/2016 |
| CN | 108047249 | 5/2018 |
| CN | 108003177 B | 4/2020 |

(Continued)

OTHER PUBLICATIONS

International Search Report and Written Opinion for PCT/US2022/012980. Mailed May 18, 2022. 10 pages.

"WHO report 2008. Global tuberculosis control: surveillance, planning, financing", World Health Organization, 2008, 304 pages.

Afonine et al., Joint X-ray and neutron refinement with phenix. refine. Acta Crystallogr D Biol Crystallogr. Nov. 2010;66(Pt 11):1153-63.

Andreu et al., Optimisation of bioluminescent reporters for use with mycobacteria. PLoS One. May 24, 2010;5(5):e10777. 16 pages.

Aristoff et al., Rifamycins—obstacles and opportunities. Tuberculosis (Edinb). Mar. 2010;90(2):94-118.

(Continued)

*Primary Examiner* — Samantha L Shterengarts

(74) *Attorney, Agent, or Firm* — Casimir Jones, S.C.; Anne M. Reynolds

(57) ABSTRACT

Provided herein are compounds that are potent inhibitors of the *Mycobacterium tuberculosis* (MTB) RNA polymerase (RNAP), which exhibit significantly reduced activation of the human pregnane X receptor (hPXR), resulting in dramatically reduced C induction of hepatic cytochromes P450 2C9 and 3A4 (CYP2C9, CYP3A4), as well as a number of Phase II metabolism enzymes. Also provided herein are pharmaceutical compositions comprising the compounds, and methods of treating tuberculosis using the compounds.

28 Claims, 5 Drawing Sheets

(56) References Cited

FOREIGN PATENT DOCUMENTS

| | | |
|---|---|---|
| WO | WO 99/00669 | 1/1999 |
| WO | WO 2007/148713 | 12/2007 |
| WO | WO 2007/148714 | 12/2007 |
| WO | WO 2013/086415 A1 | 6/2013 |
| WO | WO 2017/197056 | 11/2017 |

OTHER PUBLICATIONS

Artsimovitch et al., Allosteric modulation of the RNA polymerase catalytic reaction is an essential component of transcription control by rifamycins. Cell. Aug. 12, 2005;122(3):351-63.
Barrera. The basics of clinical bacteriology, In Tuberculosis 2007 From Basic Science to Patient Care (Palomino, J. C., Leão, S. C., and Ritacco, V., Eds.), 2007, pp. 93-112.
Barry et al., Novel agents in the management of *Mycobacterium tuberculosis* disease. Curr Med Chem. 2007;14(18):2000-8.
Basu et al., Structural basis of transcription initiation by bacterial RNA polymerase holoenzyme. J Biol Chem. Aug. 29, 2014;289(35):24549-59.
Bell et al., Optimization of novel nipecotic bis(amide) inhibitors of the Rho/MKL1/SRF transcriptional pathway as potential anti-metastasis agents. Bioorg Med Chem Lett. Jul. 1, 2013;23(13):3826-32.
Benedetti. Inducing properties of rifabutin, and effects on the pharmacokinetics and metabolism of concomitant drugs. Pharmacol Res. Oct. 1995;32(4):177-87.
Bepler et al., Positive-unlabeled convolutional neural networks for particle picking in cryo-electron micrographs. Nat Methods. Nov. 2019;16(11):1153-1160.
Brooks et al., Evaluation of once-weekly therapy for tuberculosis using isoniazid plus rifamycins in the mouse aerosol infection model. Antimicrob Agents Chemother. Nov. 1998;42(11):3047-8.
Campbell et al., Structural mechanism for rifampicin inhibition of bacterial rna polymerase. Cell. Mar. 23, 2001;104(6):901-12.
Carpino et al., The uronium/guanidinium Peptide coupling reagents: finally the true uronium salts. Angew Chem Int Ed Engl. Feb. 1, 2002;41(3):441-5.
Chemical Computing Group, I. Molecular Operating Environment (MOE), Aug. 2014, 1010 Sherbooke St. West, Suite #910, Montreal, QC, Canada, H3A 2R7, 2014. Retrieved from internet Aug. 21, 2024. 15 pages.
CHEMSRC, CAS No. 105396-63-2, Modify Date Mar. 13, 2021. Retrieved Apr. 28, 2022. 2 pages.
Chen et al., Lack of effect of rifalazil on ethinyl estradiol pharmacokinetics in healthy postmenopausal women. Int J Clin Pharmacol Ther. Jul. 2007;45(7):418-22.
Cho et al., Microplate Alamar Blue Assay (MABA) and Low Oxygen Recovery Assay (LORA) for *Mycobacterium tuberculosis*. Methods Mol Biol. 2015:1285:281-92.
Cho et al., Low-Oxygen-Recovery Assay for High-Throughput Screening of Compounds against Nonreplicating *Mycobacterium tuberculosis*. Antimicrob. Agents Chemother. 2007, 51, 1380-1385.
Choules et al., Rufomycin Targets ClpC1 Proteolysis in *Mycobacterium tuberculosis* and *M. abscessus*. Antimicrob. Agents Chemother. 2019, 63, e02204-02218.
Chrencik et al., Structural disorder in the complex of human pregnane X receptor and the macrolide antibiotic rifampicin. Mol Endocrinol. May 2005;19(5):1125-34.
Collins et al., Microplate alamar blue assay versus BACTEC 460 system for high-throughput screening of compounds against *Mycobacterium tuberculosis* and *Mycobacterium avium*. Antimicrob. Agents Chemother. 1997, 41, 1004-1009.
Cross et al., Rules for the nomenclature of organic chemistry. Pure Appl. Chem., 1976, 45: 13-30.
Dietze et al., Safety and bactericidal activity of rifalazil in patients with pulmonary tuberculosis. Antimicrob Agents Chemother. Jul. 2001;45(7):1972-6.
Dyavar et al., Hepatocytic transcriptional signatures predict comparative drug interaction potential of rifamycin antibiotics. Sci Rep. Jul. 28, 2020;10(1):12565. 12 pages.
Emsley et al., Coot: model-building tools for molecular graphics. Acta Crystallogr D Biol Crystallogr. Dec. 2004;60(Pt 12 Pt 1):2126-32.
Everard et al., Guidelines for devices and choices. J Aerosol Med. 2001:14 Suppl 1:S59-64.
Garcia et al., Strong in vitro activities of two new rifabutin analogs against multidrug-resistant *Mycobacterium tuberculosis*. Antimicrob Agents Chemother. Dec. 2010;54(12):5363-5.
Gill et al., Rifamycin inhibition of WT and Rif-resistant *Mycobacterium tuberculosis* and *Escherichia coli* RNA polymerases in vitro. Tuberculosis (Edinb). Sep. 2011;91(5):361-9.
Gill et al., Structure-based design of novel benzoxazinorifamycins with potent binding affinity to wild-type and rifampin-resistant mutant *Mycobacterium tuberculosis* RNA polymerases. J Med Chem. Apr. 26, 2012;55(8):3814-26.
Gillum et al., Induction of theophylline clearance by rifampin and rifabutin in healthy male volunteers. Antimicrob Agents Chemother. Aug. 1996;40(8):1866-9.
Global Alliance for TB Drug Development, Rifalazil. Tuberculosis 2008, 88 (2), 148-150.
Godreuil et al., Pulmonary Tuberculosis and *Mycobacterium tuberculosis*: Modern Molecular Epidemiology and Perspectives, In Encyclopedia of Infectious Diseases: Modern Methodologies (Tibayrenc, M., Ed.), John Wiley & Sons, 2007, pp. 1-30.
Jones et al., Development and validation of a genetic algorithm for flexible docking. J Mol Biol. Apr. 4, 1997;267(3):727-48.
Kakita et al., Unambiguous determination of conformation and relative configuration of a multiple stereo-centre molecule Rifamycin-S by using scaled residual dipolar couplings: A case study. Journal of Molecular Structure 2013, 1053, 122-126.
Keller. Innovations and perspectives of metered dose inhalers in pulmonary drug delivery. Int J Pharm. Sep. 10, 1999;186(1):81-90.
Kelly et al., Low-dose aerosol infection model for testing drugs for efficacy against *Mycobacterium tuberculosis*. Antimicrob Agents Chemother. Dec. 1996;40(12):2809-12.
Keung et al., Enzyme induction observed in healthy volunteers after repeated administration of rifapentine and its lack of effect on steady- state rifapentine pharmacokinetics: part I. Int J Tuberc Lung Dis. May 1999;3(5):426-36.
Klemens et al., Activity of KRM-1648 in combination with isoniazid against *Mycobacterium tuberculosis* in a murine model. Antimicrob Agents Chemother. Feb. 1996;40(2):298-301.
Klemens et al., Activity of KRM-1648, a new benzoxazinorifamycin, against *Mycobacterium tuberculosis* in a murine model. Antimicrob Agents Chemother. Oct. 1994;38(10):2245-8.
Koul et al., The challenge of new drug discovery for tuberculosis. Nature. Jan. 27, 2011;469(7331):483-90.
Lenaerts et al., Evaluation of rifalazil in a combination treatment regimen as an alternative to isoniazid-rifampin therapy in a mouse tuberculosis model. Antimicrob Agents Chemother. Nov. 2000;44(11):3167-8.
Li et al., Preparation and in vitro anti-staphylococcal activity of novel 11-deoxy-11-hydroxyiminorifamycins. Bioorg. Med. Chem. Lett., 2007, 17, 5510-5513.
Li et al., Primary human hepatocytes as a tool for the evaluation of structure-activity relationship in cytochrome P450 induction potential of xenobiotics: evaluation of rifampin, rifapentine and rifabutin. Chem Biol Interact. Nov. 6, 1997;107(1-2):17-30.
Liebschner et al., Polder maps: improving OMIT maps by excluding bulk solvent. Acta crystallographica. Section D, Structural Biology, 2017, 73, 148-157.
Lienhardt et al., New drugs and new regimens for the treatment of tuberculosis: review of the drug development pipeline and implications for national programmes. Curr Opin Pulm Med. May 2010;16(3):186-93.
Lin et al., Structural Basis of Mycobacterium tuberculosis Transcription and Transcription Inhibition. Mol Cell. Apr. 20, 2017;66(2):169-179.e8.

(56) References Cited

OTHER PUBLICATIONS

Lounis et al., In vitro and in vivo activities of new rifamycin derivatives against mycobacterial infections. Curr Pharm Des. 2004;10(26):3229-38.
Luna-Herrera et al., In vitro activity of the benzoxazinorifamycin KRM-1648 against drug-susceptible and multidrug-resistant tubercle bacilli. Antimicrob Agents Chemother. Feb. 1995;39(2):440-4.
Madan et al., Effects of prototypical microsomal enzyme inducers on cytochrome P450 expression in cultured human hepatocytes. Drug Metab Dispos. Apr. 2003;31(4):421-31.
Mae et al., Effect of a new rifamycin derivative, rifalazil, on liver microsomal enzyme induction in rat and dog. Xenobiotica. Aug. 1998;28(8):759-66.
Moghazeh et al., Comparative antimycobacterial activities of rifampin, rifapentine, and KRM-1648 against a collection of rifampin-resistant *Mycobacterium tuberculosis* isolates with known rpoB mutations. Antimicrob Agents Chemother. Nov. 1996;40(11):2655-7.
Molodtsov et al., Structural basis for rifamycin resistance of bacterial RNA polymerase by the three most clinically important RpoB mutations found in *Mycobacterium tuberculosis*. Mol Microbiol. Mar. 2017;103(6):1034-1045.
Molodtsov et al., X-ray crystal structures of *Escherichia coli* RNA polymerase with switch region binding inhibitors enable rational design of squaramides with an improved fraction unbound to human plasma protein. J Med Chem. Apr. 9, 2015;58(7):3156-71.
Molodtsov et al., X-ray crystal structures of the *Escherichia coli* RNA polymerase in complex with benzoxazinorifamycins. J Med Chem. Jun. 13, 2013;56(11):4758-63.
Mullin et al., Activity of novel benzoxazinorifamycins against rifamycin-resistant *Streptococcus pyogenes*. Antimicrob Agents Chemother. May 2006;50(5):1908-9.
Murakami et al., X-ray crystal structure of a reiterative transcription complex reveals an atypical RNA extension pathway. Proceedings of the National Academy of Sciences of the United States of America, 2017, 114, 8211-8216.
Murakami. X-ray crystal structure of *Escherichia coli* RNA polymerase σ70 holoenzyme. J Biol Chem. Mar. 29, 2013;288(13):9126-34.
Peek et al., A Semisynthetic Kanglemycin Shows In Vivo Efficacy against High-Burden Rifampicin Resistant Pathogens. ACS Infect Dis. Sep. 11, 2020;6(9):2431-2440.
Pettersen et al., UCSF Chimera—a visualization system for exploratory research and analysis. J Comput Chem. Oct. 2004;25(13):1605-12.
Portero et al., New anti-tuberculosis therapies, Expert Opin. Ther. Patents, 2007, 17, 617-637.
Pubchem, Substance record for SID 324821510, Available date: Jan. 25, 2017. Retrieved Apr. 28, 2022. 7 pages.
Punjani et al., cryoSPARC: algorithms for rapid unsupervised cryo-EM structure determination. Nat Methods. Mar. 2017;14(3):290-296.
Pyta et al., Intramolecular proton transfer impact on antibacterial properties of ansamycin antibiotic rifampicin and its new amino analogues. Org Biomol Chem. Mar. 28, 2012;10(12):2385-8.
Pyta et al., Synthesis, docking and antibacterial studies of more potent amine and hydrazone rifamycin congeners than rifampicin. Eur J Med Chem. Apr. 1, 2019:167:96-104.
Roblin et al., In vitro activities of rifamycin derivatives ABI-1648 (Rifalazil, KRM-1648), ABI-1657, and ABI-1131 against Chlamydia trachomatis and recent clinical isolates of Chlamydia pneumoniae. Antimicrob Agents Chemother. Mar. 2003;47(3):1135-6.
Rohou et al., CTFFIND4: Fast and accurate defocus estimation from electron micrographs. J Struct Biol. Nov. 2015; 192(2):216-21.
Rothstein et al., Development potential of rifalazil and other benzoxazinorifamycins. Expert Opin Investig Drugs. Jun. 2006;15(6):603-23.
Rubinstein et al., Alignment of cryo-EM movies of individual particles by optimization of image translations. J Struct Biol. Nov. 2015;192(2):188-95.
Saito et al., In vitro antimycobacterial activities of newly synthesized benzoxazinorifamycins. Antimicrob Agents Chemother. Mar. 1991;35(3):542-7.
Scharf et al., Novel Chemical Scaffolds for Inhibition of Rifamycin-Resistant RNA Polymerase Discovered from High-Throughput Screening. SLAS Discov. Mar. 2017;22(3):287-297.
Scharf, Identification and Evaluation of Bacterial RNA Polymerase Inhibitors Using a Novel Plasmid-based Transcription Assay, Dissertation, University of Michigan, 2017. 23 pages.
Schuetz et al., Modulators and substrates of P-glycoprotein and cytochrome P4503A coordinately up-regulate these proteins in human colon carcinoma cells. Mol Pharmacol. Feb. 1996;49(2):311-8.
Shetye et al., In Vitro Profiling of Antitubercular Compounds by Rapid, Efficient, and Nondestructive Assays Using Autoluminescent *Mycobacterium tuberculosis*. Antimicrob Agents Chemother. Jul. 16, 2021;65(8):e0028221. 13 pages.
Shin et al., Structural basis of ribosomal RNA transcription regulation. Nat Commun. Jan. 22, 2021;12(1):528. 12 pages.
Shoen et al., Evaluation of rifalazil in long-term treatment regimens for tuberculosis in mice. Antimicrob Agents Chemother. Jun. 2000;44(6):1458-62.
Siddiqi et al., Review of knowledge for rational design and identification of anti-tubercular compounds. Expert Opin Drug Discov. Oct. 2009;4(10):1005-15.
Svensson et al., Rifampicin and rifapentine significantly reduce concentrations of bedaquiline, a new anti-TB drug. J Antimicrob Chemother. Apr. 2015;70(4):1106-14.
Togger et al., Metered dose inhalers. Am J Nurs. Oct. 2001;101(10):26-32.
Tomioka. Current status of some antituberculosis drugs and the development of new antituberculous agents with special reference to their in vitro and in vivo antimicrobial activities. Curr Pharm Des. 2006;12(31):4047-70.
Traxler et al., Hypolipidemic activity of rifamycin derivatives. J Med Chem. Feb. 1990;33(2):552-60.
Wang, J., Huang, J., Li, H., and Zhang, S. (2003) "Synthesis of benzoxazinorifamycin derivatives and preliminary study of antibacterial activity", Huaxi Yaoxue Zazhi 18, 241-243.
Watkins et al., The human nuclear xenobiotic receptor PXR: structural determinants of directed promiscuity. Science. Jun. 22, 2001;292(5525):2329-33.
Wicher et al., Redetermination of rifampicin pentahydrate revealing a zwitterionic form of the antibiotic. Acta Crystallogr C. May 2012;68(Pt 5):0209-12.
World-Health-Organization Global Tuberculosis Report 2020. 232 pages.
Yamamoto et al., In vitro bactericidal and in vivo therapeutic activities of a new rifamycin derivative, KRM-1648, against *Mycobacterium tuberculosis*. Antimicrob Agents Chemother. Feb. 1996;40(2):426-8.
Yamane et al., Synthesis and biological activity of 3'-hydroxy-5'-aminobenzoxazinorifamycin derivatives. Chem Pharm Bull (Tokyo). Jan. 1993;41(1):148-55.
Yang et al., Relationship between antimycobacterial activities of rifampicin, rifabutin and KRM-1648 and rpoB mutations of *Mycobacterium tuberculosis*. J Antimicrob Chemother. Nov. 1998;42(5):621-8.
Zhou et al., Induction of polymorphic 4'-hydroxylation of S-mephenytoin by rifampicin. Br J Clin Pharmacol. Sep. 1990;30(3):471-5.
Zilly et al., Stimulation of drug metabolism by rifampicin in patients with cirrhosis or cholestasis measured by increased hexobarbital and tolbutamide clearance. Eur J Clin Pharmacol. Apr. 20, 1977;11(4):287-93.

Rifalazil (RLZ)

Rifampin (RMP)

RIFAMYCIN ANALOGS

CROSS-REFERENCE TO RELATED APPLICATIONS

This application is a national stage filing under 35 U.S.C. § 371 of international patent application no. PCT/US2022/012980, filed on Jan. 19, 2022, which claims priority to and the benefit of U.S. Provisional Patent Application No. 63/139,119, filed on Jan. 19, 2021, which is incorporated herein by reference in its entirety.

STATEMENT REGARDING FEDERALLY SPONSORED RESEARCH

This invention was made with government support under AI110780 and GM087350 awarded by the National Institutes of Health. The government has certain rights in the invention.

FIELD

Provided herein are compounds that are potent inhibitors of the *Mycobacterium tuberculosis* (MTB) RNA polymerase (RNAP), which exhibit significantly reduced activation of the human pregnane X receptor (hPXR), resulting in dramatically reduced induction of hepatic cytochromes P450 2C9 and 3A4 (CYP2C9, CYP3A4), as well as a number of Phase II metabolism enzymes. Also provided herein are pharmaceutical compositions comprising the compounds, and methods of treating tuberculosis using the compounds.

BACKGROUND

Tuberculosis (TB) is a contagious and deadly disease that has reached pandemic proportions. According to the World Health Organization (WHO), 8-10 million new cases of tuberculosis (TB) are diagnosed each year, making *Mycobacterium tuberculosis* (MTB) a leading cause of death in adults (2-3 million/year) due to an infectious agent. A high proportion of these new cases and deaths occurs in HIV-positive people with a significant number of AIDS deaths in Africa being attributed to TB infections. Global population growth is increasing the disease burden, posing a continuing health and financial burden in various parts of the world, particularly Asia and Africa.

TB is caused by MTB, an obligate aerobic bacillus that divides at an extremely slow rate. The chemical composition of its cell wall includes peptidoglycans and complex lipids, in particular mycolic acids, which are significant determinants of its virulence. The unique structure of the MTB cell wall contributes to its ability to lie dormant for many years as a latent infection, particularly inside macrophage-containing nodules called granulomas, hiding it from the host's immune system.

The continuing rise in multidrug-resistant TB has further contributed to the need for new TB antibiotics. Currently available second-line drugs that are active against first-line drug resistant forms of TB tend to be less potent, more toxic, more expensive, or need to be taken for an extended period of time (≥18 months). The recent emergence of virtually untreatable extensively drug-resistant TB (XDR-TB) poses a new threat to TB control worldwide. Furthermore, effective treatment of TB in persons co-infected with HIV is complicated due to drug-drug interactions. Shorter and simpler regimens that are safe, well tolerated, effective against drug-susceptible and drug-resistant TB, appropriate for treatment of HIV-TB co-infection and amenable to routine clinical settings, are needed.

The rifamycins (RIFs) are the most commonly used drugs for TB and are very potent inhibitors of the MTB RNA polymerase (RNAP). When rifamycins were introduced, they reduced the tuberculosis treatment time from 2 years to 9 months. However, even in combination with other TB drugs as they are used today, they still require 3- to 9-month treatment times and suffer from other serious drawbacks including: Cyp450 induction (which is particularly problematic for HIV-MTB co-infection), and the existence of resistant mutations within RNAP that yield RIF-resistant ($RIF^R$) MTB strains. Semisynthetic rifamycin derivatives have been reported that show improved antimycobacterial activities. These include rifampin (RMP, FIG. 1), which is the cornerstone of current short-term TB treatment. Among newer derivatives, rifalazil (RLZ, FIG. 1) has proved most interesting, not just because of its excellent potency but also its relative lack of toxicity in early rodent studies. RLZ is an exceedingly potent rifamycin derivative, being 29-fold more potent than RMP against MTB H37Rv in vitro. Several studies involving strains with various RMP-resistant mutations in the rpoB gene, encoding the RNAP β subunit, indicated that two mutations resistant to RMP and rifapentine (RFP) retained substantial sensitivity to rifabutin (RFB) and RLZ. However, all RIFs, including RLZ, are ineffective against the most prevalent $RIF^R$ MTB mutant (rpoB S450L) (see, e.g., *Tuberculosis* (2008) 88(2) 148-150). RLZ and its benzoxazino-rifamycin analogues also have showed excellent activity against other organisms with RMP-resistant mutations, including *Streptococcus pyogenes, Chlamydia trachomatis*, and *Chlamydia pneumonia.*

In mouse in vivo efficacy studies, RLZ has been shown to be clearly more potent than RMP including activity against some RMP-resistant strains, and longer term MTB studies in combination with other agents indicated the same level of cure could be achieved with shorter (at least two-fold) duration of treatment with RLZ as compared to RMP. In pharmacokinetic (PK) studies, RLZ has shown a high volume of distribution and produced tissue levels in rats up to 200 times those in plasma. It displayed a very long half-life (60-100 h) in human trials.

As mentioned above, one major downside to using rifamycins to treat TB is their many drug-drug interactions due to extremely potent activation of the human pregnane X receptor (hPXR) leading to a dramatic induction of CYP2C9, CYP3A4 and other hepatic metabolizing enzymes and transporters. This effect appears to be minimized with RLZ, which does not activate the hPXR (nor induce CYPs) at concentrations 100,000 times greater than its minimum inhibitory concentration (MIC) for MTB H37Rv. However, in a series of phase I and phase II clinical trials, RLZ proved to be quite toxic, with most adverse effects associated with a flu-like syndrome and leucopenia even at lower dose levels. Its development for TB indications has been suspended.

SUMMARY

In one aspect, disclosed herein is a compound of formula (I):

(I)

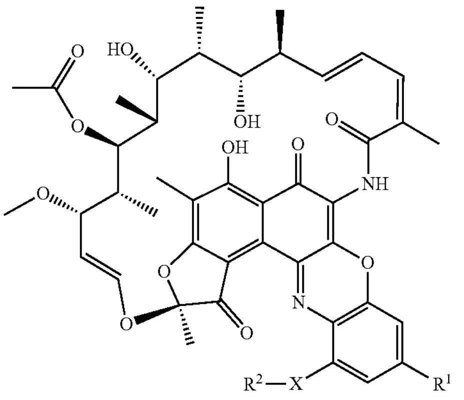

or a pharmaceutically acceptable salt thereof, wherein:

$R^1$ is selected from hydrogen, $C_1$-$C_6$ alkyl, $C_1$-$C_6$ heteroalkyl, —C(O)$R^a$, —N($R^b$)$_2$, —O$R^c$, —S$R^d$, —CH═N—Z, and heterocyclyl, wherein the heterocyclyl is unsubstituted or substituted with one substituent selected from $C_1$-$C_6$ alkyl, $C_1$-$C_6$ alkenyl, —C(O)$R^{a1}$, —C(O)O$R^{b1}$, —C(O)NH$R^{c1}$, —$(CH_2)_{n1}$—$X^{1a}$, —$SO_2$—$X^{1b}$, aryl, heteroaryl, cycloalkyl, and heterocyclyl, wherein when the substituent is aryl, heteroaryl, cycloalkyl, or heterocyclyl, the substituent is optionally further substituted with $C_1$-$C_6$ alkyl or —O—$X^{1c}$;

X is selected from O, S, $SO_2$, $NHSO_2$, $NR^X$, and a bond;

$R^X$ is selected from hydrogen and $C_1$-$C_3$ alkyl;

$R^2$ is selected from hydrogen, $C_1$-$C_6$ alkyl, $C_1$-$C_6$ alkenyl, $C_3$-$C_6$ cycloalkyl, heterocyclyl, aryl, heteroaryl, —$(CH_2)_{m1}$-aryl, —$(CH_2)_{m2}$-heterocyclyl, and —$CH_2$-Ph-$CH_2$-heterocyclyl, wherein each alkyl, alkenyl, cycloalkyl, heterocyclyl, aryl, and heteroaryl is independently unsubstituted or substituted with one or two substituents independently selected from $C_1$-$C_6$ alkyl, hydroxy, amino, —C(O)$R^{a2}$, —C(O)O$R^{b2}$, —C(O)NH$R^{c2}$, —$(CH_2)_{n2}$—$X^{2a}$, —$SO_2$—$X^{2b}$, aryl, heteroaryl, cycloalkyl, and heterocyclyl;

each $R^a$, $R^b$, $R^c$, and $R^d$ is independently selected from hydrogen, $C_1$-$C_6$ alkyl, $C_3$-$C_6$ cycloalkyl, and aryl;

$R^{a1}$ and $R^{a2}$ are each independently selected from hydrogen, $C_1$-$C_6$ alkyl, $C_1$-$C_6$ alkenyl, cycloalkyl, heterocyclyl, aryl, heteroaryl, and —$(CH_2)_p$—Y, wherein each alkyl, alkenyl, cycloalkyl, heterocyclyl, aryl, and heteroaryl is independently unsubstituted or substituted with one substituent selected from aryl, heteroaryl, $C_1$-$C_6$ alkyl, halo, and nitro, and when the substituent is aryl or heteroaryl, it is unsubstituted or substituted with one substituent selected from halo, hydroxy, and —$CONH_2$;

$R^{b1}$ and $R^{b2}$ are each independently selected from hydrogen, $C_1$-$C_6$ alkyl, and heterocyclyl, wherein the heterocyclyl is optionally further substituted with one substituent selected from $C_1$-$C_6$ alkyl, hydroxy, halo, and nitro;

$R^{c1}$ and $R^{c2}$ are each independently selected from hydrogen, $C_1$-$C_6$ alkyl, and aryl, wherein the aryl is unsubstituted or substituted with one substituent selected from $C_1$-$C_6$ alkyl, halo, and nitro;

$X^{1a}$, $X^{1b}$, $X^{1c}$, $X^{2a}$, and $X^{2b}$ are each independently selected from aryl, heteroaryl, cycloalkyl, heterocyclyl, —O-heterocyclyl, —COOH, and —N($CH_3$)$_2$, wherein each aryl, heteroaryl, cycloalkyl, or heterocyclyl is independently unsubstituted or substituted with one substituent selected from $C_1$-$C_6$ alkyl, hydroxy, halo, and nitro;

Y is selected from aryl, heteroaryl, cycloalkyl, and heterocyclyl, each of which is independently unsubstituted or substituted with one substituent selected from $C_1$-$C_6$ alkyl, halo, and nitro;

Z is selected from aryl and heteroaryl, each of which is optionally substituted with one substituent selected from heterocyclyl; and m1, m2, n1, n2, and p are each independently 1, 2, 3, 4, 5, or 6;

wherein when $R^1$ is hydrogen, —X—$R^2$ is not:

—$CH_3$,

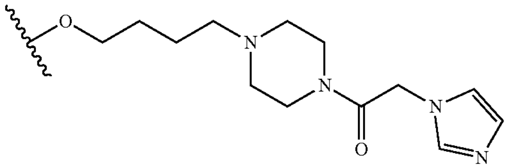

or

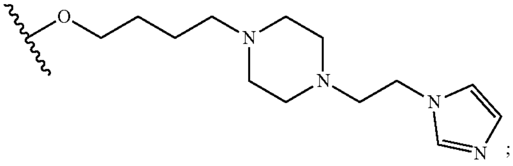

;

and when $R^1$ is

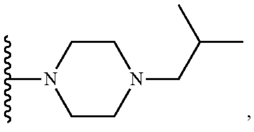 [SMILES: *N1CCN(CC(C)C)CC1]

,

—X—$R^2$ is not: —$CH_3$, —SH, or

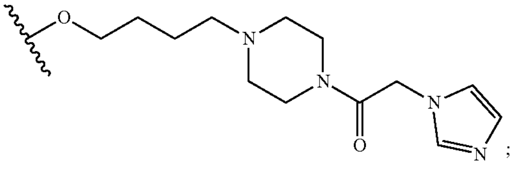 [SMILES: *OCCCCN1CCN(C(=O)Cn2ccnc2)CC1]

;

and when $R^1$ is

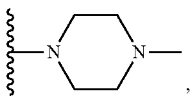

,

—X—$R^2$ is not —$CH_3$;

and when $R^1$ is $CH_3$, —X—$R^2$ is not hydrogen;

and when X is O, $R^2$ is not hydrogen.

In some embodiments, $R^1$ is selected from hydrogen and methyl. In some embodiments, $R^1$ is heterocyclyl, wherein the heterocyclyl is unsubstituted or substituted with one substituent selected from $C_1$-$C_6$ alkyl, —C(O)$R^{a1}$, —C(O)O$R^{b1}$, —C(O)NH$R^{c1}$, —$(CH_2)_{n1}$—$X^{1a}$, and heterocyclyl, wherein when the substituent is heterocyclyl, the heterocyclyl substituent is optionally further substituted with $C_1$-$C_6$ alkyl. In some embodiments, $R^1$ is a monocyclic 6-membered heterocyclyl having 1 or 2 heteroatoms independently selected from N, O, and S, wherein the heterocyclyl is unsubstituted or substituted with one substituent selected from $C_1$-$C_6$ alkyl, —C(O)$R^{a1}$, —C(O)O$R^{b1}$, and —$(CH_2)_{n1}$—$X^{1a}$. In some embodiments, the heterocyclyl is unsubstituted or substituted with one substituent selected from $C_1$-$C_4$ alkyl, —C(O)$R^{a1}$, and —C(O)O$R^{b1}$; wherein: $R^{a1}$ is selected from $C_1$-$C_4$ alkyl, aryl, and heteroaryl, wherein the aryl is unsubstituted or substituted with one heteroaryl substituent; and $R^{b1}$ is selected from hydrogen and $C_1$-$C_4$ alkyl.

In some embodiments, $R^1$ is:

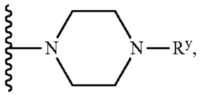

wherein $R^y$ is selected from $C_1$-$C_4$ alkyl, —C(O)$R^{a1}$, and —C(O)O$R^{b1}$; wherein: $R^{a1}$ is selected from $C_1$-$C_4$ alkyl, aryl, and heteroaryl, wherein the aryl is unsubstituted or substituted with one heteroaryl substituent; and $R^{b1}$ is selected from hydrogen and $C_1$-$C_4$ alkyl.

In some embodiments, $R^1$ is selected from:

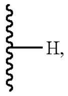 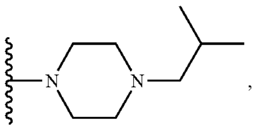 [SMILES: *N1CCN(CC(C)C)CC1], 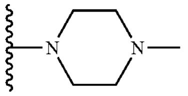,

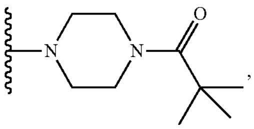, 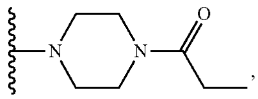,

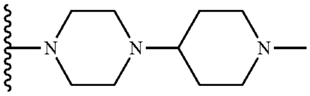 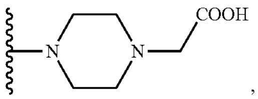,

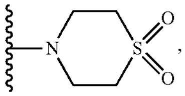, 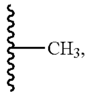

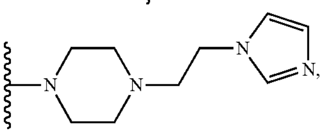 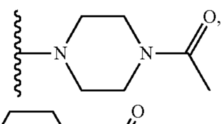

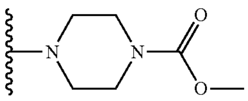, 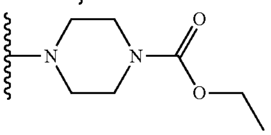,

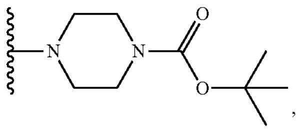,

-continued

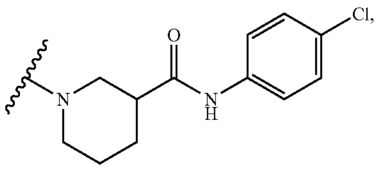

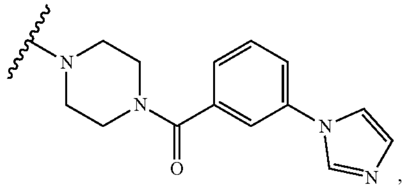,

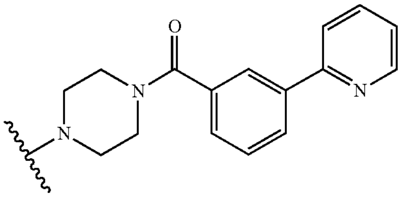,

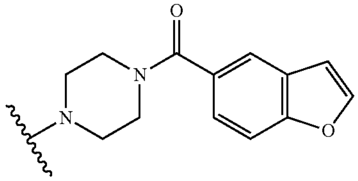

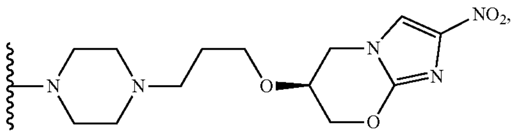

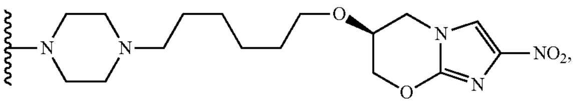

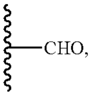 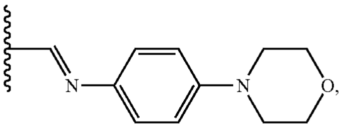

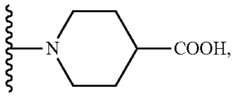 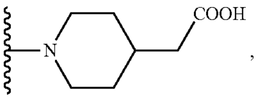,

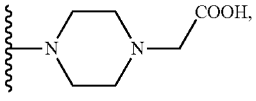 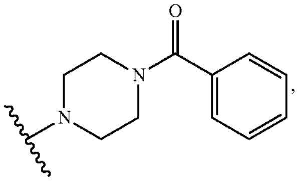

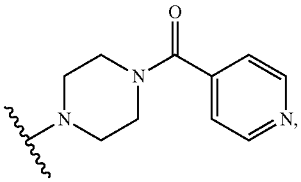 and 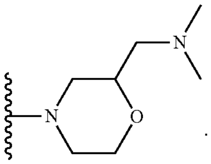.

In some embodiments, $R^1$ is:

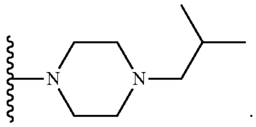

.

In some embodiments, X is O or a bond.

In some embodiments, $R^2$ is selected from hydrogen, $C_1$-$C_6$ alkyl, heterocyclyl, and —$CH_2$-Ph-$CH_2$-heterocyclyl, wherein each heterocyclyl is independently unsubstituted or substituted with one substituent selected from $C_1$-$C_6$ alkyl, —C(O)$R^2$, —C(O)$OR^{b2}$, —C(O)$NHR^{c2}$, —$(CH_2)_{n2}$—$X^{2a}$, and heterocyclyl.

In some embodiments, X is O; $R^2$ is —$CH_2$-Ph-$CH_2$-heterocyclyl, wherein the heterocyclyl is unsubstituted or substituted with one substituent selected from $C_1$-$C_6$ alkyl and —C(O)$R^{a2}$; $R^{a2}$ is selected from $C_1$-$C_6$ alkyl and —$(CH_2)_p$—Y; Y is selected from aryl, heteroaryl, and heterocyclyl; and p is 1 or 2.

In some embodiments, X is O; $R^2$ is —$CH_2$-Ph-$CH_2$-heterocyclyl, wherein the heterocyclyl is a monocyclic 6-membered heterocyclyl having 1 or 2 heteroatoms independently selected from N and O, and is unsubstituted or substituted with one substituent selected from $C_1$-$C_6$ alkyl and —C(O)$R^{a2}$; $R^{a2}$ is selected from $C_1$-$C_6$ alkyl and —$(CH_2)_p$—Y; Y is selected from phenyl, monocyclic 5- or 6-membered heteroaryl, and monocyclic 5- or 6-membered heterocyclyl; and p is 1 or 2.

In some embodiments, wherein —X—$R^2$ is selected from:

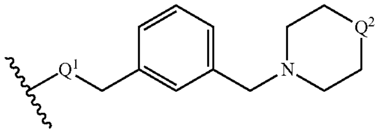

and

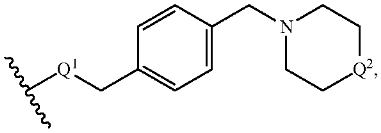

wherein: each $Q^1$ is independently selected from O, $NR^{q1}$, S, and $SO_2$; each $Q^2$ is independently selected from O, $NR^{q2}$, S, SO, and $SO_2$; $R^{q1}$ and $R^{q2}$ are each independently selected from hydrogen, $C_1$-$C_4$ alkyl, and —C(O)$R^{a2}$; $R^{a2}$ is selected from $C_1$-$C_4$ alkyl and —$(CH_2)_p$—Y; Y is selected from aryl, heteroaryl, cycloalkyl, and heterocyclyl; p is 1 or 2.

In some embodiments, $R^2$ is $C_1$-$C_6$ alkyl. In some embodiments, $R^2$ is methyl. In some embodiments, $R^2$ is heterocyclyl, which is unsubstituted or substituted with one substituent selected from $C_1$-$C_6$ alkyl, —C(O)$R^2$, and —$(CH_2)_{n2}$—$X^{2a}$.

In some embodiments, $R^2$ is a 6-membered monocyclic heterocyclyl having 1 or 2 heteroatoms independently selected from N and O, wherein the heterocyclyl is unsubstituted or substituted with one substituent selected from $C_1$-$C_4$ alkyl, —C(O)$R^{a2}$, and —$(CH_2)_{n2}$—$X^{2a}$; $R^{a2}$ is selected from aryl and heteroaryl, each of which is independently unsubstituted or substituted with one substituent selected from heteroaryl; $X^{2a}$ is selected from heteroaryl and —COOH; and n2 is 1 or 2.

In some embodiments, —X—$R^2$ is selected from:

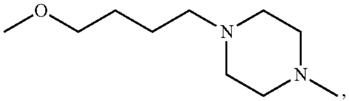

,

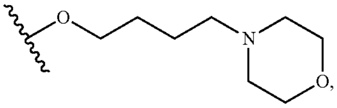

,

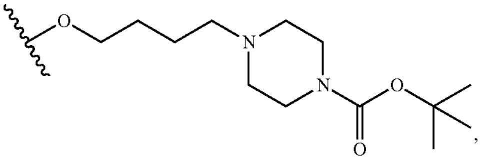

,

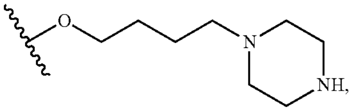

,

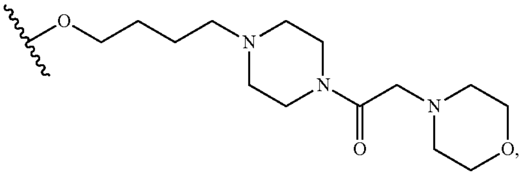

,

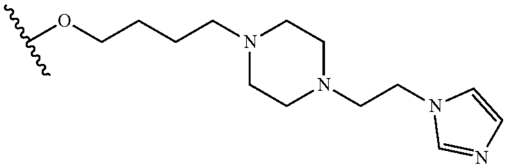

,

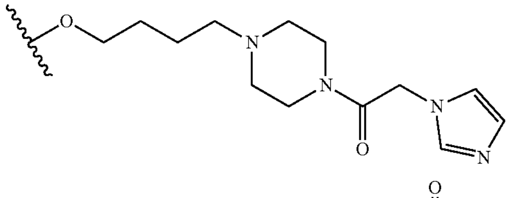

,

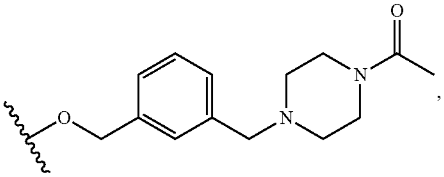

,

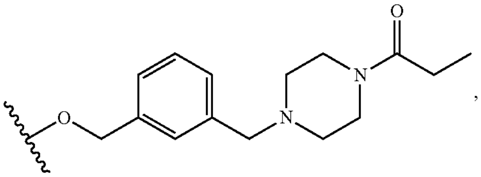

,

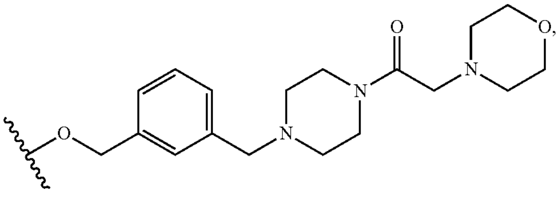

,

-continued
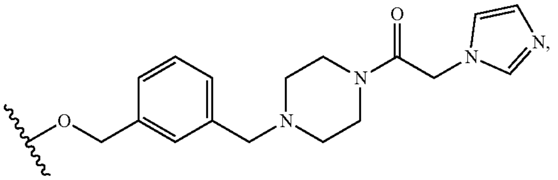
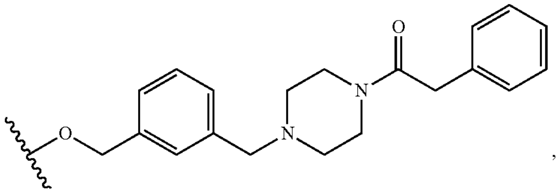
,
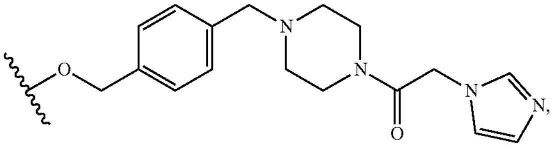
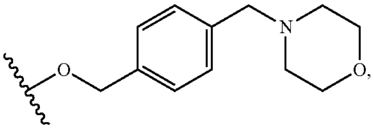
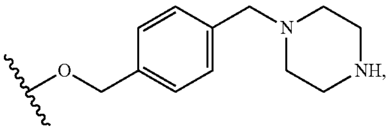
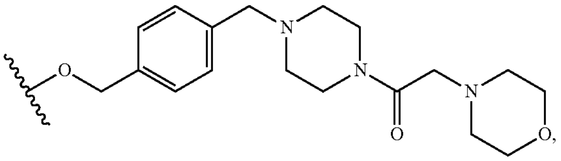
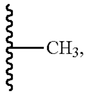
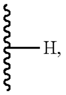
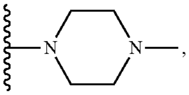
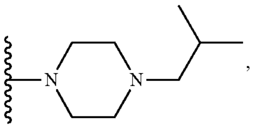
,
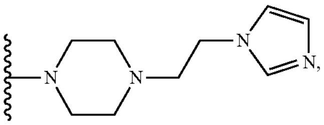
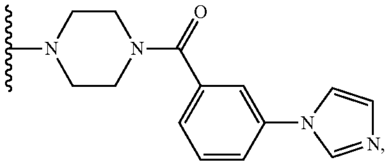
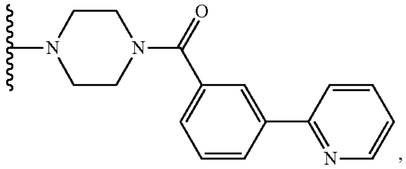
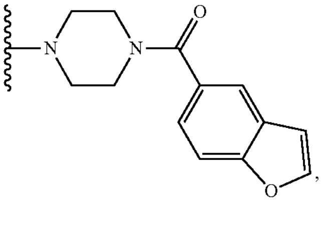
-continued
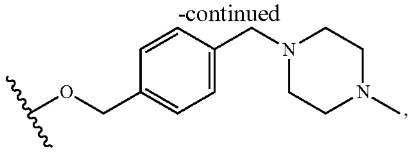
and
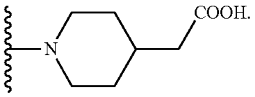
In some embodiments, —X—$R^2$ is:
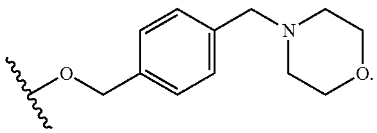 [SMILES: *OCc1ccc(CN2CCOCC2)cc1]
In one aspect, disclosed herein is a method of manufacturing a compound of formula (I) or a pharmaceutically acceptable salt thereof, comprising:
(a) reacting rifamycin S with a compound of formula (A), followed by treatment with manganese dioxide, to provide a compound of formula (B):
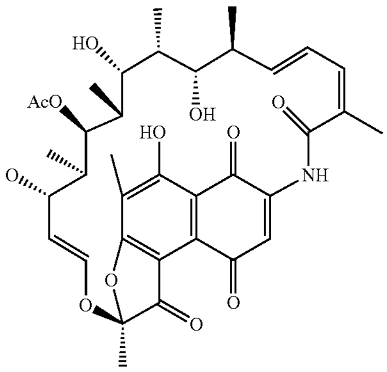
rifamycin S
+
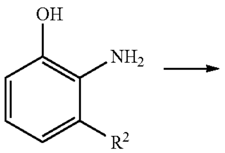
(A)

-continued

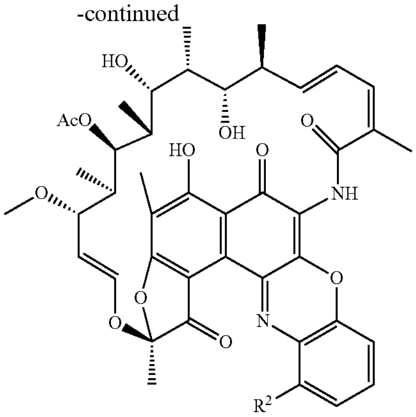

(B)

(b) reacting the compound of formula (B) with a compound of formula $R^1$—H, followed by treatment with manganese dioxide, to provide a compound of formula (I).

In one aspect, disclosed herein is a pharmaceutical composition comprising a compound of formula (I), or a pharmaceutically acceptable salt thereof, and a pharmaceutically acceptable excipient.

In one aspect, disclosed herein is a method of treating tuberculosis in a subject in need thereof, comprising administering to the subject a therapeutically effective amount of a compound of formula (I), or a pharmaceutically acceptable salt thereof, or a pharmaceutical composition comprising a compound of formula (I), or a pharmaceutically acceptable salt thereof.

In some embodiments, the subject is infected with human immunodeficiency virus. In some embodiments, the subject has acquired immune deficiency syndrome. In some embodiments, the subject is infected with *Mycobacterium tuberculosis*. In some embodiments, the subject is infected with a drug-resistant strain of *Mycobacterium tuberculosis*. In some embodiments, the subject is infected with a rifampin-resistant strain of *Mycobacterium tuberculosis*. In some embodiments, the subject has a persistent tuberculosis infection.

In one aspect, disclosed herein is a compound of formula (I), or a pharmaceutically acceptable salt thereof, for use in treatment of tuberculosis. In some embodiments, the tuberculosis is caused by *Mycobacterium tuberculosis*. In some embodiments, the tuberculosis is caused by a drug-resistant strain of *Mycobacterium tuberculosis*. In some embodiments, the tuberculosis is caused by a rifampin-resistant strain of *Mycobacterium tuberculosis*. In some embodiments, the tuberculosis is persistent tuberculosis. In some embodiments, the compound is for use in treatment of tuberculosis in a subject infected with human immunodeficiency virus. In some embodiments, the compound is for use in treatment of tuberculosis in a subject having acquired immune deficiency syndrome.

In one aspect, disclosed herein is a method of killing *Mycobacterium tuberculosis* in a sample, comprising contacting the sample with an effective amount of a compound of formula (I), or a pharmaceutically acceptable salt thereof. In some embodiments, the sample comprises a drug-resistant strain of *Mycobacterium tuberculosis*. In some embodiments, the sample comprises a rifampin-resistant strain of *Mycobacterium tuberculosis*.

DETAILED DESCRIPTION

Figure 1:
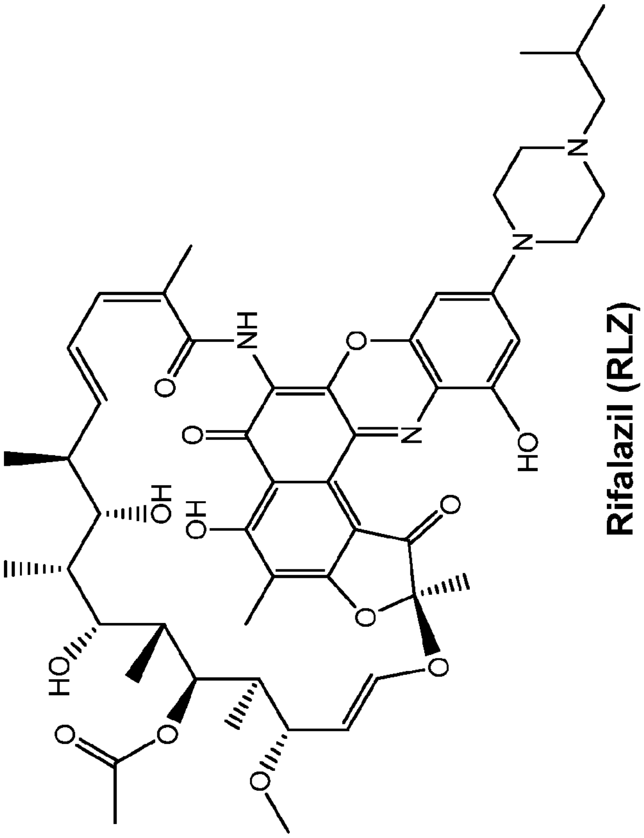
FIG. 1 shows the structures of rifampin (RMP) and rifalazil (RLZ).
Figure 1:
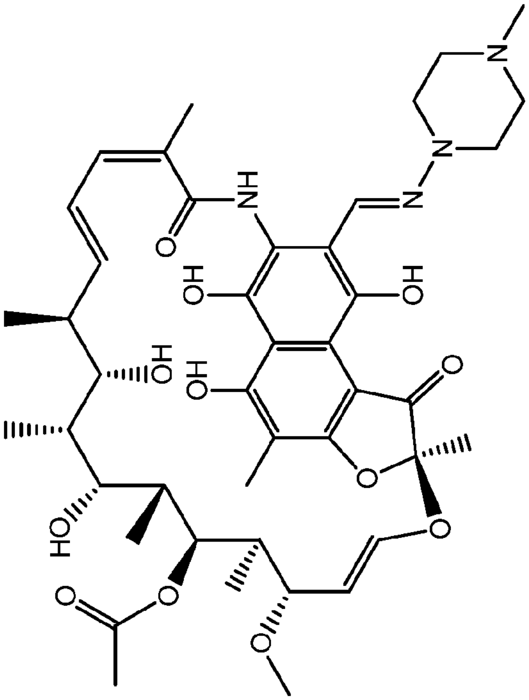

The present disclosure relates to compounds that are potent inhibitors of the *Mycobacterium tuberculosis* (MTB) RNA polymerase (RNAP), which exhibit significantly reduced activation of the human pregnane X receptor (hPXR), resulting in reduced induction of hepatic cytochromes P450 2C9 and 3A4 (CYP2C9, CYP3A4). The compounds are benzoxazino-rifamycins (bxRif), congeners of the clinical candidate rifalazil, that extend the rifamycin core to target a locus of the RNAP enzyme that has not previously been exploited. The compounds have antimicrobial activity against "normal" replicating MTB as well as non-replicating persistor (NRP) MTB, which mimics the latent state of MTB. The compounds also exhibit significantly reduced activation of the human pregnane X receptor (hPXR), which reduces or effectively eliminates induction of Cyp450s.

The present disclosure also relates to pharmaceutical compositions comprising the compounds, methods of using the compounds, and methods of preparing the compounds.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, $3^{rd}$ Edition, John Wiley & Sons, Inc., New York, 2018; and Carruthers, Some Modern Methods of Organic Synthesis, $3^{rd}$ Edition, Cambridge University Press, Cambridge, 1987; the entire contents of each of which are incorporated herein by reference.

As used herein, the term "alkyl" means a straight or branched saturated hydrocarbon chain containing from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), 1 to 4 carbon atoms ($C_1$-$C_4$ alkyl), 6 to 20 carbon atoms ($C_6$-$C_{20}$ alkyl), or 8 to 14 carbon atoms ($C_8$-$C_{14}$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkenyl" refers to a straight or branched hydrocarbon chain containing from 2 to 30 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "aryl" refers to an aromatic carbocyclic ring system having a single ring (monocyclic) or multiple rings (bicyclic or tricyclic) including fused ring systems, and zero heteroatoms. As used herein, aryl contains 6-20 carbon atoms ($C_6$-$C_{20}$ aryl), 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl). Representative examples of aryl groups include, but are not limited to, phenyl, naphthyl, anthracenyl, and phenanthrenyl.

As used herein, the term "cycloalkyl" refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "halogen" or "halo" means F, Cl, Br, or I.

As used herein, the term "haloalkyl" means an alkyl group, as defined herein, in which at least one hydrogen atom (e.g., one, two, three, four, five, six, seven or eight hydrogen atoms) is replaced by a halogen. Representative examples of haloalkyl include, but are not limited to, fluoromethyl, difluoromethyl, trifluoromethyl, and 2,2,2-trifluoroethyl.

As used herein, the term "heteroalkyl" means an alkyl group, as defined herein, in which one or more of the carbon atoms (and any associated hydrogen atoms) are each independently replaced with a heteroatom group such as —NR—, —O—, —S—, —S(O)—, —$S(O)_2$—, and the like, where R is H, alkyl, aryl, cycloalkyl, heteroalkyl, heteroaryl, or heterocyclyl, each of which may be optionally substituted. By way of example, 1, 2, or 3 carbon atoms may be independently replaced with the same or different heteroatomic group. Examples of heteroalkyl groups include, but are not limited to, —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. Heteroalkyl also includes groups in which a carbon atom of the alkyl is oxidized (i.e., is —C(O)—).

As used herein, the term "heteroaryl" refers to an aromatic group having a single ring (monocyclic) or multiple rings (bicyclic or tricyclic) having one or more ring heteroatoms independently selected from O, N, and S. The aromatic monocyclic rings are five- or six-membered rings containing at least one heteroatom independently selected from O, N, and S (e.g. 1, 2, 3, or 4 heteroatoms independently selected from O, N, and S). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, and a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

As used herein, the term "heterocycle" or "heterocyclic" refers to a saturated or partially unsaturated non-aromatic cyclic group having one or more ring heteroatoms independently selected from O, N, and S. The heterocycle can be a monocyclic heterocycle, a bicyclic heterocycle, or a tricyclic heterocycle. The monocyclic heterocycle is a three-, four-, five-, six-, seven-, or eight-membered ring containing at least one heteroatom independently selected from O, N, and S. The three- or four-membered ring contains zero or one double bond, and one heteroatom selected from O, N, and S. The five-membered ring contains zero or one double bond and one, two or three heteroatoms selected from O, N, and S. The six-membered ring contains zero, one, or two double bonds and one, two, or three heteroatoms selected from O, N, and S. The seven- and eight-membered rings contains zero, one, two, or three double bonds and one, two, or three heteroatoms selected from O, N, and S. The heteroatom in the ring can be oxidized (e.g., if the ring heteroatom is S, it can be oxidized to SO or $SO_2$). Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

As used herein, the term "hydroxy" means an —OH group.

As used herein, the term "nitro" means an —$NO_2$ group.

As used herein, the term "substituent" refers to a group substituted on an atom of the indicated group. When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroalkyl, heteroaryl, heterocyclyl, hydroxy, hydrazino, imino, oxo, nitro, phosphate, phosphonate, sulfonic acid, thiol, thione, or combinations thereof.

As used herein, in chemical structures the indication:

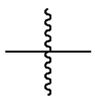

represents a point of attachment of one moiety to another moiety (e.g., a substituent group to the core compound).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —$CH_2O$— optionally also recites —$OCH_2$—, and —OC(O)NH— also optionally recites —NHC(O)O—.

The terms "administer," "administering," "administered," or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Effective amount," as used herein, refers to a dosage of a compound or a composition effective for eliciting a desired effect. This term as used herein may also refer to an amount effective at bringing about a desired in vivo effect in a subject, such as a human.

As used herein, the term "subject" is intended to include human and non-human animals. Exemplary human subjects include a human patient having a disease or disorder, e.g., an infection. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Compounds

The present disclosure provides a compound of formula (I):

(I)

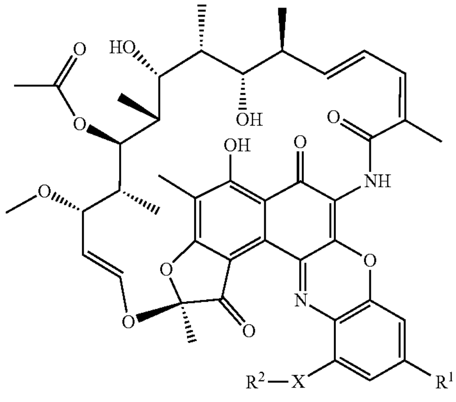

or a pharmaceutically acceptable salt thereof, wherein:

$R^1$ is selected from hydrogen, $C_1$-$C_6$ alkyl, $C_1$-$C_6$ heteroalkyl, —C(O)$R^a$, —N($R^b$)$_2$, —O$R^c$, —S$R^d$, —CH═N—Z, and heterocyclyl, wherein the heterocyclyl is unsubstituted or substituted with one substituent selected from $C_1$-$C_6$ alkyl, $C_1$-$C_6$ alkenyl, —C(O)$R^{a1}$, —C(O)O$R^{b1}$, —C(O)NH$R^{c1}$, —($CH_2$)$_{n1}$—$X^{1a}$, —$SO_2$—$X^{1b}$, aryl, heteroaryl, cycloalkyl, and heterocyclyl, wherein when the substituent is aryl, heteroaryl, cycloalkyl, or heterocyclyl, the substituent is optionally further substituted with $C_1$-$C_6$ alkyl or —O—$X^{1c}$;

X is selected from O, S, $SO_2$, $NHSO_2$, $NR^X$, and a bond;

$R^X$ is selected from hydrogen and $C_1$-$C_3$ alkyl;

$R^2$ is selected from hydrogen, $C_1$-$C_6$ alkyl, $C_1$-$C_6$ alkenyl, $C_3$-$C_6$ cycloalkyl, heterocyclyl, aryl, heteroaryl, —($CH_2$)$_{m1}$-aryl, —($CH_2$)$_{m2}$-heterocyclyl, and —$CH_2$-Ph-$CH_2$-heterocyclyl, wherein each alkyl, alkenyl, cycloalkyl, heterocyclyl, aryl, and heteroaryl is independently unsubstituted or substituted with one or two substituents independently selected from $C_1$-$C_6$ alkyl, hydroxy, amino, —C(O)$R^{a2}$, —C(O)O$R^{b2}$, —C(O)NH$R^{c2}$, —($CH_2$)$_{n2}$—$X^{2a}$, —$SO_2$—$X^{2b}$, aryl, heteroaryl, cycloalkyl, and heterocyclyl;

each $R^a$, $R^b$, $R^c$, and $R^d$ is independently selected from hydrogen, $C_1$-$C_6$ alkyl, $C_3$-$C_6$ cycloalkyl, and aryl;

$R^{a1}$ and $R^{a2}$ are each independently selected from hydrogen, $C_1$-$C_6$ alkyl, $C_1$-$C_6$ alkenyl, cycloalkyl, heterocyclyl, aryl, heteroaryl, and —($CH_2$)$_p$—Y, wherein each alkyl, alkenyl, cycloalkyl, heterocyclyl, aryl, and heteroaryl is independently unsubstituted or substituted with one substituent selected from aryl, heteroaryl, $C_1$-$C_6$ alkyl, halo, and nitro, and when the substituent is aryl or heteroaryl, it is unsubstituted or substituted with one substituent selected from halo, hydroxy, and —$CONH_2$;

$R^{b1}$ and $R^{b2}$ are each independently selected from hydrogen, $C_1$-$C_6$ alkyl, and heterocyclyl, wherein the heterocyclyl is optionally further substituted with one substituent selected from $C_1$-$C_6$ alkyl, hydroxy, halo, and nitro;

$R^{c1}$ and $R^{c2}$ are each independently selected from hydrogen, $C_1$-$C_6$ alkyl, and aryl, wherein the aryl is unsubstituted or substituted with one substituent selected from $C_1$-$C_6$ alkyl, halo, and nitro;

$X^{1a}$, $X^{1b}$, $X^{1c}$, $X^{2a}$, and $X^{2b}$ are each independently selected from aryl, heteroaryl, cycloalkyl, heterocyclyl, —O-heterocyclyl, —COOH, and —N($CH_3$)$_2$, wherein each aryl, heteroaryl, cycloalkyl, or heterocyclyl is independently unsubstituted or substituted with one substituent selected from $C_1$-$C_6$ alkyl, hydroxy, halo, and nitro;

Y is selected from aryl, heteroaryl, cycloalkyl, and heterocyclyl, each of which is independently unsubstituted or substituted with one substituent selected from $C_1$-$C_6$ alkyl, halo, and nitro;

Z is selected from aryl and heteroaryl, each of which is optionally substituted with one substituent selected from heterocyclyl; and m1, m2, n1, n2, and p are each independently 1, 2, 3, 4, 5, or 6;

wherein when $R^1$ is hydrogen, —X—$R^2$ is not:

—$CH_3$,

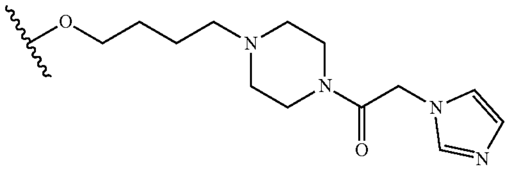

or

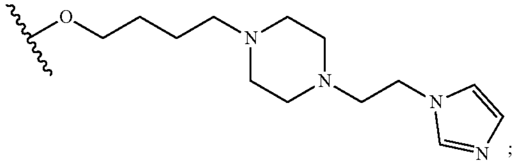

;

and when $R^1$ is

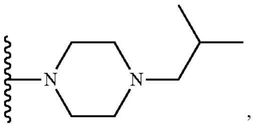 [SMILES: *N1CCN(CC(C)C)CC1]

,

—X—$R^2$ is not: —$CH_3$, —SH, or

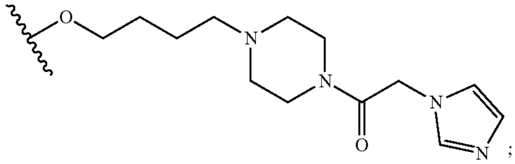 [SMILES: *OCCCCN1CCN(C(=O)Cn2ccnc2)CC1]

;

and when $R^1$ is

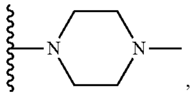 [SMILES: *N1CCN(C)CC1]

,

—X—$R^2$ is not —$CH_3$;

and when $R^1$ is $CH_3$, —X—$R^2$ is not hydrogen;

and when X is O, $R^2$ is not hydrogen.

In some embodiments, $R^1$ is selected from hydrogen and methyl. In some embodiments, $R^1$ is hydrogen. In some embodiments, $R^1$ is methyl. In some embodiments, $R^1$ is —CHO. In some embodiments, $R^1$ is —CH═N—Z, wherein Z is aryl, which is optionally substituted with one substituent selected from heterocyclyl. In some embodiments, $R^1$ is —CH═N—Z, wherein Z is phenyl, which is optionally substituted with a monocyclic 6-membered heterocyclyl having 1 or 2 heteroatoms independently selected from N, O, and S. In some embodiments, $R^1$ is —CH═N—Z, wherein Z is phenyl, which is substituted with a monocyclic 6-membered heterocyclyl having 1 or 2 heteroatoms independently selected from N and O.

In some embodiments, $R^1$ is heterocyclyl, wherein the heterocyclyl is unsubstituted or substituted with one substituent selected from $C_1$-$C_6$ alkyl, —C(O)$R^{a1}$, —C(O)O$R^b$, —C(O)NH$R^{c1}$, —($CH_2$)$_{n1}$—$X^{1a}$, and heterocyclyl, wherein when the substituent is heterocyclyl, the heterocyclyl substituent is optionally further substituted with $C_1$-$C_6$ alkyl. In some embodiments, $R^1$ is a monocyclic 6-membered heterocyclyl having 1 or 2 heteroatoms independently selected from N, O, and S, wherein the heterocyclyl is unsubstituted or substituted with one substituent selected from $C_1$-$C_6$ alkyl, —C(O)$R^{a1}$, —C(O)O$R^b$, and —$(CH_2)_{n1}$—$X^{1a}$. In some embodiments, the heterocyclyl is unsubstituted or substituted with one substituent selected from $C_1$-$C_4$ alkyl, —C(O)$R^{a1}$, and —C(O)O$R^{b1}$; wherein: $R^{a1}$ is selected from $C_1$-$C_4$ alkyl, aryl, and heteroaryl, wherein the aryl is unsubstituted or substituted with one heteroaryl substituent; and $R^{b1}$ is selected from hydrogen and $C_1$-$C_4$ alkyl. In some embodiments, $R^1$ is selected from piperazinyl, piperidinyl, morpholino, and 1,1-dioxothiomorpholino, each of which is unsubstituted or substituted with one substituent selected from $C_1$-$C_6$ alkyl, —C(O)$R^{a1}$, —C(O)O$R^b$, and —$(CH_2)_{n1}$—$X^{1a}$. In some embodiments, $R^1$ is selected from piperazinyl, piperidinyl, morpholino, and 1,1-dioxothiomorpholino, each of which is unsubstituted or substituted with one substituent selected from $C_1$-$C_4$ alkyl (e.g., methyl, isobutyl), —C(O)$R^{a1}$, and —C(O)O$R^{b1}$; wherein: $R^{a1}$ is selected from $C_1$-$C_4$ alkyl (e.g., methyl, ethyl, tert-butyl), aryl (e.g., phenyl), and heteroaryl (e.g., pyridyl or benzofuranyl), wherein the aryl is unsubstituted or substituted with one heteroaryl substituent (e.g., pyridyl or imidazolyl); and $R^{b1}$ is selected from hydrogen and $C_1$-$C_4$ alkyl (e.g., methyl, ethyl, tert-butyl).

In some embodiments, $R^1$ is:

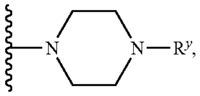

wherein $R^y$ is selected from $C_1$-$C_4$ alkyl, —C(O)$R^{a1}$, and —C(O)O$R^{b1}$; wherein $R^{a1}$ is selected from $C_1$-$C_4$ alkyl, aryl, and heteroaryl, wherein the aryl is unsubstituted or substituted with one heteroaryl substituent; and $R^{b1}$ is selected from hydrogen and $C_1$-$C_4$ alkyl.

In some embodiments, $R^1$ is selected from:

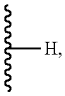 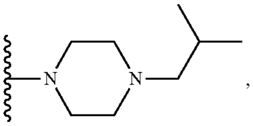, 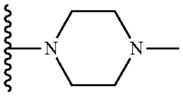,

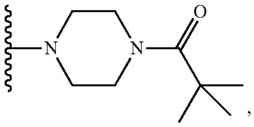, 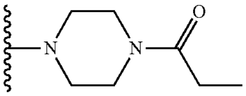,

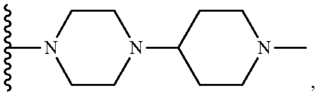, 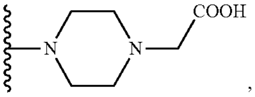,

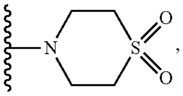, 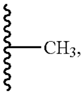

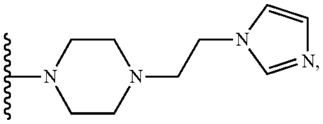 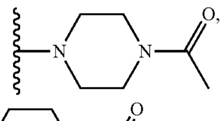

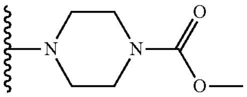, 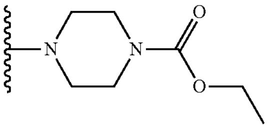,

-continued

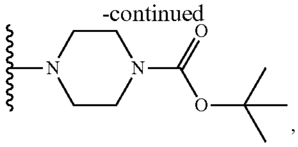,

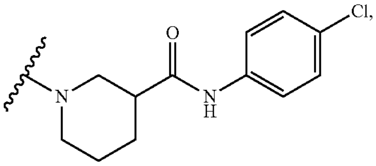

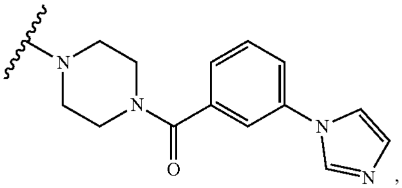,

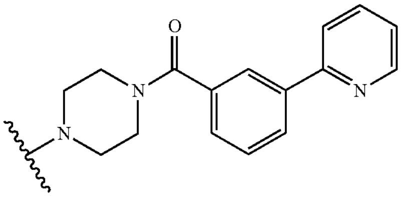,

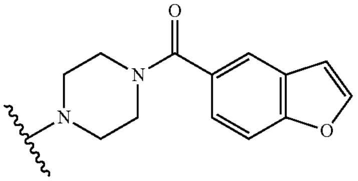

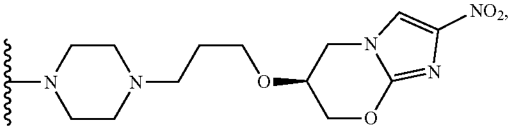

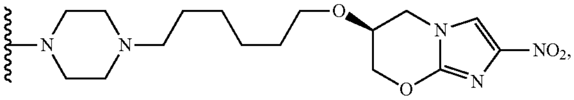

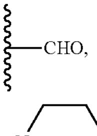 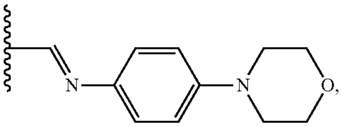

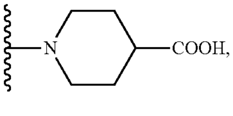 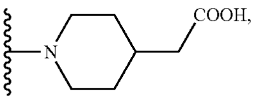

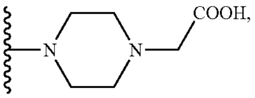 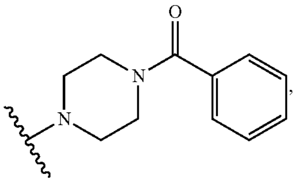

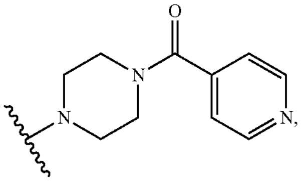 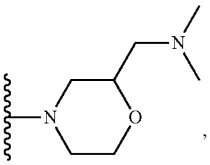,

-continued

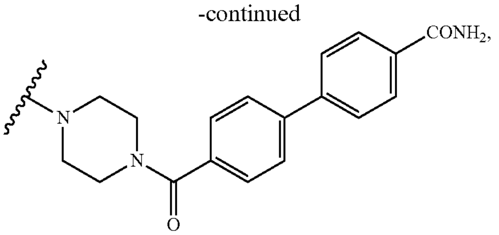

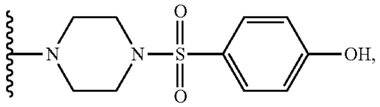

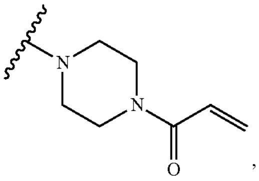
,
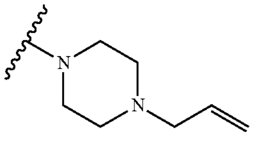
,

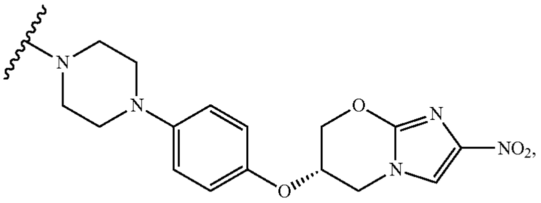

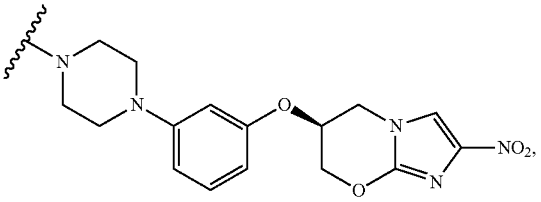

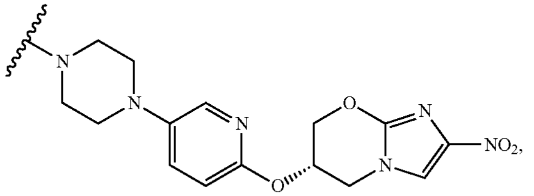
and

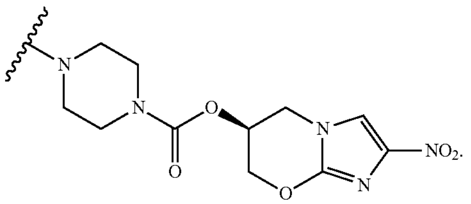

In some embodiments, $R^1$ is:

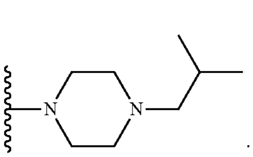
.

In some embodiments, X is O. In some embodiments, X is S. In some embodiments, X is $SO_2$. In some embodiments, X is $NHSO_2$. In some embodiments, X is NH. In some embodiments, X is a bond.

In some embodiments, $R^2$ is selected from hydrogen, $C_1$-$C_6$ alkyl, heterocyclyl, —$CH_2$-Ph-$CH_2$-heterocyclyl, wherein each heterocyclyl is independently unsubstituted or substituted with one substituent selected from $C_1$-$C_6$ alkyl, —C(O)$R^{a2}$, —C(O)O$R^{b2}$, —C(O)NH$R^{c2}$, —$(CH_2)_{n2}$—$X^{2a}$, and heterocyclyl.

In some embodiments, $R^2$ is —$CH_2$-Ph-$CH_2$-heterocyclyl, wherein the heterocyclyl is unsubstituted or substituted with one substituent selected from $C_1$-$C_6$ alkyl and —C(O)$R^{a2}$; $R^{a2}$ is selected from $C_1$-$C_6$ alkyl and —$(CH_2)_p$—Y; Y is selected from aryl, heteroaryl, and heterocyclyl; and p is 1 or 2. In some embodiments, $R^2$ is —$CH_2$-Ph-$CH_2$-heterocyclyl, wherein the heterocyclyl is a monocyclic 6-membered heterocyclyl having 1 or 2 heteroatoms independently selected from N and O, and is unsubstituted or substituted with one substituent selected from $C_1$-$C_6$ alkyl and —C(O)$R^{a2}$; $R^{a2}$ is selected from $C_1$-$C_6$ alkyl and —$(CH_2)_p$—Y; Y is selected from phenyl, monocyclic 5- or 6-membered heteroaryl, and monocyclic 5- or 6-membered heterocyclyl; and p is 1 or 2. In some embodiments, $R^2$ is —$CH_2$-Ph-$CH_2$-heterocyclyl, wherein the heterocyclyl is morpholino or piperazinyl, wherein the piperazinyl is unsubstituted or substituted with one substituent selected from $C_1$-$C_6$ alkyl and —C(O)$R^{a2}$; $R^{a2}$ is selected from $C_1$-$C_6$ alkyl and —$(CH_2)_p$—Y; Y is selected from phenyl, monocyclic 5- or 6-membered heteroaryl, and monocyclic 5- or 6-membered heterocyclyl; and p is 1 or 2.

In some embodiments, —X—$R^2$ is selected from:

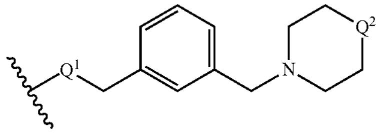
and
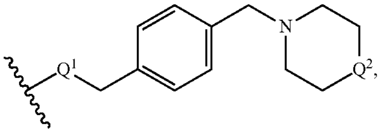

wherein each $Q^1$ is independently selected from O, $NR^{q1}$, S, and $SO_2$; and each $Q^2$ is independently selected from O, $NR^{q2}$, S, SO, and $SO_2$; $R^{q1}$ and $R^{q2}$ are each independently selected from hydrogen, $C_1$-$C_4$ alkyl, and —C(O)$R^{a2}$; $R^{a2}$ is selected from $C_1$-$C_4$ alkyl and —$(CH_2)_p$—Y; Y is selected from aryl, heteroaryl, cycloalkyl, and heterocyclyl; and p is 1 or 2. In some embodiments, $Q^1$ is O. In some embodiments, $Q^1$ is $NR^{q1}$. In some embodiments, $R^{q1}$ is selected from hydrogen, methyl, and —C(O)$R^{a2}$, wherein $R^{a2}$ is selected from $C_1$-$C_4$ alkyl (e.g., methyl) and —$(CH_2)_p$—Y; wherein Y is selected from phenyl, morpholino, and imidazolyl, and p is 1. In some embodiments, $Q^1$ is S. In some embodiments, $Q^1$ is $SO_2$. In some embodiments, $Q^2$ is O. In some embodiments, $Q^2$ is S. In some embodiments, $Q^2$ is SO. In some embodiments, $Q^2$ is $SO_2$.

In some embodiments, $R^2$ is $C_1$-$C_6$ alkyl. In some embodiments, $R^2$ is methyl.

In some embodiments, $R^2$ is heterocyclyl, which is unsubstituted or substituted with one substituent selected from $C_1$-$C_6$ alkyl, —C(O)$R^{a2}$, and —$(CH_2)_{n2}$—$X^{2a}$. In some embodiments, $R^2$ is a 6-membered monocyclic heterocyclyl having 1 or 2 heteroatoms independently selected from N and O, wherein the heterocyclyl is unsubstituted or substituted with one substituent selected from $C_1$-$C_4$ alkyl, —C(O)$R^{a2}$, and —$(CH_2)_{n2}$—$X^{2a}$; $R^{a2}$ is selected from aryl and heteroaryl, each of which is independently unsubstituted or substituted with one substituent selected from heteroaryl; $X^{2a}$ is selected from heteroaryl and —COOH; and n is 1 or 2. In some embodiments, $R^2$ is piperidinyl or piperazinyl, each of which is independently unsubstituted or substituted with one substituent selected from $C_1$-$C_4$ alkyl (e.g., methyl, iso-butyl), —C(O)$R^{a2}$, and —$(CH_2)_{n2}$—$X^{2a}$; $R^{a2}$ is selected from aryl (e.g., phenyl) and heteroaryl (e.g., benzofuranyl), each of which is independently unsubstituted or substituted with one substituent selected from heteroaryl (e.g., imidazolyl or pyridyl); $X^{2a}$ is selected from heteroaryl (e.g., imidazolyl) and —COOH; and n is 1 or 2.

In some embodiments, —X—$R^2$ is selected from:

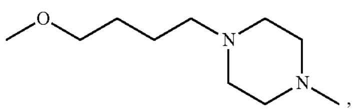

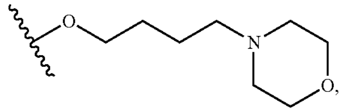

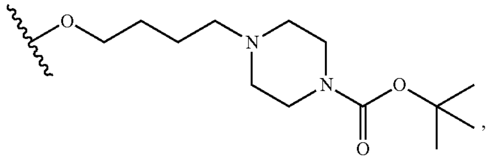

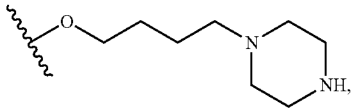

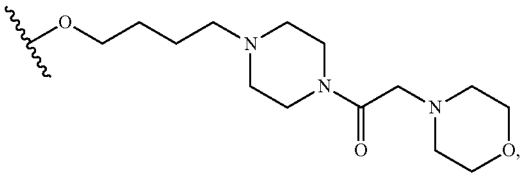

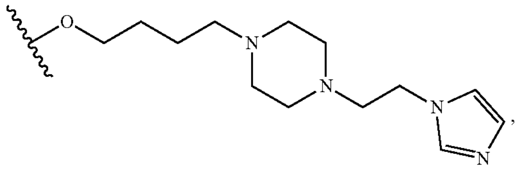

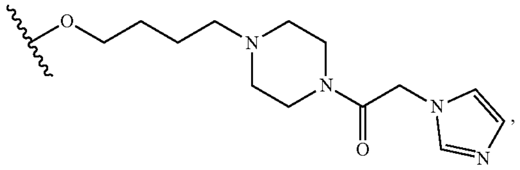

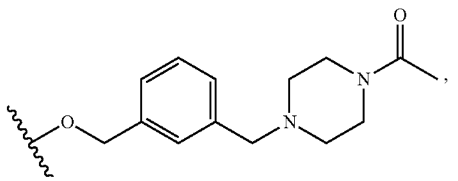

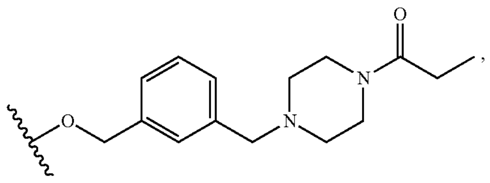

-continued

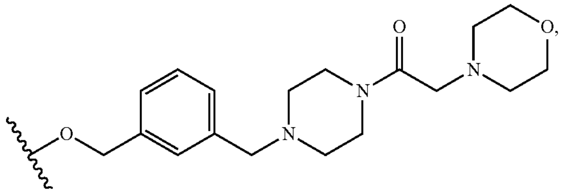

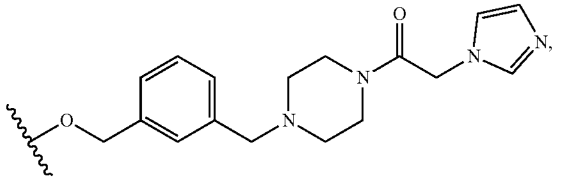

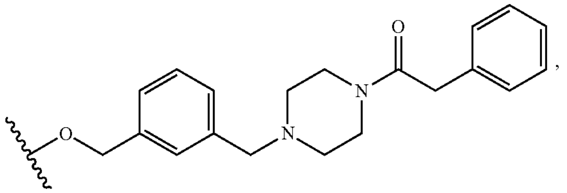

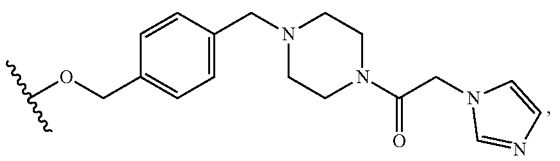

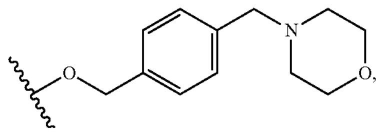

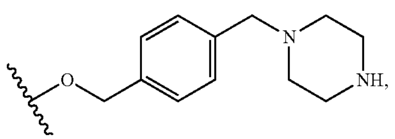

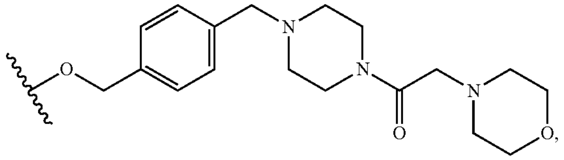

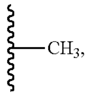

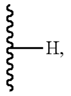

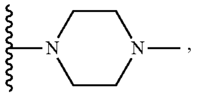

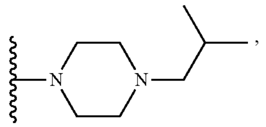

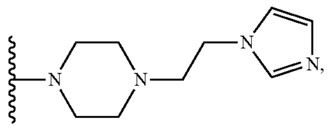

-continued
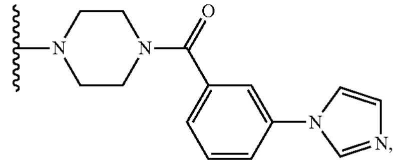
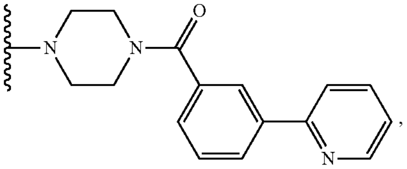
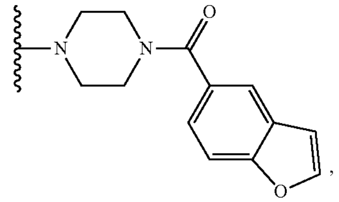
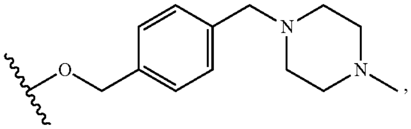
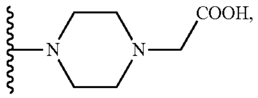
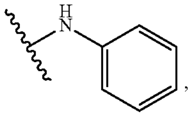
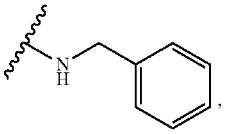
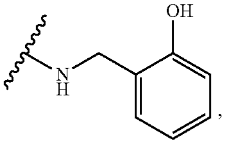
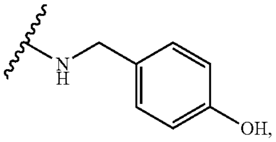
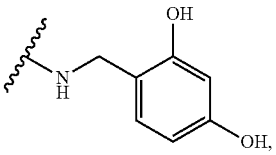
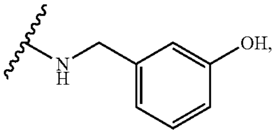
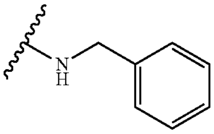
-continued
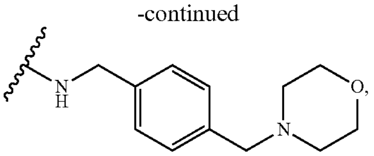
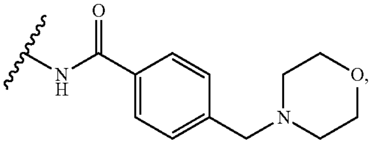
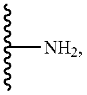
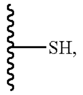
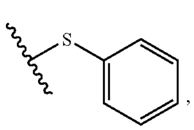
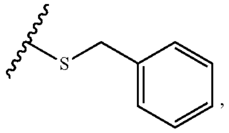
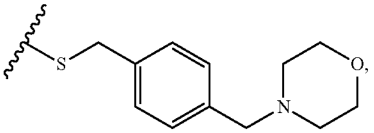
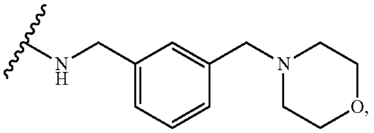
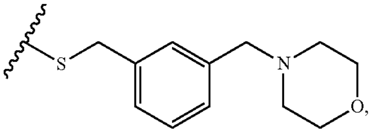
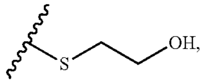
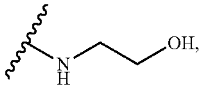
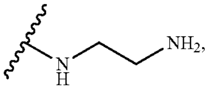
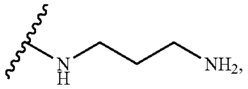
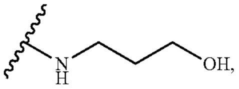
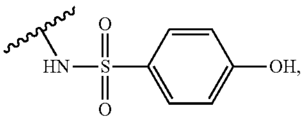
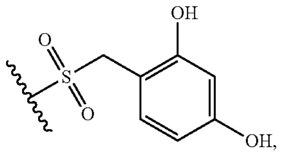
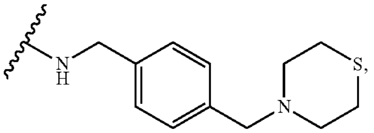
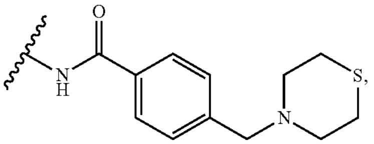

-continued
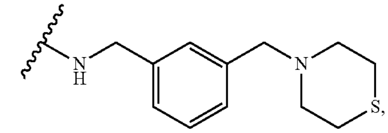,
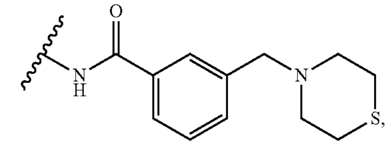,
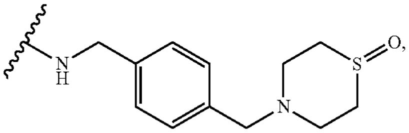,
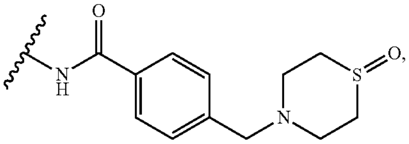,
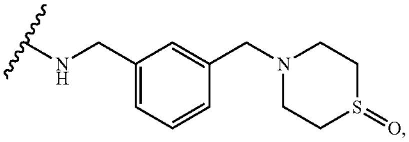,
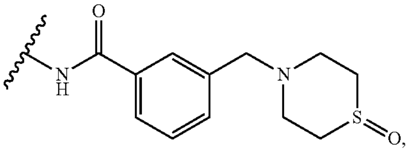,
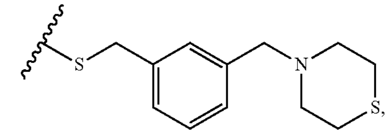,
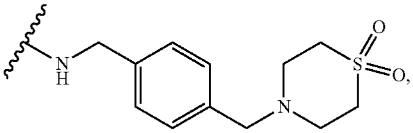,
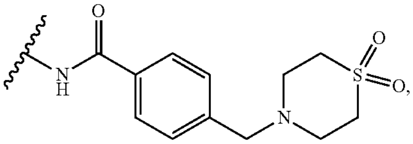,
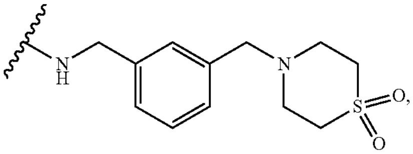,
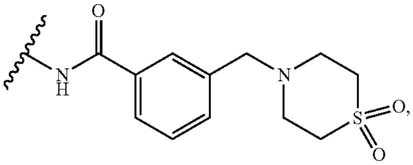,
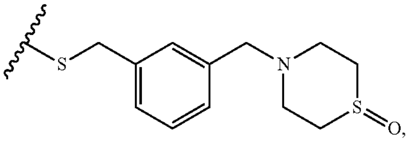,
-continued
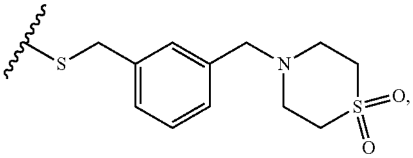,
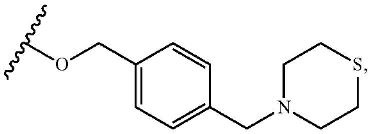,
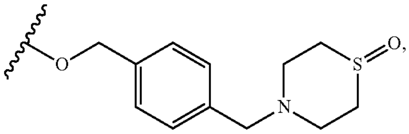,
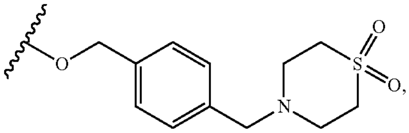,
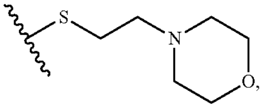,
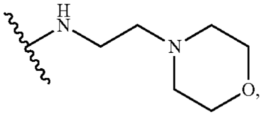,
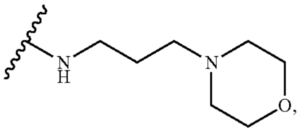,
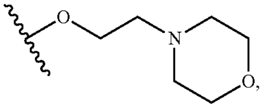,
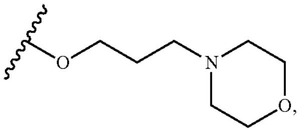,
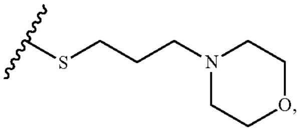,
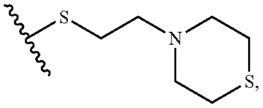,
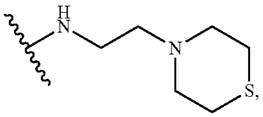,
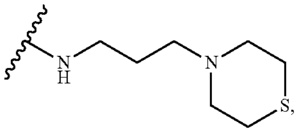, -continued
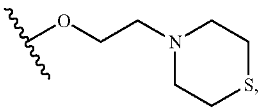
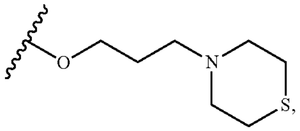
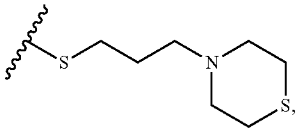
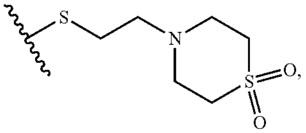
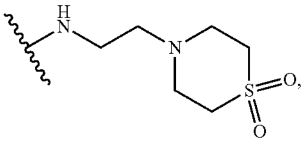
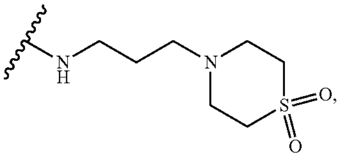
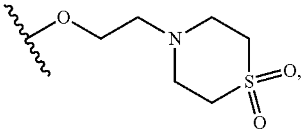
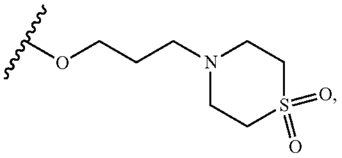
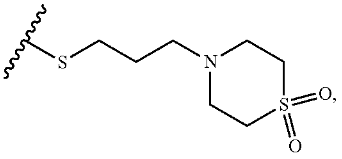
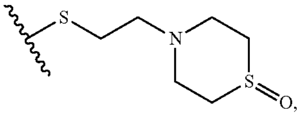
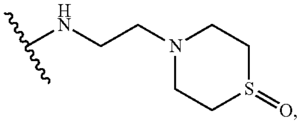
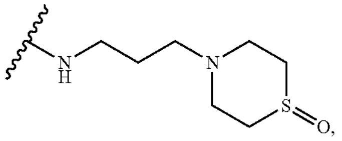
-continued
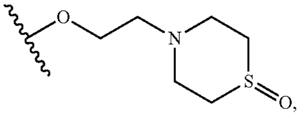
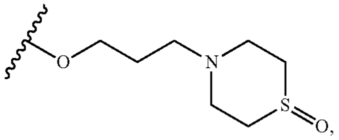
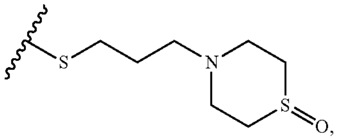
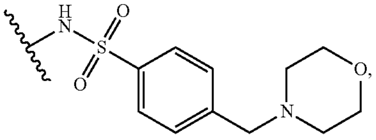
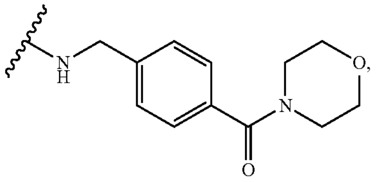
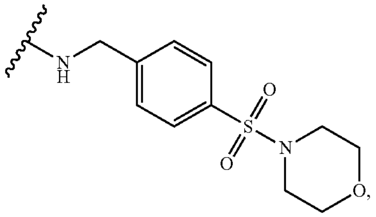
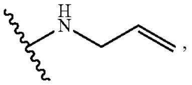
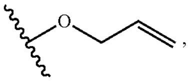
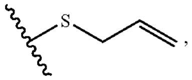
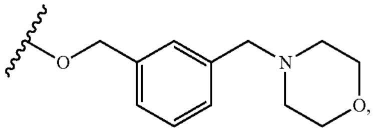
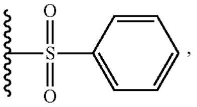
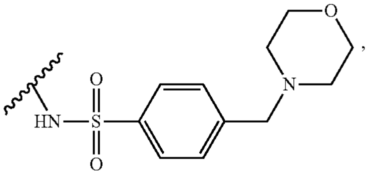
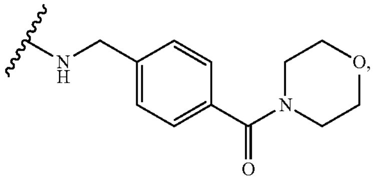

-continued

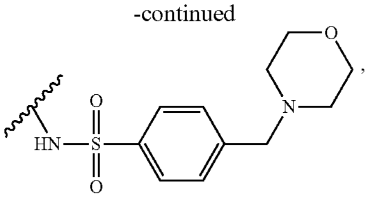

,

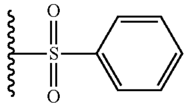

,

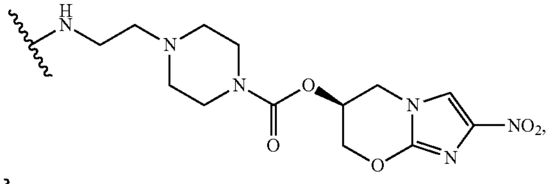

,

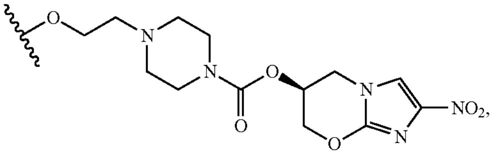

, and

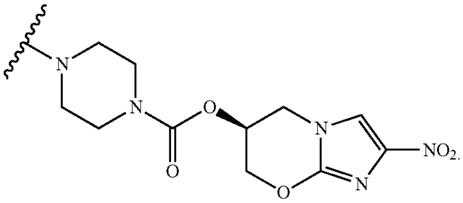

.

In some embodiments, —X—$R^2$ is selected from:

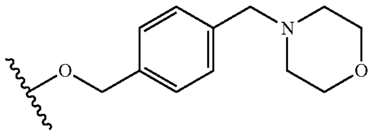

and

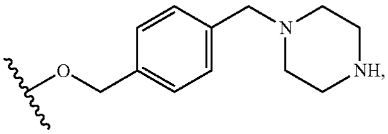

,

In some embodiments, $R^1$ is

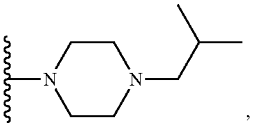

, and $R^2$ is

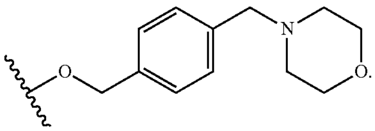 [SMILES: *OCc1ccc(CN2CCOCC2)cc1]

.

In some embodiments, $R^1$ and $R^2$ are not simultaneously hydrogen.

In some embodiments, when $R^1$ is hydrogen, —X—$R^2$ is not —O—$(CH_2)_m$-heterocyclyl. In some embodiments, when $R^1$ is hydrogen and —X—$R^2$ is —O—$(CH_2)_m$-heterocyclyl, the heterocyclyl is not substituted with —C(O)$R^{a2}$ or —$(CH_2)_{n2}$—$X^{2a}$. In some embodiments, when $R^1$ is hydrogen and —X—$R^2$ is —O—$(CH_2)_m$-heterocyclyl, the heterocyclyl is unsubstituted or substituted with one substituent selected from $C_1$-$C_6$ alkyl, —C(O)O$R^{b2}$, —C(O)NH$R^{c2}$, and heterocyclyl. In some embodiments, when $R^1$ is hydrogen, —X—$R^2$ is not:

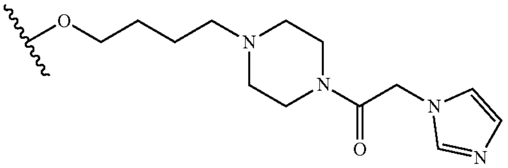

or

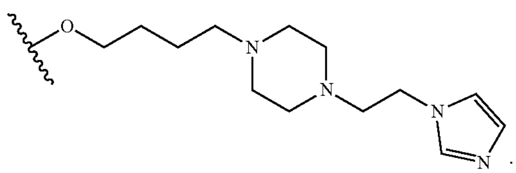

.

In some embodiments, when $R^1$ is

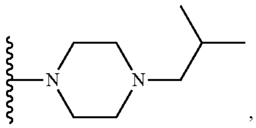

,

—X—$R^2$ is not —O—$(CH_2)_m$-heterocyclyl. In some embodiments, when $R^1$ is

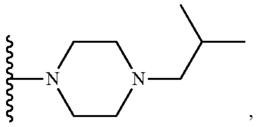 [SMILES: *N1CCN(CC(C)C)CC1]

,

—X—$R^2$ is —O—$(CH_2)_m$-heterocyclyl, wherein the heterocyclyl is not substituted with —C(O)$R^{a2}$ or —$(CH_2)_{n2}$—$X^{2a}$. In some embodiments, when $R^1$ is

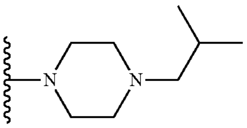

,

—X—$R^2$ is —O—$(CH_2)_m$-heterocyclyl, wherein the heterocyclyl is not substituted with —C(O)$R^{a2}$. In some embodiments, when $R^1$ is

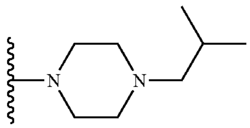,

—X—$R^2$ is —O—$(CH_2)_m$-heterocyclyl, wherein the heterocyclyl is unsubstituted or substituted with one substituent selected from $C_1$-$C_6$ alkyl, —C(O)$OR^{b2}$, —C(O)$NHR^{c2}$, and heterocyclyl. In some embodiments, when $R^1$ is

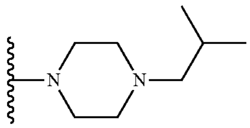,

—X—$R^2$ is not:

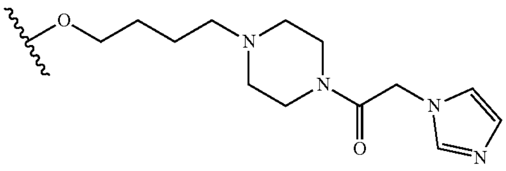

or

-continued

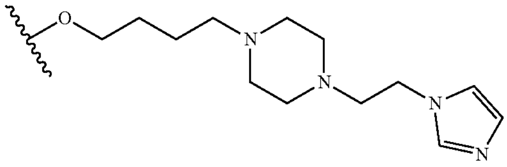.

In some embodiments, when $R^1$ is

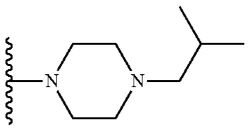,

—X—$R^2$ is not:

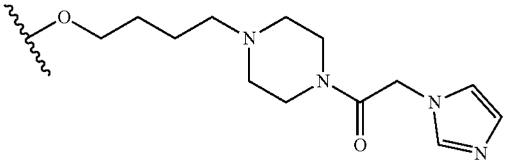.

In some embodiments, the compound of formula (I) is selected from compounds in Table 1.

TABLE 1

Exemplary Compounds

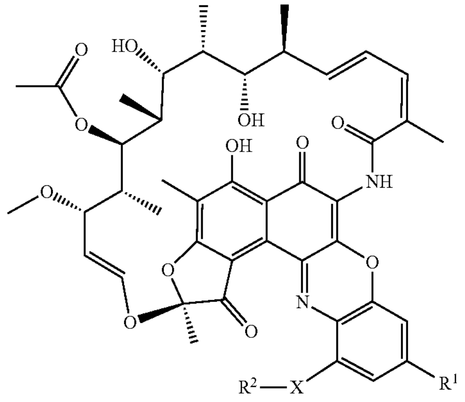

| Compound | $R^1$ | —X—$R^2$ |
| --- | --- | --- |
| 5a | H | 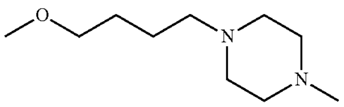 |
| 5b | H | 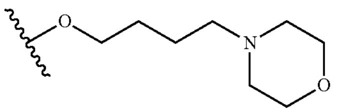 [SMILES: *OCCCCN1CCOCC1] |

TABLE 1-continued
Exemplary Compounds
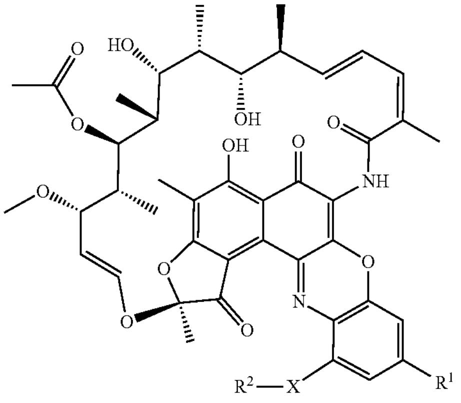
| Compound | $R^1$ | —X—$R^2$ |
|---|---|---|
| 5c | H | 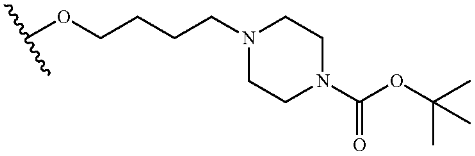 [SMILES: *OCCCCN1CCN(C(=O)OC(C)(C)C)CC1] |
| 5d | H | 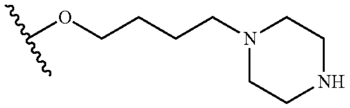 [SMILES: *OCCCCN1CCNCC1] |
| 5e | H | 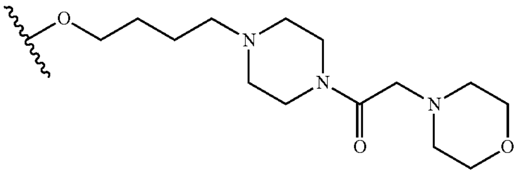 [SMILES: *OCCCCN1CCN(C(=O)CN2CCOCC2)CC1] |
| 6a | 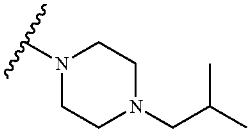 [SMILES: *N1CCN(CC(C)C)CC1] | 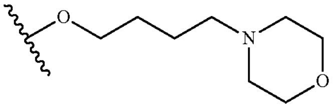 [SMILES: *OCCCCN1CCOCC1] |
| 6b | 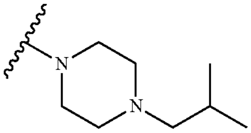 [SMILES: *N1CCN(CC(C)C)CC1] | 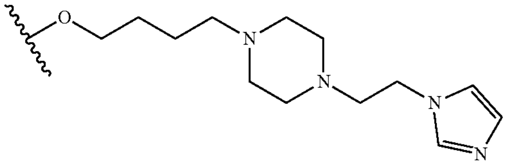 [SMILES: *OCCCCN1CCN(CCn2ccnc2)CC1] |
| 6c | 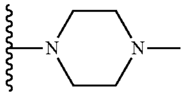 | 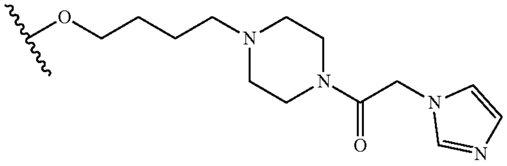 [SMILES: *OCCCCN1CCN(C(=O)Cn2ccnc2)CC1] |
| 6d | 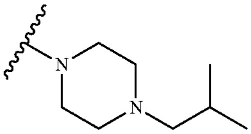 [SMILES: *N1CCN(CC(C)C)CC1] | 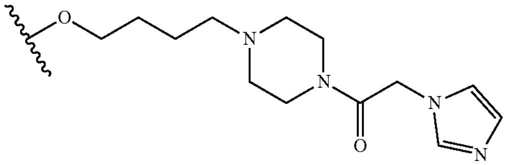 [SMILES: *OCCCCN1CCN(C(=O)Cn2ccnc2)CC1] |

TABLE 1-continued
Exemplary Compounds
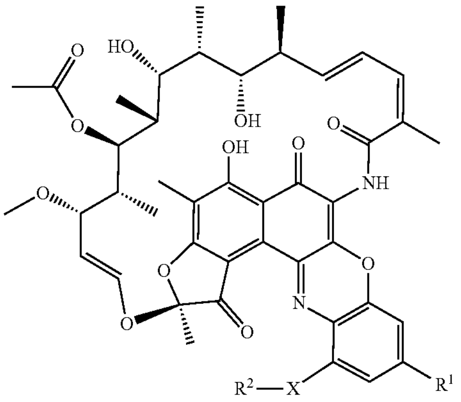
| Compound | $R^1$ | —X—$R^2$ |
| --- | --- | --- |
| 11c | H | 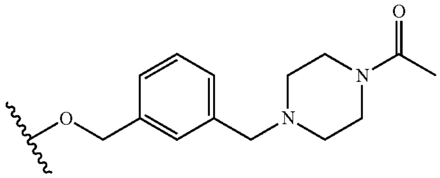 [SMILES: *OCc1cccc(CN2CCN(C(C)=O)CC2)c1] |
| 11d | H | 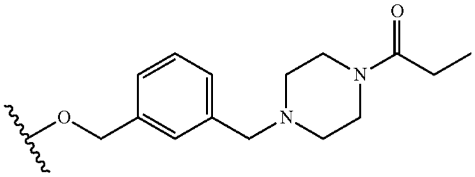 [SMILES: *OCc1cccc(CN2CCN(C(=O)CC)CC2)c1] |
| 11e | H | 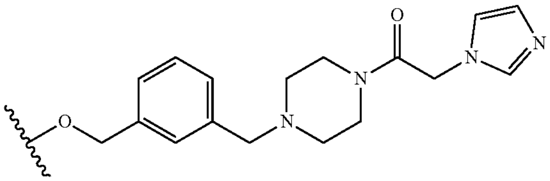 [SMILES: *OCc1cccc(CN2CCN(C(=O)Cn3ccnc3)CC2)c1] |
| 11f | H | 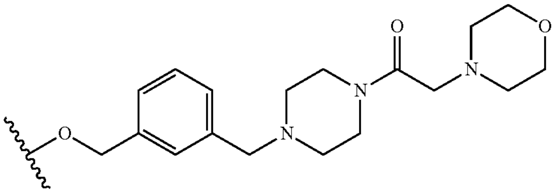 [SMILES: *OCc1cccc(CN2CCN(C(=O)CN3CCOCC3)CC2)c1] |
| 11g | H | 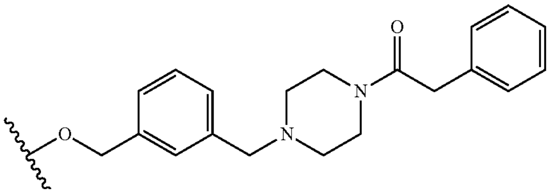 [SMILES: *OCc1cccc(CN2CCN(C(=O)Cc3ccccc3)CC2)c1] |

TABLE 1-continued
Exemplary Compounds
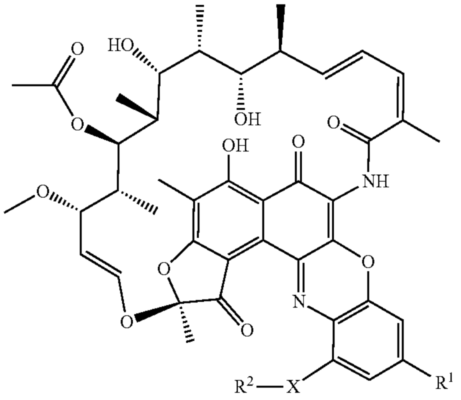
| Compound | $R^1$ | —X—$R^2$ |
|---|---|---|
| 12c | 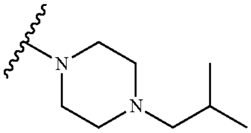 [SMILES: *N1CCN(CC(C)C)CC1] | 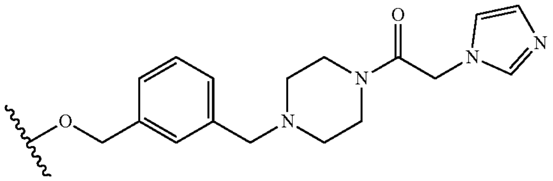 [SMILES: *OCc1cccc(CN2CCN(C(=O)Cn3ccnc3)CC2)c1] |
| 16b | H | 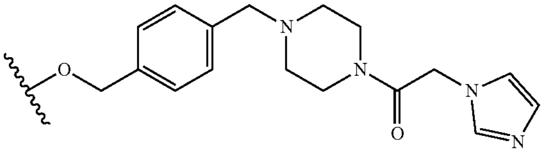 [SMILES: *OCc1ccc(CN2CCN(C(=O)Cn3ccnc3)CC2)cc1] |
| 16c | H | 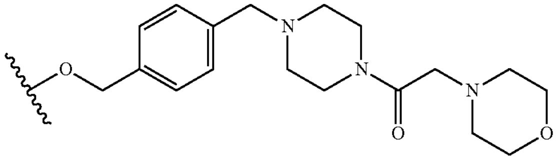 [SMILES: *OCc1ccc(CN2CCN(C(=O)CN3CCOCC3)CC2)cc1] |
| 16d | H | 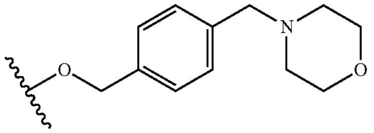 [SMILES: *OCc1ccc(CN2CCOCC2)cc1] |
| 16e | H | 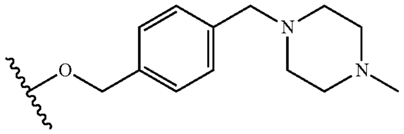 [SMILES: *OCc1ccc(CN2CCN(C)CC2)cc1] |
| 17b | 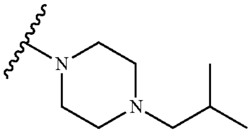 [SMILES: *N1CCN(CC(C)C)CC1] | 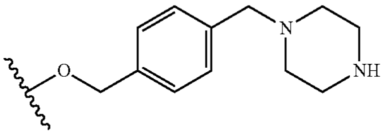 [SMILES: *OCc1ccc(CN2CCNCC2)cc1] |
| 17c | 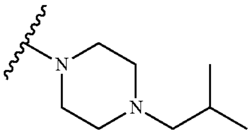 [SMILES: *N1CCN(CC(C)C)CC1] | 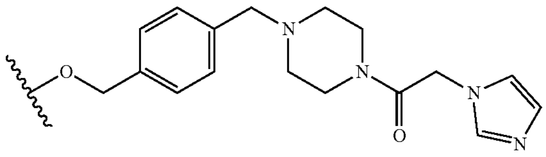 [SMILES: *OCc1ccc(CN2CCN(C(=O)Cn3ccnc3)CC2)cc1] |

TABLE 1-continued
Exemplary Compounds
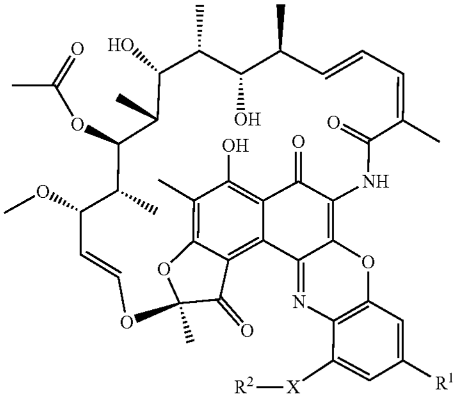
| Compound | $R^1$ | —X—$R^2$ |
|---|---|---|
| 17d | 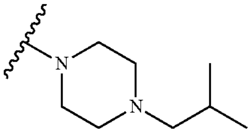 [SMILES: *N1CCN(CC(C)C)CC1] | 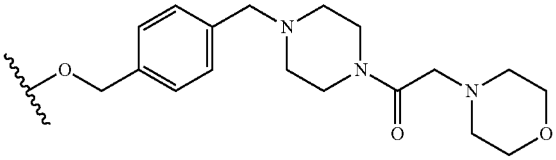 [SMILES: *OCc1ccc(CN2CCN(C(=O)CN3CCOCC3)CC2)cc1] |
| 17e | 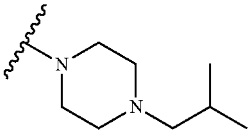 [SMILES: *N1CCN(CC(C)C)CC1] | 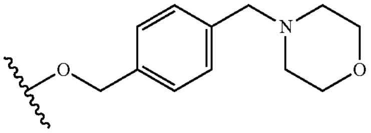 [SMILES: *OCc1ccc(CN2CCOCC2)cc1] |
| 17f | 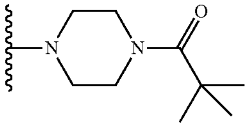 | 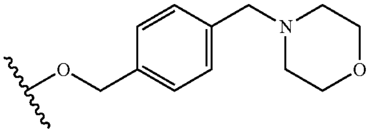 [SMILES: *OCc1ccc(CN2CCOCC2)cc1] |
| 17g | 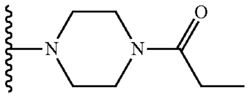 | 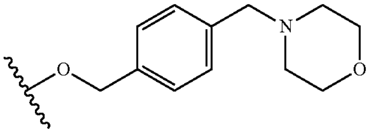 [SMILES: *OCc1ccc(CN2CCOCC2)cc1] |
| 17h | 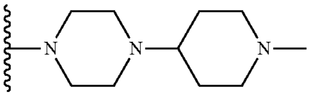 [SMILES: *N1CCN(C2CCN(C)CC2)CC1] | 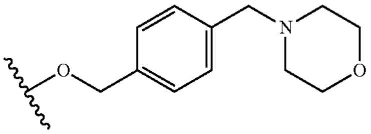 [SMILES: *OCc1ccc(CN2CCOCC2)cc1] |
| 17i | 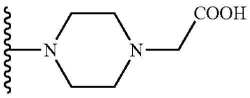 | 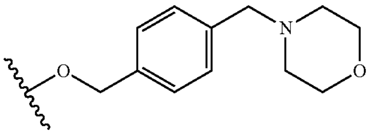 [SMILES: *OCc1ccc(CN2CCOCC2)cc1] |
| 17j | 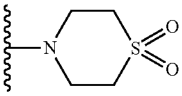 | 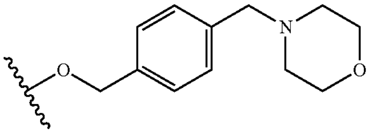 [SMILES: *OCc1ccc(CN2CCOCC2)cc1] |

TABLE 1-continued
Exemplary Compounds
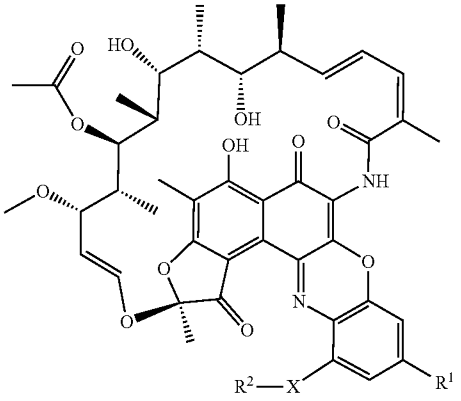
| Compound | $R^1$ | —X—$R^2$ |
|---|---|---|
| 17k | 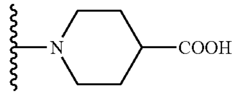 [SMILES: *N1CCC(C(=O)O)CC1] | 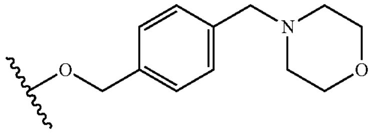 [SMILES: *OCc1ccc(CN2CCOCC2)cc1] |
| 17l | 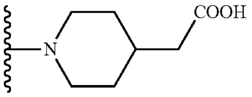 | 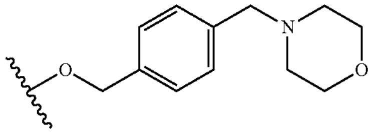 [SMILES: *OCc1ccc(CN2CCOCC2)cc1] |
| 17m | 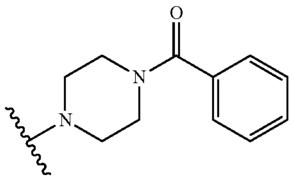 [SMILES: *N1CCN(C(=O)c2ccccc2)CC1] | 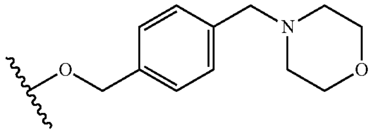 [SMILES: *OCc1ccc(CN2CCOCC2)cc1] |
| 17n | 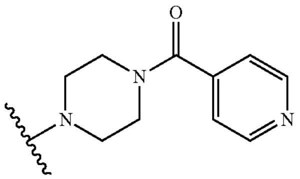 [SMILES: *N1CCN(C(=O)c2ccncc2)CC1] | 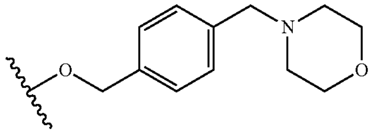 [SMILES: *OCc1ccc(CN2CCOCC2)cc1] |
| 17o | 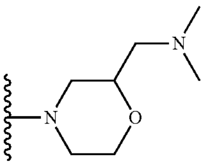 [SMILES: *N1CCOC(CN(C)C)C1] | 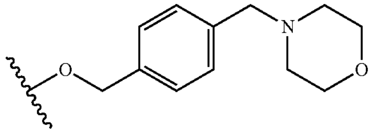 [SMILES: *OCc1ccc(CN2CCOCC2)cc1] |
| 17p | 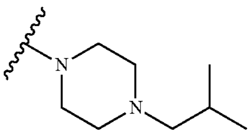 [SMILES: *N1CCN(CC(C)C)CC1] | 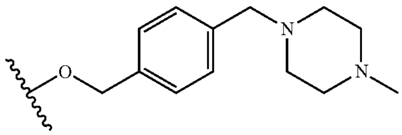 [SMILES: *OCc1ccc(CN2CCN(C)CC2)cc1] |
| 17q | 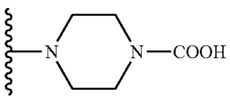 [SMILES: *N1CCN(C(=O)O)CC1] | 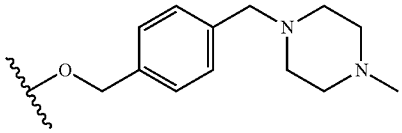 [SMILES: *OCc1ccc(CN2CCN(C)CC2)cc1] |

TABLE 1-continued
Exemplary Compounds
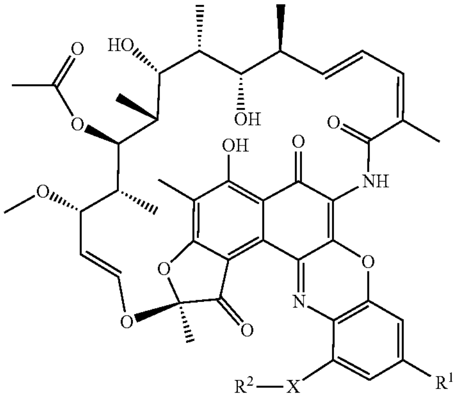
| Compound | $R^1$ | —X—$R^2$ |
| --- | --- | --- |
| 17r | 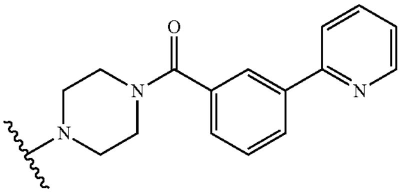 [SMILES: *N1CCN(C(=O)c2cccc(-c3ccccn3)c2)CC1] | 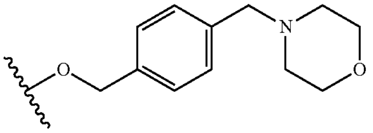 [SMILES: *OCc1ccc(CN2CCOCC2)cc1] |
| 17s | 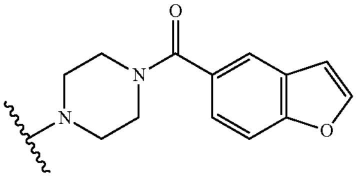 [SMILES: *N1CCN(C(=O)c2ccc3occc3c2)CC1] | 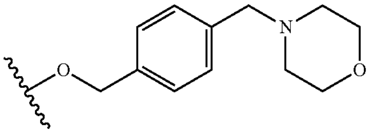 [SMILES: *OCc1ccc(CN2CCOCC2)cc1] |
| 17t | 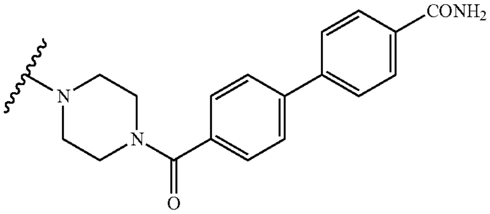 [SMILES: *N1CCN(C(=O)c2ccc(-c3ccc(C(N)=O)cc3)cc2)CC1] | 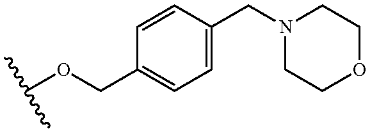 [SMILES: *OCc1ccc(CN2CCOCC2)cc1] |
| 17u | 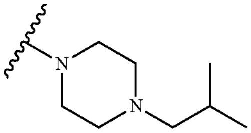 [SMILES: *N1CCN(CC(C)C)CC1] | 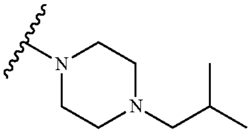 [SMILES: *N1CCN(CC(C)C)CC1] |
| 17v | 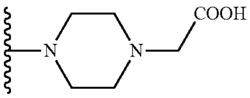 [SMILES: *N1CCN(CC(=O)O)CC1] | 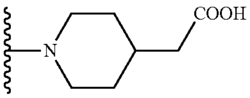 [SMILES: *N1CCC(CC(=O)O)CC1] |
| 26c | 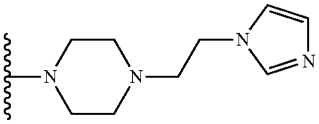 [SMILES: *N1CCN(CCn2ccnc2)CC1] | $CH_3$ |
| 26d | 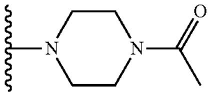 | $CH_3$ |

TABLE 1-continued
Exemplary Compounds
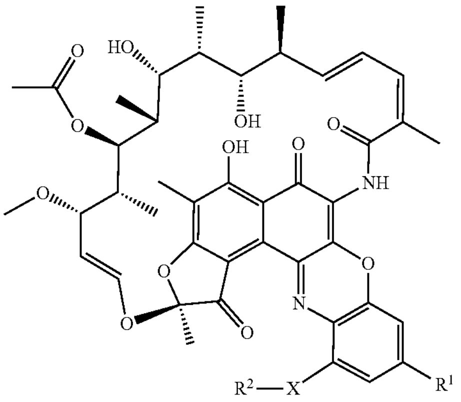
| Compound | $R^1$ | —X—$R^2$ |
|---|---|---|
| 26e | 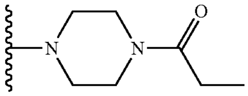 | $CH_3$ |
| 26f | 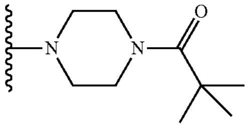 | $CH_3$ |
| 26g | 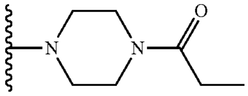 | $CH_3$ |
| 26h | 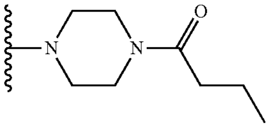 | $CH_3$ |
| 26i | 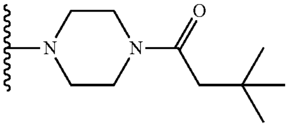 [SMILES: *N1CCN(C(=O)CC(C)(C)C)CC1] | $CH_3$ |
| 28 | 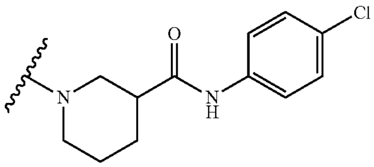 [SMILES: *N1CCCC(C(=O)Nc2ccc(Cl)cc2)C1] | $CH_3$ |
| 29a | 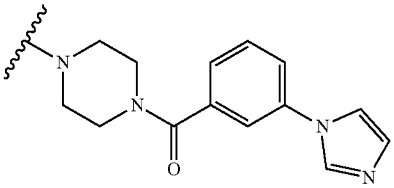 [SMILES: *N1CCN(C(=O)c2cccc(-n3ccnc3)c2)CC1] | $CH_3$ |

TABLE 1-continued
Exemplary Compounds
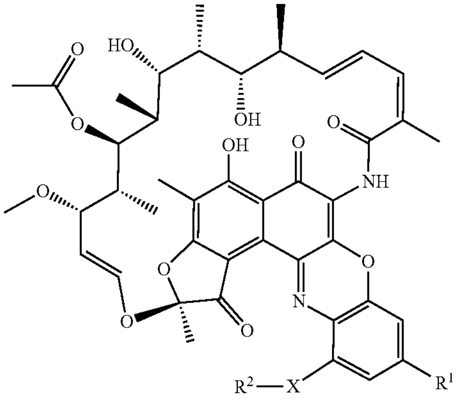
| Compound | $R^1$ | —X—$R^2$ |
| --- | --- | --- |
| 29b | 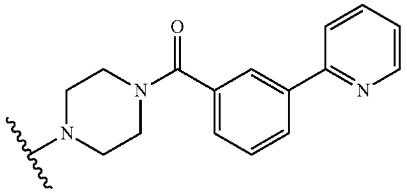 [SMILES: *N1CCN(C(=O)c2cccc(-c3ccccn3)c2)CC1] | $CH_3$ |
| 29c | 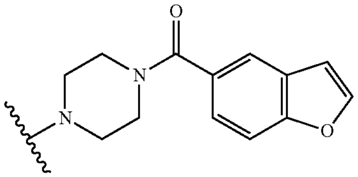 [SMILES: *N1CCN(C(=O)c2ccc3occc3c2)CC1] | $CH_3$ |
| 29d | 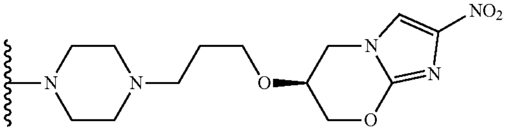 [SMILES: *N1CCN(CCCO[C@@H]2COc3nc([N+](=O)[O-])cn3C2)CC1] | $CH_3$ |
| 29e | 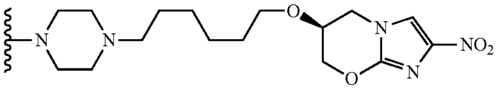 [SMILES: *N1CCN(CCCCCCO[C@@H]2COc3nc([N+](=O)[O-])cn3C2)CC1] | $CH_3$ |
| 29f | 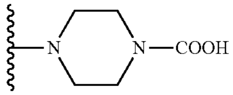 | —$CH_3$ |
| 29g | 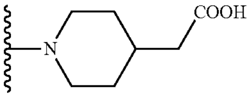 | —$CH_3$ |
| 29h | 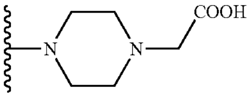 | —$CH_3$ |
| 30a | $CH_3$ | 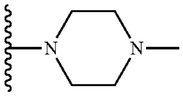 |

TABLE 1-continued
Exemplary Compounds
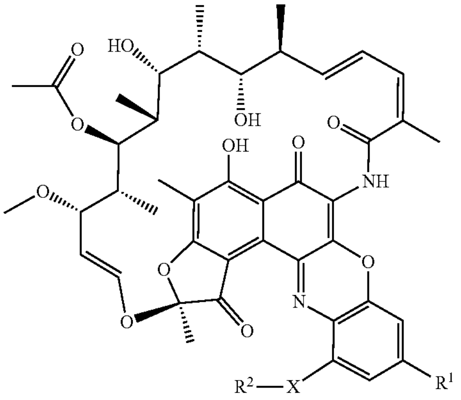
| Compound | $R^1$ | —X—$R^2$ |
| --- | --- | --- |
| 30b | —CHO | 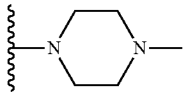 |
| 30c | $CH_3$ | 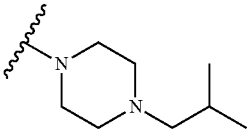 [SMILES: *N1CCN(CC(C)C)CC1] |
| 30d | —CHO | 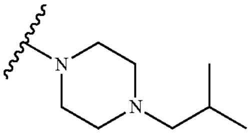 [SMILES: *N1CCN(CC(C)C)CC1] |
| 30e | $CH_3$ | 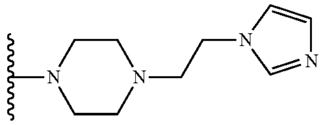 |
| 30f | $CH_3$ | 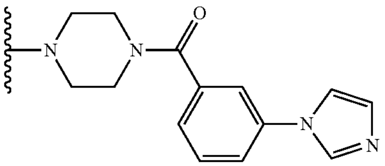 [SMILES: *N1CCN(C(=O)c2cccc(-n3ccnc3)c2)CC1] |
| 30g | $CH_3$ | 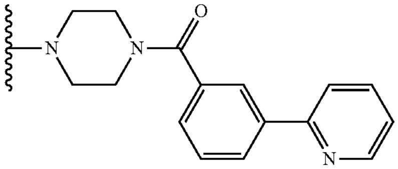 [SMILES: *N1CCN(C(=O)c2cccc(-c3ccccn3)c2)CC1] |
| 30h | $CH_3$ | 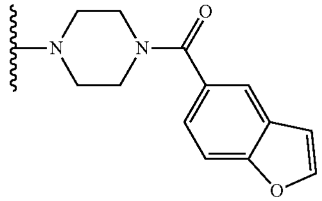 [SMILES: *N1CCN(C(=O)c2ccc3occc3c2)CC1] |

TABLE 1-continued
Exemplary Compounds
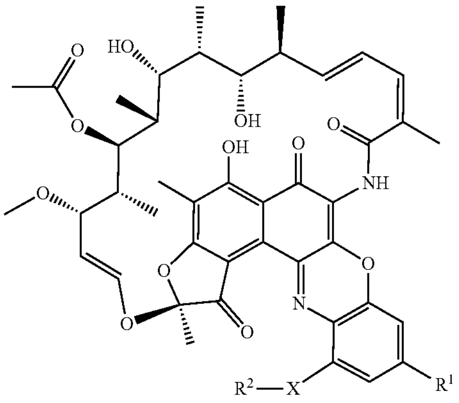
| Compound | $R^1$ | —X—$R^2$ |
|---|---|---|
| 32 | 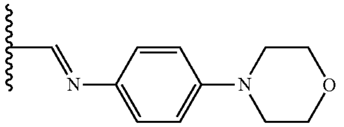 [SMILES: */C=N/c1ccc(N2CCOCC2)cc1] | 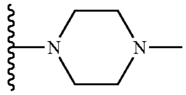 [SMILES: *N1CCN(C)CC1] |
Additional compounds of formula (I) are shown in Table 2.
TABLE 2
Additional Compounds
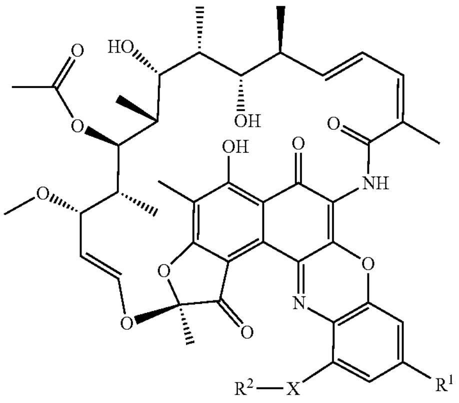
| $R^1$ | —X—$R^2$ |
|---|---|
| 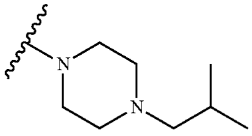 [SMILES: *N1CCN(CC(C)C)CC1] | 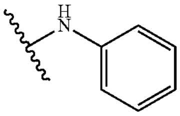 [SMILES: *Nc1ccccc1] |
| 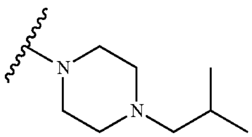 [SMILES: *N1CCN(CC(C)C)CC1] | 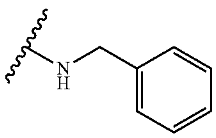 [SMILES: *NCc1ccccc1] |

TABLE 2-continued
| Additional Compounds | |
|---|---|
| 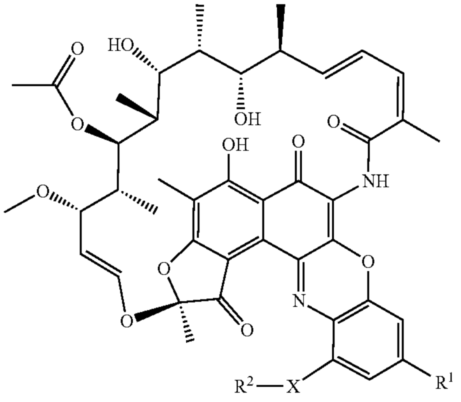 | |
| $R^1$ | —X—$R^2$ |
| 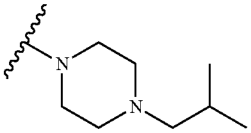 [SMILES: *N1CCN(CC(C)C)CC1] | 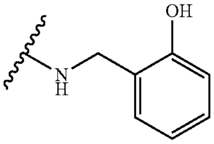 [SMILES: *NCc1ccccc1O] |
| 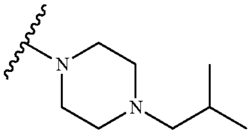 [SMILES: *N1CCN(CC(C)C)CC1] | 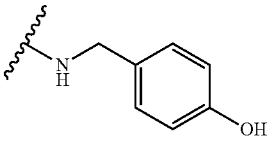 [SMILES: *NCc1ccc(O)cc1] |
| 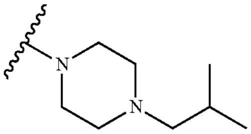 [SMILES: *N1CCN(CC(C)C)CC1] | 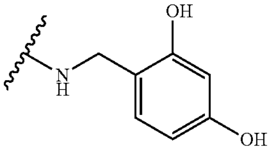 [SMILES: *NCc1ccc(O)cc1O] |
| 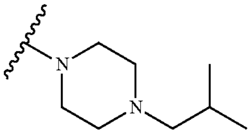 | 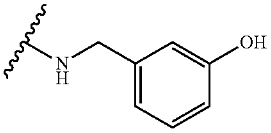 [SMILES: *NCc1cccc(O)c1] |
| 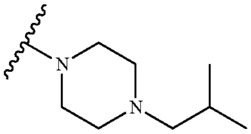 [SMILES: *N1CCN(CC(C)C)CC1] | 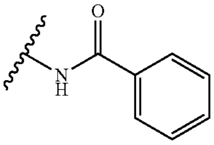 [SMILES: *NC(=O)c1ccccc1] |
| 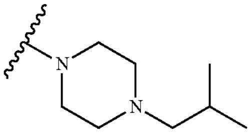 [SMILES: *N1CCN(CC(C)C)CC1] | 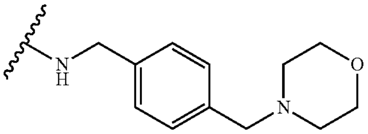 [SMILES: *NCc1ccc(CN2CCOCC2)cc1] |
| 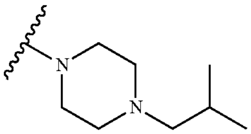 [SMILES: *N1CCN(CC(C)C)CC1] | 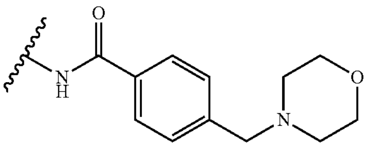 [SMILES: *NC(=O)c1ccc(CN2CCOCC2)cc1] |

TABLE 2-continued
Additional Compounds
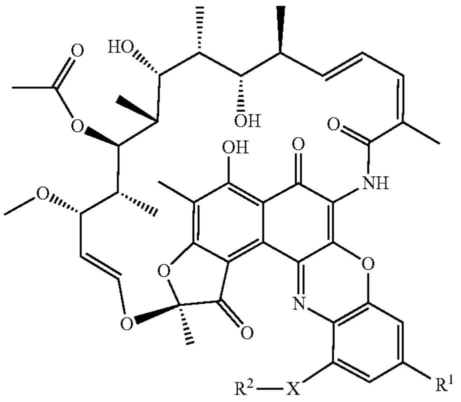
| $R^1$ | —X—$R^2$ |
|---|---|
| 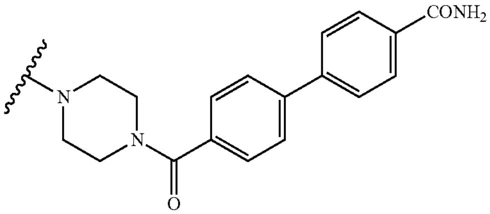 [SMILES: *N1CCN(C(=O)c2ccc(-c3ccc(C(N)=O)cc3)cc2)CC1] | —$CH_3$ |
| 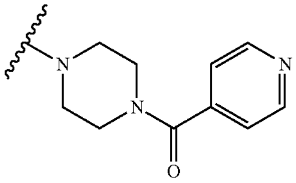 [SMILES: *N1CCN(C(=O)c2ccncc2)CC1] | —$CH_3$ |
| 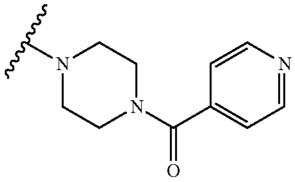 [SMILES: *N1CCN(C(=O)c2ccncc2)CC1] | 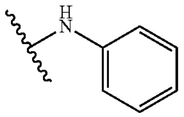 [SMILES: *Nc1ccccc1] |
| 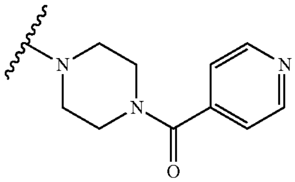 [SMILES: *N1CCN(C(=O)c2ccncc2)CC1] | 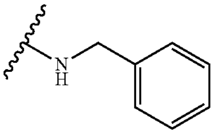 [SMILES: *NCc1ccccc1] |
| 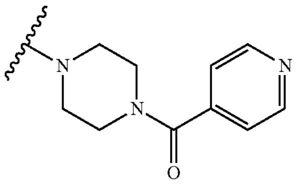 [SMILES: *N1CCN(C(=O)c2ccncc2)CC1] | 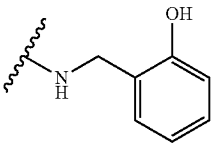 [SMILES: *NCc1ccccc1O] |

TABLE 2-continued
Additional Compounds
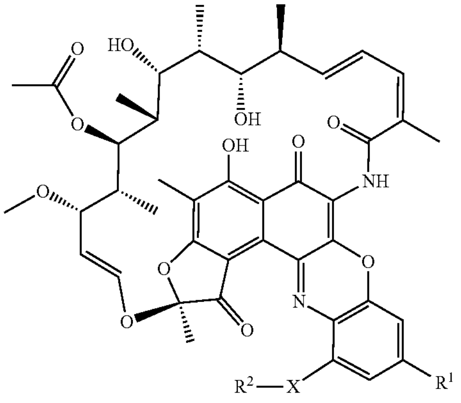
| $R^1$ | —X—$R^2$ |
| --- | --- |
| 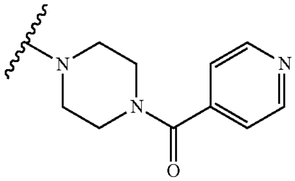 [SMILES: *N1CCN(C(=O)c2ccncc2)CC1] | 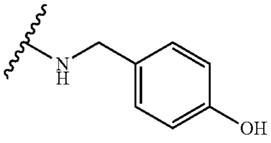 [SMILES: *NCc1ccc(O)cc1] |
| 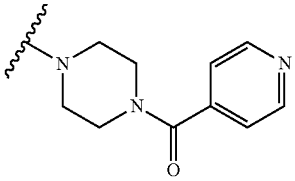 [SMILES: *N1CCN(C(=O)c2ccncc2)CC1] | 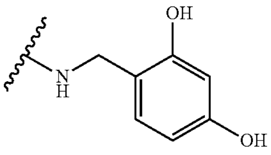 [SMILES: *NCc1ccc(O)cc1O] |
| 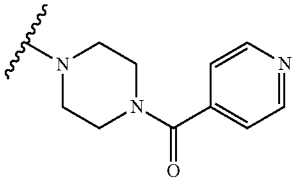 [SMILES: *N1CCN(C(=O)c2ccncc2)CC1] | 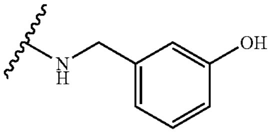 [SMILES: *NCc1cccc(O)c1] |
| 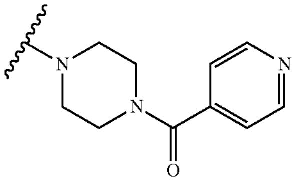 [SMILES: *N1CCN(C(=O)c2ccncc2)CC1] | 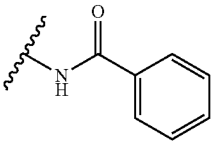 [SMILES: *NC(=O)c1ccccc1] |
| 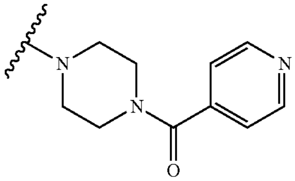 [SMILES: *N1CCN(C(=O)c2ccncc2)CC1] | 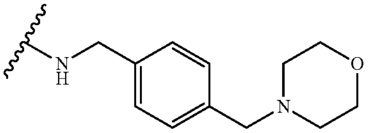 [SMILES: *NCc1ccc(CN2CCOCC2)cc1] |
| 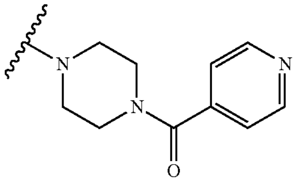 [SMILES: *N1CCN(C(=O)c2ccncc2)CC1] | 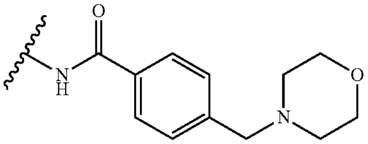 [SMILES: *NC(=O)c1ccc(CN2CCOCC2)cc1] |

TABLE 2-continued
Additional Compounds
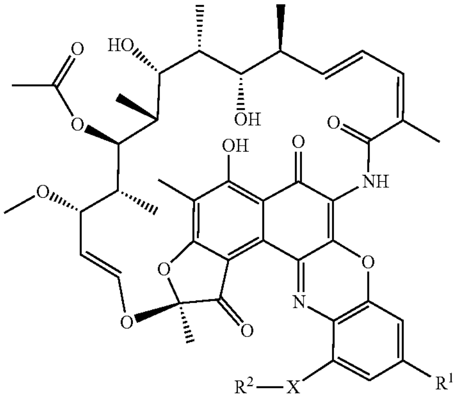
| $R^1$ | —X—$R^2$ |
| --- | --- |
| 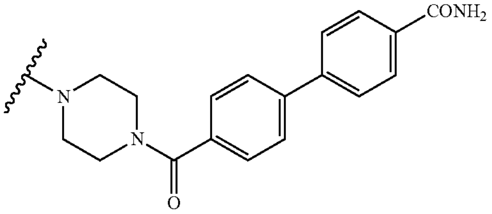 [SMILES: *N1CCN(C(=O)c2ccc(-c3ccc(C(N)=O)cc3)cc2)CC1] | 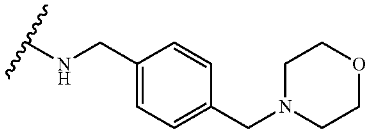 [SMILES: *NCc1ccc(CN2CCOCC2)cc1] |
| 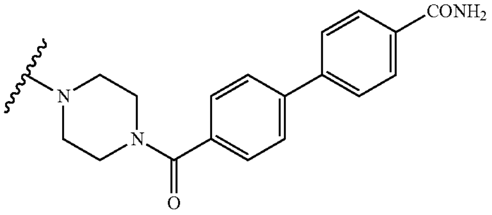 [SMILES: *N1CCN(C(=O)c2ccc(-c3ccc(C(N)=O)cc3)cc2)CC1] | 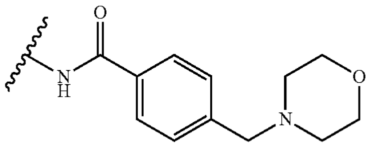 [SMILES: *NC(=O)c1ccc(CN2CCOCC2)cc1] |
| 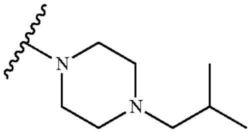 [SMILES: *N1CCN(CC(C)C)CC1] | —$NH_2$ |
| 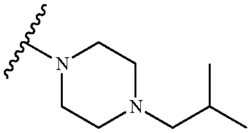 [SMILES: *N1CCN(CC(C)C)CC1] | 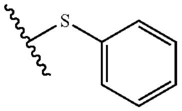 [SMILES: *Sc1ccccc1] |
| 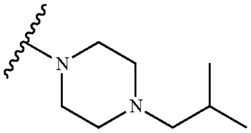 [SMILES: *N1CCN(CC(C)C)CC1] | 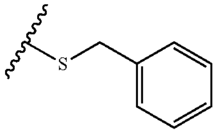 [SMILES: *SCc1ccccc1] |
| 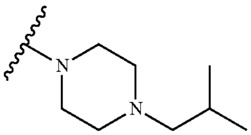 [SMILES: *N1CCN(CC(C)C)CC1] | 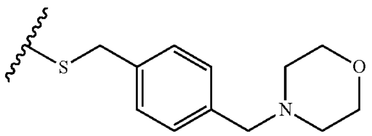 [SMILES: *SCc1ccc(CN2CCOCC2)cc1] |

TABLE 2-continued
Additional Compounds
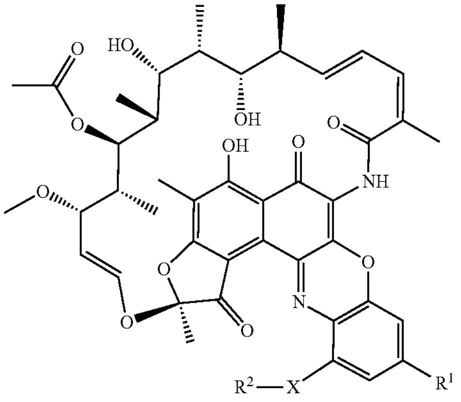
| $R^1$ | —X—$R^2$ |
| --- | --- |
| 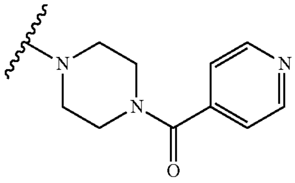 [SMILES: *N1CCN(C(=O)c2ccncc2)CC1] | 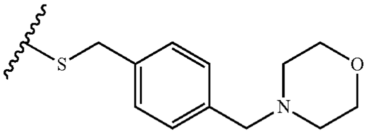 [SMILES: *SCc1ccc(CN2CCOCC2)cc1] |
| 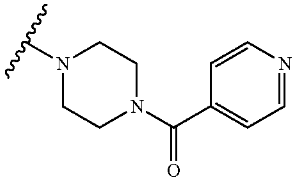 [SMILES: *N1CCN(C(=O)c2ccncc2)CC1] | —SH |
| 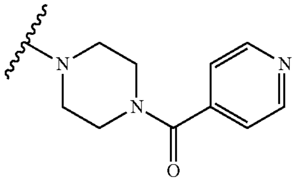 [SMILES: *N1CCN(C(=O)c2ccncc2)CC1] | —$NH_2$ |
| 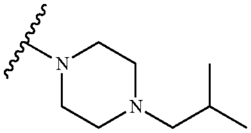 [SMILES: *N1CCN(CC(C)C)CC1] | 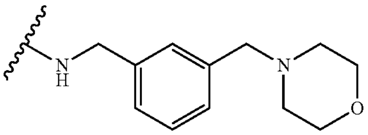 [SMILES: *NCc1cccc(CN2CCOCC2)c1] |
| 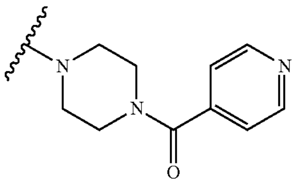 [SMILES: *N1CCN(C(=O)c2ccncc2)CC1] | 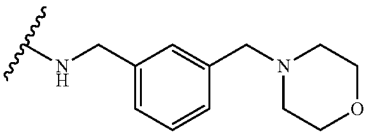 [SMILES: *NCc1cccc(CN2CCOCC2)c1] |
| 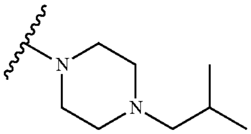 [SMILES: *N1CCN(CC(C)C)CC1] | 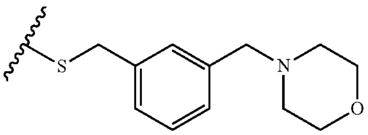 [SMILES: *SCc1cccc(CN2CCOCC2)c1] |

TABLE 2-continued
Additional Compounds
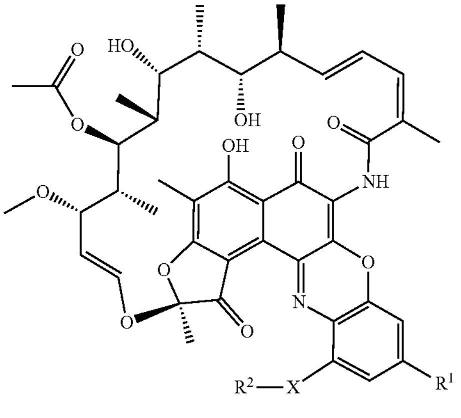
| R[1] | —X—R[2] |
|---|---|
| 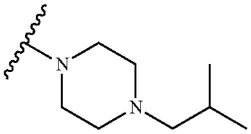 | 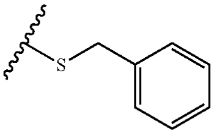 [SMILES: *SCc1ccccc1] |
| 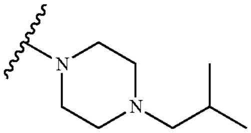 [SMILES: *N1CCN(CC(C)C)CC1] | 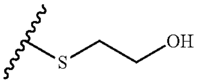 [SMILES: *SCCO] |
| 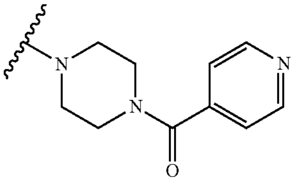 [SMILES: *N1CCN(C(=O)c2ccncc2)CC1] | 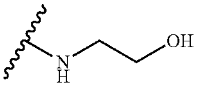 [SMILES: *NCCO] |
| 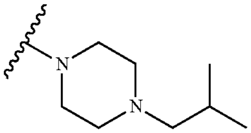 [SMILES: *N1CCN(CC(C)C)CC1] | 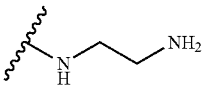 |
| 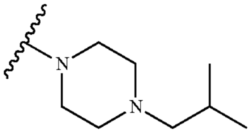 [SMILES: *N1CCN(CC(C)C)CC1] | 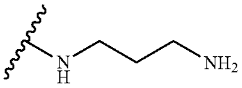 [SMILES: *NCCCN] |
| 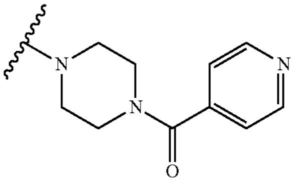 [SMILES: *N1CCN(C(=O)c2ccncc2)CC1] | 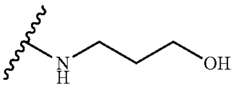 [SMILES: *NCCCO] |
| 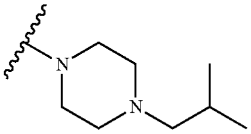 [SMILES: *N1CCN(CC(C)C)CC1] | 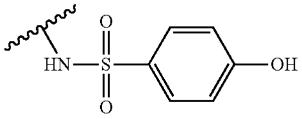 [SMILES: *NS(=O)(=O)c1ccc(O)cc1] |

TABLE 2-continued
Additional Compounds
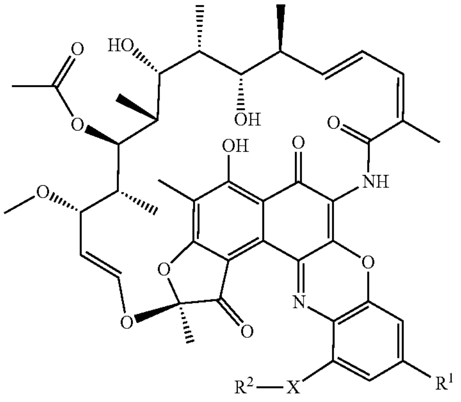
| $R^1$ | —X—$R^2$ |
|---|---|
| 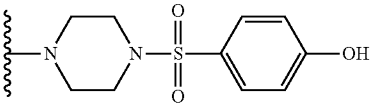 [SMILES: *N1CCN(S(=O)(=O)c2ccc(O)cc2)CC1] | 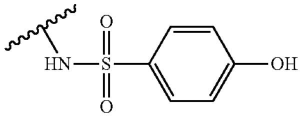 [SMILES: *NS(=O)(=O)c1ccc(O)cc1] |
| 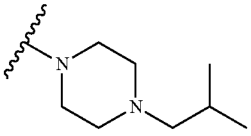 [SMILES: *N1CCN(CC(C)C)CC1] | 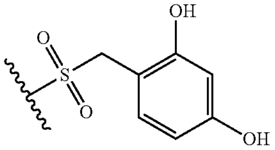 [SMILES: *S(=O)(=O)Cc1ccc(O)cc1O] |
| 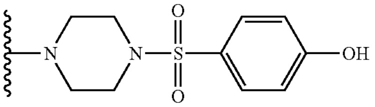 | —$CH_3$ |
| 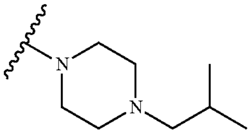 [SMILES: *N1CCN(CC(C)C)CC1] | 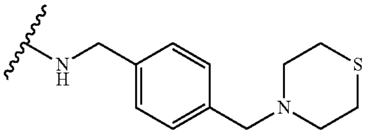 [SMILES: *NCc1ccc(CN2CCSCC2)cc1] |
| 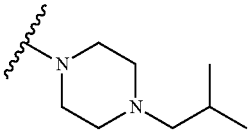 [SMILES: *N1CCN(CC(C)C)CC1] | 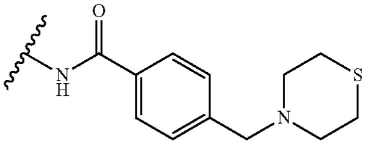 [SMILES: *NC(=O)c1ccc(CN2CCSCC2)cc1] |
| 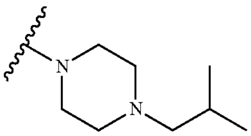 [SMILES: *N1CCN(CC(C)C)CC1] | 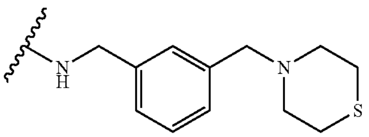 [SMILES: *NCc1cccc(CN2CCSCC2)c1] |
| 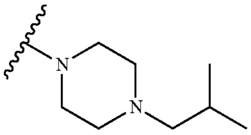 [SMILES: *N1CCN(CC(C)C)CC1] | 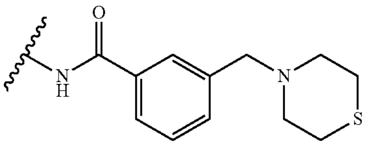 [SMILES: *NC(=O)c1cccc(CN2CCSCC2)c1] |

TABLE 2-continued
Additional Compounds
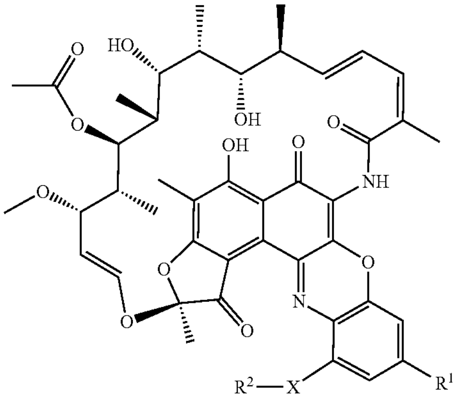
| $R^1$ | —X—$R^2$ |
|---|---|
| 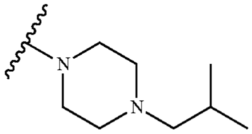 [SMILES: *N1CCN(CC(C)C)CC1] | 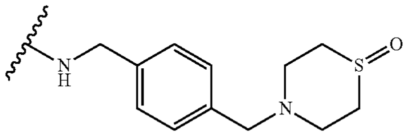 [SMILES: *NCc1ccc(CN2CCS(=O)CC2)cc1] |
| 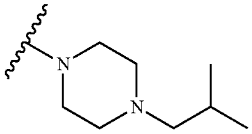 [SMILES: *N1CCN(CC(C)C)CC1] | 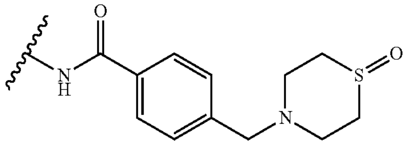 [SMILES: *NC(=O)c1ccc(CN2CCS(=O)CC2)cc1] |
| 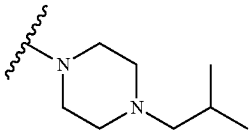 [SMILES: *N1CCN(CC(C)C)CC1] | 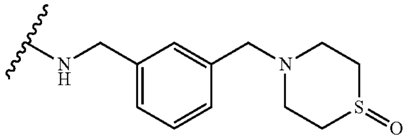 [SMILES: *NCc1cccc(CN2CCS(=O)CC2)c1] |
| 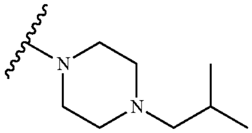 [SMILES: *N1CCN(CC(C)C)CC1] | 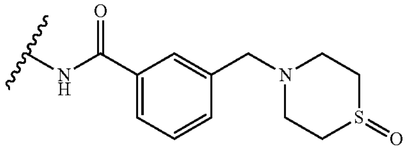 [SMILES: *NC(=O)c1cccc(CN2CCS(=O)CC2)c1] |
| 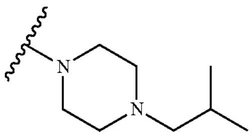 [SMILES: *N1CCN(CC(C)C)CC1] | 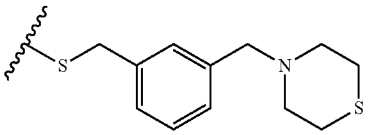 [SMILES: *SCc1cccc(CN2CCSCC2)c1] |
| 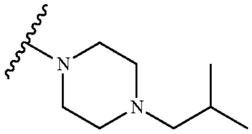 [SMILES: *N1CCN(CC(C)C)CC1] | 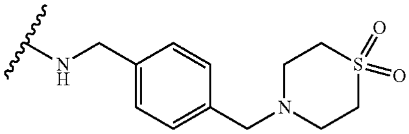 [SMILES: *NCc1ccc(CN2CCS(=O)(=O)CC2)cc1] |
| 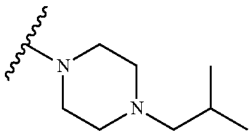 [SMILES: *N1CCN(CC(C)C)CC1] | 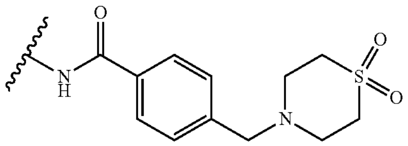 [SMILES: *NC(=O)c1ccc(CN2CCS(=O)(=O)CC2)cc1] |

TABLE 2-continued
Additional Compounds
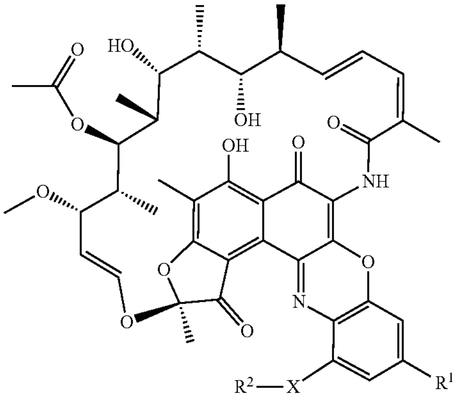
| $R^1$ | —X—$R^2$ |
|---|---|
| 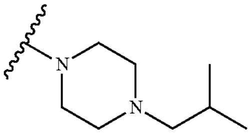 | 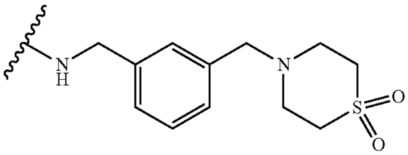 [SMILES: *NCc1cccc(CN2CCS(=O)(=O)CC2)c1] |
| 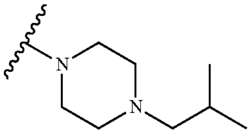 [SMILES: *N1CCN(CC(C)C)CC1] | 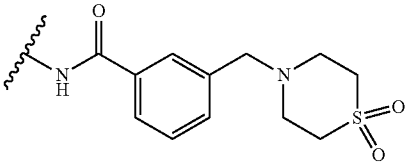 [SMILES: *NC(=O)c1cccc(CN2CCS(=O)(=O)CC2)c1] |
| 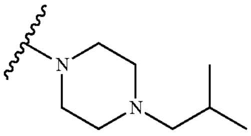 [SMILES: *N1CCN(CC(C)C)CC1] | 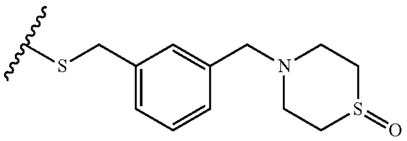 [SMILES: *SCc1cccc(CN2CCS(=O)CC2)c1] |
| 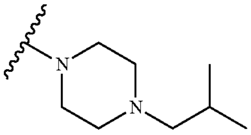 [SMILES: *N1CCN(CC(C)C)CC1] | 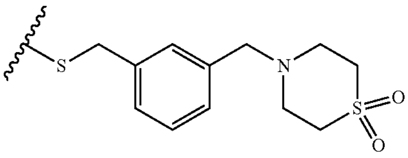 [SMILES: *SCc1cccc(CN2CCS(=O)(=O)CC2)c1] |
| 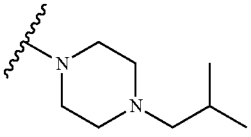 [SMILES: *N1CCN(CC(C)C)CC1] | 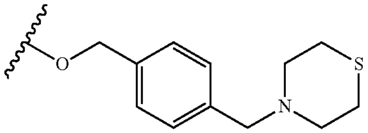 |
| 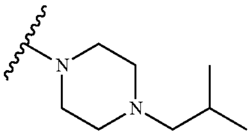 [SMILES: *N1CCN(CC(C)C)CC1] | 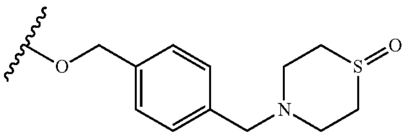 [SMILES: *OCc1ccc(CN2CCS(=O)CC2)cc1] |
| 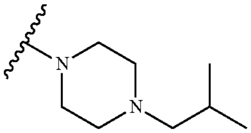 [SMILES: *N1CCN(CC(C)C)CC1] | 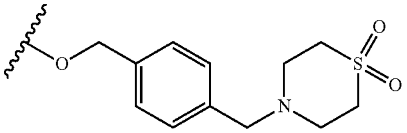 [SMILES: *OCc1ccc(CN2CCS(=O)(=O)CC2)cc1] |

TABLE 2-continued
Additional Compounds
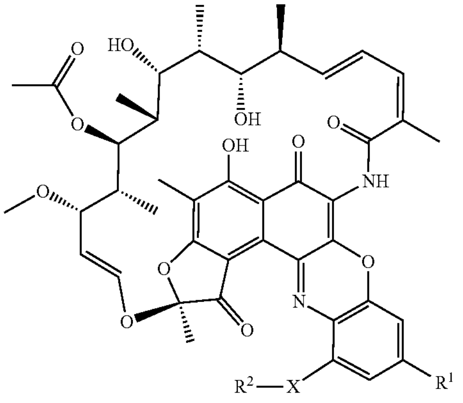
| $R^1$ | —X—$R^2$ |
| --- | --- |
| 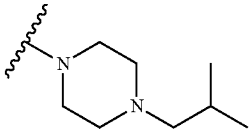 [SMILES: *N1CCN(CC(C)C)CC1] | 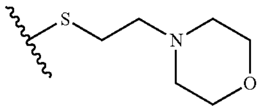 [SMILES: *SCCN1CCOCC1] |
| 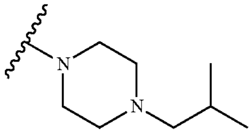 [SMILES: *N1CCN(CC(C)C)CC1] | 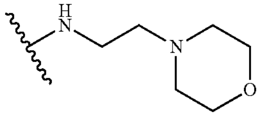 [SMILES: *NCCN1CCOCC1] |
| 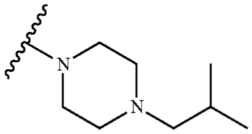 [SMILES: *N1CCN(CC(C)C)CC1] | 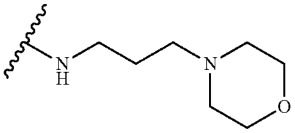 [SMILES: *NCCCN1CCOCC1] |
| 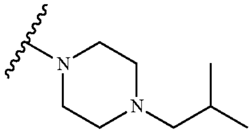 [SMILES: *N1CCN(CC(C)C)CC1] | 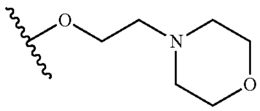 [SMILES: *OCCN1CCOCC1] |
| 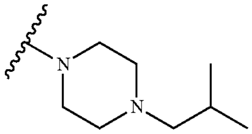 [SMILES: *N1CCN(CC(C)C)CC1] | 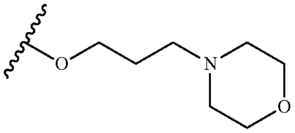 [SMILES: *OCCCN1CCOCC1] |
| 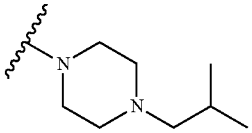 [SMILES: *N1CCN(CC(C)C)CC1] | 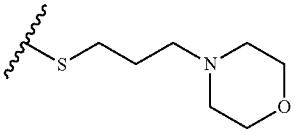 [SMILES: *SCCCN1CCOCC1] |
| 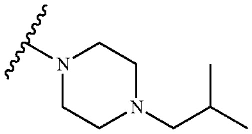 [SMILES: *N1CCN(CC(C)C)CC1] | 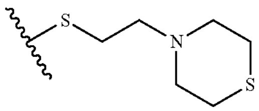 [SMILES: *SCCN1CCSCC1] |
| 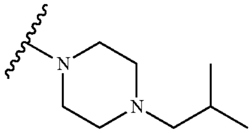 [SMILES: *N1CCN(CC(C)C)CC1] | 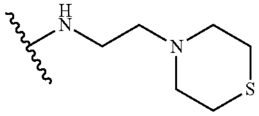 [SMILES: *NCCN1CCSCC1] |

TABLE 2-continued
| Additional Compounds | |
|---|---|
| 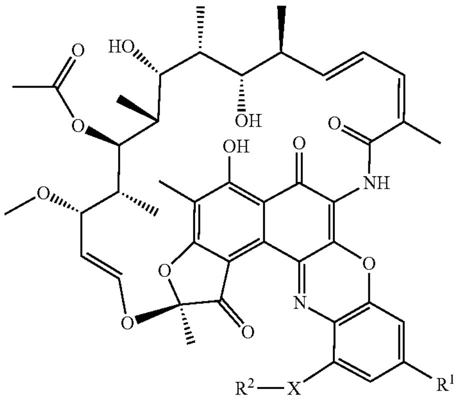 | |
| $R^1$ | —X—$R^2$ |
| 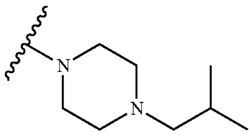 [SMILES: *N1CCN(CC(C)C)CC1] | 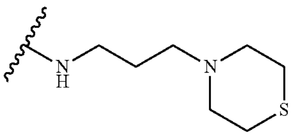 [SMILES: *NCCCN1CCSCC1] |
| 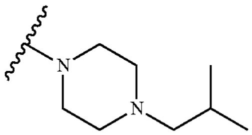 | 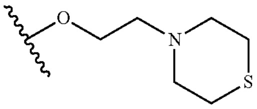 [SMILES: *OCCN1CCSCC1] |
| 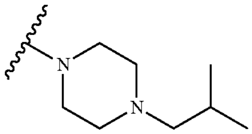 [SMILES: *N1CCN(CC(C)C)CC1] | 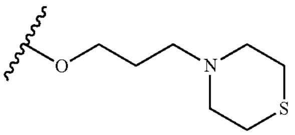 [SMILES: *OCCCN1CCSCC1] |
| 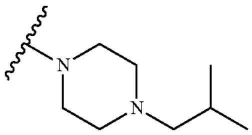 [SMILES: *N1CCN(CC(C)C)CC1] | 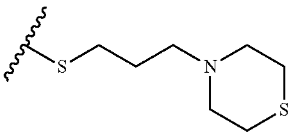 [SMILES: *SCCCN1CCSCC1] |
| 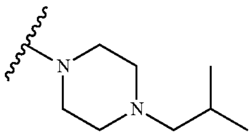 [SMILES: *N1CCN(CC(C)C)CC1] | 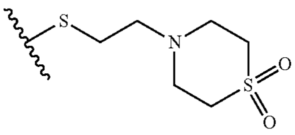 [SMILES: *SCCN1CCS(=O)(=O)CC1] |
| 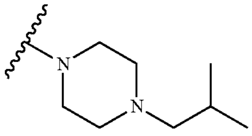 [SMILES: *N1CCN(CC(C)C)CC1] | 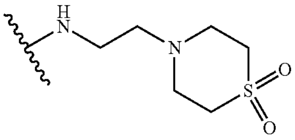 [SMILES: *NCCN1CCS(=O)(=O)CC1] |
| 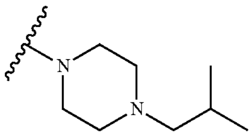 [SMILES: *N1CCN(CC(C)C)CC1] | 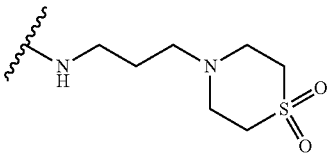 [SMILES: *NCCCN1CCS(=O)(=O)CC1] |

TABLE 2-continued
Additional Compounds
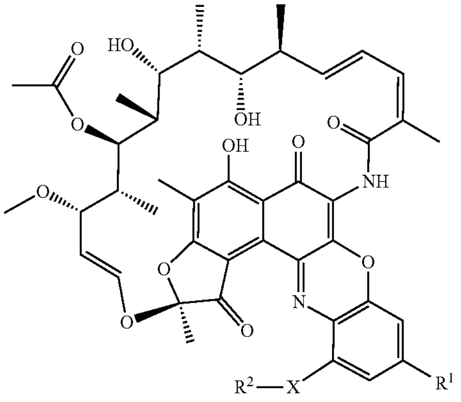
| R[1] | —X—R[2] |
| --- | --- |
| 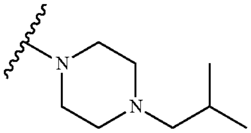 [SMILES: *N1CCN(CC(C)C)CC1] | 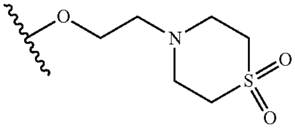 [SMILES: *OCCN1CCS(=O)(=O)CC1] |
| 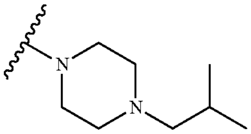 [SMILES: *N1CCN(CC(C)C)CC1] | 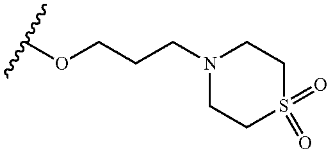 [SMILES: *OCCCN1CCS(=O)(=O)CC1] |
| 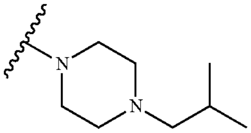 [SMILES: *N1CCN(CC(C)C)CC1] | 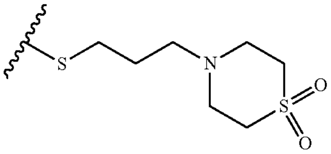 [SMILES: *SCCCN1CCS(=O)(=O)CC1] |
| 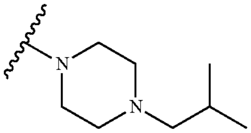 [SMILES: *N1CCN(CC(C)C)CC1] | 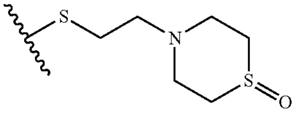 [SMILES: *SCCN1CCS(=O)CC1] |
| 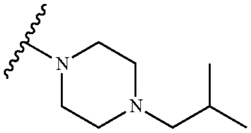 [SMILES: *N1CCN(CC(C)C)CC1] | 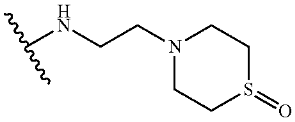 [SMILES: *NCCN1CCS(=O)CC1] |
| 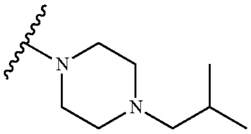 [SMILES: *N1CCN(CC(C)C)CC1] | 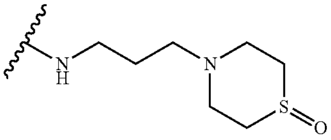 [SMILES: *NCCCN1CCS(=O)CC1] |
| 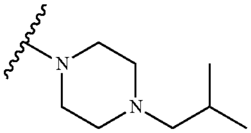 [SMILES: *N1CCN(CC(C)C)CC1] | 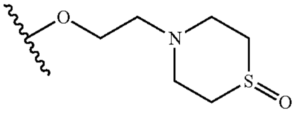 [SMILES: *OCCN1CCS(=O)CC1] |

TABLE 2-continued
Additional Compounds
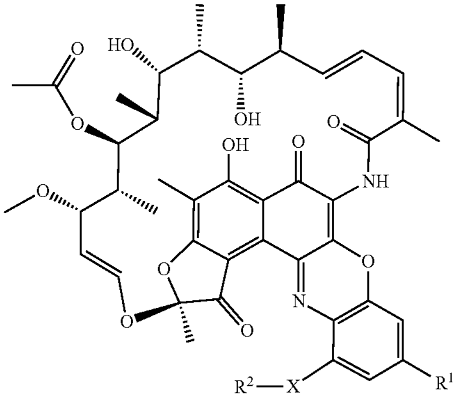
| $R^1$ | —X—$R^2$ |
|---|---|
| 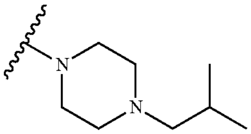 [SMILES: *N1CCN(CC(C)C)CC1] | 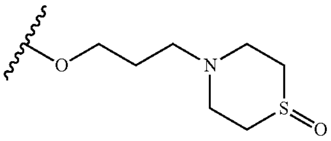 [SMILES: *OCCCN1CCS(=O)CC1] |
| 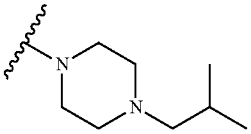 | 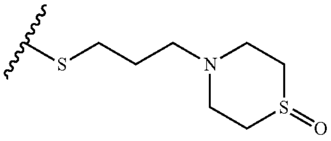 [SMILES: *SCCCN1CCS(=O)CC1] |
| 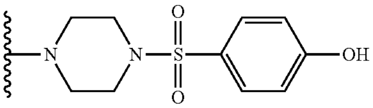 [SMILES: *N1CCN(S(=O)(=O)c2ccc(O)cc2)CC1] | 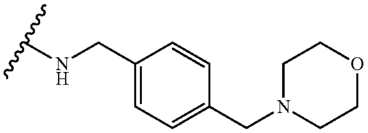 [SMILES: *NCc1ccc(CN2CCOCC2)cc1] |
| 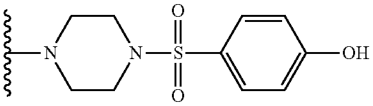 [SMILES: *N1CCN(S(=O)(=O)c2ccc(O)cc2)CC1] | 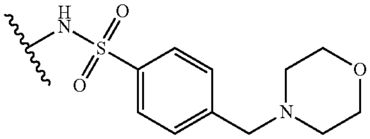 [SMILES: *NS(=O)(=O)c1ccc(CN2CCOCC2)cc1] |
| 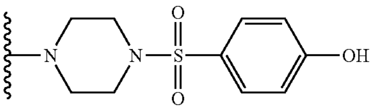 [SMILES: *N1CCN(S(=O)(=O)c2ccc(O)cc2)CC1] | 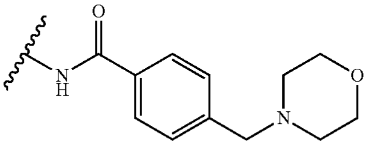 [SMILES: *NC(=O)c1ccc(CN2CCOCC2)cc1] |
| 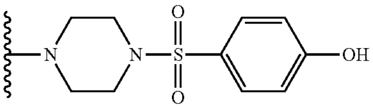 [SMILES: *N1CCN(S(=O)(=O)c2ccc(O)cc2)CC1] | 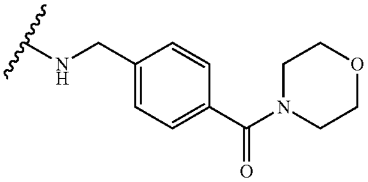 [SMILES: *NCc1ccc(C(=O)N2CCOCC2)cc1] |

TABLE 2-continued
Additional Compounds
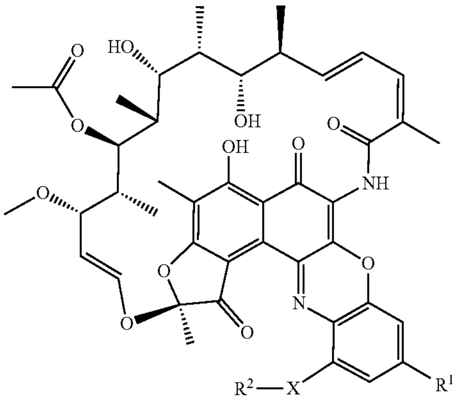
| R[1] | —X—R[2] |
| --- | --- |
| 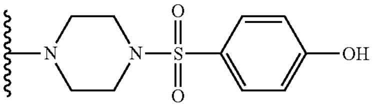 | 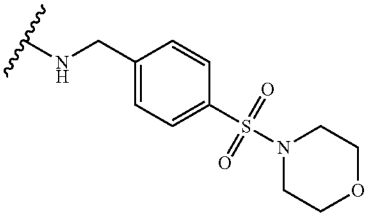 [SMILES: *NCc1ccc(S(=O)(=O)N2CCOCC2)cc1] |
| 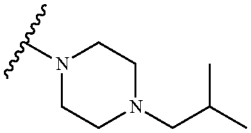 [SMILES: *N1CCN(CC(C)C)CC1] | 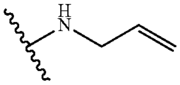 [SMILES: *NCC=C] |
| 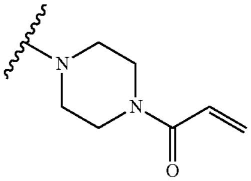 [SMILES: *N1CCN(C(=O)C=C)CC1] | 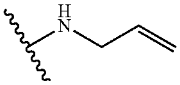 |
| 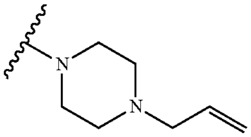 [SMILES: *N1CCN(CC=C)CC1] | 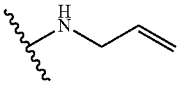 [SMILES: *NCC=C] |
| 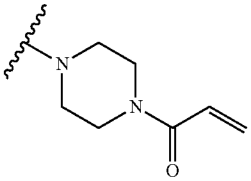 [SMILES: *N1CCN(C(=O)C=C)CC1] | 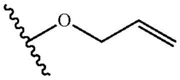 [SMILES: *OCC=C] |
| 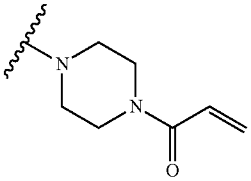 [SMILES: *N1CCN(C(=O)C=C)CC1] | 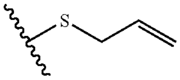 [SMILES: *SCC=C] |

TABLE 2-continued
Additional Compounds
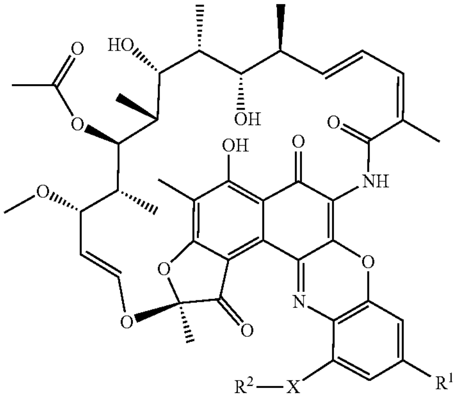
| $R^1$ | —X—$R^2$ |
| --- | --- |
| 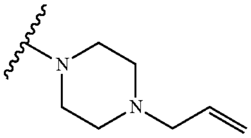 [SMILES: *N1CCN(CC=C)CC1] | 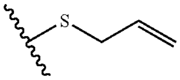 [SMILES: *SCC=C] |
| 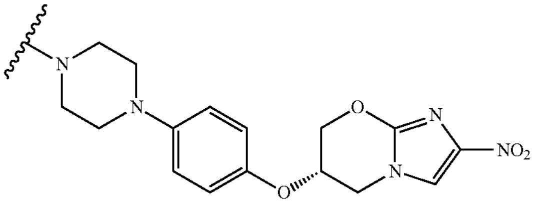 | —$CH_3$ |
| 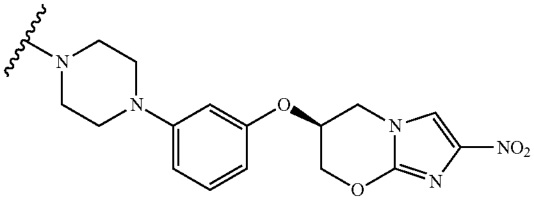 [SMILES: *N1CCN(c2cccc(O[C@@H]3COc4nc([N+](=O)[O-])cn4C3)c2)CC1] | —$CH_3$ |
| 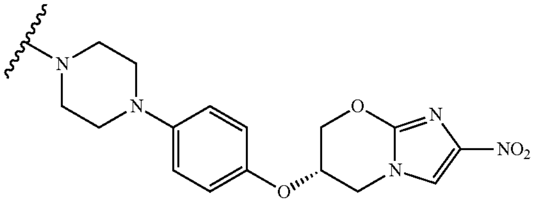 [SMILES: *N1CCN(c2ccc(O[C@@H]3COc4nc([N+](=O)[O-])cn4C3)cc2)CC1] | 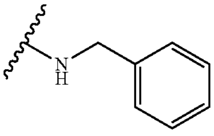 [SMILES: *NCc1ccccc1] |
| 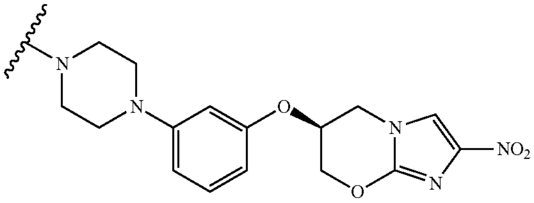 [SMILES: *N1CCN(c2cccc(O[C@@H]3COc4nc([N+](=O)[O-])cn4C3)c2)CC1] | 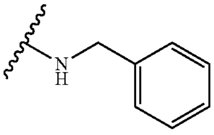 [SMILES: *NCc1ccccc1] |

TABLE 2-continued
Additional Compounds
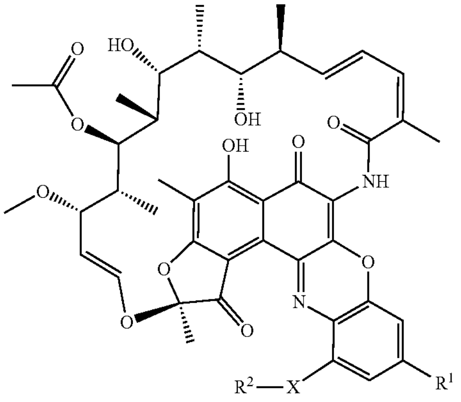
| $R^1$ | —X—$R^2$ |
| --- | --- |
| 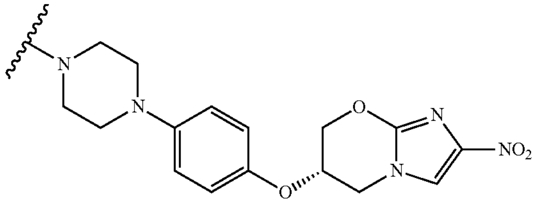 | 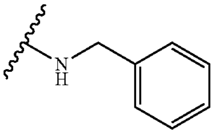 [SMILES: *NCc1ccccc1] |
| 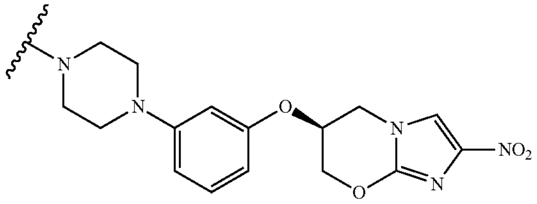 [SMILES: *N1CCN(c2cccc(O[C@@H]3COc4nc([N+](=O)[O-])cn4C3)c2)CC1] | 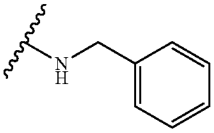 [SMILES: *NCc1ccccc1] |
| 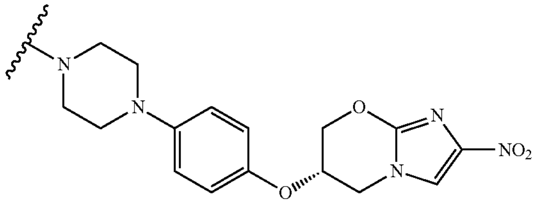 [SMILES: *N1CCN(c2ccc(O[C@@H]3COc4nc([N+](=O)[O-])cn4C3)cc2)CC1] | 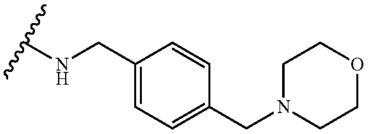 [SMILES: *NCc1ccc(CN2CCOCC2)cc1] |
| 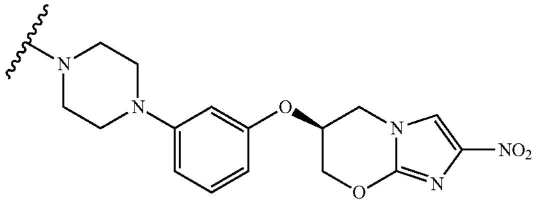 [SMILES: *N1CCN(c2cccc(O[C@@H]3COc4nc([N+](=O)[O-])cn4C3)c2)CC1] | 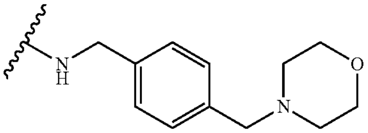 [SMILES: *NCc1ccc(CN2CCOCC2)cc1] |
| 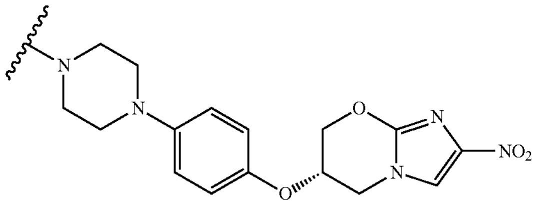 | 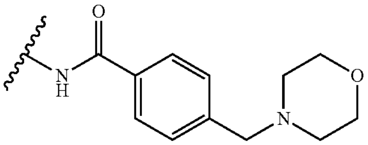 [SMILES: *NC(=O)c1ccc(CN2CCOCC2)cc1] |

TABLE 2-continued
Additional Compounds
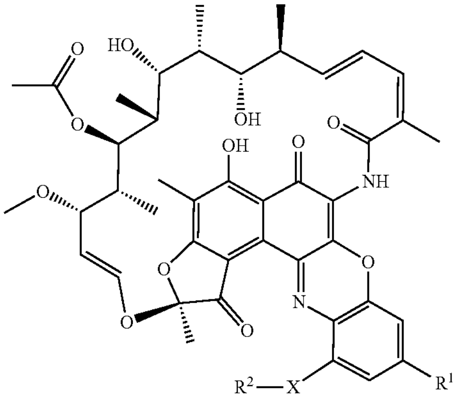
| $R^1$ | —X—$R^2$ |
| --- | --- |
| 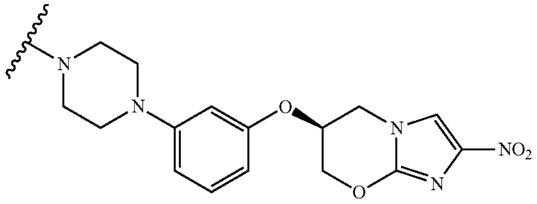 [SMILES: *N1CCN(c2cccc(O[C@@H]3COc4nc([N+](=O)[O-])cn4C3)c2)CC1] | 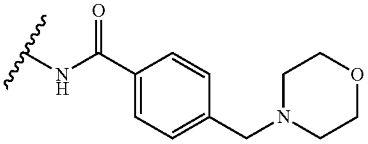 [SMILES: *NC(=O)c1ccc(CN2CCOCC2)cc1] |
| 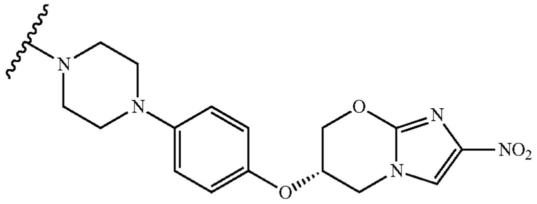 [SMILES: *N1CCN(c2ccc(O[C@@H]3COc4nc([N+](=O)[O-])cn4C3)cc2)CC1] | 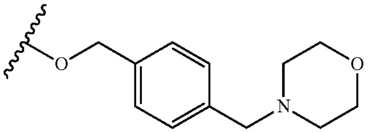 [SMILES: *OCc1ccc(CN2CCOCC2)cc1] |
| 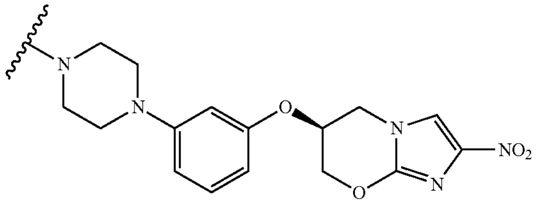 [SMILES: *N1CCN(c2cccc(O[C@@H]3COc4nc([N+](=O)[O-])cn4C3)c2)CC1] | 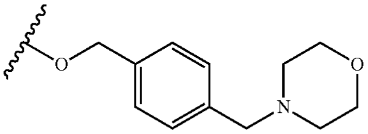 |
| 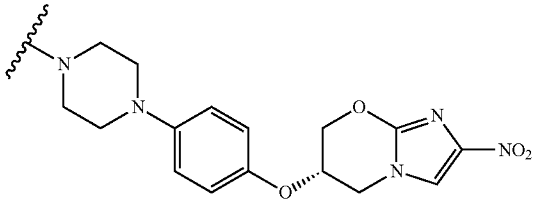 | —$NH_2$ |
| 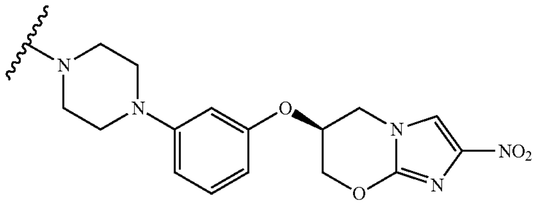 [SMILES: *N1CCN(c2cccc(O[C@@H]3COc4nc([N+](=O)[O-])cn4C3)c2)CC1] | —$NH_2$ |

TABLE 2-continued
Additional Compounds
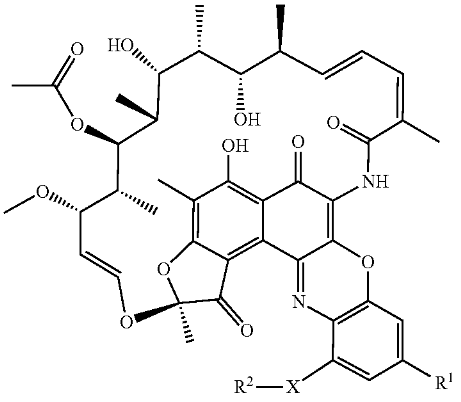
| $R^1$ | —X—$R^2$ |
| --- | --- |
| 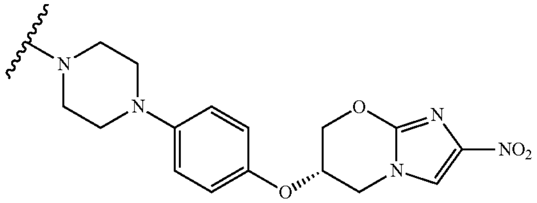 | 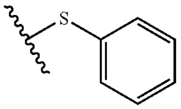 [SMILES: *Sc1ccccc1] |
| 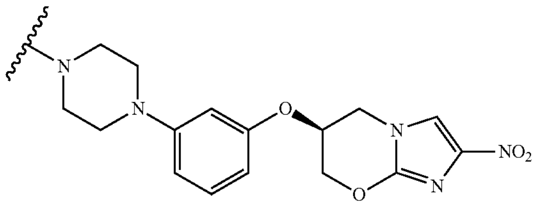 [SMILES: *N1CCN(c2cccc(O[C@@H]3COc4nc([N+](=O)[O-])cn4C3)c2)CC1] | 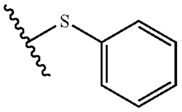 [SMILES: *Sc1ccccc1] |
| 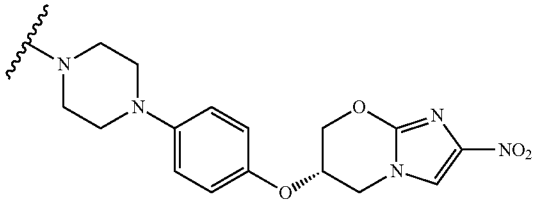 [SMILES: *N1CCN(c2ccc(O[C@@H]3COc4nc([N+](=O)[O-])cn4C3)cc2)CC1] | 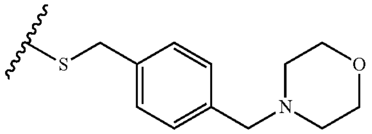 |
| 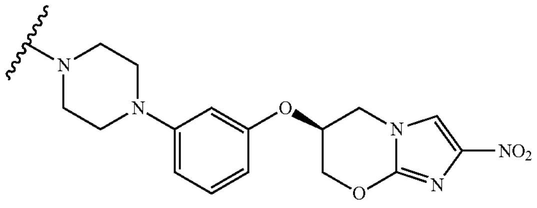 [SMILES: *N1CCN(c2cccc(O[C@@H]3COc4nc([N+](=O)[O-])cn4C3)c2)CC1] | 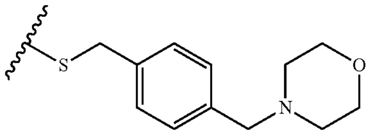 [SMILES: *SCc1ccc(CN2CCOCC2)cc1] |
| 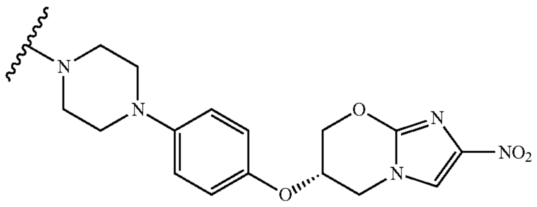 | 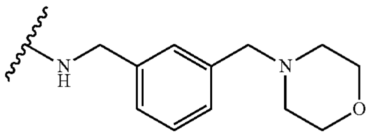 [SMILES: *NCc1cccc(CN2CCOCC2)c1] |

TABLE 2-continued
Additional Compounds
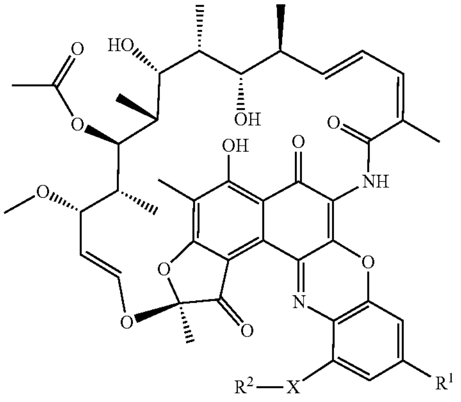
| $R^1$ | —X—$R^2$ |
|---|---|
| 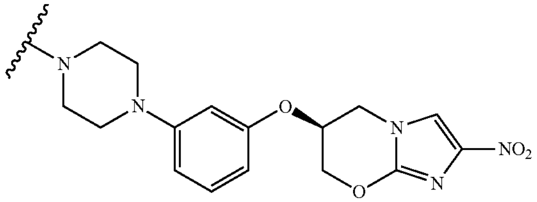 [SMILES: *N1CCN(c2cccc(O[C@@H]3COc4nc([N+](=O)[O-])cn4C3)c2)CC1] | 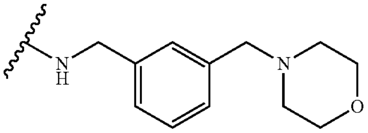 [SMILES: *NCc1cccc(CN2CCOCC2)c1] |
| 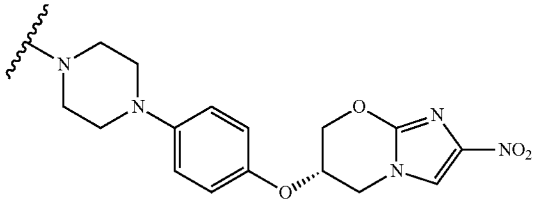 [SMILES: *N1CCN(c2ccc(O[C@@H]3COc4nc([N+](=O)[O-])cn4C3)cc2)CC1] | 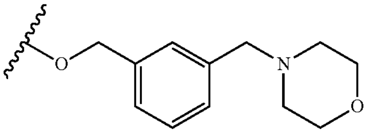 [SMILES: *OCc1cccc(CN2CCOCC2)c1] |
| 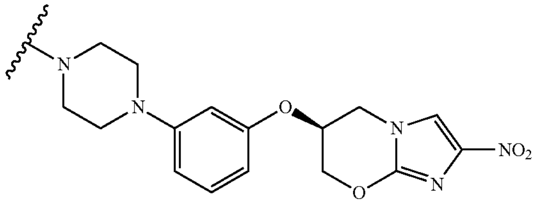 [SMILES: *N1CCN(c2cccc(O[C@@H]3COc4nc([N+](=O)[O-])cn4C3)c2)CC1] | 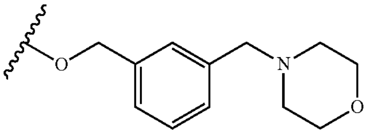 [SMILES: *OCc1cccc(CN2CCOCC2)c1] |
| 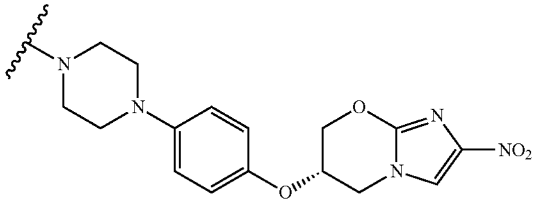 | 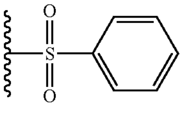 [SMILES: *S(=O)(=O)c1ccccc1] |
| 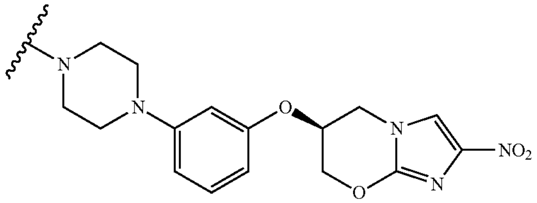 [SMILES: *N1CCN(c2cccc(O[C@@H]3COc4nc([N+](=O)[O-])cn4C3)c2)CC1] | 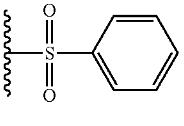 [SMILES: *S(=O)(=O)c1ccccc1] |

TABLE 2-continued
Additional Compounds
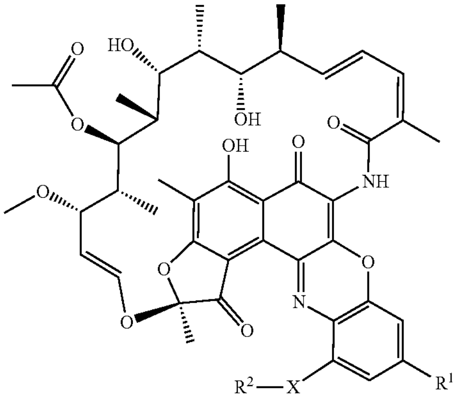
| $R^1$ | —X—$R^2$ |
|---|---|
| 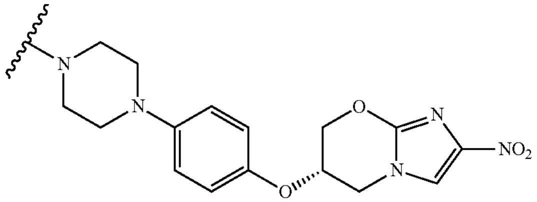 | 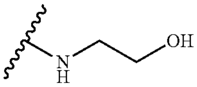 [SMILES: *NCCO] |
| 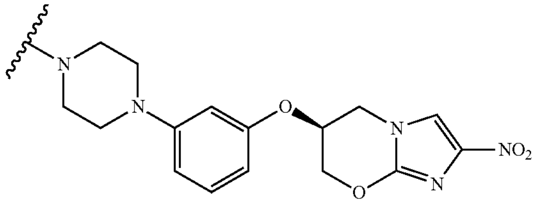 [SMILES: *N1CCN(c2cccc(O[C@@H]3COc4nc([N+](=O)[O-])cn4C3)c2)CC1] | 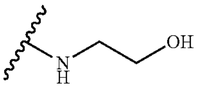 [SMILES: *NCCO] |
| 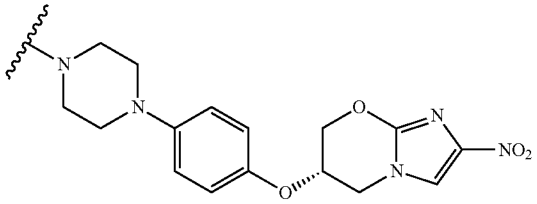 [SMILES: *N1CCN(c2ccc(O[C@@H]3COc4nc([N+](=O)[O-])cn4C3)cc2)CC1] | 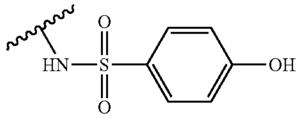 |
| 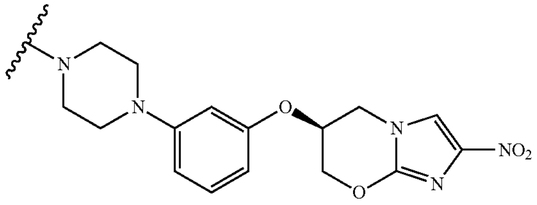 [SMILES: *N1CCN(c2cccc(O[C@@H]3COc4nc([N+](=O)[O-])cn4C3)c2)CC1] | 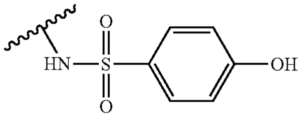 |
| 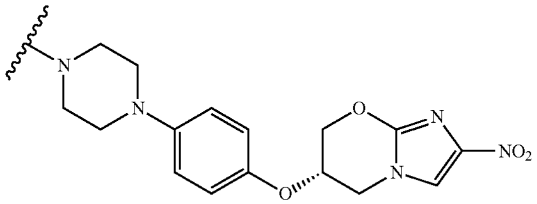 | 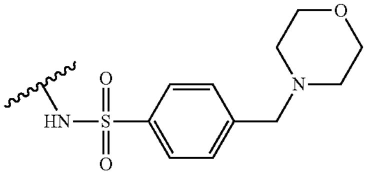 [SMILES: *NS(=O)(=O)c1ccc(CN2CCOCC2)cc1] |

TABLE 2-continued
Additional Compounds
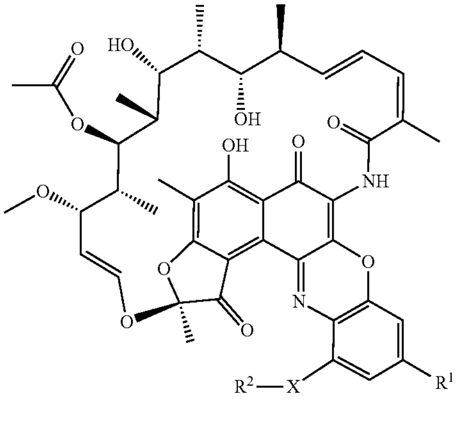
| R[1] | —X—R[2] |
| --- | --- |
| 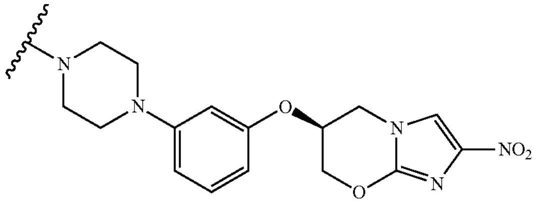 [SMILES: *N1CCN(c2cccc(O[C@@H]3COc4nc([N+](=O)[O-])cn4C3)c2)CC1] | 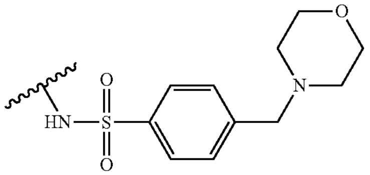 [SMILES: *NS(=O)(=O)c1ccc(CN2CCOCC2)cc1] |
| 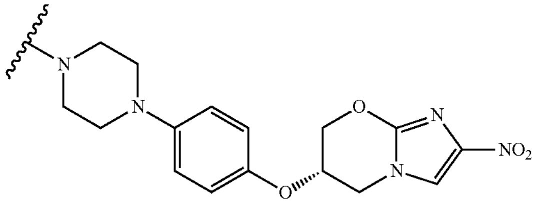 [SMILES: *N1CCN(c2ccc(O[C@@H]3COc4nc([N+](=O)[O-])cn4C3)cc2)CC1] | 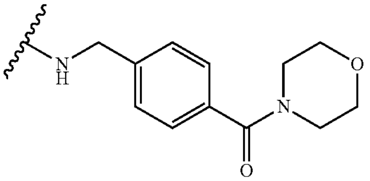 [SMILES: *NCc1ccc(C(=O)N2CCOCC2)cc1] |
| 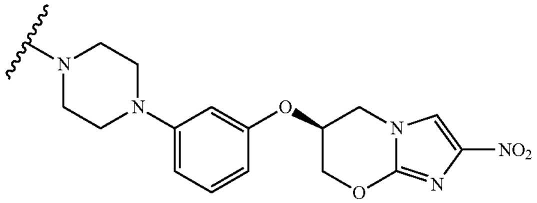 [SMILES: *N1CCN(c2cccc(O[C@@H]3COc4nc([N+](=O)[O-])cn4C3)c2)CC1] | 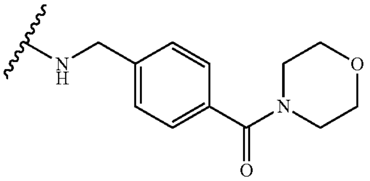 [SMILES: *NCc1ccc(C(=O)N2CCOCC2)cc1] |
| 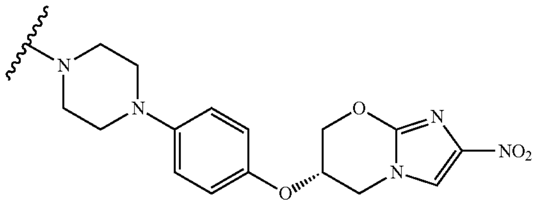 | 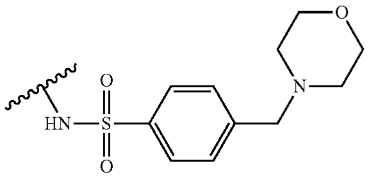 [SMILES: *NS(=O)(=O)c1ccc(CN2CCOCC2)cc1] |
| 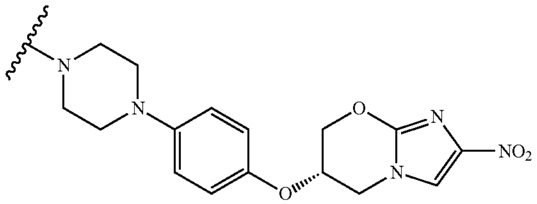 | 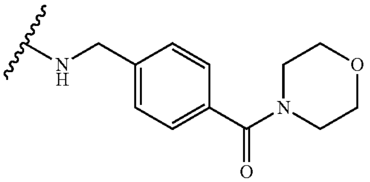 [SMILES: *NCc1ccc(C(=O)N2CCOCC2)cc1] |

TABLE 2-continued
Additional Compounds
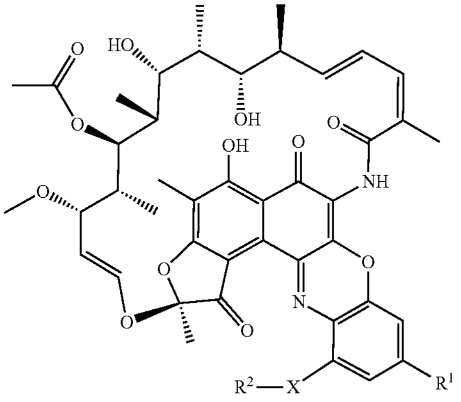
| $R^1$ | $-X-R^2$ |
| --- | --- |
| 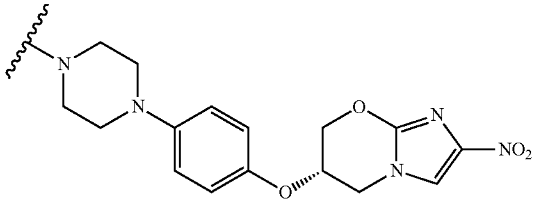 | $-CH_3$ |
| 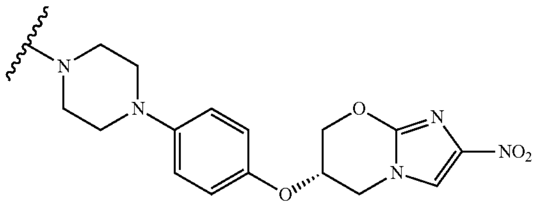 [SMILES: *N1CCN(c2ccc(O[C@@H]3COc4nc([N+](=O)[O-])cn4C3)cc2)CC1] | 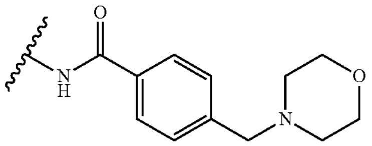 [SMILES: *NC(=O)c1ccc(CN2CCOCC2)cc1] |
| 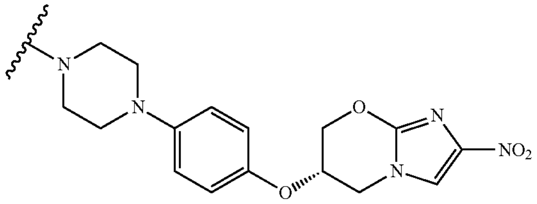 [SMILES: *N1CCN(c2ccc(O[C@@H]3COc4nc([N+](=O)[O-])cn4C3)cc2)CC1] | 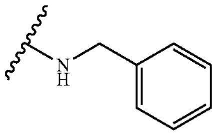 [SMILES: *NCc1ccccc1] |
| 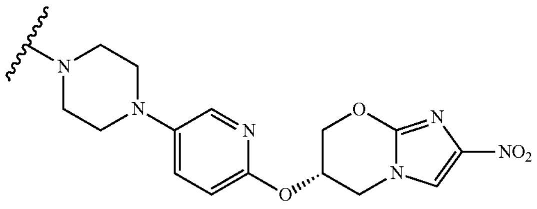 [SMILES: *N1CCN(c2ccc(O[C@@H]3COc4nc([N+](=O)[O-])cn4C3)nc2)CC1] | 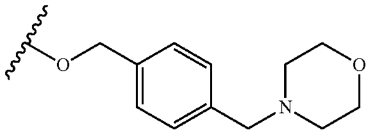 [SMILES: *OCc1ccc(CN2CCOCC2)cc1] |
| 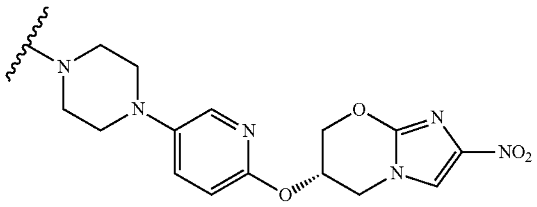 [SMILES: *N1CCN(c2ccc(O[C@@H]3COc4nc([N+](=O)[O-])cn4C3)nc2)CC1] | 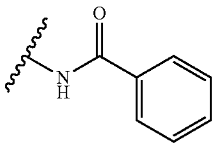 [SMILES: *NC(=O)c1ccccc1] |

TABLE 2-continued
Additional Compounds
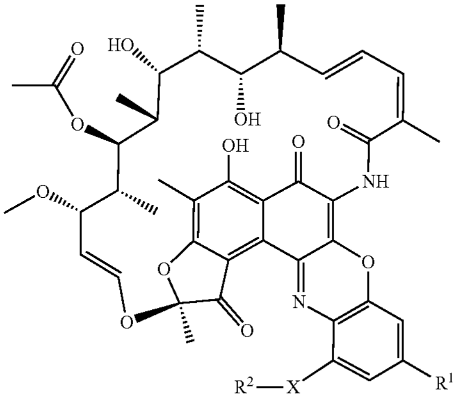
| $R^1$ | —X—$R^2$ |
|---|---|
| 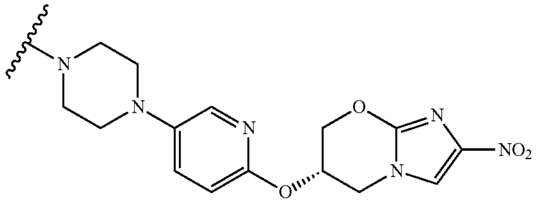 [SMILES: *N1CCN(c2ccc(O[C@@H]3COc4nc([N+](=O)[O-])cn4C3)nc2)CC1] | —$NH_2$ |
| 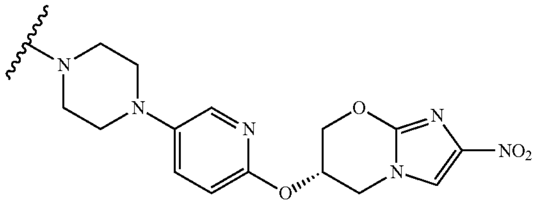 [SMILES: *N1CCN(c2ccc(O[C@@H]3COc4nc([N+](=O)[O-])cn4C3)nc2)CC1] | 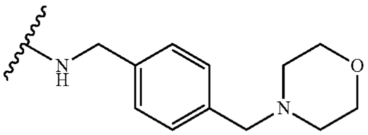 [SMILES: *NCc1ccc(CN2CCOCC2)cc1] |
| 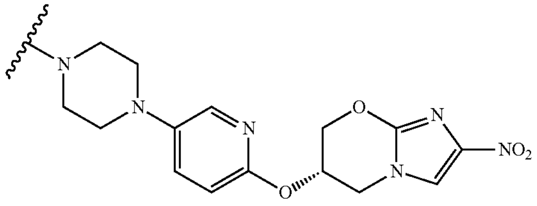 [SMILES: *N1CCN(c2ccc(O[C@@H]3COc4nc([N+](=O)[O-])cn4C3)nc2)CC1] | 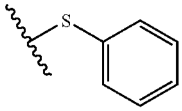 [SMILES: *Sc1ccccc1] |
| 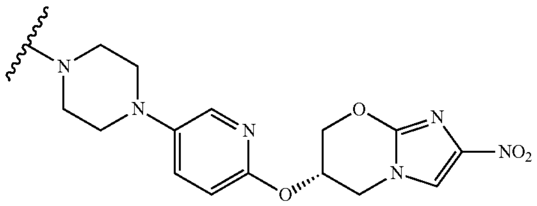 [SMILES: *N1CCN(c2ccc(O[C@@H]3COc4nc([N+](=O)[O-])cn4C3)nc2)CC1] | 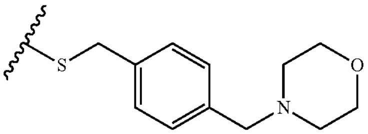 [SMILES: *SCc1ccc(CN2CCOCC2)cc1] |
| 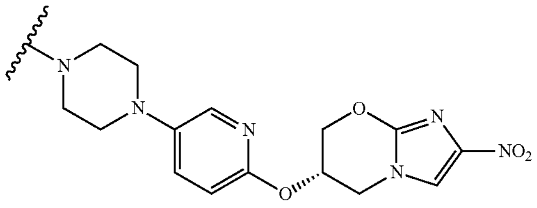 [SMILES: *N1CCN(c2ccc(O[C@@H]3COc4nc([N+](=O)[O-])cn4C3)nc2)CC1] | 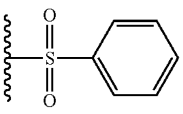 [SMILES: *S(=O)(=O)c1ccccc1] |

TABLE 2-continued
Additional Compounds
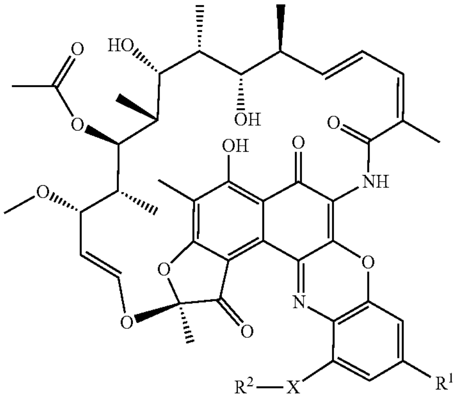
| $R^1$ | —X—$R^2$ |
| --- | --- |
| 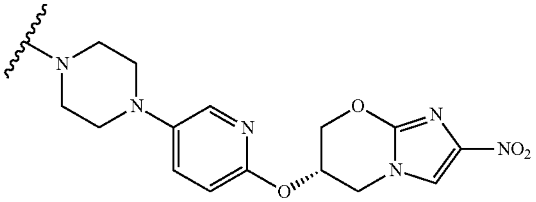 [SMILES: *N1CCN(c2ccc(O[C@@H]3COc4nc([N+](=O)[O-])cn4C3)nc2)CC1] | 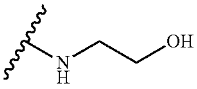 [SMILES: *NCCO] |
| 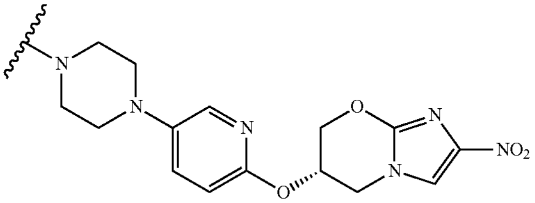 [SMILES: *N1CCN(c2ccc(O[C@@H]3COc4nc([N+](=O)[O-])cn4C3)nc2)CC1] | 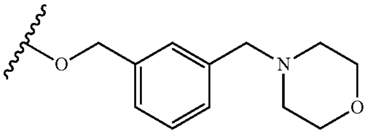 [SMILES: *OCc1cccc(CN2CCOCC2)c1] |
| 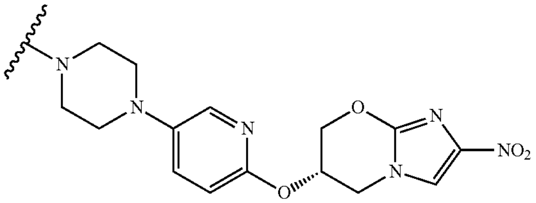 [SMILES: *N1CCN(c2ccc(O[C@@H]3COc4nc([N+](=O)[O-])cn4C3)nc2)CC1] | 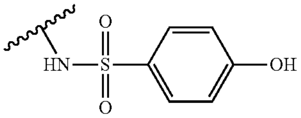 [SMILES: *NS(=O)(=O)c1ccc(O)cc1] |
| 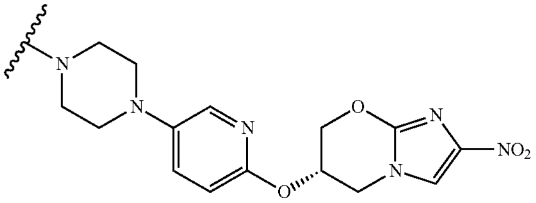 [SMILES: *N1CCN(c2ccc(O[C@@H]3COc4nc([N+](=O)[O-])cn4C3)nc2)CC1] | 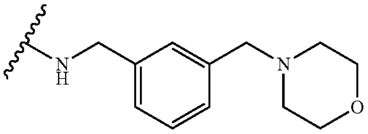 [SMILES: *NCc1cccc(CN2CCOCC2)c1] |
| 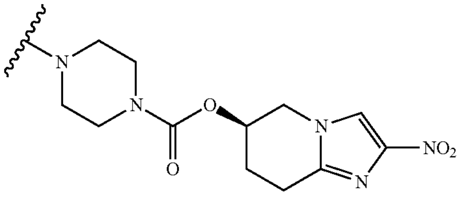 [SMILES: *N1CCN(C(=O)O[C@@H]2CCc3nc([N+](=O)[O-])cn3C2)CC1] | $-CH_3$ |

TABLE 2-continued
Additional Compounds
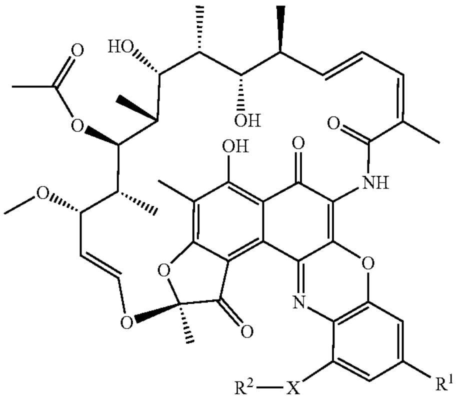
| R¹ | —X—R² |
| --- | --- |
| 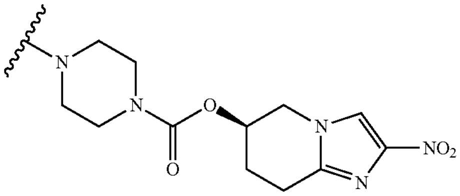 [SMILES: *N1CCN(C(=O)O[C@@H]2CCc3nc([N+](=O)[O-])cn3C2)CC1] | 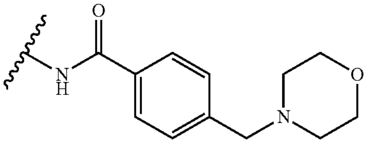 [SMILES: *NC(=O)c1ccc(CN2CCOCC2)cc1] |
| 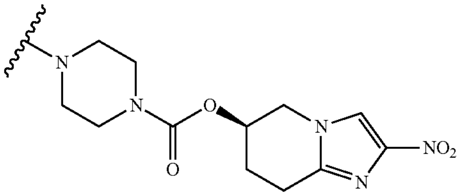 [SMILES: *N1CCN(C(=O)O[C@@H]2CCc3nc([N+](=O)[O-])cn3C2)CC1] | 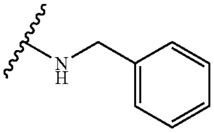 [SMILES: *NCc1ccccc1] |
| 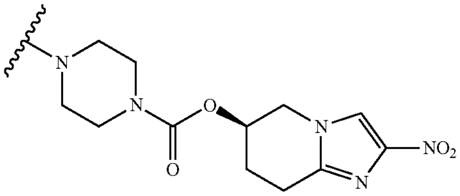 [SMILES: *N1CCN(C(=O)O[C@@H]2CCc3nc([N+](=O)[O-])cn3C2)CC1] | 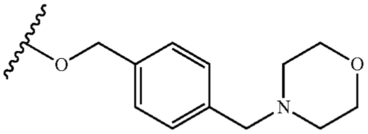 [SMILES: *OCc1ccc(CN2CCOCC2)cc1] |
| 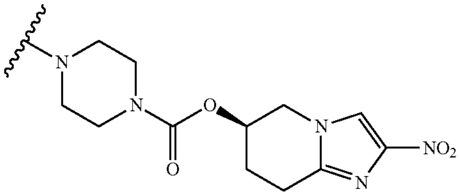 [SMILES: *N1CCN(C(=O)O[C@@H]2CCc3nc([N+](=O)[O-])cn3C2)CC1] | 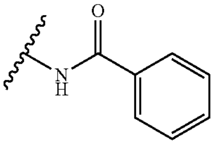 [SMILES: *NC(=O)c1ccccc1] |
| 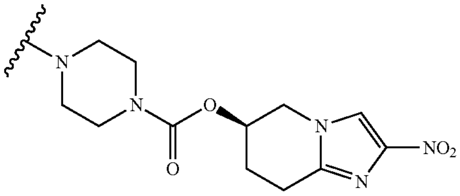 [SMILES: *N1CCN(C(=O)O[C@@H]2CCc3nc([N+](=O)[O-])cn3C2)CC1] | 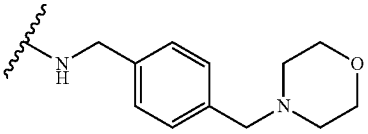 [SMILES: *NCc1ccc(CN2CCOCC2)cc1] |

TABLE 2-continued
| Additional Compounds | |
|---|---|
| 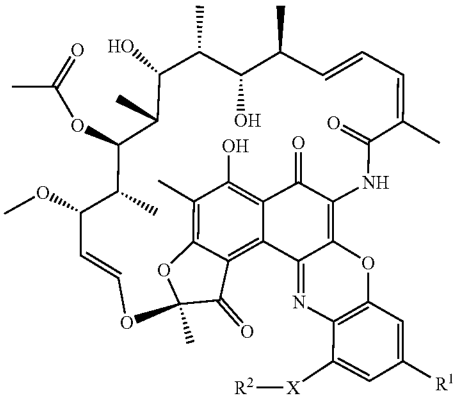 | |
| $R^1$ | —X—$R^2$ |
| 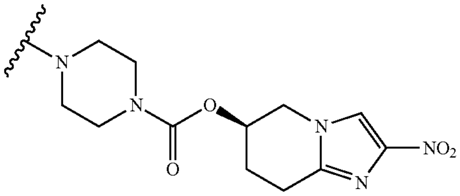 [SMILES: *N1CCN(C(=O)O[C@@H]2CCc3nc([N+](=O)[O-])cn3C2)CC1] | —$NH_2$ |
| 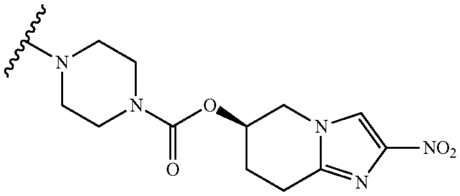 [SMILES: *N1CCN(C(=O)O[C@@H]2CCc3nc([N+](=O)[O-])cn3C2)CC1] | 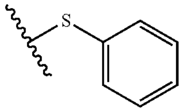 [SMILES: *Sc1ccccc1] |
| 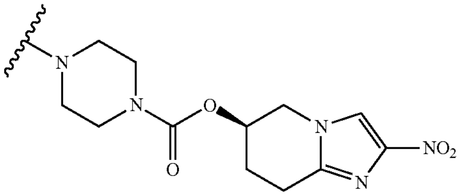 [SMILES: *N1CCN(C(=O)O[C@@H]2CCc3nc([N+](=O)[O-])cn3C2)CC1] | 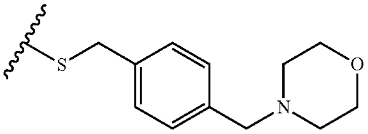 [SMILES: *SCc1ccc(CN2CCOCC2)cc1] |
| 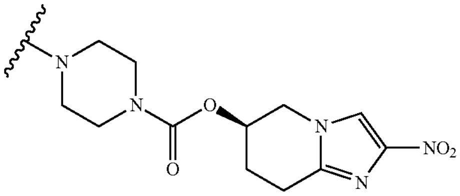 [SMILES: *N1CCN(C(=O)O[C@@H]2CCc3nc([N+](=O)[O-])cn3C2)CC1] | 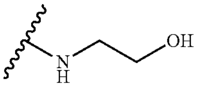 [SMILES: *NCCO] |
| 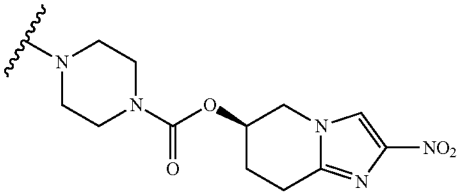 [SMILES: *N1CCN(C(=O)O[C@@H]2CCc3nc([N+](=O)[O-])cn3C2)CC1] | 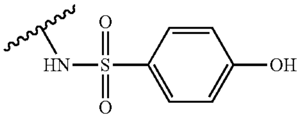 |

TABLE 2-continued
Additional Compounds
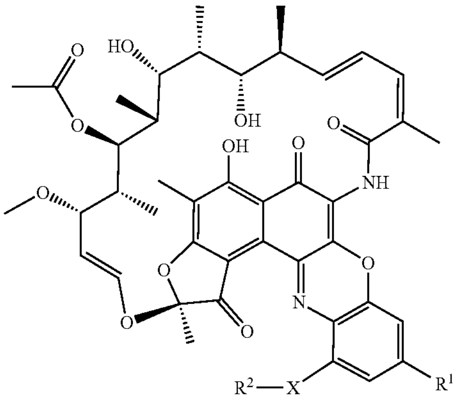
| $R^1$ | —X—$R^2$ |
| --- | --- |
| 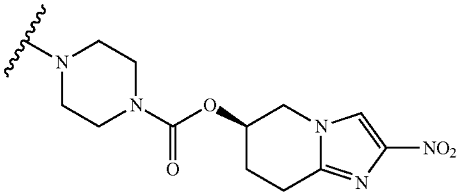 [SMILES: *N1CCN(C(=O)O[C@@H]2CCc3nc([N+](=O)[O-])cn3C2)CC1] | 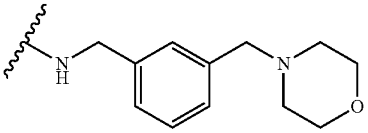 [SMILES: *NCc1cccc(CN2CCOCC2)c1] |
| 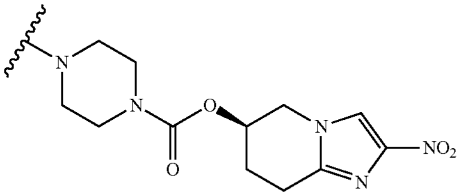 [SMILES: *N1CCN(C(=O)O[C@@H]2CCc3nc([N+](=O)[O-])cn3C2)CC1] | 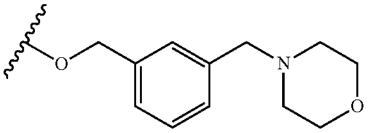 [SMILES: *OCc1cccc(CN2CCOCC2)c1] |
| 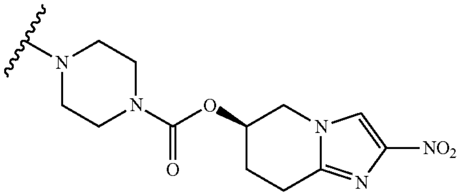 [SMILES: *N1CCN(C(=O)O[C@@H]2CCc3nc([N+](=O)[O-])cn3C2)CC1] | 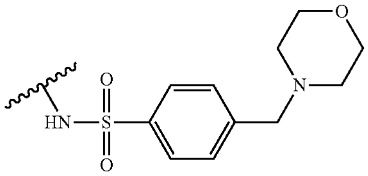 [SMILES: *NS(=O)(=O)c1ccc(CN2CCOCC2)cc1] |
| 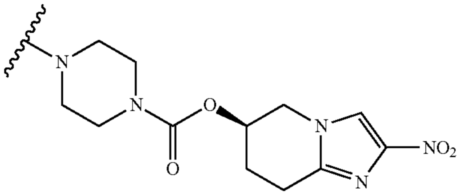 [SMILES: *N1CCN(C(=O)O[C@@H]2CCc3nc([N+](=O)[O-])cn3C2)CC1] | 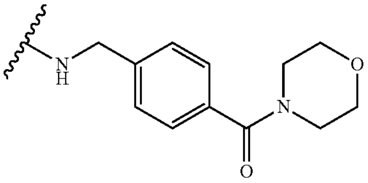 [SMILES: *NCc1ccc(C(=O)N2CCOCC2)cc1] |
| 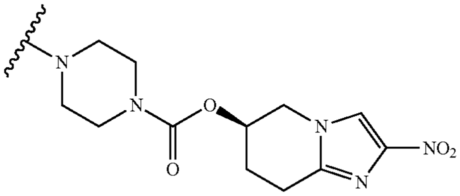 [SMILES: *N1CCN(C(=O)O[C@@H]2CCc3nc([N+](=O)[O-])cn3C2)CC1] | 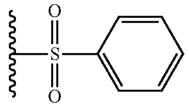 |

TABLE 2-continued
Additional Compounds
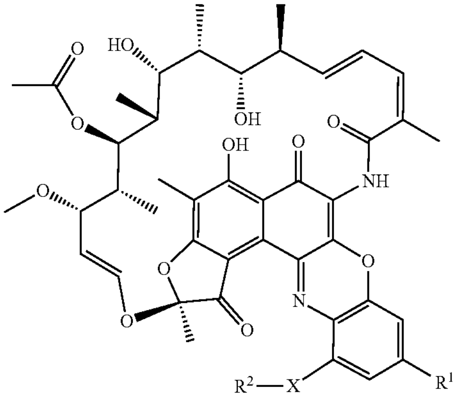
| $R^1$ | —X—$R^2$ |
| --- | --- |
| 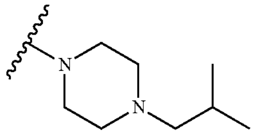 [SMILES: *N1CCN(CC(C)C)CC1] | 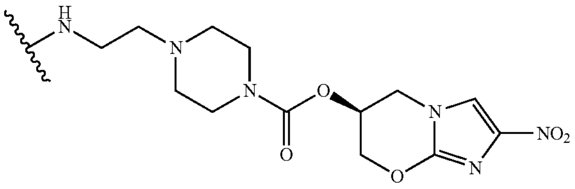 [SMILES: *NCCN1CCN(C(=O)O[C@@H]2COc3nc([N+](=O)[O-])cn3C2)CC1] |
| 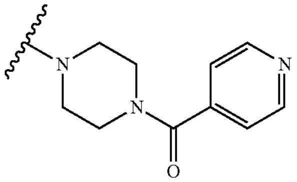 [SMILES: *N1CCN(C(=O)c2ccncc2)CC1] | 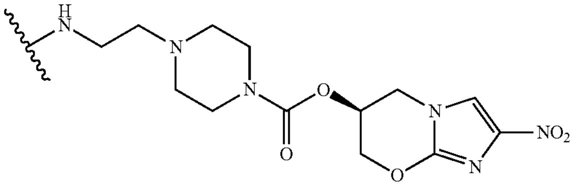 [SMILES: *NCCN1CCN(C(=O)O[C@@H]2COc3nc([N+](=O)[O-])cn3C2)CC1] |
| 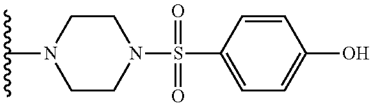 [SMILES: *N1CCN(S(=O)(=O)c2ccc(O)cc2)CC1] | 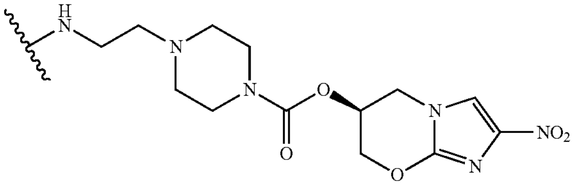 [SMILES: *NCCN1CCN(C(=O)O[C@@H]2COc3nc([N+](=O)[O-])cn3C2)CC1] |
| 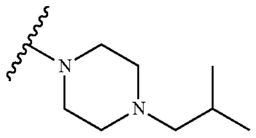 [SMILES: *N1CCN(CC(C)C)CC1] | 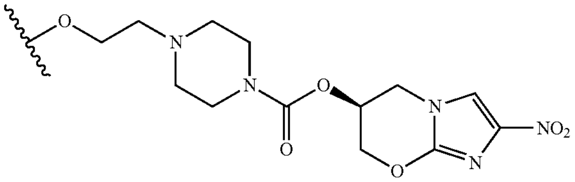 [SMILES: *OCCN1CCN(C(=O)O[C@@H]2COc3nc([N+](=O)[O-])cn3C2)CC1] |
| 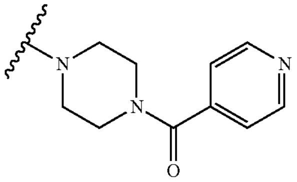 [SMILES: *N1CCN(C(=O)c2ccncc2)CC1] | 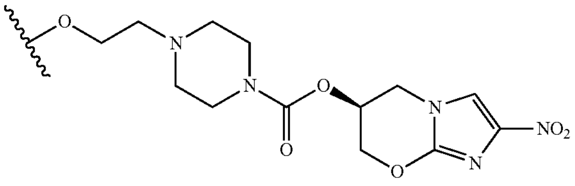 [SMILES: *OCCN1CCN(C(=O)O[C@@H]2COc3nc([N+](=O)[O-])cn3C2)CC1] |

TABLE 2-continued
Additional Compounds
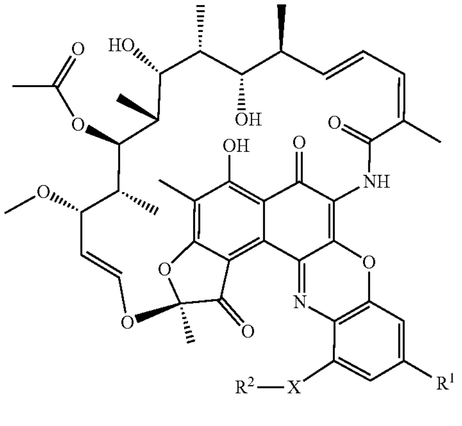
| $R^1$ | —X—$R^2$ |
| --- | --- |
| 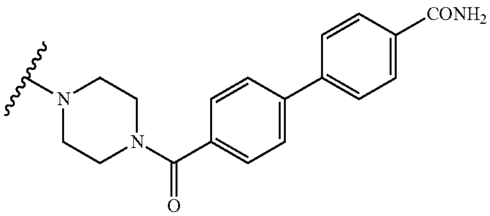 [SMILES: *N1CCN(C(=O)c2ccc(-c3ccc(C(N)=O)cc3)cc2)CC1] | 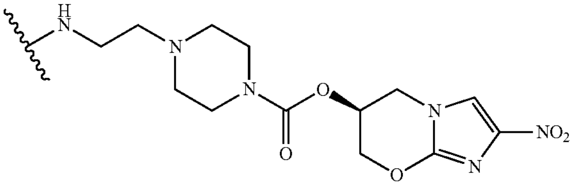 [SMILES: *NCCN1CCN(C(=O)O[C@@H]2COc3nc([N+](=O)[O-])cn3C2)CC1] |
| 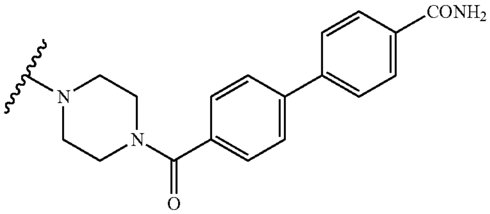 [SMILES: *N1CCN(C(=O)c2ccc(-c3ccc(C(N)=O)cc3)cc2)CC1] | 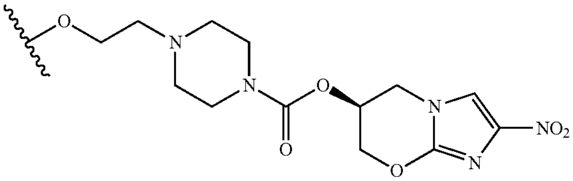 [SMILES: *OCCN1CCN(C(=O)O[C@@H]2COc3nc([N+](=O)[O-])cn3C2)CC1] |
| 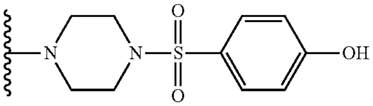 [SMILES: *N1CCN(S(=O)(=O)c2ccc(O)cc2)CC1] | 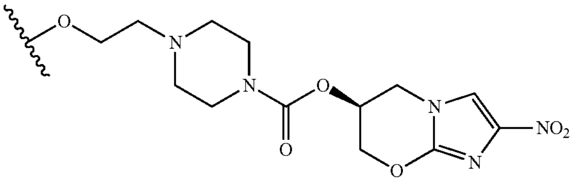 [SMILES: *OCCN1CCN(C(=O)O[C@@H]2COc3nc([N+](=O)[O-])cn3C2)CC1] |
| 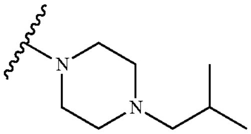 [SMILES: *N1CCN(CC(C)C)CC1] | 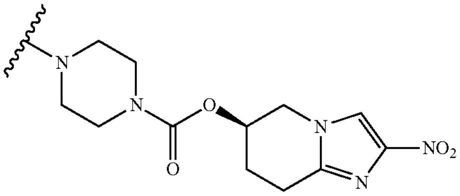 [SMILES: *N1CCN(C(=O)O[C@@H]2CCc3nc([N+](=O)[O-])cn3C2)CC1] |
| 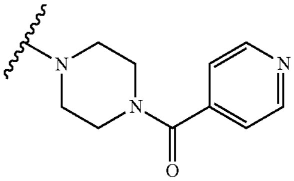 [SMILES: *N1CCN(C(=O)c2ccncc2)CC1] | 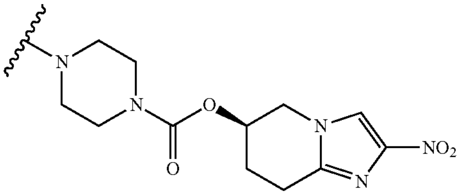 [SMILES: *N1CCN(C(=O)O[C@@H]2CCc3nc([N+](=O)[O-])cn3C2)CC1] |

TABLE 2-continued

Additional Compounds

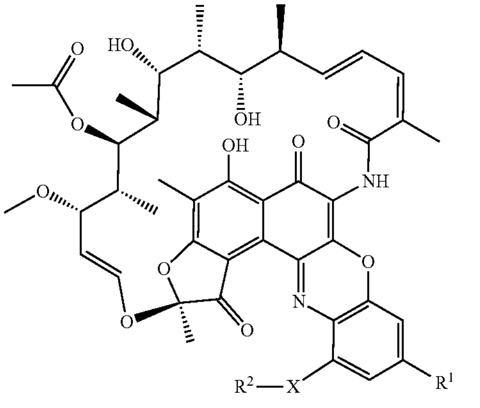

| $R^1$ | —X—$R^2$ |
| --- | --- |
| 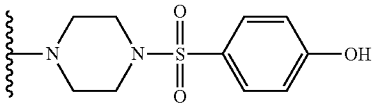 | 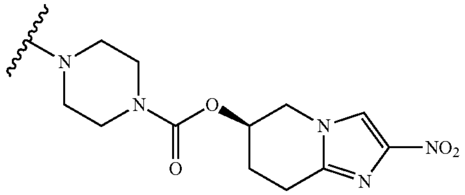 [SMILES: *N1CCN(C(=O)O[C@@H]2CCc3nc([N+](=O)[O-])cn3C2)CC1] |
| 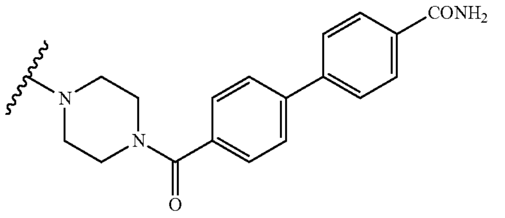 [SMILES: *N1CCN(C(=O)c2ccc(-c3ccc(C(N)=O)cc3)cc2)CC1] | 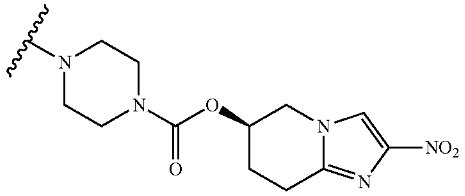 [SMILES: *N1CCN(C(=O)O[C@@H]2CCc3nc([N+](=O)[O-])cn3C2)CC1] |

The compound (e.g., a compound of formula (I)) may exist as a stereoisomer wherein asymmetric or chiral centers are present, in addition to the chiral centers already specified in formula (I). The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45:13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

The compound (e.g., a compound of formula (I)) may possess tautomeric forms, and tautomers also constitute embodiments of the disclosure.

The present disclosure also includes isotopically-labeled compounds (e.g., an isotopically-labeled compound of formula (I)), which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}$H, $^{3}$H, $^{13}$C, $^{14}$C, $^{15}$N, $^{18}$O, $^{31}$P, $^{35}$S, $^{18}$F, and $^{3}$Cl, respectively. Substitution with heavier isotopes such as deuterium, i.e. $^{2}$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$, and $^{18}$F. Isotopically-labeled compounds of formula (I) can generally be prepared by conventional techniques known to those skilled in the art or by processes analogous to those described herein using an appropriate isotopically-labeled reagent in place of a non-isotopically-labeled reagent.

Compounds of formula (I) can be synthesized by a variety of methods. For example, compounds can be synthesized as shown in the general synthetic method shown in Scheme 1.

Scheme 1

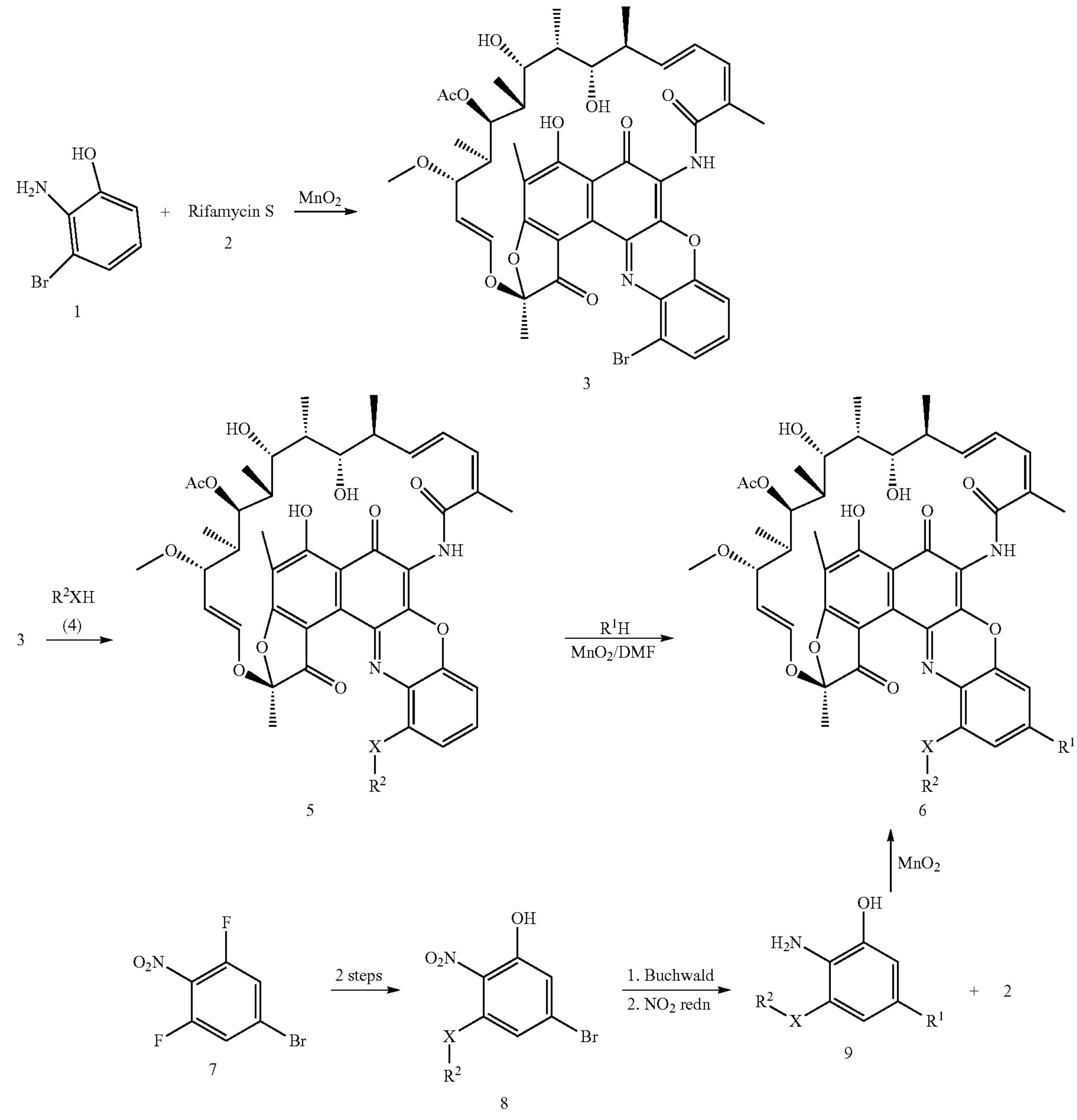

1 + 2 → 3; 3 → 5 → 6; 7 → 8 → 9 + 2 → 6

Methods of synthesizing compounds of formula (I) also include those illustrated in the Examples. For example, as shown in Scheme 2, hydrogenation of compound 2a utilizing Pearlman's catalyst simultaneously reduced the nitro function and hydrogenolyzed the benzyl protecting group to give the 2-aminoresorcinol ether compound 3a. A similar sequence of reactions was followed to provide ether compounds 3b-3c. t-Boc deprotection of compound 3c provided secondary amine compound 3d. Each 2-aminoresorcinol ether (compounds 3a-3d) was then annulated onto rifamycin S (compound 4) to provide intermediate compounds 5a-5d. Acylation of compound 5d with 4-morpholineacetic acid gave elaborated side chain amide compound 5e. Condensation of compound 5b with i-butylpiperazine followed by manganese oxide treatment provided the fully elaborated "two armed" target compound 6a following purification utilizing silica gel chromatography. Similar reaction of known intermediate compounds 5f and 5g (Showalter et al. *J. Med. Chem.* 2012, 55, 3814-3826) with appropriate N-alkylpiperazines provided compounds 6b-6d. A similar strategy to make two-armed (—X—$R^2$, $R^1$) target compounds with a wide combination of diverse side chains is outlined in Schemes 3-5. In Scheme 6, the same types of chemical transformations shown in Schemes 2-5 were made on a benzoxazino-rifamycin core with a methyl group replacing the more elaborate —X—$R^2$ ether moieties, but employing generally more complex $R^1$ amine side chains than i-butylpiperazine found in RLZ. Scheme 7 shows the synthesis of selected target compounds in which the side chain moieties of target compounds in Scheme 6 have been swapped.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Standard experimentation, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006).

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the procedures described herein using a pure geometric isomer as a starting material, or by resolution of a mixture of the geometric isomers of the compound or intermediates using a standard procedure such as chromatographic separation.

The synthetic schemes and specific examples as described are illustrative and are not to be read as limiting the scope of the invention as it is defined in the claims. All alternatives, modifications, and equivalents of the synthetic methods and specific examples are included within the scope of the claims.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Compounds disclosed herein can exist in unsolvated forms as well as solvated forms, including hydrated forms. In general, the solvated forms are equivalent to unsolvated forms and are encompassed within the scope of the present disclosure. Certain compounds of the disclosure may also exist in multiple crystalline or amorphous forms. In general, all physical forms are equivalent for the uses contemplated by the present disclosure and are intended to be within the scope of the present disclosure.

The present invention also provides compounds that are in a prodrug form. Prodrugs of the compounds described herein are those compounds that readily undergo chemical changes under physiological conditions to provide the compounds disclosed herein (e.g., a compound of formula (I)). Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Pharmaceutical Compositions

The disclosed compounds may be incorporated into pharmaceutical compositions suitable for administration to a subject (such as a patient, which may be a human or non-human). The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease or condition, the prophylactically effective amount will be less than the therapeutically effective amount.

For example, a therapeutically effective amount of a compound of formula (I) may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their pharmaceutically acceptable salts may be formulated for administration by, for example, solid dosing, eye drop, in a topical oil-based formulation, injection, inhalation (either through the mouth or the nose), implants, or oral, buccal, parenteral, or rectal administration. For example, the compounds and their pharmaceutically acceptable salts may be formulated for pulmonary administration via inhalation, for treatment of tuberculosis. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, inhalation, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerin, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)), and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I), or a pharmaceutically acceptable salt thereof), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

In some embodiments, the compounds and their pharmaceutically acceptable salts may be formulated for administration by inhalation. Methods of administration of pharmaceuticals and other substances by inhalation are well-known. In general, compounds delivered as aerosols have a particle range of about 0.5 to about 6 sm. Methods known in the art to generate and deliver such aerosols include nebulizers (liquid formulations), dry powder inhalers (dry powder formulations), and metered dose inhalers (drug formulation suspended in a propellant that evaporates virtually instantaneously). Such delivery methods are well-known in the art. See, e.g., M. Keller (1999) *Int. J. Pharmaceutics* 186:81-90; M. Everard (2001) J. *Aerosol Med.* 14 (Suppl 1):S-59-S-64; Togger and Brenner (2001) *Am. J. Nursing* 101:26-32. Commercially available aerosolizers for liquid formulations, including jet nebulizers and ultrasonic nebulizers, are useful in the methods of the invention. For delivery in liquid form, liquid formulations can be directly aerosolized and lyophilized powder can be aerosolized after reconstitution. For delivery in dry powder form, the formulation may be prepared as a lyophilized and milled powder. In additions, formulations may be delivered using a fluorocarbon formulation or other propellant and a metered dose dispenser. For delivery devices and methods, see, e.g., U.S. Pat. Nos. 4,137,914; 4,174,712; 4,524,769; 4,667,688; 5,672,581; 5,709,202; 5,780,014; 5,672,581; 5,915,378; 5,997,848; 6,123,068; 6,123,936; 6,397,838.

Methods of Use

Compounds disclosed herein are potent inhibitors of *Mycobacterium tuberculosis* RNAP, and accordingly can be used in methods of treating tuberculosis in a subject, as well as methods of killing *Mycobacterium tuberculosis* in a sample. Compounds disclosed herein also exhibit significantly reduced activation of the human pregnane X receptor (hPXR), resulting in reduced induction of hepatic cytochromes P450 2C9 and 3A4 (CYP2C9, CYP3A4). CYP3A4 is known to metabolize several classes of drugs used to treat HIV infections, including protease inhibitors and non-nucleoside reverse transcriptase inhibitors. Accordingly, compounds disclosed herein are particularly useful in methods of treating a subject co-infected with tuberculosis and HIV.

Accordingly, disclosed herein is a method of treating tuberculosis in a subject in need thereof, comprising administering to the subject a therapeutically effective amount of a compound disclosed herein (e.g., a compound of formula (I) or a pharmaceutically acceptable salt thereof), or a pharmaceutical composition disclosed herein (e.g., a pharmaceutical composition comprising a compound of formula (I) or a pharmaceutically acceptable salt thereof). In some embodiments, the subject is infected with *Mycobacterium tuberculosis*, such as a drug-resistant strain of *Mycobacterium tuberculosis* (e.g., a rifampin-resistant strain of *Mycobacterium tuberculosis*). In some embodiments, the subject has a persistent tuberculosis infection. In some embodiments, the subject is also infected with human immunodeficiency virus. In some embodiments, the subject has acquired immune deficiency syndrome.

Also disclosed herein is a method of killing *Mycobacterium tuberculosis* in a sample, comprising contacting the sample with an effective amount of a compound disclosed herein (e.g., a compound of formula (I) or a pharmaceutically acceptable salt thereof), or a pharmaceutical composition disclosed herein (e.g., a pharmaceutical composition comprising a compound of formula (I) or a pharmaceutically acceptable salt thereof). In some embodiments, the sample comprises a drug-resistant strain of *Mycobacterium tuberculosis* (e.g., a rifampin-resistant strain of *Mycobacterium tuberculosis*).

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those skilled in the art and will vary with the formulation used for therapy, the purpose of the therapy, the target cell being treated, and the subject being treated. Single or multiple administrations can be carried out with the dose level and pattern being selected by the treating physician.

A compound described herein may be used in combination with other known therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound described herein and the, at least one, additional therapeutic agent can be administered simultaneously, in the same or in separate compositions, or sequentially. For sequential administration, the compound described herein can be administered first, and the additional agent can be administered subsequently, or the order of administration can be reversed.

In some embodiments, a compound described herein is co-administered with an antibiotic such as, e.g., isoniazid, pyrazinamide, ethambutol, or streptomycin. In some embodiments, the antibiotic co-administered with the compound described herein is an aminoglycoside (e.g., amikacin, kanamycin), a polypeptide (e.g., capreomycin, viomycin, enviomycin), a fluoroquinolone (e.g., ciprofloxacin, levofloxacin, moxifloxacin), a thioamide (e.g., ethionamide, prothionamide, tiocarlide), cycloserine, or p-aminosalicylic acid. In some embodiments, the antibiotic co-administered with compound described herein is rifabutin, a macrolide (e.g., clarithromycin), linezolid, thioacetazone, thioridazine, arginine, vitamin D, or R207910. In some embodiments, a steroid (e.g., a corticosteroid (e.g., prednisolone or dexamethasone)) is co-administered with the compound.

In some embodiments, a compound described herein is co-administered with thalidomide. In some embodiments, a compound described herein is co-administered with interferon-γ. In some embodiments, a compound described herein is co-administered with meropenem, morinamide, terizidone, or clavulanic acid. In some embodiments, a compound described herein is co-administered with co-amoxiclav, clofazimine, prochlorperazine, metronidazole, delamanid, or pretomanid (PA-824). In some embodiments, a compound described herein is co-administered with Dzherelo, Anemin, Svitanok, Lizorm, Immunoxel, or Immunitor.

Kits

For use in methods described herein, kits and articles of manufacture are also provided, which include a compound or pharmaceutical composition described herein (e.g., a compound of formula (I) or a pharmaceutically acceptable salt thereof, or a pharmaceutical composition comprising a compound of formula (I) or a pharmaceutically acceptable salt thereof). In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, in some embodiments the container(s) includes a compound of formula (I) or a pharmaceutically acceptable salt thereof, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

The following examples further illustrate aspects of the disclosure but, of course, should not be construed as in any way limiting its scope.

EXAMPLES

Example 1: Compound Syntheses

All reagents were commercially available and used without further purification, unless otherwise indicated. Rifalazil was synthesized according to a disclosed method (*Chem. Pharm. Bull.* 1993, 41 (1), 148-155). Column chromatographic purifications were carried out using Teledyne-Isco's combiflash Rf+ or Rf+ Lumen systems. Teledyne-Isco Redisep gold silica gel columns with 20-40 micron particle size or Silicycle high performance silica gel columns with 25 micron particle size were used for separations. $^1H$ and $^{13}C$ NMR spectra were obtained on Varian 700, 500 or 400 MHz spectrometers with $CDCl_3$ or $d_6$-DMSO as solvent and chemical shifts are reported relative to TMS peak in δ (ppm). Mass spectrometry analysis was performed using a Waters LCT time-of-flight mass spectrometry instrument. High resolution mass spectrometry (HRMS) analysis was performed on an Agilent Q-TOF system. Compound purities were determined by analytical HPLC performed on an Agilent 1100 series system with an Agilent Eclipse plus C18 (4.6+7.5 mm, 3.5 mm particle size) column. The mobile phase was a 13 min binary gradient of acetonitrile (containing 0.1% TFA) and water (20-90%). Thin-layer chromatography (TLC) was performed on silica gel GHLF plates (250 microns) purchased from Analtech. Extraction solutions were dried over $Na_2SO_4$ prior to concentration. Compounds embedded with a rifamycin core were assigned IUPAC nomenclature using Marvin Sketch version 20.19.0.

Compounds 5a-5g and 6a-6d were synthesized as illustrated in Scheme 2.

Scheme 2

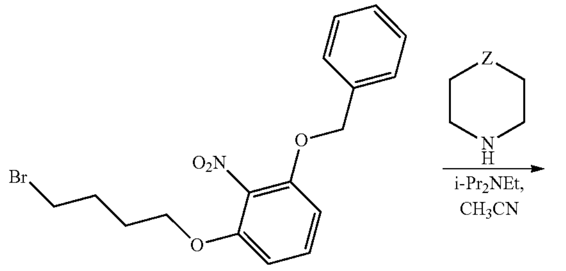

1

-continued

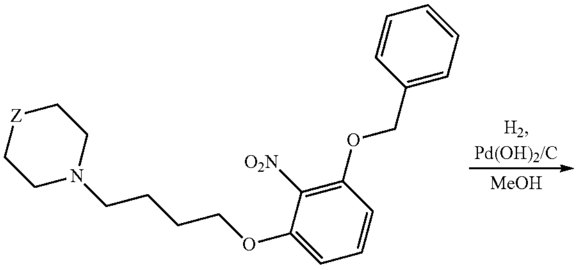

2 a: Z = NMe
b: Z = O
c: Z = NBoc
d: Z = $NCO_2(CH_2)_2SiMe_3$

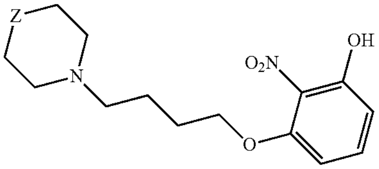

3 a: Z = NMe
b: Z = O
c: Z = NBoc
d: Z = NH
TFA/DCM
e: Z = $NCO_2(CH_2)_2SiMe_3$

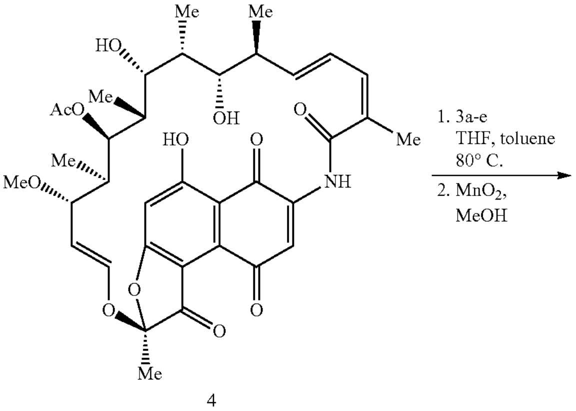

4
(rifamycin S)

-continued

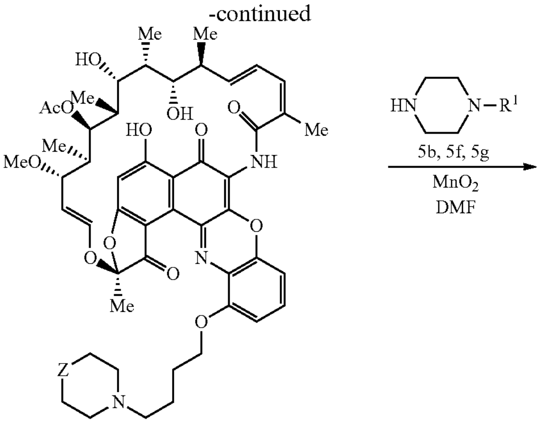

5 a: Z = NMe
b: Z = O
c: Z = NBoc
d: Z = NH
e: = $NC(O)CH_2$-(morpholin-4-yl)
f: Z = $N(CH_2)_2$-(1H-imidazol-1-yl)
g: Z = $NC(O)CH_2$-(1H-imidazol-1-yl)
h: Z = $NCO_2(CH_2)_2SiMe_3$ 4-morpholineacetic acid
HATU, HOBT
$NEt_3$, DMF

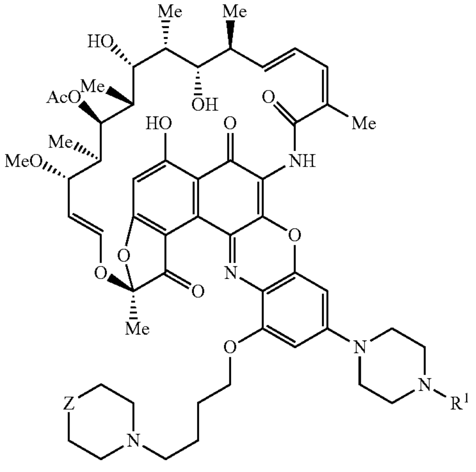

6 a: Z = O; $R^1$ = i-Bu
b: Z = $N(CH_2)_2$-(1H-imidazol-1-yl); $R^1$ = i-Bu
c: Z = $NC(O)CH_2$-(1H-imidazol-1-yl); $R^1$ = Me
d: Z = $NC(O)CH_2$-(1H-imidazol-1-yl); $R^1$ = i-Bu 1-{4-[3-(Benzyloxy)-2-nitrophenoxy]butyl}-4-methylpiperazine (2a). A solution of bromo compound 1 (Showalter et al., *J. Med. Chem.* 2012, 55, 3814-3826; 0.25 g, 0.736 mmol), N-methylpiperazine (0.072 g, 0.810 mmol), N,N-diisopropylethylamine (0.35 mL, 2.21 mmol) and acetonitrile (8 mL) was stirred at 85° C. for 3 h. The mixture was concentrated to a crude residue that was loaded onto a precolumn of silica gel attached to a 24 g column and eluted with 2-10% methanol/dichloromethane over 30 min and then up to 15% methanol/dichloromethane for a further 10 min. Combined product fractions were concentrated to give 2a (0.143 g, 79%). $^1H$ NMR (700 MHz, chloroform-d) δ 7.38-7.35 (m, 3H), 7.33-7.30 (m, 1H), 7.27-7.24 (m, 2H), 6.63 (d, J=8.5 Hz, 1H), 6.60 (d, J=8.5 Hz, 1H), 5.16 (s, 2H), 4.07 (t, J=6.1 Hz, 2H), 2.86-2.54 (m, 8H), 2.51-2.46 (m, 2H), 2.40-2.35 (m, 3H), 1.81 (p, J=6.6 Hz, 2H), 1.70 (s, 2H). ESI (+) MS: 400.2 ($M+H^+$).

4-{4-[3-(Benzyloxy)-2-nitrophenoxy]butyl}morpholine (2b). A solution of the bromo compound 1 (0.3 g, 0.789 mmol), morpholine (0.08 mL, 0.868 mmol), N,N-diisopropylethylamine (0.4 mL, 2.37 mmol) and acetonitrile (8 mL) was heated at 80° C. in a sealed tube for 4.5 h. The mixture was concentrated to a residue that was loaded onto a precolumn of silica gel attached to a 25 g column and eluted with ethyl acetate over 33 min followed by 4% isopropanol/ethyl acetate over 17 min. Combined product fractions were concentrated to give 2b (0.252 g, 83%). $^1H$ NMR (700 MHz, chloroform-d) δ 7.37-7.35 (m, 3H), 7.33-7.29 (m, 1H), 7.28-7.23 (m, 2H), 6.62 (d, J=8.5 Hz, 1H), 6.60 (d, J=8.5 Hz, 1H), 5.16 (s, 2H), 4.07 (t, J=6.2 Hz, 2H), 3.73-3.66 (m, 4H), 2.47-2.39 (m, 4H), 2.37 (t, J=7.4 Hz, 2H), 1.84-1.78 (m, 2H), 1.66-1.59 (m, 2H). ESI (+) MS: 387.2 ($M+H^+$).

2-(Trimethylsilyl)ethyl 4-(4-(3-(benzyloxy)-2-nitrophenoxy)butyl)piperazine-1-carboxylate (2d). A solution of compound 1 (1.22 g, 3.21 mmol), 2-(trimethylsilyl)ethyl piperazine-1-carboxylate (see U.S. Pat. No. 6,991,902) (0.812 g, 3.53 mmol) and triethylamine (1.34 mL, 9.62 mmol) in acetonitrile (50 mL) was heated at reflux for 12 h. The mixture was concentrated and the residue was purified by flash silica gel chromatography eluting with 50-100% ethyl acetate/hexanes. Combined product fractions were concentrated to give 2d (1.10 g, 65%). $^1H$ NMR (700 MHz, chloroform-d): δ 7.41-7.29 (m, 5H), 7.27-7.23 (m, 1H), 6.62 (d, J=8.5 Hz, 1H), 6.60 (d, J=8.5 Hz, 1H), 5.16 (s, 2H), 4.19-4.15 (m, 2H), 4.07 (t, J=6.2 Hz, 2H), 3.50-3.42 (m, 4H), 2.43-2.32 (m, 6H), 1.80 (p, J=6.5 Hz, 2H), 1.62 (p, J=7.4 Hz, 2H), 1.03-0.98 (m, 2H), 0.04 (s, 9H).

2-Amino-3-[4-(4-methylpiperazin-1-yl)butoxy]phenol (3a). To a solution of 2a (0.222 g, 0.556 mmol) in methanol (12 mL) was added 20% palladium hydroxide on carbon (31 mg, 0.044 mmol), and the mixture was hydrogenated at 52 psi for 20 h. The mixture was filtered over Celite and the filtrate was concentrated to leave 3a (0.155 g, 100%). $^1H$ NMR (700 MHz, $(CD_3)_2SO$) δ 8.97 (s, 1H), 6.45-6.30 (m, 3H), 3.90 (t, J=6.2 Hz, 2H), 3.12-2.38 (m, 15H), 1.74-1.58 (m, 4H). MS: 280.2 ($M+H^+$).

2-Amino-3-[4-(morpholin-4-yl)butoxy]phenol (3b). To a solution of 2b (0.152 g, 0.393 mmol) in methanol (15 mL) was added 20% palladium hydroxide on carbon (22 mg, 0.031 mmol). The mixture was hydrogenated at 52 psi 16 h, filtered over Celite and the filtrate concentrated to give 3b (0.104 g, 99%). $^1H$ NMR (700 MHz, chloroform-d) δ 6.60 (d, J=8.2 Hz, 1H), 6.43 (d, J=8.2 Hz, 1H), 6.39 (d, J=8.0 Hz, 1H), 3.99 (t, J=6.2 Hz, 2H), 3.73 (t, J=4.7 Hz, 4H), 2.48 (s, 4H), 2.45-2.40 (m, 2H), 1.86-1.79 (m, 2H), 1.75-1.67 (m, 2H). MS: 267.1744 ($M+H^+$).

tert-Butyl 4-[4-(2-amino-3-hydroxyphenoxy)butyl]piperazine-1-carboxylate (3c). To a solution of the nitro compound 2c (Showalter et al., *J. Med. Chem.* 2012, 55, 3814-3826; 0.500 g, 1.03 mmol) in methanol (15 mL) was added 20% palladium hydroxide on carbon (40 mg, 0.057 mmol). The mixture was hydrogenated at 53 psi for 20 h, filtered over Celite, and the filtrate concentrated to give 3c (0.363 g, 96%). $^1H$ NMR (500 MHz, chloroform-d) δ 6.61-6.54 (m, 1H), 6.43-6.36 (m, 2H), 3.99 (t, J=6.2 Hz, 2H), 3.45 (t, J=5.2 Hz, 4H), 2.47-2.39 (m, 6H), 1.85-1.77 (m, 2H), 1.74-1.67 (m, 2H), 1.46 (s, 91). MS: 366.2 ($M+H^+$) and 388.2 ($M+Na^+$).

2-(Trimethylsilyl)ethyl 4-(4-(2-amino-3-hydroxyphenoxy)butyl)piperazine-1-carboxylate (3e). To a solution of 2d (0.472 g, 0.891 mmol) in methanol (22 mL) was added 20% palladium hydroxide on carbon (40 mg, 0.057 mmol), and the mixture was hydrogenated at 55 psi for 18 h. Workup as described for the synthesis of 3b gave 3e (0.363 g, 99%).

$^1$H NMR (400 MHz, chloroform-d): δ 6.65-6.57 (m, 1H), 6.42 (d, J=8.1 Hz, 2H), 4.23-4.14 (m, 2H), 3.99 (t, J=6.1 Hz, 2H), 3.70 (s, 3H), 3.50 (t, J=5.1 Hz, 4H), 2.53-2.38 (m, 6H), 1.88-1.77 (m, 2H), 1.76-1.65 (m, 2H), 1.05-0.95 (m, 2H), 0.04 (s, 9H). HRMS: 410.2485 ($M+H^+$).

(7S,9E,11S,12R,13S,14R,15R,16R,17S,18S,19E,21Z)-2,15,17-Trihydroxy-11-methoxy-3,7,12,14,16,18,22-heptamethyl-32-[4-(4-methylpiperazin-1-yl)butoxy]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-13-yl acetate (5a). A solution of 3a (0.05 g, 0.179 mmol) and rifamycin S (4; 0.19 g, 0.268 mmol) in tetrahydrofuran (5 mL) and toluene (1 mL) was stirred at 80° C. for 75 h. The mixture was concentrated to a residue that was dissolved in methanol (5 mL). The solution was treated with manganese dioxide (31 mg. 0.358 mmol), stirred for 1 h at 25° C. and filtered over Celite. The filtrate was concentrated to a crude residue that was applied to a 4 g Silicycle column and eluted with 1-10% 2N $NH_3$ in methanol/dichloromethane. Combined product fractions were concentrated to give 5a (11 mg, 6.4%). HPLC $t_R$, 5.92, purity 74.8%. MS: 955.4705 ($M+H^+$)

(7S,9E,11S,12R,13S,14R,15R,16R,17S,18S,19E,21Z)-2,15,17-Trihydroxy-11-methoxy-3,7,12,14,16,18,22-heptamethyl-32-[4-(morpholin-4-yl)butoxy]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-13-yl acetate (5b). A solution of 3b (0.044 g, 0.165 mmol), rifamycin S (4; 0.17 g, 0.248 mmol), tetrahydrofuran (3 mL) and toluene (0.6 mL) was stirred at 80° C. 16 h. Additional rifamycin S (20 mg) was added and reaction was continued for 90 min more at 80° C. The mixture was concentrated to a residue that was dissolved in methanol (3 mL) and treated with manganese dioxide (0.029 g, 0.330 mmol). The mixture was stirred at 25° C. for 2 h and filtered over Celite. The filtrate was concentrated to a crude residue that was loaded onto a precolumn attached to a 12 g Silicycle column and eluted with 2% methanol/ethyl acetate over 15 min at 25 mL/min to remove the unreacted starting material and impurities followed by 2-4% methanol/dichloromethane for 10 min at 25 mL/min and then by 4-6% 2N $NH_3$ in methanol/dichloromethane for 10 min and finally by 6% 2N $NH_3$ in methanol/dichloromethane for 6 min. Combined product fractions were concentrated to give 5b (49 mg, 32%). HPLC $t_R$, 6.30, purity 85.8%. MS: 942.4394 ($M+H^+$).

Tert-Butyl 4-(4-{[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-32-yl]oxy}butyl)piperazine-1-carboxylate (5c). A solution of 3c (0.085 g, 0.233 mmol), rifamycin S (0.23 g), tetrahydrofuran (5 mL) and toluene (1 mL) was stirred at 80° C. for 15 h. Additional rifamycin S (30 mg) was added and the reaction was continued at 80° C. for 4 h more. The mixture was concentrated to a residue that was dissolved in methanol (5 mL) and treated with manganese dioxide (40 mg). The mixture was stirred at 25° C. for 1 h, filtered over Celite and the filtrate concentrated to a crude residue that was loaded onto a precolumn attached to a 12 g Silicycle column and eluted with 1-7% methanol/dichloromethane. Combined product fractions were concentrated to give 5c (0.086 g, 36%). HPLC $t_R$, 6.35, purity 80.9%. MS: 1041.5058 ($M+H^+$) and 1063.4873 ($M+Na^+$)

(7S,9E,11S,12R,13S,14R,15R,16R,17S,18S,19E,21Z)-2,15,17-Trihydroxy-11-methoxy-3,7,12,14,16,18,22-heptamethyl-6,23,37-trioxo-32-[4-(piperazin-1-yl)butoxy]-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (5d). To a solution of the compound 3c (0.034 g, 0.093 mmole) in dichloromethane (2 mL) at 25° C. was added trifluoroacetic acid (0.1 mL, 1.30 mmol) slowly. The reaction mixture was stirred at 25° C. for 2 h. The volatiles were removed under reduced pressure to leave the debocylated compound 3d (99%), which was used as such. A solution of the aminophenol 3d (0.035 g, 0.092 mmol), N,N-diisopropylethylamine (0.08 mL, 0.461 mmole) and rifamycin S (0.090 g, 0.129 mmol) in THE (3 mL) and toluene (1 mL) was stirred at 80° C. for 30 h. The mixture was concentrated and the residue was dissolved in methanol (2 mL). Manganese dioxide (24 mg, 0.277 mmole) was added and the reaction mixture was stirred at 25° C. for 15 h. The reaction mixture was filtered through Celite and the filtrate was concentrated. The residue was applied on a 12 g column that was eluted with 2-20% 2N $NH_3$ in methanol/dichloromethane over 33 min. The collected fractions were pooled and concentrated. The residue was applied to a preparative silica gel plate and eluted with 15% 2N $NH_3$ in methanol/dichloromethane. The separated band was extracted using 25% methanol/dichloromethane and the solvent concentrated to give 5d (1 mg, 1% yield). MS: 941.6 ($M+H^+$) and 963.6 ($M+Na^+$). As an alternate method, a solution of 5h (see below) (0.155 g, 0.143 mmol) and cesium fluoride (0.128 g, 0.843 mmol) in N, N-dimethylformamide (15 mL) stirred at 60° C. for 5 h and then concentrated in vacuo. The residue was diluted with dichloromethane and the solution was washed with water (2×) and brine, dried and concentrated. The residue was purified by flash silica gel chromatography eluting with 0 to 3:17 (2N ammonia in methanol)/dichloromethane. The combined product fractions were concentrated to give 5d (23 mg, 17%). HPLC: $t_R$ 5.74 min, purity 74.6%. HRMS: 941.4539 ($M+H^+$).

(7S,9E,11S,12R,13S,14R,15R,16R,17S,18S,19E,21Z)-2,15,17-Trihydroxy-11-methoxy-3,7,12,14,16,18,22-heptamethyl-32-(4-{4-[2-(morpholin-4-yl)acetyl]piperazin-1-yl}butoxy)-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-13-yl acetate (5e). Benzoxazino-rifamycin 5d (19 mg, 0.020 mmol) was added to a solution of 4-morpholineacetic acid (3 mg, 0.020 mmol), triethylamine (0.02 mL, 0.121 mmol), 2-(3H-[1,2,3]triazolo[4,5-b]pyridin-3-yl)-1,1,3,3-tetramethylisouronium hexafluorophosphate(V) (HATU; 8 mg, 0.022 mmol), 1-hydroxy-1H-benzotriazole (HOBT; 3 mg, 0.020 mmol) and N,N-dimethylformamide (0.5 mL), and the mixture was stirred at 25° C. for 2 h. The solution was concentrated under reduced pressure and ice water was added to the residue, which was extracted with dichloromethane (2×). The combined extracts were washed with brine, dried ($Na_2SO_4$) and concentrated to a crude residue that was purified by flash silica gel chromatography, eluting with 1-10% methanol/dichloromethane over 30 min. Combined product fractions were concentrated to give 5e (7 mg, 33%). HPLC $t_R$, 5.72, purity 93.5%. MS: 1068.5180 ($M+H^+$); 1090.4992 ($M+Na^+$).

2-(Trimethylsilyl)ethyl 4-(4-{[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-32-yl]oxy}butyl)piperazine-1-carboxylate (5h). A solution of 3e (0.165 g, 0.403 mmol), rifamycin S (4; 0.336 g, 0.483 mmole) and manganese dioxide (0.070 g) in dioxane (13 mL) was stirred at 80° C.

in a sealed tube for 10 h. The solution was filtered over Celite® followed by a dichloromethane wash. The filtrate was concentrated to a residue that was purified by flash silica gel chromatography eluting with 1-10% methanol/dichloromethane at 30 ml/min. The combined product fractions were concentrated to give 5h (160 mg, 37%). HPLC: $t_R$ 7.69 min, purity 94.9%. HRMS: 1085.5145 (M+H$^+$).

(7S,9E,11S,12R,13S,14R,15R,16R,17S,18S,19E,21Z)-2,15,17-Trihydroxy-11-methoxy-3,7,12,14,16,18,22-heptamethyl-30-[4-(2-methylpropyl)piperazin-1-yl]-32-[4-(morpholin-4-yl)butoxy]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-13-yl acetate (6a). A mixture of 5b (20.8 mg, 0.022 mmol), N-i-butylpiperazine (19 mg, 0.132 mmol), manganese dioxide (21 mg, 0.243 mmol) and N,N-dimethylformamide (1.1 mL) was stirred at 25° C. for 15 h. The mixture was filtered over Celite and the filtrate was concentrated to a residue that was dissolved in dichloromethane and applied to a 4 g Silicycle column and eluted with 2-15% methanol/dichloromethane over 25 min at 20 mL/min. Combined product fractions were concentrated to give 6a (16 mg, 67%). HPLC $t_R$, 5.80, purity 91.8%. MS: 1082.5689 (M+H$^+$).

(7S,9E,11S,12R,13S,14R,15R,16R,17S,18S,19E,21Z)-2,15,17-trihydroxy-32-(4-{4-[2-(1H-imidazol-1-yl)ethyl]piperazin-1-yl}butoxy)-11-methoxy-3,7,12,14,16,18,22-heptamethyl-30-[4-(2-methylpropyl)piperazin-1-yl]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-13-yl acetate (6b). A mixture of compound 5f (Showalter et al., *J. Med. Chem.* 2012, 55, 3814-3826; 22 mg, 0.021 mmol), N-i-butylpiperazine (15 mg, 0.106 mmol), manganese dioxide (20 mg, 0.234 mmol) and N,N-dimethylformamide (0.8 mL) was stirred at 25° C. for 15 h. The mixture was filtered over Celite and the filtrate concentrated to a residue that was dissolved in dichloromethane and applied to a preparative silica gel plate. It was eluted with 10% 2N $NH_3$ in methanol/dichloromethane and the product band was extracted with 50% methanol/dichloromethane to give 6b (12 mg, 48%); HPLC $t_R$, 5.64, purity 98.2%; MS: 1175.6376 (M+H$^+$).

(7S,9E,11S,12R,13S,14R,15R,16R,17S,18S,19E,21Z)-2,15,17-Trihydroxy-32-(4-{4-[2-(1H-imidazol-1-yl)acetyl]piperazin-1-yl}butoxy)-11-methoxy-3,7,12,14,16,18,22-heptamethyl-30-(4-methylpiperazin-1-yl)-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28(33)29,31,34-undecaen-13-yl acetate (6c). A solution of compound 5g (Showalter et al., *J. Med. Chem.* 2012, 55, 3814-3826; 22 mg, 0.021 mmol), N-methylpiperazine (11 mg, 0.105 mmol) and N,N-dimethylformamide (1.3 mL) was treated with manganese dioxide (20 mg, 0.231 mmol) and the mixture was stirred at 25° C. for 16 h. The mixture was filtered over Celite, washing the pad well with dichloromethane. The filtrate was concentrated to a residue that was dissolved in dichloromethane and purified via preparative plate silica gel chromatography eluting with 15% 2N $NH_3$ in methanol/dichloromethane. The product band was extracted with 50% methanol/dichloromethane to give impure product that was subjected to a second preparative plate purification under the same conditions. Extraction of the product band gave 6c (8 mg, 33%). HPLC $t_R$, 5.06, purity 86.6%. MS: 1147.5709 (M+H$^+$).

(7S,9E,11S,12R,13S,14R,15R,16R,17S,18S,19E,21Z)-2,15,17-Trihydroxy-32-(4-{4-[2-(1H-imidazol-1-yl)acetyl]piperazin-1-yl}butoxy)-11-methoxy-3,7,12,14,16,18,22-heptamethyl-30-[4-(2-methylpropyl)piperazin-1-yl]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (6d). A solution of compound 5g (Showalter et al., *J. Med. Chem.* 2012, 55, 3814-3826; 10 mg, 0.001 mmol), N-isobutylpiperazine (7 mg, 0.049 mmol) and dimethylsulfoxide (0.8 mL) was treated with manganese dioxide (9 mg, 0.104 mmol) and the mixture was stirred at 25° C. for 16 h. The mixture was filtered over Celite, washing the pad well with dichloromethane. The filtrate was concentrated to a residue that was diluted with water, extracted with ethyl acetate (5×10 mL), dried ($Na_2SO_4$) and the combined extracts concentrated. The crude product was purified via preparative plate silica gel chromatography eluting with 15% 2N $NH_3$ in methanol/dichloromethane. The product band was extracted with 50% methanol/dichloromethane to give 6d (5 mg, 44.1%). HPLC $t_R$, 5.35, purity 99.2%. MS: 1189.6153 (M+H$^+$).

Compounds 11a-11g and 12a-12c were synthesized as shown in Scheme 3.

Scheme 3

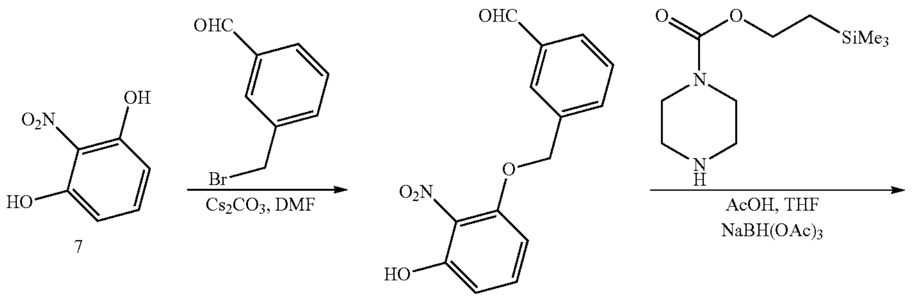

7

8

-continued
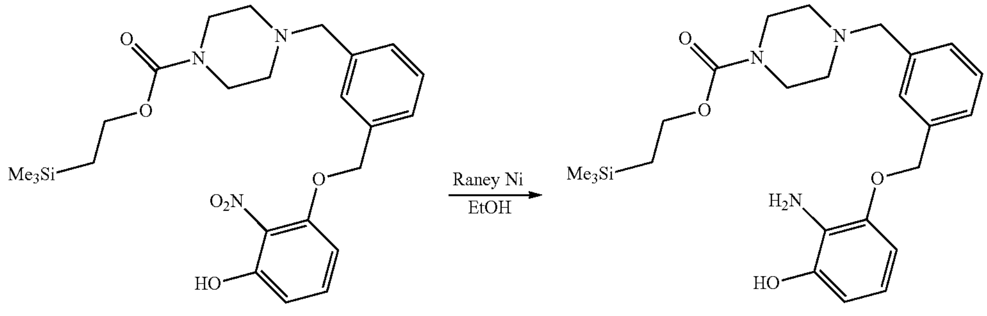
9 10
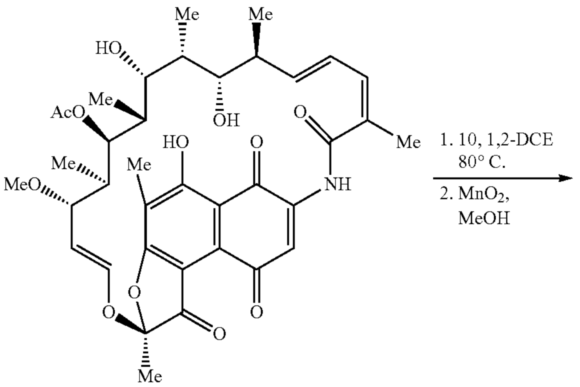
4
(rifamycin S)
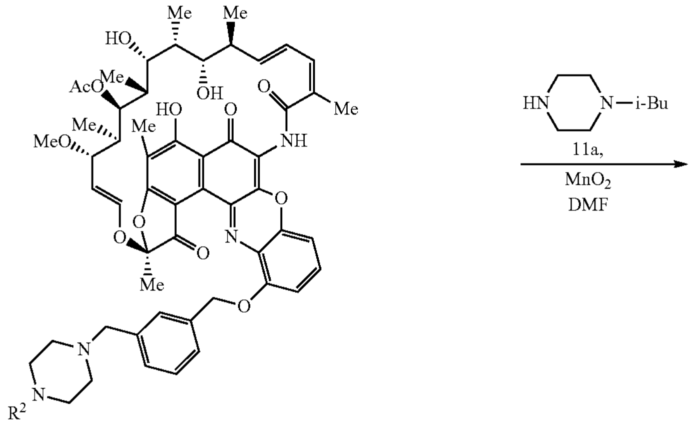
11
a: $R^2 = C(O)O(CH_2)_2SiMe_3$
CsF
DMF
b: $R^2 = H$
RCO2H
HATU, HOBT
i-Pr2NEt or NEt3
DMF
c: $R^2 = CO(O)Me$
d: $R^2 = C(O)Et$
e: = $R^2 = C(O)CH_2$-(1H-imidazol-1-yl)
f: $R^2 = C(O)CH_2$-(morpholin-4-yl)
g: $R^2 = C(O)CH_2$-phenyl -continued

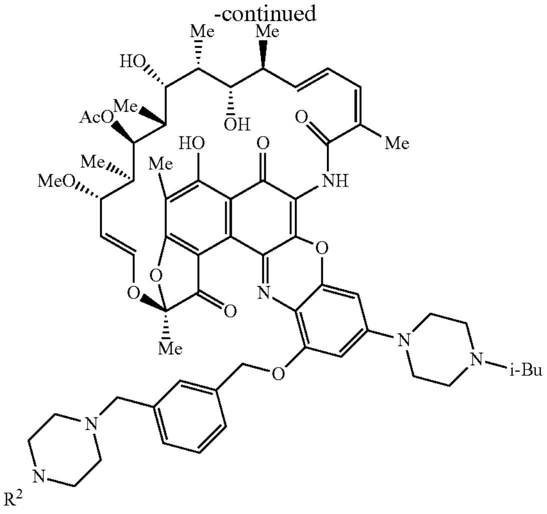

12

3-[(3-Hydroxy-2-nitrophenoxy)methyl]benzaldehyde (8). A suspension of 2-nitroresorcinol 7 (22.44 g, 145 mmol), 3-(bromomethyl)benzaldehyde (3.20 g, 16.08 mmol), cesium carbonate (10.48 g, 32.2 mmol) and N,N-dimethylformamide (100 mL) was stirred at 25° C. for 6 h. The mixture was poured over ice water, acidified with 1% aq. HCl, and extracted with dichloromethane (3×). The combined extracts were washed with water and brine, dried ($Na_2SO_4$) and concentrated to leave a residue that was loaded onto a 25 g precolumn attached to an 80 g Gold column. The column was eluted first with 50% dichloromethane/hexanes until all the nitroresorcinol starting materials had eluted. Then, the column was eluted with 25-75% ethyl acetate/hexanes over 30 min at 40 mL/min. Combined product fractions were concentrated to give 8 (3.36 g). $^1$H NMR (400 MHz, chloroform-d) δ 10.19 (s, 1H), 10.06 (s, 1H), 8.00-7.97 (m, 1H), 7.88 (d, J=7.8 Hz, 1H), 7.82 (d, J=7.8 Hz, 1H), 7.61 (t, J=7.6 Hz, 1H), 7.41 (d, J=8.1 Hz, 1H), 6.76 (d, J=8.7 Hz, 1H), 6.61 (d, J=8.4 Hz, 1H), 5.27 (s, 2H). MS: 296.0534 (M+Na$^+$).

2-(Trimethylsilyl)ethyl 4-({3-[(3-hydroxy-2-nitrophenoxy)methyl]phenyl}methyl)-piperazine-1-carboxylate (9). To a solution of 8 (0.700 g, 2.56 mmol), 2-(trimethylsilyl)ethyl piperazine-1-carboxylate (WO 99/00669; 0.59 g, 2.69 mmol), acetic acid (0.15 mL, 2.56 mmol) and tetrahydrofuran (40 mL) was added sodium triacetoxyborohydride (2.17 g, 10.25 mmol). The mixture was stirred at 25° C. for 15 h and then quenched with methanol (10 mL) and water (70 mL). The solution was extracted with ether and the organic extract was washed with water and brine, dried ($Na_2SO_4$) and concentrated to give a residue that was loaded onto a precolumn (15 g) attached to a 24 g Gold column. Elution was carried out with 30-75% ethyl acetate/hexanes over 30 min. Combined product fractions were concentrated to give 9 (1.08 g, 86%). $^1$H NMR (500 MHz, chloroform-d) δ 7.43 (s, 1H), 7.38-7.33 (m, 3H), 7.30-7.26 (m, 1H), 6.70 (d, J=8.4 Hz, 1H), 6.59 (d, J=8.4 Hz, 1H), 5.18 (s, 2H), 4.18 (t, J=8.4 Hz, 2H), 3.55 (s, 2H), 3.50-3.46 (m, 4H), 2.44-2.38 (m, 4H), 1.00 (t, J=8.4 Hz, 2H), 0.03 (s, 9H).

2-(Trimethylsilyl)ethyl 4-({3-[(2-amino-3-hydroxyphenoxy)methyl]phenyl}methyl)-piperazine-1-carboxylate (10). To a solution of 9 (1.07 g) in ethanol (35 mL) was added Raney nickel (4 g). The mixture was shaken in an orbital shaker for 6 h and then filtered over Celite. The filtrate was concentrated to a residue that was purified using a 40 g Gold column eluting with 25-600% ethyl acetate/dichloromethane. Combined product fractions were concentrated to give 10 (0.60 g, 60%). $^1$H NMR (500 MHz, chloroform-d) δ 7.36 (s, 1H), 7.35-7.30 (m, 2H), 7.27-7.24 (m, 1H), 6.60-6.54 (m, 1H), 6.50-6.46 (m, 1H), 6.40 (dd, J=8.1, 1.2 Hz, 1H), 5.05 (s, 2H), 4.23-4.13 (m, 2H), 3.53 (s, 2H), 3.50-3.43 (m, 4H), 2.44-2.33 (m, 4H), 1.03-0.95 (m, 2H), 0.03 (s, 9H).

2-(Trimethylsilyl)ethyl 4-{[3-({[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-32-yl]oxy}methyl)phenyl]methyl}piperazine-1-carboxylate (11a). A solution of rifamycin S 4 (0.217 g, 0.312 mmol), compound 10 (0.13 g, 0.284 mmol) and 1,2-dichloroethane (15 mL) was heated at reflux for 10 h. The mixture was concentrated to a residue that was dissolved in methanol (9 mL) and treated with manganese dioxide (0.049 g, 0.568 mmol). After stirring at 25° C. for 1 h, it was concentrated to a residue that was loaded on a precolumn attached to a 24 g Gold column. It was eluted with 2-6% methanol/dichloromethane. Combined product fractions were concentrated to give 11a (0.081 g, 25%). HPLC $t_R$, 7.99, purity 96.2%. MS: 1133.5138 (M+H$^+$); 1155.4960 (M+Na$^+$).

(7S,9E,11S,12R,13S,14R,15R,16R,17S,18S,19E,21Z)-2,15,17-Trihydroxy-11-methoxy-3,7,12,14,16,18,22-heptamethyl-6,23,37-trioxo-32-({3-[(piperazin-1-yl)methyl]phenyl}methoxy)-8,27,38-trioxa-24,34-diazahexacyclo-[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (11b). A solution of 11a (30 mg, 0.026 mmol), cesium fluoride (32 mg, 0.212 mmol) and N,N-dimethylformamide (1.5 mL) was stirred under argon at 61° C. for 3 h. The solution was diluted with ethyl acetate, washed with water (2×7 mL) and brine (7 mL), and dried ($Na_2SO_4$). Concentration under reduced pressure gave 11b (23 mg, 88%). HPLC $t_R$, 5.95, purity 90.9%. MS: 989.4537 ($M+H^+$).

(7S,9E,11S,12R,13S,14R,15R,16R,17S,18S,19E,21Z)-32-({3-[(4-Acetylpiperazin-1-yl)methyl]phenyl}methoxy)-2,15,17-trihydroxy-11-methoxy-3,7,12,14,16,18,22-heptamethyl-6,23,37-trioxo-8,27,38-trioxa-24,34-diazahexacyclo-[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (11c). A solution of 11b (25 mg, 0.025 mmol), acetic acid (1.5 mg, 0.025 mmol), triethylamine (0.02 mL, 0.152 mmol), HATU (11 mg, 0.028 mmol), HOBT (4 mg, 0.025 mmol) and N,N-dimethylformamide (1 mL) was stirred at 25° C. for 12 h. Ice water was added to the reaction mixture, which was extracted with dichloromethane (2×7 mL). The organic layer was washed with brine (10 mL), dried ($Na_2SO_4$) and concentrated to yield the crude compound. The crude compound was applied on a preparative plate silica gel chromatography and eluted with 10% methanol/dichloromethane to give 11c (10 mg, 38%). HPLC $t_R$, 6.64, purity 83.9%. MS: 1031.4646 ($M+H^+$); 1053.4452 ($M+Na^+$).

(7S,9E,11S,12R,13S,14R,15R,16R,17S,1S,19E,21Z)-2,15,17-Trihydroxy-11-methoxy-3,7,12,14,16,18,22-heptamethyl-6,23,37-trioxo-32-{(3-[(4-propanoylpiperazin-1-yl)methyl]phenyl}methoxy)-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (11d). A solution of 11b (26 mg, 0.026 mmol), propionic acid (2.2 mg, 0.025 mmol), triethylamine (0.02 mL, 0.152 mmol), HATU (11 mg, 0.028 mmol), HOBT (4 mg, 0.025 mmol) and N,N-dimethylformamide (1 mL) was stirred at 25° C. for 12 h. Ice water was added to the reaction mixture, which was extracted with dichloromethane (2×7 mL). The organic layer was washed with brine (10 mL), dried ($Na_2SO_4$) and concentrated to yield the crude compound. The crude compound was loaded on a flash silica gel column and eluted with 2-7% methanol/dichloromethane. Combined product fractions were concentrated to give 11d (10 mg, 36%). HPLC $t_R$, 6.69, purity 94.7%. MS: 1045.4786 ($M+H^+$).

(7S,9E,11S,12R,13S,14R,15R,16R,17S,18S,19E,21Z)-2,15,17-Trihydroxy-32-{[3-({4-[2-(1H-imidazol-1-yl)acetyl]piperazin-1-yl}methyl)phenyl]methoxy}-11-methoxy-3,7,12,14,16,18,22-heptamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (11e). A solution of 11b (60 mg, 0.061 mmol), N,N-diisopropylethylamine (0.1 mL, 0.575 mmol), (1H-imidazol-1-yl)acetic acid (15 mg, 0.12 mmol), HATU (35 mg, 0.091 mmol), HOBT (9 mg, 0.061 mmol) and N,N-dimethylformamide (1 mL) was stirred under argon at 25° C. for 15 h. The solution was diluted with ethyl acetate, washed with water (2×7 mL) and brine (5 mL), dried ($Na_2SO_4$) and concentrated to give a residue that was purified by preparative plate silica gel chromatography eluting with 10% methanol in dichloromethane. Extraction of the product band with 40% methanol in dichloromethane gave 11e (10 mg, 15%). HPLC $t_R$, 5.78, purity 92.2%. MS: 1097.4857 ($M+H^+$) and 1119.4673 ($M+Na^+$).

(7S,9E,11S,12R,13S,14R,15R,16R,17S,1S,19E,21Z)-2,15,17-Trihydroxy-11-methoxy-3,7,12,14,16,18,22-heptamethyl-32-{[3-({4-[2-(morpholin-4-yl)acetyl]piperazin-1-yl}methyl)phenyl]methoxy}-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (11f). A solution of 11b (35 mg, 0.035 mmol), 4-morpholinoacetic acid (5.2 mg, 0.035 mmol), triethylamine (0.03 mL, 0.212 mmol), HATU (15 mg, 0.039 mmol), HOBT (5.4 mg, 0.035 mmol) and N,N-dimethylformamide (1 mL) was stirred at 25° C. for 15 h. The mixture was diluted with ice water and then extracted with ethyl acetate (2×). The combined organic phase was washed with brine, dried ($Na_2SO_4$) and concentrated to give a residue that was purified by silica gel flash chromatography eluting with 1-10% methanol in dichloromethane. Product fractions were combined and further purified by preparative plate silica gel chromatography eluting with 10% methanol in dichloromethane. The product band was extracted with 50% methanol in dichloromethane to give 11f (4 mg, 10%). HPLC $t_R$, 6.05, purity 96.6%. MS: 1116.5175 ($M+H^+$).

(7S,9E,11S,12R,13S,14R,15R,16R,17S,18S,19E,21Z)-2,15,17-Trihydroxy-11-methoxy-3,7,12,14,16,18,22-heptamethyl-6,23,37-trioxo-32-[(3-{[4-(2-phenylacetyl)-piperazin-1-yl]methyl}phenyl)methoxy]-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (11g). A solution of 11b (23 mg, 0.023 mmol), phenylacetic acid (3.2 mg, 0.023 mmol), triethylamine (0.02 mL, 0.140 mmol), HATU (9.3 mg, 0.026 mmol), HOBT (3.6 mg, 0.023 mmol) and N,N-dimethylformamide (1 mL) was stirred at 25° C. for 12 h. The mixture was diluted with ice water and extracted with dichloromethane. The organic phase was washed successively with sat. aqueous $NaHCO_3$, water and brine, dried ($Na_2SO_4$) and concentrated to a residue that was loaded onto a 4 g Silicycle column and eluted with 2-7% methanol/dichloromethane over 13 min at 20 mL/min. Combined product fractions were concentrated to give 11g (11 mg, 43%). HPLC $t_R$, 6.84, purity 83.3%. MS: 1107.4957 ($M+H^+$) and 1129.4776 ($M+Na^+$).

2-(Trimethylsilyl)ethyl 4-{[3-({[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-30-[4-(2-methylpropyl)piperazin-1-yl]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-32-yl]oxy}methyl)phenyl]methyl}piperazine-1-carboxylate (12a) To a solution of 11a (30 mg, 0.026 mmol), N-i-butylpiperazine (21 mg, 0.148 mmol) and N,N-dimethylformamide (1.1 mL) was added manganese dioxide (25 mg, 0.291 mmol) and the mixture was stirred at 25° C. for 16 h. The mixture was diluted with dichloromethane and washed successively with water and brine, dried ($Na_2SO_4$), and concentrated to a residue that was applied to a 4 g Silicycle column eluting with 2-8% methanol/dichloromethane over 30 min. Product fractions were concentrated to leave 12a (21 mg, 62%). MS: 1273.6458 ($M+H^+$) and 1295.6276 ($M+Na^+$).

(7S,9E,11S,12R,13S,14R,15R,16R,17S,18S,19E,21Z)-2,15,17-Trihydroxy-11-methoxy-3,7,12,14,16,18,22-heptamethyl-30-[4-(2-methylpropyl)piperazin-1-yl]-6,23,37-trioxo-32-({3-[(piperazin-1-yl)methyl]phenyl}methoxy)-8,27,38-trioxa-24,34-diazahexacyclo[23.11.1.1$^{4,7}$.0$^{5,36}$.0$^{26,35}$.0$^{28,33}$]octatriaconta-(36)2,4,9,19,21,25,28,30,32,34-undecaen-13-yl acetate (12b). A solution of 12a (21 mg, 0.016 mmol), cesium fluoride (18 mg, 0.115 mmol) and N,N-dimethylformamide (I mL) was stirred at 61° C. for 4 h. The mixture was diluted with dichloromethane and the organic phase was washed with water (2×) and brine, and dried ($Na_2SO_4$). Concentration under reduced pressure gave 12b (19 mg, 100%). HPLC $t_R$, 5.49, purity 89%. MS: 1129.5850 ($M+H^+$) and 1151.5664 ($M+Na^+$).

(7S,9E,11S,12R,13S,14R,15R,16R,17S,18S,19E,21Z)-2,15,17-Trihydroxy-32-{[3-({4-[2-(1H-imidazol-1-yl)acetyl]piperazin-1-yl}methyl)phenyl]methoxy}-11-methoxy-3,7,12,14,16,18,22-heptamethyl-30-[4-(2-methylpropyl)piperazin-1-yl]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (12c). A solution of 12b (19 mg, 0.017 mmol), (1H-imidazol-1-yl)acetic acid (4.2 mg, 0.034 mmol), N,N-diisopropylethylamine (0.02 mL, 0.101 mmol), HATU (9.6 mg, 0.025 mmol), HOBT (2.6 mg, 0.017 mmol) and N,N-dimethylformamide (1 mL) was stirred at 25° C. for 4 h. The mixture was diluted with dichloromethane and the organic phase was washed with water (2×) and dried ($Na_2SO_4$). Concentration under reduced pressure gave a residue that was applied to a 4 g Silicycle column and eluted with 2-100% methanol/dichloromethane over 30 min. Combined product fractions were concentrated to give 12c (16 mg, 77%). HPLC $t_R$, 5.43, purity 99.2%. MS: 1237.6173 (M+H$^+$).

Compounds 16a-16d and 17a-17j were synthesized as shown in Scheme 4.

Scheme 4

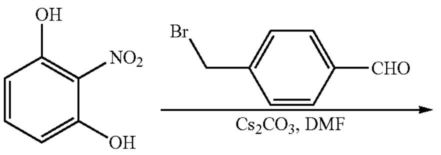

7

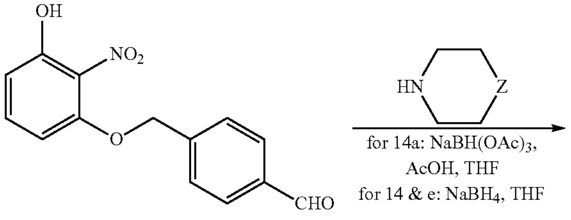

13

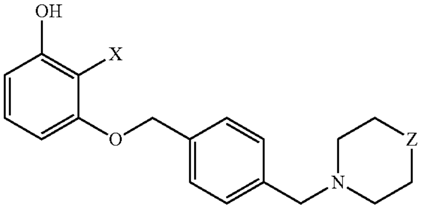

14

Raney Ni EtOH a: X = $NO_2$; Z = $NCO_2(CH_2)_2SiMe_3$
b: X = $NH_2$; Z = $NCO_2(CH_2)_2SiMe_3$
Zn, AcOH DCM c: X = $NO_2$; Z = O
d: X = $NH_2$; Z = O
Raney Ni EtOH e: X = $NO_2$; Z = NMe
f: X = $NH_2$; Z = NMe 14a

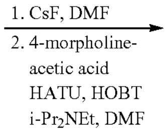

-continued

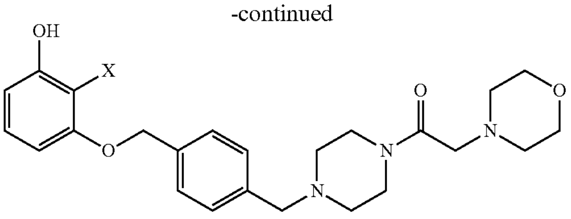

15

Zn, AcOH DCM a: X = $NO_2$
b: X = $NH_2$

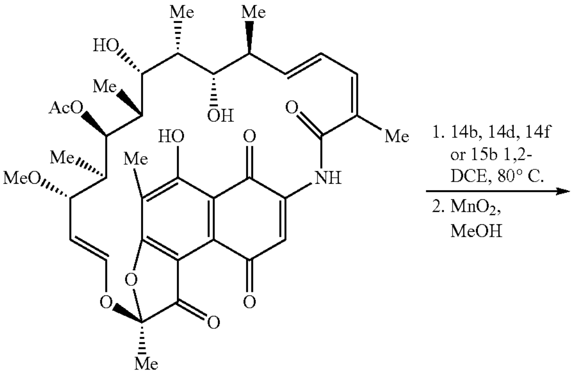

4

(rifamycin S)

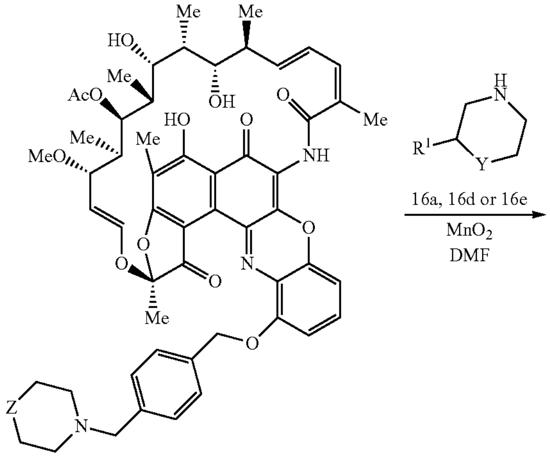

16

1. CsF, DMF
2. $RCO_2H$
HATU, HOBT
i-$PrN_2Et$, DMF a: Z = $NCO_2(CH_2)_2SiMe_3$
b: Z = $NC(O)CH_2$-(1H-imidazol-1-yl)
c: Z = $NC(O)CH_2$-(morpholin-4-yl)
d: Z = O
e: Z = NMe -continued

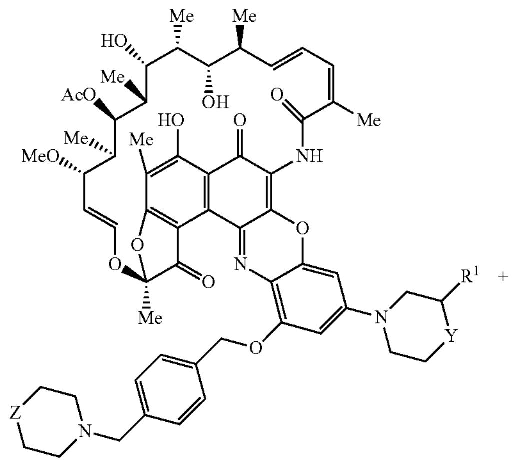

17

RCO$_2$H
HATU,
HOBT
i-Pr$_2$NEt,
DMF a: $R^1$ = H; Y = N(i-Bu); Z = $NCO_2(CH_2)_2SiMe_3$
CsF, DMF
b: $R^1$ = H; Y = N(i-Bu); Z = NH
c: $R^1$ = H; Y = N(i-Bu); Z = NC(O)$CH_2$-(1H-imidazol-1-yl)
d: $R^1$ = H; Y = N(i-Bu); Z = NC(O)$CH_2$-(morpholin-4-yl)
e: $R^1$ = H; Y = N(i-Bu); Z = O f: $R^1$ = H; Y = N—C(O)-t-Bu; Z = O
g: $R^1$ = H; Y = N—C(O)Et; Z = O
h: $R^1$ = H; Y = N-(1-Me)piperidin-4-yl; Z = O
i: $R^1$ = H; Y = N—$CH_2CO_2H$; Z = O
j: $R^1$ = H; Y = $SO_2$; Z = O
k: $R^1$ = H; Y = $CHCO_2H$; Z = O
l: $R^1$ = H; Y = CH—$CH_2CO_2H$; Z = O
m: $R^1$ = H; Y = N-benzoyl; Z = O
n: $R^1$ = H; Y = N-4-pyridoyl; Z = O
o: $R^1$ = $CH_2N(Me)_2$; Y = O; Z = O;
p: $R^1$ = H: Y = N(i-Bu); Z = NMe
q: $R^1$ = H; Y = $CHCO_2H$; Z = NMe r: $R^1$ = H; Y = 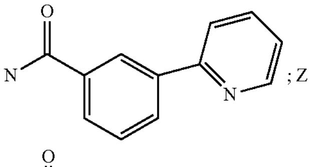 ; Z = O s: $R^1$ = H; Y = 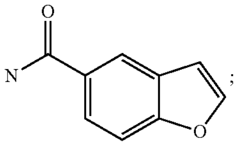 ; Z = O t: $R^1$ = H; Y = 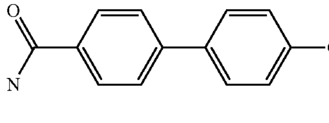 Z = O -continued

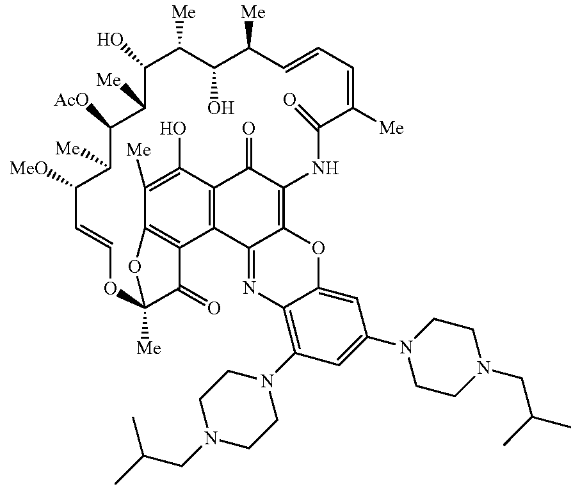

17u

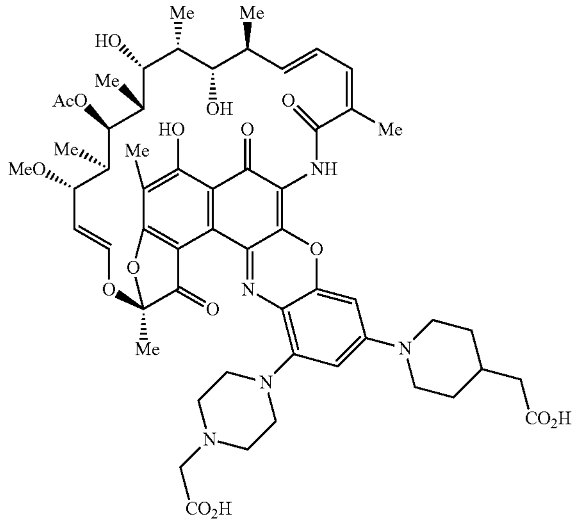

17v

4-[(3-Hydroxy-2-nitrophenoxy)methyl]benzaldehyde (13). To a mixture of 2-nitroresorcinol (7; 5.45 g, 35.2 mmol) and cesium carbonate (3.27 g, 10.05 mmol) in N,N-dimethylformamide (30 mL) was added a solution of 4-(bromomethyl)benzaldehyde (1 g, 5.02 mmol) in N,N-dimethylformamide (12 mL) slowly over a period of 20 min. The reaction was further stirred at 25° C. for 3 h. The reaction mixture was poured into ice water, acidified to pH 4 with 1% aqueous HCl and extracted with ether (2×). The combined extracts were washed with water (2×) and brine, dried ($Na_2SO_4$) concentrated to yield crude product, which was triturated in dichloromethane. The solids were collected to give pure 13. The mother liquor was applied to a 25 g precolumn attached to an 80 g Gold column and first eluted with 30-50% dichloromethane/hexanes until all the nitroresorcinol starting material was stripped from the column. Further elution with 5% ethyl acetate/dichloromethane over 30 min at 40 mL/min provided product fractions that were combined and concentrated to a residue that was triturated in 50% dichloromethane/hexanes and collected. Product lots were combined to leave 13 (0.62 g, 45%). $^1H$ NMR (400 MHz, chloroform-d) δ 10.20 (s, 1H), 10.04 (s, 1H), 7.94 (d, J=8.2 Hz, 2H), 7.68 (d, J=7.8 Hz, 2H), 7.40 (t, J=8.5 Hz, 1H), 6.77 (d, J=8.6 Hz, 1H), 6.58 (d, J=8.4 Hz, 1H), 5.28 (s, 2H).

2-(Trimethylsilyl)ethyl 4-({4-[(3-hydroxy-2-nitrophenoxy)methyl]phenyl}methyl)-piperazine-1-carboxylate (14a). To a solution of 13 (0.22 g, 0.805 mmol), acetic acid (0.05 mL, 0.805 mmol) and 2-(trimethylsilyl)ethyl piperazine-1-carboxylate (WO 99/00669; 0.21 g, 0.886 mmol) in tetrahydrofuran (14 mL) was added sodium triacetoxyborohydride (0.68 g, 3.22 mmol). The mixture was stirred at 25° C. for 10 h and quenched with 20 mL of 1:3 methanol:water. The solution was extracted with ether and the organic phase was washed with water and brine, dried ($Na_2SO_4$) and concentrated to a residue that was applied to a precolumn (5 g) attached to a 24 g Gold column and eluted with 40-75% ethyl acetate/hexanes over 21 min. Combined product fractions were concentrated to give 14a (0.361 g, 92%). $^1$H NMR (500 MHz, chloroform-d) δ 7.46-7.41 (m, 2H), 7.40-7.33 (m, 3H), 6.73-6.69 (m, 1H), 6.62-6.57 (m, 1H), 5.18 (s, 2H), 4.23-4.12 (m, 2H), 3.56-3.44 (m, 6H), 2.49-2.32 (m, 4H), 1.08-0.94 (m, 2H), 0.03 (s, 9H). MS: 488.2315 ($M+H^+$) and 510.2031 ($M+Na^+$).

2-(Trimethylsilyl)ethyl 4-(4-[(2-amino-3-hydroxyphenoxy)methyl]phenyl)methyl)-piperazine-1-carboxylate (14b). To a solution of nitro compound 14a (0.505 g, 1.04 mmol) in dichloromethane (15 mL) were added zinc powder (0.474 g, 7.25 mmole) and acetic acid (2.5 mL, 43.7 mmole). The reaction mixture was stirred at 25° C. for 45 mi. The mixture was filtered over Celite and the filtrate was washed with satd. $NaHCO_3$ (2×25 mL) and brine (25 mL). The separated organic layer was dried ($Na_2SO_4$) and concentrated to yield 14b (0.440 g, 93%). $^1$H NMR (400 MHz, chloroform-d) δ 7.46-7.26 (m, 4H), 6.60 (t, J=8.1 Hz, 1H), 6.51 (d, J=8.2 Hz, 1H), 6.43 (d, J=8.0 Hz, 1H), 5.05 (s, 2H), 4.22-4.13 (m, 2H), 3.60-3.39 (m, 6H), 2.60-2.25 (m, 4H), 0.99 (d, J=8.4 Hz, 2H), 0.03 (s, 9H).

3-((4-(Morpholinomethyl)benzyl)oxy)-2-nitrophenol (14c). To a solution of aldehyde 13 (1.03 g, 3.77 mmol), acetic acid (0.22 mL, 3.77 mmol) and morpholine (0.35 mL, 3.96 mmol) in THF (25 mL) was added $NaBH(OAc)_3$ (3.196 g, 15.08 mmole). The reaction mixture was stirred at 25° C. for 2.5 h. The reaction was quenched with methanol (5 mL) and water (15 mL) and extracted with ether/ethyl acetate (100 mL) The separated organic layer was washed with water (2×25 mL), brine (20 mL), dried ($Na_2SO_4$) and concentrated to yield the crude product. It was applied on a precolumn (25 g) attached to a 40 g Gold column and eluted with 50% ethyl acetate/hexanes for 10 min followed by up to 100% ethyl acetate/hexanes over 15 min and then ethyl acetate for 10 min at 40 mL/minute. Eluted product fractions were combined, and concentrated to yield 14c (0.63 g, 49%). $^1$H NMR (700 MHz, chloroform-d) δ 7.44-7.39 (m, 2H), 7.37-7.32 (m, 3H), 6.68 (dd, J=8.6, 1.5 Hz, 1H), 6.58 (d, J=8.3 Hz, 1H), 5.17 (s, 2H), 3.71 (d, J=5.0 Hz, 4H), 3.52 (s, 2H), 2.46 (s, 4H).

2-Amino-3-((4-(morpholinomethyl)benzyl)oxy)phenol (14d). To a solution of the nitro compound 14c (0.61 g, 1.77 mmol) in dichloromethane (14 mL) were added zinc powder (0.81 g, 12.4 mmol) and acetic acid (2.2 mL, 38.4 mmol). The reaction was stirred at 25° C. for 1 h and filtered over Celite. The filtrate was washed with saturated $NaHCO_3$ (2×25 mL) and brine (15 mL). The separated organic layer was dried ($Na_2SO_4$) and concentrated to yield the product 14d (0.52 g, 93%). HPLC $t_R$, 3.34, purity 90.8%. $^1$H NMR (700 MHz, chloroform-d) δ 7.54-7.28 (m, 5H), 6.60-6.56 (m, 1H), 6.50 (d, J=8.1 Hz, 1H), 6.38 (d, J=7.9 Hz, 1H), 5.04 (s, 2H), 4.37 (bs, 2H), 3.75-3.68 (m, 4H), 3.53 (s, 2H), 2.53-2.42 (m, 4H).

3-((4-((4-Methylpiperazin-1-yl)methyl)benzyl)oxy)-2-nitrophenol (14e). The compound was synthesized by the procedure as described for 14c. Yield: 0.21 g (64%); $^1$H NMR (500 MHz, chloroform-d) δ 7.45-7.40 (m, 2H), 7.37-7.31 (m, 3H), 6.74 (d, J=8.5 Hz, 1H), 6.58 (d, J=8.4 Hz, 1H), 5.16 (s, 2H), 3.60 (s, 2H), 2.98 (s, 4H), 2.80 (s, 4H), 2.64 (s, 3H); MS: 358.1755 ($M+H^+$).

2-Amino-3-((4-((4-methylpiperazin-1-yl)methyl)benzyl)oxy)phenol (14f). a solution of the nitro compound (0.196 g) in EtOH (12 mL) was added Raney Nickel (2g). The reaction was shaken in an orbital shaker at RT for 15 h. TLC indicated completion of reaction. Nickel was filtered off and the solvent was removed from the filtrate to yield the product. The crude was purified using about 5 g of silica gel bed with 10% methanol/dichloromethane as eluent. Solvent was removed from the combined fractions to yield 14f (0.106 g, 59%). $^1$H NMR (500 MHz, chloroform-d) δ 7.40-7.35 (m, 2H), 7.33-7.29 (m, 2H), 6.61-6.56 (m, 1H), 6.53-6.49 (m, 1H), 6.41-6.37 (m, 1H), 5.04 (s, 2H), 3.53 (s, 2H), 2.53 (s, 10H), 2.33-2.30 (m, 3H); MS: 328.2014 ($M+H^+$)

1-[4-({4-[(3-Hydroxy-2-nitrophenoxy)methyl]phenyl}methyl)piperazin-1-yl]-2-(morpholin-4-yl)ethan-1-one (15a). A suspension of 14a (97 mg, 0.199 mmol), cesium fluoride (212 mg, 1.392 mmol) and N,N-dimethylformamide (2 mL) was stirred at 63° C. for 7 h. The mixture was filtered using a syringe filter and treated with N,N-diisopropyethylamine (0.2 mL, 1.19 mmol), 4-morpholineacetic acid (44 mg, 0.30 mmol), HATU (112 mg, 0.30 mmol) and HOBT (30 mg, 0.20 mmol). The mixture was stirred at 25° C. for 3 h, diluted with dichloromethane (8 mL), washed successively with water, saturated aqueous sodium bicarbonate and brine, and dried ($Na_2SO_4$). Concentration left a residue that was applied to a flash silica gel column and eluted with 1-9% methanol/dichloromethane. Fractions containing a mixture of N- and N,O-diacylated products were concentrated to a residue that was dissolved in methanol (4 mL) and treated with 10% aqueous sodium hydroxide (0.6 mL). The solution was stirred at 25° C. for 1 h, concentrated, diluted with water, adjusted to pH 7 with 1N aqueous HCl and extracted with dichloromethane (2×). Concentration of the combined dried organic extracts gave 15a (34 mg, 37%). $^1$H NMR (500 MHz, chloroform-d) δ 7.46-7.41 (m, 2H), 7.40-7.34 (m, 3H), 6.75-6.69 (m, 1H), 6.63-6.58 (m, 1H), 5.18 (s, 2H), 3.71 (t, J=4.5 Hz, 4H), 3.65-3.58 (m, 4H), 3.53 (s, 2H), 3.18 (s, 2H), 2.55-2.47 (m, 4H), 2.46-2.40 (m, 4H). MS: 471.2240 ($M+H^+$), 493.2059 ($M+Na^+$).

1-[4-({4-[(2-Amino-3-hydroxyphenoxy)methyl]phenyl}methyl)piperazin-1-yl]-2-(morpholin-4-yl)ethan-1-one (15b). To a solution of 15a (15 mg, 0.032 mmol) in dichloromethane (1.5 mL) and acetic acid (0.1 mL, 1.753 mmol) was added zinc powder (15 mg, 0.223 mmol). The mixture was stirred at 25° C. for 20 min and filtered over Celite. The filtrate was diluted with dichloromethane, washed with saturated aqueous sodium bicarbonate and brine, dried ($Na_2SO_4$) and concentrated to give 15b (14 mg, 100%). 1H NMR (500 MHz, chloroform-d) δ 7.38 (d, J=7.7 Hz, 2H), 7.33 (d, J=7.7 Hz, 2H), 6.63 (t, J=7.3 Hz, 1H), 6.48 (d, J=8.1 Hz, 2H), 5.03 (s, 2H), 3.70 (q, J=3.6, 2.7 Hz, 4H), 3.61 (dt, J=10.5, 4.7 Hz, 4H), 3.53 (s, 2H), 3.18 (s, 2H), 2.51 (t, J=4.4 Hz, 4H), 2.43 (dt, J=15.8, 5.0 Hz, 4H).

2-(Trimethylsilyl)ethyl 4-([4-({[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-4, 23,37-trioxo-8,27,38-trioxa-24,34-diazahexacyclo [23.11.1.$1^{4,7}$.$0^{5,36}$.$0^{26,35}$.$0^{28,33}$]octatriaconta-1(36)2,4,9,19, 21,25,28,30,32,34-undecaen-32-yl]oxy}methyl)phenyl] methyl)piperazine-1-carboxylate (16a). A solution of rifamycin S (4; 0.19 g, 0.273 mmol) and 14b (112 mg, 0.245 mmol) in 1,2-dichloroethane (25 mL) was heated at reflux for 8 h and then concentrated. The residue was dissolved in methanol (15 mL), treated with manganese dioxide (43 mg, 0.489 mmol) and the mixture was stirred at 25° C. for 45 min, and then concentrated. The residue was applied on a pre-column attached to a 24 g Gold column. It was eluted with 2-6% dichloromethane/methanol. Combined product fractions were concentrated to give 16a (0.113 g, 41%). HPLC $t_R$, 7.99, purity 96.1%. MS: 1133.5141 ($M+H^+$).

(7S,9E,11S,12R,13S,14R,15R,16R,17S,18S,19E,21Z)-2, 15,17-Trihydroxy-32-{[4-({4-[2-(1H-imidazol-1-yl)acetyl] piperazin-1-yl}methyl)phenyl]methoxy}-11-methoxy-3,7, 12,14,16,18,22-heptamethyl-6,23,37-trioxo-8,27,38-trioxa-24,34-diazahexacyclo[23.11.1.$1^{4,7}$.$0^{5,36}$.$0^{26,35}$.$0^{28,33}$] octatriaconta-1(36)2,4,9,19,21,25,28,30,32,34-undecaen-13-yl acetate (16b). A solution of benzoxazino-rifamycin 16a (27 mg, 0.024 mmol), cesium fluoride (34 mg, 0.224 mmol) and N,N-dimethylformamide (1.2 mL) was stirred at 63° C. for 4.5 h under argon. The cooled solution was treated with N,N-diisopropylethylamine (0.025 mL, 0.146 mmol), (1H-imidazol-1-yl)acetic acid (6.1 mg, 0.049 mmol), HATU (14 mg, 0.036 mmol) and HOBT (3.7 mg, 0.024 mmol) and stirred at 25° C. for 3 h. The mixture was diluted with dichloromethane and washed with water (2×) and brine, and dried ($Na_2SO_4$). The organic phase was concentrated to a residue that was purified by preparative plate silica gel chromatography, eluting with 10% methanol/dichloromethane. The product band was extracted with 50% methanol/ dichloromethane to give 16b (5 mg, 19%). HPLC $t_R$, 6.02, purity 96.3%. MS: 1097.4859 ($M+H^+$).

(7S,9E,11S,12R,13S,14R,15R,16R,17S,18S,19E,21Z)-2, 15,17-Trihydroxy-11-methoxy-3,7,12,14,16,18,22-heptamethyl-32-{[4-({4-[2-(morpholin-4-yl)acetyl]piperazin-1-yl}methyl)phenyl]methoxy}-6,23,37-trioxo-8,27,38-trioxa-24,34-diazahexacyclo[23.11.1.$1^{4,7}$.$0^{5,36}$.$0^{26,35}$.$0^{28,33}$] octatriaconta-1(36)2,4,9,19,21,25,28,30,32,34-undecaen-13-yl acetate (16c). A solution of the rifamycin S (4; 23 mg, 0.032 mmol) and 15b (13 mg, 0.030 mmol) in 1,2-dichloroethane (2.5 mL) was heated at reflux for 13 h and concentrated. The residue was dissolved in methanol (1 mL), treated with manganese dioxide (3 mg, 0.035 mmol) and the mixture was stirred for 30 min. The mixture was concentrated to a residue that was purified by preparative plate silica gel chromatography eluting with 10% methanol/ dichloromethane. The product band was extracted with 50% methanol/dichloromethane, which was concentrated to give 16c (5 mg, 15%). HPLC $t_R$, 6.02, purity 93.1%. MS: 1116.5174 ($M+H^+$).

(7S,9E,11S,12R,13S,14R,15R,16R,17S,18S,19E,21Z)-2, 15,17-Trihydroxy-11-methoxy-3,7,12,14,16,18,22-heptamethyl-32-({4-[(morpholin-4-yl)methyl]phenyl}methoxy)-6, 23,37-trioxo-8,27,38-trioxa-24,34-diazahexacyclo [23.11.1.$1^{4,7}$.$0^{5,36}$.$0^{26,35}$.$0^{28,33}$]octatriaconta-1(36)2,4,9,19, 21,25,28,30,32,34-undecaen-13-yl acetate (16d). A solution of the rifamycin S (4; 1.16 g, 1.66 mmol) and 14d (0.475 g, 1.51 mmol) in 1,2-dichloroethane (50 mL) was heated at reflux for 10 h. More rifamycin S (4; 0.1 g) was added and with further refluxing for 1 h. The solution was concentrated, and the residue was dissolved in methanol (50 mL), treated with manganese dioxide (0.263 g, 3.02 mmol) and the mixture was stirred for 30 min. The mixture was concentrated to a residue that was applied to a pre-column attached to an 80 g Gold column and eluted first with 50% ethyl acetate/dichloromethane. Then it was rapidly ramped up to 70% ethyl acetate/dichloromethane over 3 min and then up to 100% ethyl acetate. Combined product fractions were concentrated to give 16d (0.61 g, 41%). HPLC $t_R$, 6.70, purity 95.9%. MS: 990.4370 ($M+H^+$) and 1012.4193 ($M+Na^+$).

(7S,9E,11S,12R,13S,14R,15R,16R,17S,18S,19E,21Z)-2, 15,17-trihydroxy-11-methoxy-3,7,12,14,16,18,22-heptamethyl-32-({4-[(4-methylpiperazin-1-yl)methyl] phenyl}methoxy)-6,23,37-trioxo-8,27,38-trioxa-24,34-diazahexacyclo[23.11.1.$1^{4,7}$.$0^{5,36}$.$0^{26,35}$.$0^{28,33}$] octatriaconta-1,3,5(36)9,19,21,25,28,30,32,34-undecaen-13-yl acetate (16e), This was synthesized from 4 and 14f following the procedure to make 16d to give 16e (71 mg, 23%). HPLC $t_R$, 6.19, purity 92.1%. MS: 1003.4691 ($M+H^+$) and 1025.4516 ($M+Na^+$).

2-(Trimethylsilyl)ethyl 4-([4-({[(7S,9E,11S,12R,13S, 14R,15R,16R,17S,18S,19E,21Z)-13-(acetyloxy)-2,15,17-trihydroxy-11-methoxy-3,7,12,14,16,18,22-heptamethyl-30-[4-(2-methylpropyl)piperazin-1-yl]-6,23,37-trioxo-8,27, 38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-32-yl]oxy}methyl)phenyl]methyl}piperazine-1-carboxylate (17a) and 7S,9E,11S,12R,13S,14R,15R,16R, 17S,18S,19E,21Z)-2,15,17-trihydroxy-11-methoxy-3,7,12, 14,16,18,22-heptamethyl-30,32-bis[4-(2-methylpropyl) piperazin-1-yl]-6,23,37-trioxo-8,27,38-trioxa-24,34-diazahexacyclo[23.11.1.$1^{4,7}$.$0^{5,36}$.$0^{26,35}$.$0^{28,33}$] octatriaconta-1,3,5(36)9,19,21,25,28,30,32,34-undecaen-13-yl acetate (17u) A mixture of 16a (356 mg, 0.314 mmol), N-i-butylpiperazine (179 mg, 1.26 mmol), manganese dioxide (55 mg, 0.628 mmol) and N,N-dimethylformamide (2 mL) was stirred at 25° C. for 16 h. The mixture was diluted with ethyl acetate, washed successively with water (2×) and brine, dried and concentrated. The residue was loaded onto a 40 g gold column and eluted with 2-4% methanol/dichloromethane over 25 min. Combined product fractions were concentrated to give 17a (250 mg, 63%) and 17u (58 mg, 17%). 17a: HPLC $t_R$, 6.28, purity 97.1%. MS: 1273.6468 ($M+H^+$) and 1295.6275 ($M+Na^+$). 17u: HPLC $t_R$, 5.56, purity 96.2%. MS: 1065.5907 ($M+H^+$) and 1087.5715 ($M+Na^+$).

(7S,9E,11S,12R,13S,14R,15R,16R,17S,18S,19E,21Z)-2, 15,17-Trihydroxy-11-methoxy-3,7,12,14,16,18,22-heptamethyl-30-[4-(2-methylpropyl)piperazin-1-yl]-6,23,37-trioxo-32-({4-[(piperazin-1-yl)methyl]phenyl}methoxy)-8,27, 38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (17b). A mixture of 17a (27 mg, 0.021 mmol), cesium fluoride (29 mg, 0.190 mmol) and N,N-dimethylformamide (0.7 mL) was stirred at 63° C. for 5 h. The mixture was diluted with ethyl acetate, washed successively with water (2×) and brine, dried and concentrated to give 17b (23 mg, 96%). HPLC $t_R$, 5.26, purity 91.9%. MS: 1129.5820 ($M+H^+$) and 1151.5618 ($M+Na^+$).

(7S,9E,11S,12R,13S,14R,15R,16R,17S,18S,19E,21Z)-2, 15,17-Trihydroxy-32-{[4-({4-[2-(1H-imidazol-1-yl)acetyl] piperazin-1-yl}methyl)phenyl]methoxy}-11-methoxy-3,7, 12,14,16,18,22-heptamethyl-30-[4-(2-methylpropyl) piperazin-1-yl]-6,23,37-trioxo-8,27,38-trioxa-24,34-diazahexacyclo[23.11.1.$1^{4,7}$.$0^{5,36}$.$0^{26,35}$.$0^{28,33}$] octatriaconta-1(36)2,4,9,19,21,25,28,30,32,34-undecaen-13-yl acetate (17c). A solution of 17b (23 mg, 0.020 mmol), N,N-diisopropylethylamine (0.02 mL, 0.120 mmol), (1H-imidazol-1-yl)acetic acid (5.1 mg, 0.041 mmol), HATU (12 mg, 0.031 mmol), HOBT (3 mg, 0.020 mmol) and N,N-dimethylformamide (0.7 mL) was stirred at 25° C. for 6 h. The mixture was diluted with ethyl acetate, washed successively with water (2×) and brine (5 mL), dried ($Na_2SO_4$) and concentrated to a residue that was purified by preparative plate silica gel chromatography eluting with 10% methanol/dichloromethane. The product band was extracted with 40% methanol/dichloromethane to give 17c (11 mg, 44%). HPLC $t_R$, 5.14, purity 99.4%. MS: 1237.6150 ($M+H^+$) and 1259.5943 ($M+Na^+$).

(7S,9E,11S,12R,13S,14R,15R,16R,17S,18S,19E,21Z)-2,15,17-Trihydroxy-11-methoxy-3,7,12,14,16,18,22-heptamethyl-30-[4-(2-methylpropyl)piperazin-1-yl]-32-{[4-({4-[2-(morpholin-4-yl)acetyl]piperazin-1-yl}methyl)phenyl]methoxy}-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (17d). A solution of 17b (19 mg, 0.017 mmol), N,N-diisopropyethylamine (0.02 mL, 0.1 mmol), 4-morpholineacetic acid (5 mg, 0.034 mmol), HATU (10 mg, 0.025 mmol), HOBT (3 mg, 0.017 mmol) and N,N-dimethylformamide (0.7 mL) was stirred at 25° C. for 12 h. The mixture was diluted with ethyl acetate, washed successively with water (2×) and brine (5 mL), dried ($Na_2SO_4$) and concentrated to a residue that was purified by preparative plate silica gel chromatography eluting with 10% methanol/dichloromethane. The product band was extracted with 40% methanol/dichloromethane to give 17d (16 mg, 76%). HPLC $t_R$, 5.41, purity 99.2%. MS: 1256.6438 ($M+H^+$), 1278.6230 ($M+Na^+$).

(7S,9E,11S,12R,13S,14R,15R,16R,17S,18S,19E,21Z)-2,15,17-Trihydroxy-11-methoxy-3,7,12,14,16,18,22-heptamethyl-30-[4-(2-methylpropyl)piperazin-1-yl]-32-({4-[(morpholin-4-yl)methyl]phenyl}methoxy)-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (17e). A mixture of 16d (100 mg, 0.101 mmol), N-i-butylpiperazine (57 mg, 0.404 mmol), manganese dioxide (18 mg, 0.202 mmol) and N,N-dimethylformamide (1 mL) was stirred at 25° C. for 15 h. The mixture was diluted with ethyl acetate, washed successively with water (2×) and brine, dried and concentrated. The residue was loaded onto a precolumn that was attached to a 12 g Gold column and eluted with 2-5% methanol/ethyl acetate. Combined product fractions were concentrated and applied again to a precolumn attached to a 12 g Gold column. The column was eluted first with ethyl acetate followed by 2% methanol/ethyl acetate. Combined product fractions were concentrated to give 17e (48 mg, 42%). HPLC $t_R$, 5.88, purity 97.1%. MS: 1130.5070 ($M+H^+$) and 1152.4868 ($M+Na^+$).

(7S,9E,11S,12R,13S,14R,15R,16R,17S,18S,19E,21Z)-30-[4-(2,2-Dimethylpropanoyl)-piperazin-1-yl]-2,15,17-trihydroxy-11-methoxy-3,7,12,14,16,18,22-heptamethyl-32-({4-[(morpholin-4-yl)methyl]phenyl}methoxy)-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (17f). A mixture of 16d (50 mg, 0.050 mmol), piperazine derivative (34 mg, 0.200 mmol), manganese dioxide (9 mg, 0.100 mmol) and N,N-dimethylformamide (0.6 mL) was stirred at 25° C. for 15 h. The mixture was diluted with ethyl acetate, washed successively with water (2×) and brine, dried and concentrated. The residue was loaded onto a precolumn that was attached to a 12 g Gold column and eluted with 2% methanol/dichloromethane followed by 2-6% methanol/dichloromethane. Combined product fractions were concentrated to give 17f (51 mg, 87%). HPLC $t_R$, 6.76, purity 98.9%. MS: 1158.4995 ($M+H^+$) and 1180.4807 ($M+Na^+$).

(7S,9E,11S,12R,13S,14R,15R,16R,17S,18S,19E,21Z)-2,15,17-Trihydroxy-11-methoxy-3,7,12,14,16,18,22-heptamethyl-32-({4-[(morpholin-4-yl)methyl]phenyl}methoxy)-6,23,37-trioxo-30-(4-propanoylpiperazin-1-yl)-8,27,38-trioxa-24,34-diazahexacyclo-[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (17g). A mixture of 16d (50 mg, 0.050 mmol), piperazine derivative (29 mg, 0.200 mmol), manganese dioxide (9 mg, 0.100 mmol) and N,N-dimethylformamide (0.6 mL) was stirred at 25° C. for 15 h. The mixture was diluted with ethyl acetate, washed successively with water (2×) and brine, dried and concentrated. The residue was loaded onto a precolumn that was attached to a 12 g Gold column and eluted with ethyl acetate followed by 2-7% methanol/ethyl acetate. Combined product fractions were concentrated to give 17g (19 mg, 33%). HPLC ta, 6.05, purity 95.2%. MS: 1130.5323 ($M+H^+$) and 1152.5112 ($M+Na^+$).

(7S,9E,11S,12R,13S,14R,15R,16R,17S,18S,19E,21Z)-2,15,17-trihydroxy-11-methoxy-3,7,12,14,16,18,22-heptamethyl-30-[4-(1-methylpiperidin-4-yl)piperazin-1-yl]-32-{[4-(morpholin-4-ylmethyl)phenyl]methoxy}-6,23,37-trioxo-8,27,38-trioxa-24,34-diazahexacyclo-[23.11.1.$1^{4,7}$.$0^{5,36}$.$0^{26,35}$.$0^{28,33}$]octatriaconta-1,3,5(36)9,19,21,25,28,30,32,34-undecaen-13-yl acetate (17h). To a solution of the compound 16d (50 mg, 0.05 mmol) in N,N-dimethylformamide (0.6 mL) were added the piperazine derivative (19 mg, 0.1 mmol) and manganese dioxide (48 mg, 0.56 mmol). The reaction mixture was stirred at 25° C. for 15 h, diluted with ethyl acetate (10 mL) and filtered through Celite. The filtrate was washed with water (2×10 mL), brine (10 mL), dried ($Na_2SO_4$) and concentrated. The residue was dissolved in 20% methanol/dichloromethane and applied to two preparative silica gel plates. The plates were developed with 15% methanol/dichloromethane. Extraction of the product band with 40% methanol/dichloromethane followed by concentration gave product 17h (41 mg, 69%). HPLC, ta 5.94, purity 98.9%. MS: 1171.5978 ($M+H^+$) and 1193.5800 ($M+Na^+$).

(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-30-[4-(1-methylpiperidin-4-yl)piperazin-1-yl]-32-{[4-(morpholin-4-ylmethyl)phenyl]methoxy)-6,23,37-trioxo-8,27,38-trioxa-24,34-diazahexacyclo-[23.11.1.$1^{4,7}$.$0^{5,36}$.$0^{26,35}$.$0^{28,33}$]octatriaconta-1,3,5(36)9,19,21,25,28,30,32,34-undecaen-30-yl]piperazin-1-yl}acetic acid (17i). Trimethylsilyl 2-(piperazin-1-yl)acetate was generated in situ by refluxing piperazin-1-ylacetic acid (28 mg, 0.19 mmole) and ammonium sulfate (2 mg, 0.02 mmol) in hexamethyldisilazane (0.6 mL, 2.83 mmol) for 1.5 h and then removing excess hexamethyldisilazane under reduced pressure at 72° C.). To a solution of this in dimethyl sulfoxide (0.6 mL) were added compound 16d (25 mg, 0.025 mmol) and manganese dioxide (24 mg, 0.28 mmol). The reaction mixture was stirred at 25° C. for 2.5 h, diluted with ethyl acetate (10 mL) and filtered through Celite. The filtrate was washed with water (2×10 mL), brine (10 mL), dried ($Na_2SO_4$) and concentrated in vacuo at or below 72° C. The residue was treated with ~50% aq. methanol and left at 25° C. for two days. The aqueous mixture was extracted with hexane (2×10 mL) and 50% ethyl acetate/hexane (2×10 mL). Volatiles were removed under reduced pressure from the aqueous solution, and the water was azeotropically removed by repeated additions of ethanol and methanol followed by concentration. The crude residue was dissolved in 20% methanol/dichloromethane (1.5 mL) and applied to a preparative silica gel plate and developed with 15% methanol/dichloromethane. The product band was extracted with 40% methanol/dichloromethane and concentrated to give product 17i (11 mg, 38%). HPLC, $t_R$ 5.82, purity, 96.4%. MS: 1132.5134 (M+H$^+$) and 1154.4915 (M+Na$^+$).

(7S,9E,11S,12R,13S,14R,15R,16R,17S,18S,19E,21Z)-30-(1,1-dioxothiomorpholin-4-yl)-2,15,17-trihydroxy-11-methoxy-3,7,12,14,16,18,22-heptamethyl-32-([4-(morpholin-4-ylmethyl)phenyl]methoxy)-6,23,37-trioxo-8,27,38-trioxa-24,34-diazahexacyclo-[23.11.1.1$^{4,7}$.0$^{5,36}$.0$^{26,35}$.0$^{28,33}$]octatriaconta-1,3,5(36)9,19,21,25,28,30,32,34-undecaen-13-yl acetate (17j). To a solution of the compound 16d (50 mg, 0.05 mmol) in N,N-dimethylformamide (0.4 mL) were added thiomorpholine-1,1-dioxide (28 mg, 0.20 mmol) and manganese dioxide (48 mg, 0.56 mmol). The reaction mixture was heated at 63° C. for 21 h. TLC showed some progress and the stirring was continued at 63° C. for 15 h. It was further heated at 63° C. for 45 h more after additional sulfone (128 mg) was added. The solution was diluted with ethyl acetate (10 mL) and filtered through Celite. The filtrate was washed with water (2×10 mL), brine (10 mL), dried ($Na_2SO_4$) and concentrated. The crude compound was applied to a 5 g precolumn that was attached to a 4 g Gold column and eluted with ethyl acetate for 7 min, followed by 2-5% methanol/ethyl acetate for 15 min. The desired product fractions were combined and concentrated to give product 17j (31 mg, 55%). HPLC, $t_R$ 6.38, purity, 95.2%. MS: 1123.4571 (M+H$^+$) and 1145.4365 (M+Na$^+$).

1-[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-32-[4-(morpholin-4-ylmethyl)phenyl]-methoxy)-6,23,37-trioxo-8,27,38-trioxa-24,34-diazahexacyclo[23.11.1.1$^{4,7}$.0$^{5,36}$.0$^{26,35}$.0$^{28,33}$]-octatriaconta-1,3,5(36)9,19,21,25,28,30,32,34-undecaen-30-yl]piperidine-4-carboxylic acid (17k). To a suspension of the pyridine-4-carboxylic acid (41 mg) in DMF (1.5 mL) was added NaH (9 mg). The reaction was stirred for 2 h. To this solution were added 16d (48 mg) and $MnO_2$ (46 mg). The reaction was stirred at 63° C. for 25 h. The solvent was removed under high vacuum. The residue was dissolved in water, and the solution washed with 50% ethyl acetate/hexane (5×7 mL) to selectively extract out the starting material. Amberlite XAD 2 resin (~10 g) was loaded onto a 25 g cartridge, which was washed with HPLC grade water (100 mL), methanol (300 mL) and water again (300 mL). The aqueous product solution was applied directly to the prepared cartridge and eluted first with water (100 mL) and then an increasing gradient of methanol/water to 100% methanol. The product fractions were pooled and concentrated to a residue that was purified by preparative plate silica gel chromatography eluting with 15% methanol/dichloromethane. The product was extracted using 25-40% methanol/dichloromethane to give 17k (0.008 g, 15%). HPLC, $t_R$ 6.05, purity, 90.5%. MS: 1117.5017 (M+H$^+$) and 1139.4808 (M+Na$^+$).

2-{1-[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-32-{[4-(morpholin-4-ylmethyl)phenyl]methoxy}-6,23,37-trioxo-8,27,38-trioxa-24,34-diazahexacyclo-[23.11.1.1$^{4,7}$.0$^{5,36}$.0$^{26,35}$.0$^{28,33}$]octatriaconta-1,3,5(36)9,19,21,25,28,30,32,34-undecaen-30-yl]piperidin-4-yl)acetic acid (17l) and 2-{1-[(7S,9E,11S,12R,13S,14R,15R,16R,17S,18S,19E,21Z)-13-(acetyloxy)-32-[4-(carboxymethyl)piperidin-1-yl]-2,15,17-trihydroxy-11-methoxy-3,7,12,14,16,18,22-heptamethyl-6,23,37-trioxo-8,27,38-trioxa-24,34-diazahexacyclo-[23.11.1.1$^{4,7}$.0$^{5,36}$.0$^{26,35}$.0$^{28,33}$]octatriaconta-1,3,5(36)9,19,21,25,28,30,32,34-undecaen-30-yl]piperidin-4-yl)acetic acid (17v). Trimethylsilyl 2-(piperidin-4-yl)acetate was generated in situ by refluxing piperidin-4-ylacetic acid (51 mg, 0.36 mmole) and ammonium sulfate (2 mg, 0.02 mmol) in hexamethyldisilazane (0.85 mL, 4.0 mmol) for 1.5 h and then removing excess hexamethyldisilazane under reduced pressure at 72° C. To a solution of this in dimethyl sulfoxide (0.6 mL) were added compound 16d (26 mg, 0.026 mmol) and manganese dioxide (25 mg, 0.29 mmol). The reaction mixture was stirred at room temperature for 25 h. The reaction mixture was diluted with ethyl acetate (10 mL), filtered with the aid of celite, and concentrated to a residue that was dissolved in water (5 mL) and methanol (8 mL). The solution was left at room temperature for two days and then concentrated via azeotropic removal of water using methanol. The compound was applied to a 5 g precolumn attached to a 5 g Gold Isco column and gradient eluted with 5-15% methanol/dichloromethane over 30 minutes. The collected product fractions were mostly a mixture of 17l and 17v. The mixture was further purified by preparative plate silica gel chromatography eluting with 15% methanol/dichloromethane. Each product band was isolated and extracted with 40% methanol/dichloromethane to give 17l (8 mg, 27%). HPLC, $t_R$ 6.44, purity, 98.4%. MS: 1131.5167 (M+H$^+$), 1153.4990 (M+Na$^+$) and 17v (11 mg, 39%). HPLC, $t_R$ 6.56, purity, 97.5%. MS: 1067.4847 (M+H$^+$).

(7S,9E,11S,12R,13S,14R,15R,16R,17S,18S,19E,21Z)-30-(4-benzoylpiperazin-1-yl)-2,15,17-trihydroxy-1-methoxy-3,7,12,14,16,18,22-heptamethyl-32-{[4-(morpholin-4-ylmethyl)phenyl]methoxy}-6,23,37-trioxo-8,27,38-trioxa-24,34-diazahexacyclo-[23.11.1.1$^{4,7}$.0$^{5,36}$.0$^{26,35}$.0$^{28,33}$]octatriaconta-1,3,5(36)9,19,21,25,28,30,32,34-undecaen-13-yl acetate (17m). This was synthesized from 16d and 1-benzoylpiperazine following the procedure for 17g to give 17m (29 mg, 81%). HPLC $t_R$, 6.66, purity 98.5%. MS: 1178.5316 (M+H$^+$) and 1200.5140 (M+Na$^+$).

7S,9E,11S,12R,13S,14R,15R,16R,17S,18S,19E,21Z)-2,15,17-trihydroxy-11-methoxy-3,7,12,14,16,18,22-heptamethyl-32-{[4-(morpholin-4-ylmethyl)phenyl]methoxy}-6,23,37-trioxo-30-{4-[(pyridin-4-yl)carbonyl]piperazin-1-yl}-8,27,38-trioxa-24,34-diazahexacyclo[23.11.1.1$^{4,7}$.0$^{5,36}$.0$^{26,35}$.0$^{28,33}$]octatriaconta-1,3,5(36)9,19,21,25,28,30,32,34-undecaen-13-yl acetate (17n). This was synthesized from 16d and piperazin-1-yl(pyridin-4-yl)methanone following the procedure for 17g to give 17n (26 mg, 73%). HPLC $t_R$, 5.69, purity 98.9%. MS: 1179.5282 (M+H$^+$) and 1201.5013 (M+Na$^+$).

(7S,9E,11S,12R,13S,14R,15R,16R,17S,18S,19E,21Z)-30-{2-[(dimethylamino)methyl]morpholin-4-yl}-2,15,17-trihydroxy-11-methoxy-3,7,12,14,16,18,22-heptamethyl-32-{[4-(morpholin-4-ylmethyl)phenyl]methoxy}-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1,3,5(36)9,19,21,25,28,30,32,34-undecaen-13-yl acetate (17o). This was synthesized from 16d and N,N-dimethyl-1-(morpholin-2-yl)methanamine following the procedure for 17g to give 17o (28 mg, 82%). HPLC $t_R$, 5.66, purity 97.3%. MS: 1132.5486 (M+H$^+$) and 1154.5309 (M+Na$^+$).

(7S,9E,11S,12R,13S,14R,15R,16R,17S,18S,19E,21Z)-2,15,17-trihydroxy-11-methoxy-3,7,12,14,16,18,22-heptamethyl-32-({4-[(4-methylpiperazin-1-yl)methyl]phenyl}methoxy)-30-[4-(2-methylpropyl)piperazin-1-yl]-6,23,37-trioxo-8,27,38-trioxa-24,34-diazahexacyclo-[23.11.1.1$^{4,7}$.0$^{5,36}$.0$^{26,35}$.0$^{28,33}$]octatriaconta-1,3,5(36)9,19,21,25,28,30,32,34-undecaen-13-yl acetate (17p). This was synthesized from 16e and 1-isobutylpiperazine following the procedure for 17g to give 17p (33 mg, 80%). HPLC $t_R$, 5.49, purity 97.6%. MS: 1143.5998 ($M+H^+$) and 1165.5788 ($M+Na^+$).

1-[(7S,9E,11S,12R,13S,14R,15R,16R,17S,18S,19E,21Z)-13-(acetyloxy)-2,15,17-trihydroxy-11-methoxy-3,7,12,14,16,18,22-heptamethyl-32-({4-[(4-methylpiperazin-1-yl)methyl]phenyl}methoxy)-6,23,37-trioxo-8,27,38-trioxa-24,34-diazahexacyclo-[23.11.1.$1^{4,7}$.$0^{5,36}$.$0^{26,35}$.$0^{28,33}$]-octatriaconta-1,3,5(36)9,19,21,25,28,30,32,34-undecaen-30-yl]piperidine-4-carboxylic acid (17q). This was synthesized from 16e and trimethylsilyl piperidine-4-carboxylate following the procedure for 17l to give 17q (12 mg, 51%). HPLC $t_R$, 6.13, purity 98.6%. MS: 1130.5327 ($M+H^+$) and 1152.5169 (M+Na).

(7S,9E,11S,12R,13S,14R,15R,16R,17S,18S,19E,21Z)-2,15,17-trihydroxy-11-methoxy-3,7,12,14,16,18,22-heptamethyl-32-{[4-(morpholin-4-ylmethyl)phenyl]methoxy}-6,23,37-trioxo-30-(4-{[3-(pyridin-2-yl)phenyl]carbonyl}piperazin-1-yl)-8,27,38-trioxa-24,34-diazahexacyclo[23.11.1.$1^{4,7}$.$0^{5,36}$.$0^{26,35}$.$0^{28,33}$]octatriaconta-1,3,5(36)9,19,21,25,28,30,32,34-undecaen-13-yl acetate (17r). This was synthesized from 16d and piperazin-1-yl(3-(pyridin-2-yl)phenyl)methanone following the procedure for 17g to give 17r (36 mg, 71%) HPLC $t_R$, 5.83, purity 98.6%. MS: 1255.5619 ($M+H^+$) and 1277.5439 ($M+Na^+$).

(7S,9E,11S,12R,13S,14R,15R,16R,17S,18S,19E,21Z)-30-{4-[(1-benzofuran-5-yl)carbonyl]piperazin-1-yl}-2,15,17-trihydroxy-11-methoxy-3,7,12,14,16,18,22-heptamethyl-32-{[4-(morpholin-4-ylmethyl)phenyl]methoxy}-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1,3,5(36)9,19,21,25,28,30,32,34-undecaen-13-yl acetate (17s). This was synthesized from 16d and benzofuran-5-yl(piperazin-1-yl) methanone following the procedure for 17g to give 17s (27 mg, 71 HPLC $t_R$, 6.77, purity 98.2%. MS: 1218.5269 ($M+H^+$) and 1240.5089 ($M+Na^+$).

(7S,9E,11S,12R,13S,14R,15R,16R,17S,18S,19E,21Z)-30-(4-{[4-(4-carbamoylphenyl)-phenyl]carbonyl}piperazin-1-yl)-2,15,17-trihydroxy-11-methoxy-3,7,12,14,16,18,22-heptamethyl-32-{[4-(morpholin-4-ylmethyl)phenyl]methoxy}-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1,3,5(36)9,19,21,25,28,30,32,34-undecaen-13-yl acetate (17t). To a solution of the compound 16d (25 mg, 0.025 mmol) in N,N-dimethylformamide (0.7 mL) were added 4'-(piperazine-1-carbonyl)-[1,1'-biphenyl]-4-carboxamide (33 mg, 0.063 mmol) and manganese dioxide (48 mg, 0.28 mmol). The reaction mixture was heated at 63° C. for 24 h, diluted with ethyl acetate and filtered through Celite. The filtrate was washed with water (2×), brine, dried and concentrated to a residue that was loaded onto a 5 g precolumn attached to a 4 g Gold column. It was eluted with dichloromethane followed by 2-7% methanol/dichloromethane over 25 minutes. Product fractions were combined and concentrated to give 17t (7 mg, 20%). HPLC, $t_R$ 5.74, purity 95.4%. MS: 1297.5694 ($M+H^+$) and 1319.5510 ($M+Na^+$).

Compounds 24a-d were synthesized as shown in Scheme 5.

Scheme 5

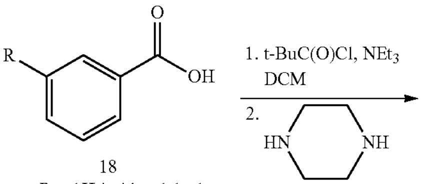

18
a: R = 1H-imidazol-1-yl
b: R = pyridin-2-yl

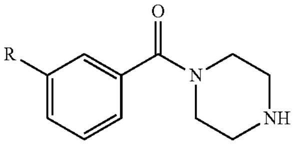

19
a: R = 1H-imidazol-1-yl
b: R = pyridin-2-yl

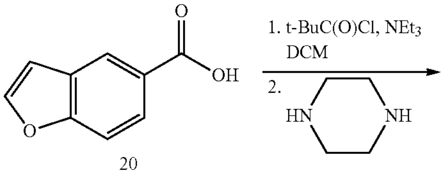

20

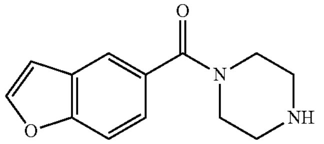

21

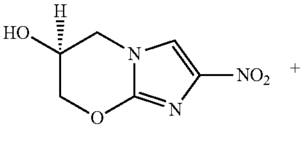

22

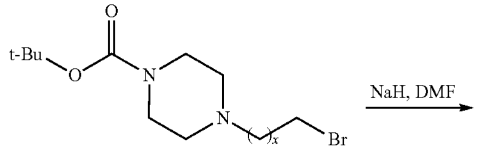

23
a: x = 2
b: x = 5

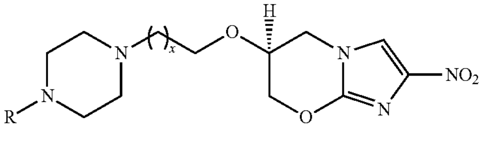

24

TFA/DCM or HCl/MeOH a: R = Boc; x = 2
b: R = Boc; x = 5
c: R = H; x = 2
d: R = H; x = 5

1-[3-(1H-Imidazol-1-yl)benzoyl]piperazine (19a). A solution of pivaloyl chloride (32 mg, 0.266 mmol), triethylamine (0.06 mL, 0.399 mmol) and dichloromethane (3 mL) was treated with 3-(1H-imidazol-1-yl)benzoic acid (18a; 50 mg, 0.266 mmol) and stirred until the mixture became a clear liquid (2 h). To this was added a solution of piperazine (0.114 g, 1.328 mmol) in ethanol (3 mL) and the mixture was stirred for 12 h. The mixture was diluted with water (2 mL), treated with conc. HCl (0.5 mL) and washed with dichloromethane (2×). The aqueous solution was basified with 10% aqueous NaOH and extracted with dichloromethane (2×). The combined extracts were washed with water and brine, dried and concentrated to give 19a (36 mg, 52%). $^1$H NMR (500 MHz, chloroform-d) δ 7.89 (s, 1H), 7.54 (t, J=7.7 Hz, 1H), 7.46 (d, J=7.9 Hz, 2H), 7.37 (d, J=7.6 Hz, 1H), 7.31 (s, 1H), 7.22 (s, 1H), 3.90-3.73 (m, 2H), 3.54-3.39 (m, 2H), 3.05-2.93 (m, 2H), 2.91-2.80 (m, 2H), 2.63 (s, 1H). MS: 257.1397 (M+H$^+$).

1-[3-(Pyridin-2-yl)benzoyl]piperazine (19b). A solution of pivaloyl chloride (121 mg, 1.004 mmol), triethylamine (0.14 mL, 1.004 mmol) and dichloromethane (8 mL) was treated with 3-(2-pyridinyl)benzoic acid (18b; 200 mg, 1.004 mmol). The mixture was stirred until it became a clear liquid (1.5 h) and then treated with a solution of piperazine (0.259 g, 3.010 mmol) in ethanol (8 mL) followed by stirring at 25° C. for 15 h. The mixture was diluted with water (5 mL), treated with conc. HCl (1 mL) and concentrated. The residue was diluted with water and the aqueous solution washed with dichloromethane. The aqueous phase was basified with 10% aqueous NaOH and extracted with dichloromethane (2×). The combined extracts were dried ($Na_2SO_4$) and concentrated to a residue that was purified by flash silica gel chromatography with gradient elution using 2-14% methanol/dichloromethane. Combined product fractions were concentrated to give 19b (0.245 g, 91%). $^1$H NMR (700 MHz, chloroform-d) δ 8.75-8.63 (m, 1H), 8.08-8.00 (m, 2H), 7.78-7.71 (m, 2H), 7.52 (td, J=7.7, 2.0 Hz, 1H), 7.46-7.41 (m, 1H), 7.27-7.24 (m, 1H), 3.80 (s, 2H), 3.55-3.40 (m, 2H), 3.03-2.92 (m, 2H), 2.86 (d, J=31.6 Hz, 2H), 2.37 (s, 1H). MS: 268.1445 (M+H$^+$).

1-(1-Benzofuran-5-carbonyl)piperazine (21). Starting from benzo[b]furan-5-carboxylic acid (20), this was synthesized following the procedure for 19b. The crude compound was purified by silica gel flash chromatography eluting with 2-12% methanol/dichloromethane. Combined product fractions were concentrated to give 21 (0.257 g, 90%). $^1$H NMR (700 MHz, chloroform-d) δ 7.67 (d, J=2.1 Hz, 2H), 7.52 (d, J=8.4 Hz, 1H), 7.34 (dd, J=8.4, 1.7 Hz, 1H), 6.80 (d, J=2.2 Hz, 1H), 3.76 (s, 2H), 3.45 (s, 2H), 2.95-2.79 (m, 4H), 1.78 (s, 1H). MS: 231.1130 (M+H$^+$), 253.0949 (M+Na$^+$).

tert-Butyl 4-(3-{[(6S)-2-nitro-5H,6H,7H-imidazo[2,1-b][1,3]oxazin-6-yl]oxy}propyl)piperazine-1-carboxylate (24a). A mixture of 60% sodium hydride (40 mg, 1.0 mmol), nitro compound 22 (U.S. Pat. No. 6,087,358) (52 mg, 0.28 mmol) and N,N-dimethylformamide (1.5 mL) was stirred at 25° C. for 15 min and then treated with bromo compound 23a (J. Med. Chem. 2004, 47, 711-719) (88 mg, 0.29 mmol). The mixture was stirred at 25° C. for 3.5 h, quenched with water and extracted with dichloromethane (2×10 mL). The combined extracts were dried ($Na_2SO_4$) and concentrated to a residue that was purified by silica gel flash chromatography eluting with dichloromethane and then 5% methanol/dichloromethane followed by 10% methanol/dichloromethane. Combined product fractions were concentrated to give 24a (65 mg, 56%). $^1$H NMR (700 MHz, chloroform-d) δ 7.42 (s, 1H), 4.66-4.57 (m, 1H), 4.37-4.32 (m, 1H), 4.25-4.18 (m, 1H), 4.16-4.10 (m, 1H), 4.05-3.99 (m, 1H), 3.73-3.66 (m, 1H), 3.64-3.57 (m, 1H), 3.41 (t, J=5.1 Hz, 4H), 2.44-2.27 (m, 6H), 1.81-1.71 (m, 2H), 1.46 (s, 9H). MS: 412.2192 (M+H$^+$), 434.2011 (M+Na$^+$).

tert-Butyl 4-(6-{[(6S)-2-nitro-5H,6H,7H-imidazo[2,1-b][1,3]oxazin-6-yl]oxy}hexyl)piperazine-1-carboxylate (24b). A suspension of 60% sodium hydride (72 mg, 1.80 mmol), the nitro compound 22 (U.S. Pat. No. 6,087,358) (111 mg, 0.600 mmol) and N,N-dimethylformamide (2 mL) was stirred at 25° C. for 15 min and then treated with bromo compound 23b (WO 2017197056) (214 mg, 0.642 mmol). The mixture was stirred at 25° C. for 3 h, quenched with water and extracted with ethyl acetate (2×10 mL). The combined extracts were washed successively with water and brine, dried ($Na_2SO_4$) and concentrated to a residue that was loaded onto a 10 g precolumn that was attached to a 24 g silica gel column and eluted with dichloromethane and then a gradient from 3%-10% methanol/dichloromethane. Combined product fractions were concentrated to give 24b (0.137 g, 50%). $^1$H NMR (500 MHz, chloroform-d) δ 7.42 (s, 1H), 4.63-4.52 (m, 1H), 4.38-4.29 (m, 1H), 4.20 (dd, J=12.7, 3.9 Hz, 1H), 4.14-4.08 (m, 1H), 4.04-3.96 (m, 1H), 3.65-3.58 (m, 1H), 3.55-3.49 (m, 1H), 3.43 (t, J=5.1 Hz, 4H), 2.43-2.28 (m, 6H), 1.61-1.55 (m, 2H), 1.51-1.44 (m, 11H), 1.37-1.26 (m, 4H). MS: 454.2660 (M+H$^+$) and 476.2473 (M+Na$^+$).

Compounds 26c-i, 28, and 29a-e were synthesized as shown in Scheme 6.

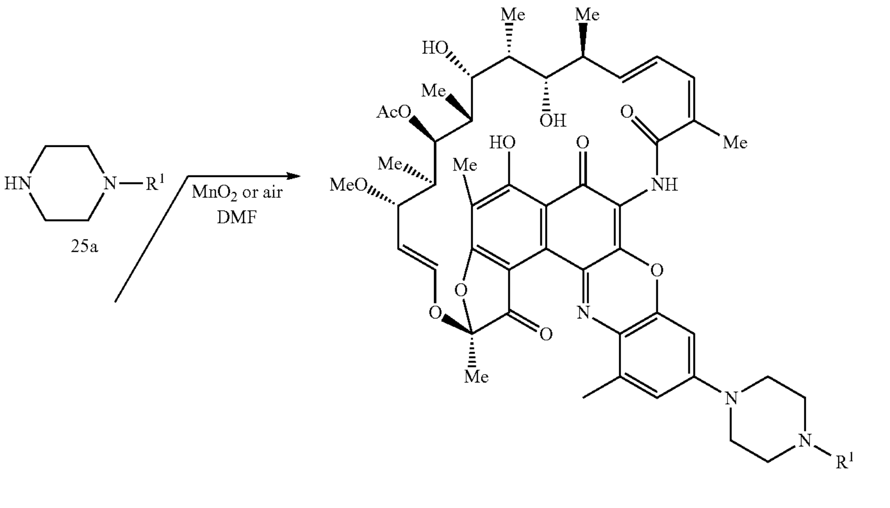

25a

-continued
a: $R^1$ = t-Bu
b: $R^1$ = Me
c: $R^1$ = $(CH_2)_2$-(1H-imidazol-1-yl)
d: $R^1$ = C(O)Me
e: $R^1$ = C(O)Et
f: $R^1$ = C(O)-t-Bu
g: $R^1$ = C(O)OMe
h: $R^1$ = C(O)OEt
i: $R^1$ = C(O)O-t-Bu
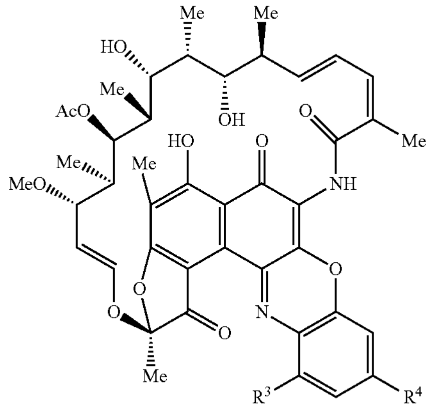
25
a: $R^3$ = Me; $R^4$ = H
b: $R^3$ = H; $R^4$ = Me
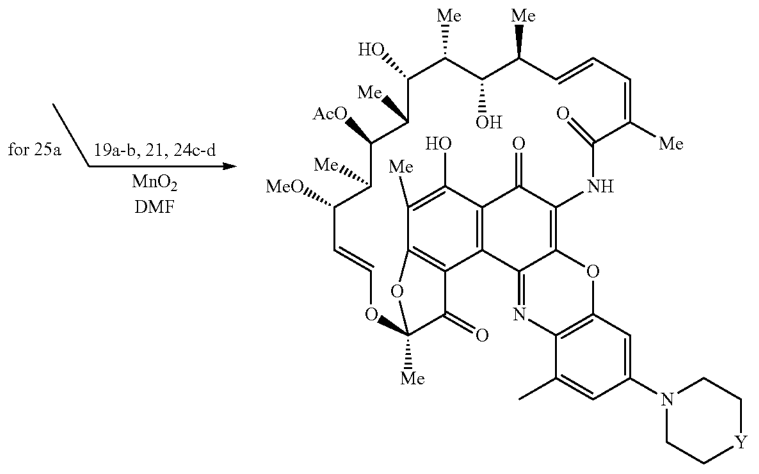
29

-continued

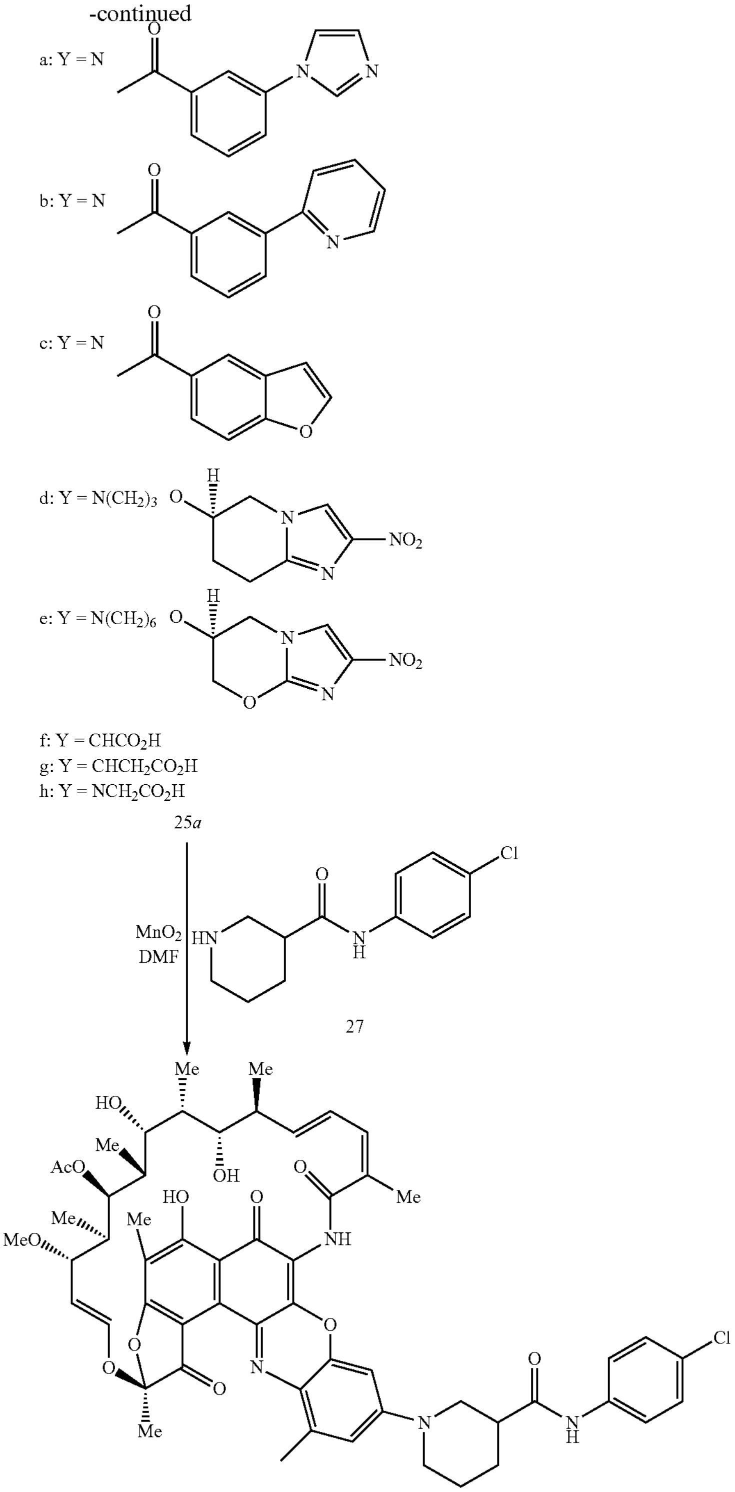

28

(7S,9E,11S,12R,13S,14R,15R,16R,17S,18S,19E,21Z)-2,15,17-Trihydroxy-11-methoxy-3,7,12,14,16,18,22,32-octamethyl-30-[4-(2-methylpropyl)piperazin-1-yl]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (26a). A solution of 25a (*Bioorg. Med. Chem. Lett.,* 2007, 17, 5510-5513) (20 mg, 0.025 mmol), N-i-butylpiperazine (20 mg, 0.138 mmol) and N,N-dimethylformamide (1 mL) was stirred at 25° C. for 12 h. The mixture was diluted with dichloromethane, washed successively with water (2×) and brine, dried ($Na_2SO_4$) and concentrated to a residue that was purified by preparative plate silica gel chromatography eluting with 10% methanol/dichloromethane. The product band was extracted with 50% methanol/dichloromethane to give 26a (15 mg, 64%) (*Bioorg. Med. Chem. Lett.*, 2007, 17, 5510-5513; U.S. Pat. No. 5,981,522). HPLC $t_R$, 6.78, purity 96.3%. MS: 939.4750 ($M+H^+$) and 961.4569 ($M+Na^+$).

(7S,9E,11S,12R,13S,14R,15R,16R,17S,18S,19E,21Z)-2,15,17-Trihydroxy-11-methoxy-3,7,12,14,16,18,22,32-octamethyl-30-(4-methylpiperazin-1-yl)-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (26b). Synthesized from 25a following the procedure for 26a to give 26b (Bioorg. Med. Chem. Lett., 2007, 17, 5510-5513; U.S. Pat. No. 5,981,522) (13 mg, 58%). HPLC $t_R$, 6.38, purity 97.8%. MS: 897.4285 ($M+H^+$) and 919.4101 ($M+Na^+$).

(7S,9E,11S,12R,13S,14R,15R,16R,17S,18S,19E,21Z)-2,15,17-trihydroxy-30-{4-[2-(1H-imidazol-1-yl)ethyl]piperazin-1-yl}-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (26c). Synthesized from 25a following the procedure for 26a to give 26c (9 mg, 37%). HPLC $t_R$, 5.97, purity 96.6%. MS: 977.4655 ($M+H^+$) and 999.4480 ($M+Na^+$).

(7S,9E,11S,12R,13S,14R,15R,16R,17S,18S,19E,21Z)-30-(4-Acetylpiperazin-1-yl)-2,15,17-trihydroxy-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (26d). A solution of 25a (100 mg, 0.125 mmol), 1-acetylpiperazine (40 mg, 0.313 mmol) and N,N-dimethylformamide (1.3 mL) was treated with manganese dioxide (22 mg, 0.250 mmol), stirred at 25° C. for 15 h and concentrated in vacuo. The residue was diluted with ethyl acetate, washed sequentially with water and brine, dried ($Na_2SO_4$) and concentrated to a residue that was loaded onto a 4 g column and eluted first with dichloromethane for 4 min followed by 3-10% methanol/dichloromethane over 25 min. Combined product fractions were concentrated to give 26d (90 mg, 78%). HPLC $t_R$, 7.45, purity 99.3%. MS: 925.4230 ($M+H^+$) and 947.4039 ($M+Na^+$).

(7S,9E,11S,12R,13S,14R,15R,16R,17S,18S,19E,21Z)-2,15,17-Trihydroxy-11-methoxy-3,7,12,14,16,18,22,32-octamethyl-6,23,37-trioxo-30-(4-propanoylpiperazin-1-yl)-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (26e). This was synthesized from 25a and 1-propionylpiperazine following the procedure for 26d to give 26e (78 mg, 88%). HPLC $t_R$, 7.82, purity 99.4%. MS: 939.4389 (M+1), 961.4206 (M+23).

(7S,9E,11S,12R,13S,14R,15R,16R,17S,18S,19E,21Z)-30-[4-(2,2-Dimethylpropanoyl)piperazin-1-yl]-2,15,17-trihydroxy-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (26f). This was synthesized from 25a and 1-pivaloylpiperazine following the procedure for 26d to give 26f (109 mg, 90%). HPLC $t_R$, 8.54, purity 97.2%. MS: 967.4700 ($M+H^+$), 989.4516 ($M+Na^+$).

Methyl 4-[(7S,9E,11S,12R,13S,14R,15R,16R,17S,18S,19E,21Z)-13-(acetyloxy)-2,15,17-trihydroxy-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-30-yl]piperazine-1-carboxylate (26g). This was synthesized from 25a and 1-(carbmethoxy)piperazine following the procedure for 26d to give 26g (51 mg, 87%). HPLC $t_R$, 8.22, purity 98.1%. MS: 941.4170 ($M+H^+$) and 963.3992 ($M+Na^+$).

Ethyl 4-[(7S,9E,11S,12R,13S,14R,15R,16R,17S,18S,19E,21Z)-13-(acetyloxy)-2,15,17-trihydroxy-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-30-yl]piperazine-1-carboxylate (26h). This was synthesized from 25a and 1-(carbethoxy)piperazine following the procedure for 26d to give 26h (53 mg, 89%). HPLC $t_R$, 8.57, purity 98.5%. MS: 955.4329 ($M+H^+$) and 977.4149 ($M+Na^+$).

tert-Butyl 4-[(7S,9E,11S,12R,13S,14R,15R,16R,17S,18S,19E,21Z)-13-(acetyloxy)-2,15,17-trihydroxy-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-30-yl]piperazine-1-carboxylate (26i). This was synthesized from 25a and 1-(ter-butoxycarbonyl)piperazine following the procedure for 26d to give 26i (60 mg, 98%). HPLC $t_R$, 9.19, purity 97.8%. MS: 983.4654 ($M+H^+$) and 1005.4467 ($M+Na^+$).

(7S,9E,11S,12R,13S,14R,15R,16R,17S,1S,19E,21Z)-30-{3-[(4-Chlorophenyl)carbamoyl]piperidin-1-yl}-2,15,17-trihydroxy-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (28). A solution of 25a (20 mg, 0.025 mmol), compound 27 (Bell et al. Bioorg. Med. Chem. Lett., 2013, 23, 3826-3832) (22 mg, 0.092 mmol) and N,N-dimethylformamide (0.9 mL) was treated with manganese dioxide (5 mg, 0.058 mmol) and stirred at 25° C. for 19 h. The mixture was concentrated in vacuo to a residue that was purified by preparative plate silica gel chromatography eluting with 10% methanol/dichloromethane. The product band was extracted with 50% methanol/dichloromethane to provide a mixture of diastereomers 28 (8 mg, 31%). HPLC $t_R$, 9.17, purity 95% (dr: 1.4:1). MS: 1035.4150 (M+1), 1057.3954 (M+23).

(7S,9E,11S,12R,13S,14R,15R,16R,17S,18S,19E,21Z)-2,15,17-Trihydroxy-30-{4-[3-(1H-imidazol-1-yl)benzoyl]piperazin-1-yl}-11-methoxy-3,7,12,14,16,18,22,32-octamethyl-6,23,37-trioxo-8,27,38-trioxa-24,34-diazahexacyclo[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (29a). A solution of 25a (40 mg, 0.050 mmol), compound 19a (30 mg, 0.115 mmol) and N,N-dimethylformamide (0.7 mL) was treated with manganese dioxide (9 mg, 0.100 mmol) and the mixture was heated at 63° C. for 4 h. Additional piperazine derivative (30 mg, 0.200 mmol) was added and stirring was continued for 5 h. The mixture was diluted with ethyl acetate, washed successively with water (2×) and brine, dried and concentrated to a residue that was purified by flash silica gel chromatography eluting with a gradient of 2-6% methanol/dichloromethane. Combined product fractions were concentrated to give 29a (23 mg, 44%). HPLC $t_R$, 6.60, purity 98.3%. MS: 1053.4585 ($M+H^+$) and 1075.4380 ($M+Na^+$).

(7S,9E,11S,12R,13S,14R,15R,16R,17S,18S,19E,21Z)-2,15,17-Trihydroxy-11-methoxy-3,7,12,14,16,18,22,32-octamethyl-6,23,37-trioxo-30-(4-[3-(pyridin-2-yl)benzoyl]piperazin-1-yl)-8,27,38-trioxa-24,34-diazahexacyclo-[23.11.1.$1^{4,7}$.$0^{5,36}$.$0^{26,35}$.$0^{28,33}$]octatriaconta-1(36)2,4,9,19,21,25,28,30,32,34-undecaen-13-yl acetate (29b). A solution of 25a (20 mg, 0.025 mmol), compound 19b (23 mg, 0.086 mmol) and N,N-dimethylformamide (0.9 mL) was treated with manganese dioxide (11 mg, 0.125 mmol) and stirred at 70° C. for 18 h. The mixture was concentrated in vacuo to a residue that was purified by preparative plate silica gel chromatography eluting with 10% methanol/dichloromethane. The product band was extracted with 50% methanol/dichloromethane to give 29b (16 mg, 60%). HPLC $t_R$, 7.23, purity 97.7%. MS: 1064.4648 (M+H$^+$).

(7S,9E,11S,12R,13S,14R,15R,16R,17S,18S,19E,21Z)-30-[4-(1-Benzofuran-5-carbonyl)piperazin-1-yl]-2,15,17-trihydroxy-11-methoxy-3,7,12,14,16,18,22,32-octamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-(36)2,4,9,19,21,25,28,30,32,34-undecaen-13-yl acetate (29c). A solution of 25a (20 mg, 0.025 mmol), piperazine compound 21 (23 mg, 0.100 mmol) and N,N-dimethylformamide (0.9 mL) was treated with manganese dioxide (6 mg, 0.069 mmol) and stirred at 25° C. for 15 h. The mixture was concentrated in vacuo and the residue was purified by preparative plate silica gel chromatography, eluting with 7% methanol/dichloromethane. The product band was extracted with 50% methanol/dichloromethane to give 29c (24 mg, 93%). HPLC $t_R$, 8.47, purity 90.0%. MS: 1027.4334 (M+H$^+$), 1049.4144 (M+Na$^+$) and 1065.3894 (M+K$^+$).

(7S,9E,11S,12R,13S,14R,15R,16R,17S,18S,19E,21Z)-2,15,17-Trihydroxy-11-methoxy-3,7,12,14,16,18,22,32-octamethyl-30-[4-(3-{[(6S)-2-nitro-5H,6H,7H-imidazo[2,1-b][1,3]oxazin-6-yl]oxy}propyl)piperazin-1-yl]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (29d). A solution of 24a (67 mg, 0.16 mmol) in dichloromethane (1 mL) was treated with trifluoroacetic acid (0.1 mL, 1.60 mmol) and the mixture was stirred at 25° C. for 3 h. The mixture was concentrated to a residue that was suspended in methanol (3 mL) and treated with potassium carbonate (92 mg, 0.64 mmol). After stirring for 30 min, the suspension was filtered and the solvent was removed from the filtrate. The residue was dissolved in N,N-dimethylformamide (0.7 mL). To this solution were added 25a (28 mg, 0.035 mmol) and manganese dioxide (6 mg, 0.071 mmol). The reaction mixture was stirred at 25° C. for 80 h. The mixture was concentrated in vacuo and the residue was dissolved in dichloromethane. The solution was loaded onto a 2 g precolumn that was attached to a 4 g Silicycle column and eluted with 3% methanol/dichloromethane followed by 3-10% methanol/dichloromethane. Combined product fractions were concentrated to give 29d (6 mg, 15%). HPLC $t_R$, 6.51, purity 96.0%. MS: 1108.4868 (M+H$^+$), 1130.4680 (M+Na$^+$).

(7S,9E,11S,12R,13S,14R,15R,16R,17S,18S,19E,21Z)-2,15,17-Trihydroxy-11-methoxy-3,7,12,14,16,18,22,32-octamethyl-30-[4-(6-{[(6S)-2-nitro-5H,6H,7H-imidazo[2,1-b][1,3]oxazin-6-yl]oxy}hexyl)piperazin-1-yl]-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (29e). A solution of 24b (0.075 g, 0.165 mmol) in 0.5N methanolic HCl (3.3 mL, 1.65 mmol) was stirred at 25° C. for 15 h followed by heating at 50° C. for 2 h. The solution was concentrated to a residue that was dissolved in methanol (5 mL) and treated with Amberlite IRA 67 resin (Sigma-Aldrich, 500 mg) The mixture was agitated in an orbital shaker for 3 h and then stored at 25° C. for 3 d. The mixture was filtered, the resin was washed with methanol, and the filtrate concentrated. The residue was dissolved in N,N-dimethylformamide (1 mL). To this solution were added 25a (75 mg, 0.094 mmol) and manganese dioxide (16 mg, 0.19 mmol) and the mixture was stirred at 25° C. for 15 h. The mixture was concentrated in vacuo and the residue was loaded onto a 4 g precolumn that was attached to a 4 g Silicycle column. Elution was carried out first with 2% methanol/dichloromethane followed by 3-7% methanol/dichloromethane. Combined product fractions were concentrated to give 29e (15 mg, 14%). HPLC $t_R$, 6.74, purity 95.1%. MS: 1150.5335 (M+H$^+$) and 1172.5156 (M+Na$^+$).

1-[(7S,9E,11S,12R,13S,14R,15R,16R,17S,18S,19E,21Z)-13-(acetyloxy)-2,15,17-trihydroxy-11-methoxy-3,7,12,14,16,18,22,32-octamethyl-6,23,37-trioxo-8,27,38-trioxa-24,34-diazahexacyclo-[23.11.1.1$^{4,7}$.0$^{5,36}$.0$^{26,35}$.0$^{28,33}$]octatriaconta-1,3,5(36)9,19,21,25,28,30,32,34-undecaen-30-yl]piperidine-4-carboxylic acid (29f). This was synthesized from 25a and trimethylsilyl piperidine-4-carboxylate following the procedure for 17l to give 29f (11 mg, 38%). HPLC $t_R$, 7.59, purity 95.3%. MS: 926.4066 (M+H$^+$) and 948.3882 (M+Na$^+$).

2-{4-[(7S,9E,11S,12R,13S,14R,15R,16R,17S,18S,19E,21Z)-13-(acetyloxy)-2,15,17-trihydroxy-11-methoxy-3,7,12,14,16,18,22,32-octamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1,3,5(36)9,19,21,25,28,30,32,34-undecaen-30-yl]piperidin-4-yl}acetic acid (29g). This was synthesized from 25a and trimethylsilyl 2-(piperidin-4-yl)acetate following the procedure for 17l to give 29g (18 mg, 59%). HPLC $t_R$, 7.71, purity 97.7%. MS: 940.4215 (M+H$^+$) and 962.4044 (M+Na$^+$).

2-{4-[(7S,9E,11S,12R,13S,14R,15R,16R,17S,18S,19E,21Z)-13-(acetyloxy)-2,15,17-trihydroxy-11-methoxy-3,7,12,14,16,18,22,32-octamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1,3,5(36)9,19,21,25,28,30,32,34-undecaen-30-yl]piperazin-1-yl}acetic acid (29h). This was synthesized from 25a and trimethylsilyl 2-(piperazin-1-yl)acetate following the procedure for 17l to give 29h (20 mg, 57%). HPLC $t_R$, 6.50, purity 98.5%. MS: 941.4166 (M+H$^+$) and 963.3996 (M+Na$^+$).

Compounds 30a-h were synthesized as shown in Scheme 7.

Scheme 7

25b
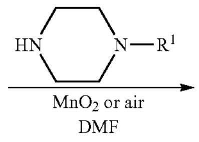

-continued

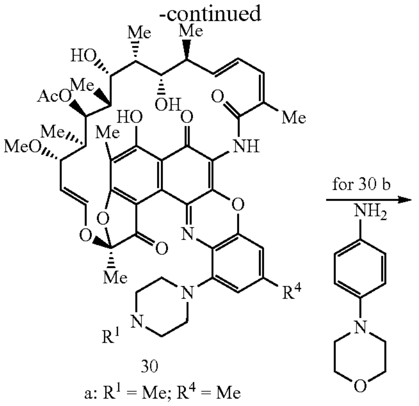

30

31 a: $R^1$ = Me; $R^4$ = Me b: $R^1$ = Me; $R^4$ = CHO c: $R^1$ = i-Bu; $R^4$ = Me d: $R^1$ = i-Bu; $R^4$ = CHO e: $R^1$ = $(CH_2)_2$-(1H-imidazol-1-yl):

$R^4$ = Me

Of: $R^1$ =

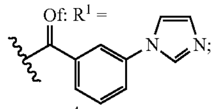

$R^4$ = Me g: $R^1$ =

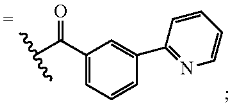

;

$R^4$ = Me h: $R^1$ =

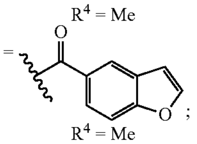

;

$R^4$ = Me

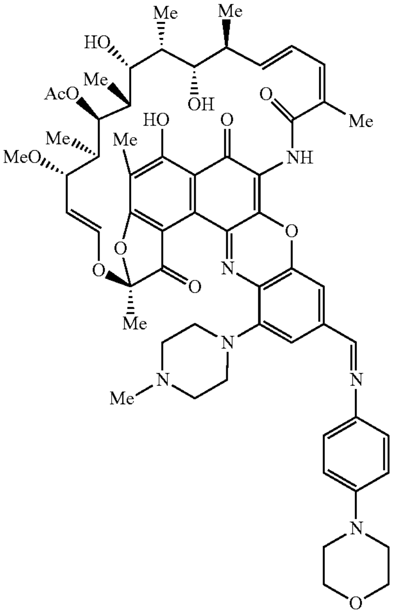

32

(7S,9E,11S,12R,13S,14R,15R,16R,17S,18S,19E,21Z)-2,15,17-Trihydroxy-11-methoxy-3,7,12,14,16,18,22,30-octamethyl-32-(4-methylpiperazin-1-yl)-6,23,37-trioxo-8,27,38-trioxa-24,34-diazahexacyclo[$23.11.1.1^{4,7}.0^{5,36}.0^{26,35}.0^{28,33}$]octatriaconta-1(36)2,4,9,19,21,25,28,30,32,34-undecaen-13-yl acetate (30a). To a solution of 25b (J. Med. Chem., 1990, 33, 552-560) (20 mg, 0.025 mmol) in N,N-dimethylformamide (1 mL) was added N-methylpiperazine (25 mg, 0.250 mmol) and manganese dioxide (1.7 mg, 0.020 mmol). The reaction mixture was stirred at 25° C. for 23 h, diluted with dichloromethane and decanted into a separatory funnel. The solution was washed with water (2×5 mL), brine (5 mL), dried ($Na_2SO_4$) and concentrated. The crude compound was purified by preparative plate silica gel chromatography, eluting with 10% methanol/dichloromethane. The product was extracted with ~50% methanol/dichloromethane to leave 30a (5 mg, 22%). HPLC $t_R$, 6.44, purity 81.4%.

(7S,9E,11S,12R,13S,14R,15R,16R,17S,18S,19E,21Z)-30-Formyl-2,15,17-trihydroxy-11-methoxy-3,7,12,14,16,18,22-heptamethyl-32-(4-methylpiperazin-1-yl)-6,23,37-trioxo-8,27,38-trioxa-24,34-diazahexacyclo[$23.11.1.1^{4,7}.0^{5,36}.0^{26,35}.0^{28,33}$]octatriaconta-1(36)2,4,9,19,21,25,28,30,32,34-undecaen-13-yl acetate (30b). A solution of 25b (20 mg, 0.025 mmol) in N,N-dimethylformamide (1 mL) was treated with N-methylpiperazine (14 mg, 0.138 mmol) and manganese dioxide (24 mg, 0.275 mmol) and then stirred at 25° C. for 15 h. The mixture was diluted with dichloromethane and washed successively with water (2×) and brine, dried ($Na_2SO_4$) and concentrated to a residue that was purified by preparative plate silica gel chromatography eluting with 10% methanol/dichloromethane. The product band was extracted with 50% methanol/dichloromethane to give 30b (5 mg, 22%). HPLC $t_R$, 6.47, purity 95.5%. MS: 911.4069 (M+1) and 943.4331 (M+methanol+$H^+$).

(7S,9E,11S,12R,13S,14R,15R,16R,17S,18S,19E,21Z)-2,15,17-Trihydroxy-11-methoxy-3,7,12,14,16,18,22,30-octamethyl-32-[4-(2-methylpropyl)piperazin-1-yl]-6,23,37-trioxo-8,27,38-trioxa-24,34-diazahexacyclo[$23.11.1.1^{4,7}.0^{5,36}.0^{26,35}.0^{28,33}$]octatriaconta-1(36)2,4,9,19,21,25,28,30,32,34-undecaen-13-yl acetate (30c) and (7S,9E,11S,12R,13S,14R,15R,16R,17S,1S,19E,21Z)-30-Formyl-2,15,17-trihydroxy-11-methoxy-3,7,12,14,16,18,22-heptamethyl-32-[4-(2-methylpropyl)piperazin-1-yl]-6,23,37-trioxo-8,27,38-trioxa-24,34-diazahexacyclo[$23.11.1.1^{4,7}.0^{5,36}.0^{26,35}.0^{28,33}$]octatriaconta-1(36)2,4,9,19,21,25,28,30,32,34-undecaen-13-yl acetate (30d). A solution of 25b (20 mg, 0.025 mmol) in N,N-dimethylformamide (1 mL) was treated with N-i-butylpiperazine (20 mg, 0.138 mmol) and manganese dioxide (24 mg, 0.275 mmol) and stirred at 25° C. for 12 h. The mixture was diluted with dichloromethane and washed successively with water (2×) and brine, dried ($Na_2SO_4$) and concentrated to a residue that was purified by preparative plate silica gel chromatography eluting with 10% Y, methanol/dichloromethane. Each product band was extracted with 50% methanol/dichloromethane to provide 30c (5 mg, 21%) and 30d (2 mg, 8%). 30c: HPLC $t_R$, 6.84, purity 96.8%; 30d: HPLC $t_R$, 7.01, purity 90.8%.

(7S,9E,11S,12R,13S,14R,15R,16R,17S,18S,19E,21Z)-2,15,17-Trihydroxy-32-{4-[3-(1H-imidazol-1-yl)ethyl]piperazin-1-yl}-11-methoxy-3,7,12,14,16,18,22,30-octamethyl-6,23,37-trioxo-8,27,38-trioxa-24,34-diazahexacyclo[$23.11.1.1^{4,7}.0^{5,36}.0^{26,35}.0^{28,33}$]octatriaconta-1(36)2,4,9,19,21,25,28,30,32,34-undecaen-13-yl acetate (30e). A solution of 25b (20 mg, 0.025 mmol), 1-[2-(1H-imidazol-1-yl)ethyl]piperazine (25 mg, 0.138 mmol) and N,N-dimethylformamide (1 mL) was stirred at 65° C. for 1 h under microwave irradiation followed by further irradiation at 70° C. for 3 h. The mixture was diluted with dichloromethane, washed successively with water and brine, dried ($Na_2SO_4$) and concentrated to a residue that was purified by preparative plate silica gel chromatography eluting with 10% methanol/dichloromethane. The product band was extracted with 50% methanol/dichloromethane to give 30e (2.2 mg, 9%). HPLC $t_R$, 5.40, purity 86.4%. MS: 977.4653 (M+H$^+$).

(7S,9E,11S,12R,13S,14R,15R,16R,17S,18S,19E,21Z)-2,15,17-Trihydroxy-32-{4-[3-(1H-imidazol-1-yl)benzoyl]piperazin-1-yl}-11-methoxy-3,7,12,14,16,18,22,30-octamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (30f). A solution of 25b (19 mg, 0.024 mmol), compound 19a (18 mg, 0.070 mmol) and N,N-dimethylformamide (1 mL) was heated at 70° C. for 15 h with exposure to atmospheric oxygen. The mixture was concentrated in vacuo and the residue was purified by preparative plate silica gel chromatography eluting with 10% methanol/dichloromethane. The product band was extracted with 50% methanol/dichloromethane to give 30f (4 mg, 16%). HPLC $t_R$, 5.60, purity 84.6%. MS: 1053.4605 (M+H$^+$) and 1075.4419 (M+Na$^+$).

(7S,9E,11S,12R,13S,14R,15R,16R,17S,18S,19E,21Z)-2,15,17-Trihydroxy-11-methoxy-3,7,12,14,16,18,22,30-octamethyl-6,23,37-trioxo-32-{4-[3-(pyridin-2-yl)benzoyl]piperazin-1-yl}-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (30g). A solution of 25b (48 mg, 0.060 mmol), compound 19b (64 mg, 0.240 mmol) and N,N-dimethylformamide (1 mL) was stirred at 60° C. for 20 h. Additional 19b (25 mg) was added and the mixture was heated for another 20 h. It was diluted with ethyl acetate, washed successively with water (2×) and brine, dried ($Na_2SO_4$) and concentrated to a residue that was purified by preparative plate silica gel chromatography eluting with 10% methanol/dichloromethane. The product band was extracted with 40% methanol/dichloromethane to give 30g (9.7 mg, 15%). HPLC $t_R$, 6.26, purity 95.7%. MS: 1064.4648 (M+H$^+$) and 1086.4467 (M+Na$^+$).

(7S,9E,11S,12R,13S,14R,15R,16R,17S,18S,19E,21Z)-32-[4-(1-Benzofuran-5-carbonyl)piperazin-1-yl]-2,15,17-trihydroxy-11-methoxy-3,7,12,14,16,18,22,30-octamethyl-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1(36)2,4,9,19,21,25,28,30,32,34-undecaen-13-yl acetate (30h). Compound 30h was synthesized from 25b and compound 21 following the procedure for 30g. The crude compound was loaded onto a 4 g precolumn attached to 4 g column and eluted with 0-5% methanol/ethyl acetate over 25 min. Combined product fractions were concentrated and further purified by preparative plate silica gel chromatography, eluting with 5% methanol/ethyl acetate to give 30h (9.6 mg, 21%). HPLC $t_R$, 6.92, purity 91.1%. MS: 1027.4328 (M+H$^+$) and 1049.4150 (M+Na$^+$).

(7S,9E,11S,12R,13S,14R,15R,16R,17S,18S,19E,21Z)-2,15,17-trihydroxy-11-methoxy-3,7,12,14,16,18,22-heptamethyl-32-(4-methylpiperazin-1-yl)-30-{N-[4-(morpholin-4-yl)phenyl]carboximidoyl}-6,23,37-trioxo-8,27,38-trioxa-24,34-diazahexacyclo[23.11.1.1$^{4,7}$.0$^{5,36}$.0$^{26,35}$.0$^{28,33}$]octatriaconta-1,3,5(36)9,19,21,25,28,30,32,34-undecaen-13-yl acetate (32). To a solution of the aldehyde 30b (3.4 mg, 0.004 mmol) in THF (0.7 mL) was added the aniline derivative 31 (1 mg, 0.006 mmole). The reaction mixture was stirred at 25° C. for 1 h. The mixture was concentrated and the residue was dissolved in dichloromethane. The solution was washed with water (2×), brine, dried and concentrated to a residue that was purified by preparative plate silica gel chromatography eluting with 10% methanol/dichloromethane. The product band was extracted with 40% methanol/dichloromethane followed by concentration to give 32 (2.7 mg, 68%). HPLC, $t_R$ 6.49, purity 97.7%. MS: 1071.5069 (M+H$^+$) and 1093.4879 (M+Na$^+$)

Example 2: In Vitro Studies

Expression and Purification of MTB RNAP (WT and RIF$^R$ Mutant) and MTB Sigma Factor A The expression system and purification protocol used for preparation of the wild-type (WT) and Rif-resistant (RIF$^R$) *E. coli* RNAP holoenzymes and the β-D435V (RIF$^R$) MTB RNAP holoenzyme used for the in vitro transcription assays were as previously described (Scharf, et al. SLAS Discovery 2017, 22 (3), 287-297). The expression system and purification protocol used for preparation of the wild-type (WT) and β-S450L (RIF$^R$) MTB RNAP holoenzymes used for the in vitro transcription assays were as previously described (Molodstov, et al. Molecular Microbiology 2017, 103 (6), 1034-1045) with minor alterations. Genes encoding rpoB and rpoC were previously subcloned into a pET duet plasmid, rpoZ was subcloned into a pRSF vector, and rpoA and sigA into a pACYC_Duet vector. A 10× His tag was placed on the N-terminus of the rpoA. BL21(DE3) cells previously transformed with these 3 expression vectors were used to overexpress the MTB RNAP enzymes purified for this study. The cells were grown in terrific broth supplemented with 1 mM $ZnSO_4$ up to an $OD_{600}$ of 0.6 and induced with 1 mM IPTG for 16 hr at 16° C. Cells were resuspended in 20 mL/L lysis buffer (20 mM Tris-HCl, 200 mM NaCl, 20 μM $ZnCl_2$, 5% glycerol, 1 mM PMSF, 2 mM β-mercaptoethanol, 1 Roche cOmplete™ ULTRA protease cocktail). Cells were lysed by sonication on ice, and centrifuged at 25,000 g for 45 min at 4° C. The pellet was discarded, and RNAP in the supernatant was precipitated by slowly adding polyethyleneimine (pH 7.9) to a final concentration of 0.6%. After centrifugation at 6000 g for 10 min at 4° C., the pellet was resuspended in wash buffer (20 mM Tris-HCl, 0.5 M NaCl, 5% glycerol, 1 mM PMSF, 2 mM β-mercaptoethanol) and incubated on ice for 20 min with mild swirling by hand. After another centrifugation at 6000 g for 10 min at 4° C., the pellet was solubilized in elution buffer (20 mM Tris-HCl, 1 M NaCl, 5% glycerol, 1 mM PMSF, 2 mM β-mercaptoethanol) and incubated on ice for 30 min with mild swirling by hand. After centrifuging again at 8000 g for 10 min at 4° C., the pellet was discarded and the RNAP was precipitated by adding ammonium sulfate to a concentration of 0.3 g/mL supernatant. The mixture was incubated at 4° C. for 30 min with mixing, followed by centrifugation at 10000 g for 30 min at 4° C. The pellet was suspended in pre-chromatography dialysis buffer (10 mM Tris-HCl (pH 8 at 4° C.), 75 mM NaCl, 5% glycerol, 20 μM $ZnCl_2$, 2 mM β-mercaptoethanol), sterile filtered and added to a dialysis cassette, and allowed to dialyze overnight. The next day, the dialyzed RNAP solution was applied to a 5 mL Source 15S column equilibrated with TGEB buffer (10 mM Tris-HCl, (pH 8.0 at 4° C.), 5% glycerol, 0.1 mM EDTA, 5 mM β-mercaptoethanol) with 50 mM NaCl. Protein was eluted over a linear gradient to 1 M NaCl in TGEB over 20 CV. Eluted RNAP was then applied to a 1 mL HisTrap column equilibrated with 10 mM Tris-HCl (pH8 at 4° C.), 200 mM NaCl, 5 mM β-mercaptoethanol, and 5% glycerol. His-tagged RNAP was then eluted over a linear gradient to 500 mM imidazole in the same buffer. The his-tagged RNAP was then applied to a 5 mL Source 15Q column (GE Healthcare) equilibrated in TGEB with 50 mM NaCl, and eluted over a linear gradient to 1 M NaCl in TGEB over 25 CV. Purified protein was dialyzed overnight into storage buffer (40 mM Tris-HCl (pH7.9 at 4° C.), 200 mM NaCl, 1 mM DTT, 0.1 mM EDTA, 20 μM $ZnCl_2$, 50% glycerol) and stored at −20° C.

A pMCSG7-SigA vector in *E. coli* BL21(DE3) cells previously prepared (Gill et al. (2012) *J. Med. Chem.* 55(8), 3814-3826) was used to overexpress MTB sigA. The BL21 (DE3) cells were grown in 2XTY at 37° C. to an $OD_{600}$ of 0.6, then induced with 1 mM IPTG at 16° C. for 16-20 hours. The cell pellet was then resuspended in 15 mL/L lysis buffer (10 mM Tris-HCl (pH 8 at 4° C.), 0.5 M NaCl, 5% glycerol, and 5 mM β-mercaptoethanol, supplemented with 2 mM PMSF). Cells were lysed by sonication on ice, and centrifuged at 21,000 g for 40 min at 4° C. The clarified lysate supernatant was then applied slowly to a 1 mL HisTrap HP column (GE Healthcare), and the column was washed with lysis buffer to allow for any non-his tagged proteins to flow through. Lysis buffer supplemented with imidazole was then used to elute the his-tagged sigA protein with a linear gradient of 10-100 mM imidazole. The eluted protein was concentrated using a 10 kDa MWCO Amicon® Ultra-15 Centrifugal Filter Unit, sterile filtered through 0.22 μm nitrocellulose, and applied to a HiPrep 16/60 Sephacryl S-200 HR size-exclusion column pre-equilibrated with the same running buffer used for elution (10 mM Tris-HCl (pH 8 at 4° C.), 200 mM NaCl, 5% glycerol, 0.1 mM EDTA, 5 mM DTT). Purified sigA was concentrated with another 10 kDa MWCO Amicon® Ultra-15 Centrifugal Filter Unit and frozen at −20° C.

In Vitro Transcription Assay

Inhibition of transcription by the MTB WT and $RIF^R$ RNAP enzymes was quantified using a previously developed plasmid-based transcription assay (Scharf, et al. SLAS Discovery 2017, 22 (3), 287-297). In this study, a previously modified version of the pTZ18U vector was used, containing the MTB rrnA P3 ribosomal RNA promoter followed by 4 repeats of DNA encoding malachite green aptamer (MGA) and 3 consecutive repeats of the synB artificial terminator sequence (Molodstov, et al. Molecular Microbiology 2017, 103 (6), 1034-1045). pMGA4-Mt-rrnA3-SynBx3 plasmid was purified using a QIAGEN® Giga Kit. In reaction buffer (40 mM Tris base (pH 7.5 at 37° C.), 10 mM $MgCl_2$, 0.1 mM EDTA, 25 μg/mL BSA, 1 mM DTT, 150 mM K-glutamate), enzyme, sigA and the pMGA4-Mt-rrnA3-SynBx3 plasmid were combined in a ratio of 1:3:1 respectively, with 15 nM or 20 nM enzyme. Total reaction volume was 50 or 25 μL, carried out in 96-well format using Corning 3686 black, flat bottom, half area microplates. Test compounds, rifampin, and 4% DMSO controls were added to the reaction buffer in the wells and allowed to incubate for 10 min at 37° C. NTP mix (ATP, CTP, GTP, UTP) was then added to a final concentration of 2 mM of each NTP to initiate transcription in the reaction mixture. The plates were incubated at 37° C. for 90 mins when testing against WT RNAP, and 180 min when testing against the $RIF^R$ βS450L MTB RNAP. The reaction was then quenched by placing the plates on ice for 5 min. Ice-cold malachite green was added to a final concentration of 75 mM, and allowed to incubate on ice for 10 min. Fluorescence was read using a BioTek Synergy H1 Hybrid Multi-Mode microplate reader, at excitation/emission wavelengths of 628/660 nm. Compounds were tested in triplicate at 10 concentrations against WT MTB RNAP (400-0.781 nM) and 11 concentrations against the βS450L MTB RNAP (1000-0.24 μM). One μM rifampin against WT MTB RNAP and blank 4% DMSO served as the positive and negative controls, respectively. Average fluorescence observed for each concentration of test compound was normalized to that of the DMSO control as percent enzyme activity, plotted as a function of log concentration. The plots were fit by non-linear regression to the following four-parameter equation using Prism (GraphPad Software).

$$\%\ \text{activity} = \text{min} + (\text{max} - \text{min}) / (1 + 10\hat{\ }((\log EC_{50} - X) * \text{Hill Slope}))$$

where max and min were the maximum and minimum plateaus of the % activity and X is the log of sample concentration. When unconstrained, the values of max, min, $EC_{50}$, and Hill slope are fit by the regression plot.

Data are shown in Table 3. The compounds inhibit the wild-type MTB RNAP in the $10^{-9}$ M (nM) range. It should be noted that the lower limit of detection of this assay is an $IC_{50}$ of ~5 nM. It is possible that the compounds have true $IC_{50}$s much lower than 5 nM. The $IC_{50}$ values for RMP and RLZ with the $Rif^R$ mutants of MTB were much higher (1.3 mM and 70 μM respectively). Most of the compounds have $IC_{50}$s for the β-S450L $Rif^R$ mutant in the 100-300 μM range, with some compounds having β-S450L $Rif^R$ mutant $IC_{50}$s less than 100 μM.

TABLE 3

In Vitro RNAP $IC_{50}$ Data (μM, except where noted)

| Cpd | *E. coli* WT (nM) | *E. coli* D516V | *E. coli* S531L | MTB WT (nM) | MTB D435V | MTB S450L |
|---|---|---|---|---|---|---|
| RMP | ND | ND | ND | <5 | 1.26 mM | 1.31 mM |
| RFB | ND | ND | ND | 28 | ND | 212 |
| RLZ | ND | ND | ND | 12 | ND | 70 |
| 5a | 6 | 27 | 790 | <5 | 400 | 610 |
| 5b | 7 | 65 | 390 | <5 | 240 | 580 |
| 5c | <5 | 22 | 300 | <5 | 190 | 200 |
| 5d | 6 | 29 | 440 | <5 | 190 | 380 |
| 5e | 7 | 23 | >1000 | <5 | 240 | 1000 |
| 6a | 6 | 39 | 80 | <5 | 120 | 140 |
| 6b | 6 | 51 | 52 | 7.0 | 110 | 170 |
| 6c | 10 | 12 | 230 | <5 | 140 | 420 |
| 6d | 8 | 59 | 93 | 6.0 | 160 | 240 |
| 11c | 19 | 8.8 | 330 | 8.0 | 61 | 640 |
| 11d | <5 | 0.9 | 94 | <5 | 21 | 180 |
| 11e | ND | ND | ND | 18 | ND | 159 |
| 11f | 10 | 39 | >500 | 7.0 | 7.4 | 340 |
| 11g | <5 | 0.58 | 28 | 7.0 | 7.2 | 94 |
| 12c | 14 | 17 | 66 | 5.0 | 20 | 150 |
| 16b | 5 | 24 | 160 | 5.0 | 53 | 220 |
| 16c | 5 | 10 | 92 | 5.0 | 43 | 150 |
| 16d | ND | ND | ND | 13 | ND | No IC50 fit |
| 16e | ND | ND | ND | 12 | ND | 14 |
| 17b | ND | ND | ND | 5.9 | ND | 16 |
| 17c | 20 | 12 | 100 | <5 | 44 | 74 |
| 17d | 16 | 7.3 | 32 | 6.0 | 57 | 110 |
| 17e | 14 | ND | ND | 7.8 | ND | 39 |
| 17f | ND | ND | ND | 12 | ND | 59 |
| 17g | ND | ND | ND | 7.7 | ND | 14 |
| 17h | ND | ND | ND | 26 | ND | 13 |
| 17i | ND | ND | ND | 18 | ND | 10 |
| 17j | ND | ND | ND | 10 | ND | 7.6 |
| 17k | ND | ND | ND | 15 | ND | 26 |
| 17l | ND | ND | ND | 13 | ND | 22 |
| 17m | ND | ND | ND | 9.6 | ND | 67 |
| 17n | ND | ND | ND | 8.9 | ND | 15 |
| 17o | ND | ND | ND | 28 | ND | 14 |
| 17p | ND | ND | ND | 11 | ND | 18 |
| 17q | ND | ND | ND | 18 | ND | 20 |
| 17r | ND | ND | ND | 9.8 | ND | 77 |
| 17s | ND | ND | ND | 12 | ND | 56 |
| 17t | ND | ND | ND | ND | ND | ND |
| 17u | ND | ND | ND | 27 | ND | 44 |
| 17v | ND | ND | ND | 27 | ND | 66 |
| 26c | ND | ND | ND | 6.9 | ND | 198 |
| 26d | ND | ND | ND | 4.8 | ND | 104 |
| 26e | ND | ND | ND | 7.4 | ND | 118 |
| 26f | ND | ND | ND | 8.2 | ND | 69 |
| 26g | ND | ND | ND | 15 | ND | 47 |
| 26h | ND | ND | ND | 17 | ND | 62 |

TABLE 3-continued

| In Vitro RNAP $IC_{50}$ Data (μM, except where noted) | | | | | | |
|---|---|---|---|---|---|---|
| Cpd | *E. coli* WT (nM) | *E. coli* D516V | *E. coli* S531L | MTB WT (nM) | MTB D435V | MTB S450L |
| 26i | ND | ND | ND | 24 | ND | 50 |
| 28 | ND | ND | ND | 24 | ND | 99 |
| 29a | ND | ND | ND | 6.5 | ND | 144 |
| 29b | ND | ND | ND | 9.0 | ND | 107 |
| 29c | ND | ND | ND | 11 | ND | 74 |
| 29d | ND | ND | ND | 8.5 | ND | 234 |
| 29e | ND | ND | ND | 8.5 | ND | 73 |
| 29f | ND | ND | ND | 16 | ND | 50 |
| 29g | ND | ND | ND | 20 | ND | 41 |
| 29h | ND | ND | ND | 22 | ND | 45 |
| 30b | ND | ND | ND | ND | ND | ND |
| 30c | 6 | 10 | 130 | <5 | 25 | 200 |
| 30d | ND | ND | ND | ND | ND | ND |
| 30e | ND | ND | ND | 12 | ND | 435 |
| 30f | ND | ND | ND | 6.9 | ND | 174 |
| 30g | ND | ND | ND | 7.0 | ND | 170 |
| 30h | ND | ND | ND | 7.1 | ND | 121 |
| 32 | 10 | 30 | 330 | 6.0 | 260 | 320 |

Human Pregnane X Receptor (hPXR) Activation and DPX2 Cell Toxicity Assay

The ability of specific compounds to activate the human pregnane X receptor (hPXR) was analyzed using DPX2 cells, a HepG2-derived cell line stably integrated with the hPXR gene (NR1I2) plus a luciferase reporter gene linked to two promotors of the CYP3A4 gene. The effect of these analogues on the viability of DPX2 cells was also assessed. These cells are available from Puracyp, Inc., as part of an hPXR activation assay system (Product DPX2-96-001) which also contains the materials needed to perform the reporter assays in a 96-well format. The manufacturer's protocol was followed with modifications made to the recommended dosage scheme.

The DPX2 cells, provided by the vendor in the assay kit (1 mL containing approximately 6 million cells), were allowed to thaw at room temperature or in a 37° C. water bath. Under sterile conditions within a biosafety cabinet, the cells were mixed with 10 mL culture media. 100 μL were transferred to each well of a 96-well plate, and the plate was incubated overnight at 37° C. in a 5% $CO_2$ incubator. The following day, dilutions of the test compounds and a provided rifampin control were prepared in neat DMSO following the scheme provided in the manual, with alterations made to allow for use of 25 mM stock concentrations of the test compounds rather than 100 mM. Dosing media was allowed to thaw at room temperature or in a 37° C. water bath, and different doses of the test compounds (100, 25, 6.25, 1.56, 0.39, and 0.098 μM) and rifampin (20, 10, 5, 1, 0.5, and 0.1 μM) were prepared in this media. The culture media was gently removed from all wells on the plate and disposed. 100 μL of dosing media containing the various dosages of test compounds and rifampin control were added to each well. On a single 96-well plate, the rifampin control and each of three analogues were added at 6 concentrations, each in triplicate, along with multiple 0.4% DMSO and blank dosing media controls. The plate was incubated at 37° C. in a 5% C02 incubator for 24 hours. The following day, CellTiter-Fluor™ and CellTiter-Fluor buffer were thawed at room temperature and mixed. The dosing media was gently removed from each of the wells and disposed, and 100 μL of CellTiter-Fluor™ mix was added to each well. The plate was incubated for 1 hour at 37° C. and 5% C02. Using a BioTek™ Synergy™ H1 Hybrid Multi-Mode Microplate Reader, the fluorescence across the wells was measured at excitation/emission wavelengths of 390/505 nm and a gain of 60. At this point, ONE-Glo™ assay substrate and ONE-Glo™ buffer had been thawed at room temperature and mixed, and 100 μL of this mixture was added to each of the wells. The plate was allowed to incubate at room temperature for 5 minutes, and using the same plate reader, was shaken linearly for 5 seconds at a frequency of 567 cpm. The luminescence was then measured with an integration time of 5 seconds and gain of 200.

The average of all luminescence readings and all fluorescence readings across the plate For the DMSO controls were used as the relative luminescence units (RLU) and relative fluorescence units (RFU) of the DMSO control. The RLU and RFU's for each dose of rifampin and each of the tested compounds were calculated in the same fashion. Normalized luciferase activity was calculated as (RLU/RFU) for the DMSO controls, and for each dose of rifampin and each of the tested compounds. The normalized luciferase activity (RLU/RFU) was divided by the normalized DMSO control to represent the data as 'fold activation' relative to the control. hPXR fold activation was plotted and fit as described above for in vitro transcription assays.

Data are shown in Table 4. RMP, as previously known, exhibits a high maximal degree of activation (~13-fold at 5 μM) and an $EC_{50}$ of ~2 μM. RLZ has been reported to have essentially no ability to activate hPXR. This data confirms that at concentrations lower than 100 M, RLZ exhibits no activation of hPXR. At 100 μM, RLZ does show ~2-fold activation; however, it also shows ~2-fold loss of cell viability (suggesting cytotoxicity) at 100 pt. For the new compounds, at position $R^1$, piperazines with 4-acetyl or larger amides exhibit negligible hPXR activation. Longer substituents on the piperazine 4-position also maintain negligible hPXR activation, indicating that the $R_1$ position is viable for elaboration to both minimize hPXR activation and to improve RNAP inhibition.

Potential toxicity of the analogues on the DPX2 cells was assessed by evaluating their percent viability after having been dosed with the compounds for 24 hours. Using the same fluorescence data points collected for hPXR activation assessment, this was calculated as the average fluorescence value measured at each concentration of compound or rifampin control, divided by that of the DMSO control. These data are also shown in Table 4.

TABLE 4

| hPXR Activation and Cytotoxicity | | | | | | | |
|---|---|---|---|---|---|---|---|
| | hPXR | | | | Cytotoxicity | | |
| Cpd | Fold Act. (lucif) @ 6.25 μM | Fold Act. (CYP 3A4) @ 6.25 μM | Fold Act. (lucif) @ 25 μM | Fold Act. (CYP 3A4) @ 25 μM | DPX2 Viability @ 6.25 μM | DPX2 Viability @ 25 μM | Vero Cell ($IC_{50}$, μM) |
| RMP | 12.9 (5 μM) | 26.9 (5 μM) | 19.9 (20 μM) | 26.0 (20 μM) | 104% (5 μM) | 96% (20 μM) | >100 |
| RLZ | 1.5 | 1.2 | 2.0 | 2.7 | 108% | 96% | ND |
| RFP | 13.4 | 20.3 | 18.6 | 20.5 | 104% | 105% | ND |
| RFB | 8.8 | 14.5 | 5.3 | 6.9 | 117% | 107% | ND |

TABLE 4-continued hPXR Activation and Cytotoxicity

| Cpd | hPXR Fold Act. (lucif) @ 6.25 μM | hPXR Fold Act. (CYP 3A4) @ 6.25 μM | hPXR Fold Act. (lucif) @ 25 μM | hPXR Fold Act. (CYP 3A4) @ 25 μM | Cytotoxicity DPX2 Viability @ 6.25 μM | Cytotoxicity DPX2 Viability @ 25 μM | Cytotoxicity Vero Cell ($IC_{50}$, μM) |
|---|---|---|---|---|---|---|---|
| 5a | 5.3 | ND | 0.4 | ND | 87% | 47% | >8 |
| 5b | 3.3 | ND | 0.3 | ND | 81% | 45% | >8 |
| 5c | ND | ND | ND | ND | ND | ND | 6.2 |
| 5d | 6.4 | ND | 4.3 | ND | 102% | 59% | >8 |
| 5e | 5.4 | ND | 0.8 | ND | 106% | 83% | >8 |
| 6a | 3.3 | ND | 8.0 (22 μM) | ND | 102% | 86% | >8 |
| 6b | 7.6 | ND | 0.8 | ND | 120% | 57% | >8 |
| 6c | 2.7 | ND | 8.3 | ND | 108% | 111% | 53 |
| 6d | 2.2 | ND | 5.9 | ND | 104% | 90% | >8 |
| 11c | 7.3 | ND | 6.9 | ND | 103% | 70% | >8 |
| 11d | 3.3 | ND | 0.9 | ND | 77% | 33% | 19.1 |
| 11e | 2.1 | ND | 6.7 | ND | 105% | 96% | >8 |
| 11f | 5.3 | ND | 0.4 (21 μM) | ND | 103% | 57% (21 μM) | 6.2 |
| 11g | 3.1 | ND | 2.5 | ND | 88% | 70% | >32 |
| 12c | 1.1 | ND | 1.2 | ND | 107% | 95 | >8 |
| 16b | 2.5 | ND | 3.4 | ND | 117% | 76 | >8 |
| 16c | 2.3 | ND | 0.4 | ND | 96% | 55 | >8 |
| 16d | 2.1 | ND | 0.9 | ND | 79% | 59% | >10 |
| 16e | 4.2 | ND | 0.3 | ND | 63% | 41% | >10 |
| 17b | 1.8 | ND | 1.0 | ND | 109% | 45% | 7.9 |
| 17c | 1.4 | ND | 4 | ND | 102% | 94 | >8 |
| 17d | 1.5 | ND | 0.3 | ND | 104% | 84 | >8 |
| 17e | 1.6 | ND | 2 | ND | 113% | 95% | >10 |
| 17f | 1.3 | ND | 1.6 | ND | 85% | 71% | >10 |
| 17g | 1 | ND | 1.2 | ND | 117% | 56% | >10 |
| 17h | 1.2 | ND | 1.2 | ND | 94% | 83% | >10 |
| 17i | 1 | ND | 1.2 | ND | 106% | 100% | >10 |
| 17j | 1.2 | ND | 2.7 | ND | 2% | 126% | >10 |
| 17k | 1 | ND | 2 | ND | 131% | 34% | >10 |
| 171 | 1.1 | ND | 1.9 | ND | 107% | 102% | >10 |
| 17m | 1.2 | ND | 1.5 | ND | 89% | 78% | >10 |
| 17n | 1.1 | ND | 1.2 | ND | 102% | 98% | >10 |
| 17o | 2.9 | ND | 0.3 | ND | 96% | 42% | >10 |
| 17p | 1.4 | ND | 1.1 | ND | 116% | 80% | >10 |
| 17q | 1.3 | ND | 1.4 | ND | 100% | 98% | >10 |
| 17r | 1 | ND | 1 | ND | 105% | 94% | >10 |
| 17s | 1.4 | ND | 1.5 | ND | 102% | 86% | >10 |
| 17t | 1.3 | ND | 2.1 | ND | 100% | ND | 55 |
| 17u | 1.3 | ND | 2.2 | ND | 106% | 90% | ND |
| 17v | 1.2 | ND | 1.6 | ND | 110% | 100% | >10 |
| 26c | 3.6 | ND | 5.5 | ND | 108% | 96% | ND |
| 26d | 1.6 | ND | 0.8 | ND | 106% | 88% | ND |
| 26e | 1.2 | ND | 0.9 | ND | 101% | 97% | ND |
| 26f | 2.5 | ND | 4.5 | ND | 111% | 102% | ND |
| 26g | 2.8 | ND | 1. | ND | 111% | 105% | ND |
| 26h | 2.9 | ND | 4.4 | ND | 118% | 110% | ND |
| 26i | 2.8 | ND | 4.6 | ND | 120% | 102% | ND |
| 28 | 5.3 | ND | 9.8 | ND | 110% | 109% | >10 |
| 29a | 1.2 | ND | 2 | ND | 144% | 149% | >10 |
| 29b | 1.2 | ND | 2.6 | ND | 136% | 128% | >10 |
| 29c | 2.1 | ND | 3.3 | ND | 121% | 114% | >10 |
| 29d | 2.1 | ND | 4.8 | ND | 114% | 101% | >10 |
| 29e | 1.4 | ND | 1.7 | ND | 112% | 99% | ND |
| 29f | 1.1 | ND | 3.6 | ND | 126% | 131% | >10 |
| 29g | 1.8 | ND | 3.6 | ND | 100% | 101% | >10 |
| 29h | 1.3 | ND | 1.9 | ND | 109% | 98% | >10 |
| 30a | 4.6 | ND | 20.4 | ND | 92% | 47 | >8 |
| 30b | ND | ND | ND | ND | ND | ND | >8 |
| 30c | 9.7 | ND | 14 | ND | 93% | 49 | >8 |
| 30d | ND | ND | ND | ND | ND | ND | >8 |
| 30e | 1.9 | ND | 9.2 | ND | 130% | 119% | >10 |
| 30f | 4.8 | ND | 0.5 | ND | 98% | 64% | >10 |
| 30g | 5.8 | ND | 2.4 | ND | 99% | 61% | >10 |
| 30h | 5.2 | ND | 6.1 | ND | 100% | 57% | >10 |
| 32 | 1.3 | ND | 3.3 | ND | 116% | 100 | >8 |

Vero Cell Toxicity

Cytotoxicity for a mammalian cell line was determined by exposing VERO cells (ATCC CRL-81) to serial dilutions of test compounds for 72 hours, followed by addition of resazurin and measurement of fluorescence after 4 hours incubation (Choules, et al., *Antimnicrob. Agents Chemother.* 2019, 63, e02204-02218). The $IC_{50}$ was defined as the concentration effecting a reduction in fluorescence of 50% relative to untreated cells. Data are shown in Table 4.

Minimum Inhibitory Concentration ($MRC_{90}$) and Minimum Bactericidal Concentration ($MBC_{99}$)

All compounds were evaluated for MIC vs. MTB H37Rv ATCC 27294 using the microplate Alamar Blue assay (MABA) (Cho et al. Antimicrobial Agents and Chemotherapy 2015, 1285, 281-92). The MIC was defined as the lowest concentration effecting a reduction in fluorescence of ≥90% relative to untreated bacteria controls. Activity against non-replicating cultures of *M. tuberculosis* H37Rv transformed with lux ABCDE (Andreu, et al., PLoS One 2010, 5, e10777) was determined using the low oxygen recovery (LORA) in vitro assay (Cho et al. *Antimicrob. Agents Chemother.* 2015, 1285, 281-92). The MIC was defined as the lowest concentration effecting a reduction in luminescence of ≥90% relative to untreated bacteria controls.

Minimum bactericidal concentration (MBC, CFU Assay) was determined by incubating test compounds with *M. tuberculosis* H37Rv for one week at 37° C. (Choules, et al., *Antimicrob. Agents Chemother.* 2019, 63, e02204-02218). Cultures were centrifuged, and pellets resuspended and serially diluted in phosphate-buffered saline and then plated on Middlebrook 7H11 agar. Colonies were enumerated following 2-3 weeks incubation at 37° C. The MBC was defined as the lowest concentration effecting a reduction in colony forming units of ≥99% relative to that observed prior to incubation with test compounds.

Time-kill studies were performed with *M. tuberculosis* transformed with luxABCDE (Andreu, et al., *PLoS One* 2010, 5, e10777) and determining luminescence at selected time intervals. The MBC (Lux Assay) at a given time point was defined as the lowest concentration effecting a reduction in luminescence of ≥99% relative to that observed prior to the addition of test compounds.

Data are shown in Table 5. The majority of the new compounds have MICs for WT MTB in the 1-10 nM range. MBCs for a number of the compounds are in the 10-50 nM range. Compounds with acidic functionalities at $R^1$ or $R^2$ and exhibited poor MICs and MBCs. A number of compounds have MBCs ~5-fold better than that of rifampin, including compounds 17b and 17e.

TABLE 5

MIC and MBC Data

| | $MIC_{90}$ | | | | | $MBC_{99}$ Day 7 (Lux Assay) | | $MBC_{99}$ Day 7 (CFU Assay) | |
|---|---|---|---|---|---|---|---|---|---|
| Cpd | MABA (nM) | LORA (nM) | LORA/MABA | MABA Rel to RMP | LORA Rel to RMP | MBC (nM) | MBC Rel to RMP | $MBC_{99}$ (CFU, nM) | $MBC_{99}$ Rel to RMP |
| RMP | 27 | 206 | 7.6 | 1 | 1 | 463 | 1 | 130 | 1 |
| RFB | 2.4 | 2.3 | 0.94 | 0.09 | 0.01 | 10 | 0.02 | ND | ND |
| RLZ | 1.1 | 2.2 | 2.0 | 0.04 | 0.01 | 30 | 0.07 | ND | ND |
| 5a | 92 | 186 | 2.0 | 3.1 | 0.57 | ND | ND | 100 | 0.77 |
| 5b | 21 | 50 | 2.4 | 0.70 | 0.15 | ND | ND | 50 | 0.38 |
| 5c | 24 | 58 | 2.4 | 0.89 | 0.22 | ND | ND | 100 | 0.77 |
| 5d | ND | ND | ND | ND | ND | ND | ND | ND | ND |
| 5e | 82 | 47 | 0.57 | 1.4 | 0.27 | 40 | 0.09 | ND | ND |
| 6a | 92 | 186 | 2.0 | 0.80 | 0.07 | ND | ND | 10 | 0.08 |
| 6b | 21 | 50 | 2.4 | 1.6 | 0.05 | ND | ND | 30 | 0.23 |
| 6c | 39 | 21 | 0.5 | 2.7 | 0.14 | ND | ND | 50 | 0.38 |
| 6d | 24 | 58 | 2.4 | 1.3 | 0.06 | ND | ND | 30 | 0.23 |
| 11c | 58 | 123 | 2.1 | 1.4 | 0.53 | ND | ND | ND | ND |
| 11d | 16 | <100 | ND | 0.43 | ND | 58 | 0.08 | ND | ND |
| 11e | 48 | 78 | 1.6 | 0.93 | 0.26 | ND | ND | 20 | 0.15 |
| 11f | 24 | 370 | 15 | 0.65 | 0.39 | 84 | 0.11 | ND | ND |
| 11g | 11 | 131 | 12 | 0.30 | 1.1 | 44 | 0.06 | ND | ND |
| 12c | 4.8 | <16 | ND | 0.12 | 0.11 | 37 | 0.08 | <20 | <0.08 |
| 16b | 29 | 57 | 2.0 | 1.6 | 0.93 | ND | ND | 20 | 0.15 |
| 16c | 19 | 32 | 1.7 | 0.51 | 0.16 | 61 | 0.08 | ND | ND |
| 16d | 3.7 | 31 | 8.4 | 0.07 | 0.62 | 92 | 0.20 | ND | ND |
| 16e | 6.4 | 36 | 5.6 | 0.16 | 1.3 | 60 | 0.14 | ND | ND |
| 17b | <16 | <16 | ND | 0.24 | 1.3 | ND | ND | 20 | 0.15 |
| 17c | 23 | 29 | 1.3 | 1.3 | 0.48 | ND | ND | 20 | 0.15 |
| 17d | <16 | <16 | ND | ND | ND | ND | ND | 20 | 0.15 |
| 17e | 5.0 | 9.4 | 1.9 | 0.12 | 0.11 | 93 | 0.20 | ND | ND |
| 17f | 27 | 369 | 14 | 1.0 | 1.8 | >100 | ND | ND | ND |
| 17g | 12 | 65 | 5.4 | 0.4 | 0.3 | >100 | ND | ND | ND |
| 17h | 35 | 318 | 9.0 | 1.3 | 12 | >100 | ND | ND | ND |
| 17i | 26 | 247 | 9.5 | 1.0 | 9.2 | >>100 | ND | ND | ND |
| 17j | >10 | >20 | ND | ND | ND | >>100 | ND | ND | ND |
| 17k | 300 | >20 | ND | 11 | ND | >100 | ND | ND | ND |
| 17l | 187 | 843 | 4.5 | 7.0 | 31 | >100 | ND | ND | ND |
| 17m | 17 | 72 | 4.2 | 0.34 | 1.4 | 217 | 0.48 | ND | ND |
| 17n | 73 | 235 | 3.2 | 1.5 | 4.7 | 315 | 0.70 | ND | ND |
| 17o | 55 | 106 | 19 | 1.1 | 2.1 | 128 | 0.28 | ND | ND |
| 17p | 9.4 | 35 | 3.7 | ND | ND | 92 | 0.20 | ND | ND |
| 17q | 415 | >20 | ND | 16 | ND | >100 | ND | ND | ND |
| 17r | 23 | 130 | 5.7 | 0.46 | 2.60 | 205 | 0.46 | ND | ND |

TABLE 5-continued

MIC and MBC Data

| | $MIC_{90}$ | | | | | $MBC_{99}$ Day 7 (Lux Assay) | | $MBC_{99}$ Day 7 (CFU Assay) | |
|---|---|---|---|---|---|---|---|---|---|
| Cpd | MABA (nM) | LORA (nM) | LORA/ MABA | MABA Rel to RMP | LORA Rel to RMP | MBC (nM) | MBC Rel to RMP | $MBC_{99}$ (CFU, nM) | $MBC_{99}$ Rel to RMP |
| 17s | 18 | 30 | 1.7 | 0.36 | 0.60 | 84 | 0.19 | ND | ND |
| 17t | 32 | 59 | 1.8 | 0.6 | 1.2 | 86 | 0.12 | ND | ND |
| 17u | ND | ND | ND | ND | ND | 25 | 0.05 | ND | ND |
| 17v | ND | ND | ND | ND | ND | >100 | ND | ND | ND |
| 26c | ND | ND | ND | ND | ND | ND | ND | ND | ND |
| 26d | 9.4 | >20 | ND | 0.35 | ND | >>100 | ND | ND | ND |
| 26e | 9.4 | >20 | ND | 0.35 | ND | 87 | 0.19 | ND | ND |
| 26f | 4.6 | 9.5 | 2.1 | 0.17 | 0.05 | 43 | 0.09 | ND | ND |
| 26g | 5.0 | 9.6 | 1.9 | 0.18 | 0.05 | 43 | 0.09 | ND | ND |
| 26h | 4.9 | 9.4 | 1.9 | 0.18 | 0.05 | 28 | 0.06 | ND | ND |
| 26i | 4.7 | 9.3 | 2.0 | 0.17 | 0.05 | 47 | 0.10 | ND | ND |
| 28 | 4.4 | 9.2 | 2.1 | 0.16 | 0.04 | 25 | 0.05 | ND | ND |
| 29a | 36 | 126 | 3.5 | 1.33 | 0.61 | ND | ND | 20 | 0.15 |
| 29b | 8.7 | 6 | 0.7 | 0.32 | 0.03 | 50 | 0.11 | ND | ND |
| 29c | 4.9 | 9.6 | 2.0 | 0.18 | 0.05 | 48 | 0.10 | ND | ND |
| 29d | 37 | 53 | 1.4 | 1.37 | 0.20 | ND | ND | 80 | 0.62 |
| 29e | 2 | 8 | 4.0 | 0.07 | 0.03 | 50 | 0.11 | ND | ND |
| 29f | 238 | 1066 | 4.5 | 8.9 | 40 | >100 | ND | ND | ND |
| 29g | 51 | 280 | 5.4 | 1.9 | 10 | >100 | ND | ND | ND |
| 29h | 18 | 133 | 7.2 | 0.69 | 5.0 | >100 | ND | ND | ND |
| 30a | <16 | <16 | ND | <0.6 | <0.06 | ND | ND | ND | ND |
| 30b | 37 | 114 | 3.1 | 1.37 | 0.44 | ND | ND | ND | ND |
| 30c | <16 | <16 | ND | <0.6 | <0.06 | ND | ND | ND | ND |
| 30d | <16 | 17 | ND | <0.6 | 0.07 | ND | ND | ND | ND |
| 30e | 84 | 180 | 2.1 | 3.11 | 0.87 | 490 | 1.06 | ND | ND |
| 30f | 44 | 117 | 2.7 | 1.63 | 0.57 | 110 | 0.24 | ND | ND |
| 30g | 26 | 32 | 1.2 | 0.96 | 0.16 | ND | ND | <20 | <0.08 |
| 30h | 19 | 42 | 2.2 | 0.70 | 0.20 | ND | ND | <20 | <0.08 |
| 32 | 47 | 118 | 2.5 | 1.74 | 0.45 | ND | ND | ND | ND |

Time-Kill MIC and MBC of 17e

Figure 2:
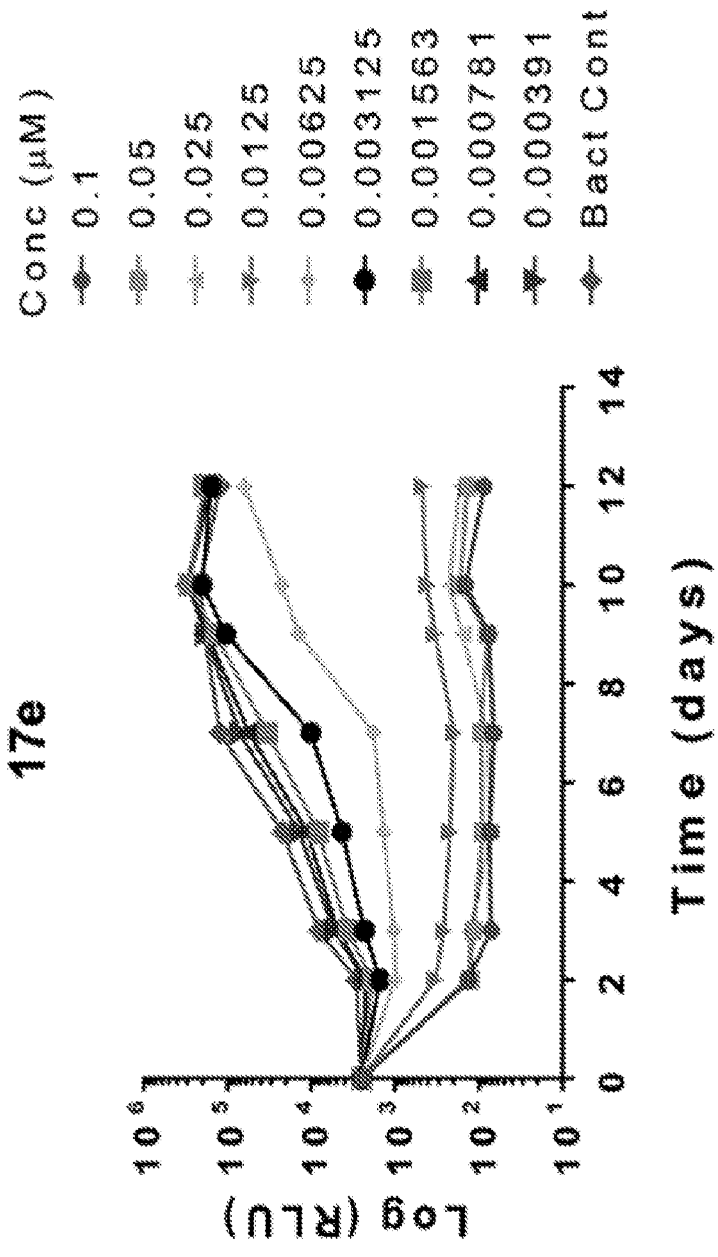
FIG. 2 shows data from a time-kill study of Compound 17e.

Compound 17e was subjected to a time-kill study where MIC and MBC were determined at day 7 of treatment in comparison to RMP and three other anti-TB drugs (Table 6 and FIG. 2). Time-kill studies were performed with *M. tuberculosis* transformed with luxABCDE (*Plos One* 2010, 5 (5), e10777) and determining luminescence at selected time intervals (*Antimicrob. Agents Chemother.* 2021, 65 (8), e0028221). The MBC at a given time point was defined as the lowest concentration effecting a reduction in luminescence of ≥99% relative to that observed prior to the addition of test compounds. Compound 17e was approximately 10-fold more potent than RMP in terms of day 7 MBC.

TABLE 6

MIC and MBC values for 17e, RMP, and other TB drugs from day 7 of a time-kill study
Day 7 MIC and MBC

| Compound ID | $MIC_{90}$ (nM) | $MBC_{99}$ (nM) |
|---|---|---|
| 17e | 9.0 | 93 |
| RMP | 30 | 463 |
| Isoniazid | 409 | 3586 |
| Bedaquiline | 31 | 124 |
| Pretomanid | 470 | 597 |

Cryo-Electron Microscopy (Cryo-EM) Structure of 17e Bound to an *E. coli* RNAP•DNA Complex To validate the specific binding of 17e to RNAP and to provide a structural basis for advanced analogue design, the Murakami lab determined the cryo-EM structure of 17e bound to an *E. coli* RNAP-DNA complex. *E. coli* RNAP•$\sigma^{70}$ holoenzyme (15 μM) was mixed with double-stranded DNA containing the rrnBP1 promoter (15 μM) in a buffer containing 5 mM $MgCl_2$, 10 mM HEPES pH 8.0, 50 mM NaCl, 0.1 mM EDTA, and 5 mM DTT and incubated at 37° C. for 5 min to form an open promoter complex. The compound 17e (final concentration 200 μM) was added to the RNAP•DNA complex and incubated at room temperature (rt) for 10 min. CHAPSO (8 mM) was added to the sample and incubated at rt for 10 min. Immediately after the 10 min incubation, 3.5 μL samples were applied to a glow-discharged C-Flat Holey Carbon grid (Cu 2/1, 400 mesh), blotted and plunge-frozen in liquid ethane using Vitrobot Mark IV (FEI, USA) at 100% humidity and 4° C. Cryo-EM data was collected using the Titan Krios (Thermo Fisher) microscope equipped with a K3 direct electron detector (Gatan) at the National Cancer Institute's Cryo-EM facility at Frederick, MD. The grid was imaged at 300 keV, with a defocus range of −1.0 μm to −2.25 μm and 81,000× magnification in electron counting mode (image pixel size=1.12 Å) with a nominal dose of 45 $e^-/Å^2$. A total of 3,110 movies were acquired.

The data were processed using cryoSPARC V3.0.0 (Punjani, et al., Nat Methods 2017, 14, 290-296). The movies were aligned and dose-weighted using Patch-motion correction and Patch-CTF estimation (Rohou and Grigorieff, J Struct Biol 2015, 192, 216-221, Rubinstein and Brubaker, J Struct Biol 2015, 192, 188-195), followed by discarding low quality micrographs that had large motions or poor CTF resolution through manual curate exposure job. A total of 2,952 movies were selected for further processing. A total of 490,843 particles were auto picked and extracted using Topaz (Bepler, et al., Nat Methods 2019, 16, 1153-1160)

with a pre-trained model and classified to hundred 2D classes. The extracted particles were classified to five 3D classes using four ab initio maps that were generated using 22 excluded 2D classes (99,692 particles) and a map of *E. coli* apo-form RNAP as reference models. The class corresponding to the RNAP was selected (285,262 particles) and refined by optimal per-particle defocus using local CTF and non-uniform refinements. The nominal resolution of the cryo-EM map was estimated by 0.143 gold standard Fourier Shell Correlation (FSC) cut off. To refine the structure, the *E. coli* RNAP holoenzyme crystal structure (PDB: 4YG2, Murakami, J Biol Chem 2013, 288, 9126-9134) was fit into the cryo-EM density map using Chimera (Pettersen, et al. *J Comput Chem* 2004, 25, 1605-1612), followed by manually building 17e and DNA using Coot (Emsley and Cowtan, *Acta Crystallogr D Biol Crystallogr* 2004, 60, 2126-2132). The structure was real-space refined by using rigid-body refinement, secondary structure, Ramachandran, rotamer and reference model restraints in Phenix (Afonine, et al., *Acta Crystallogr D Biol Crystallogr* 2010, 66, 1153-1163).

Figure 3:
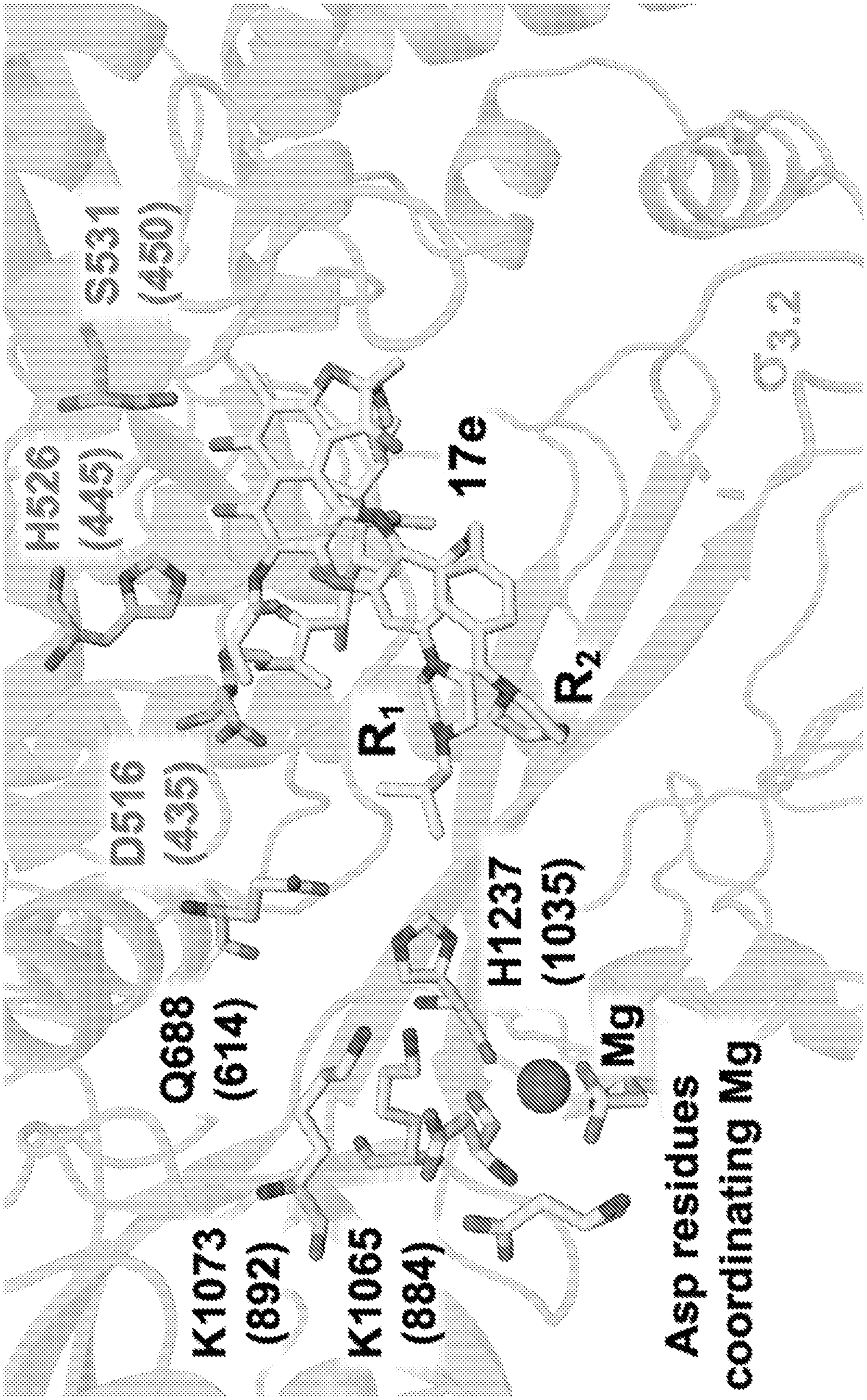
FIG. 3 shows a portion of the cryo-electron microscopy (cryo-EM) structure of a compound disclosed herein (Compound 17e) with the RNAP from *E. coli* in complex with DNA.

The RMP-binding pocket of RNAP is highly conserved in bacteria, therefore, the structure of *E. coli* RNAP-DNA and compound 17e complex can provide a framework for understanding its interaction with MTB RNAP. The cryo-EM map shows a clear density for 17e at the RMP-binding pocket of p subunit of RNAP (FIG. 3). The naphthalene core of the compound 17e fits into the RMP-binding pocket of RNAP similar to rifampin. Additionally, two large, modified side chains attached to the naphthalene ring extend toward the σ region 3.2 and the active site of RNAP. The density of the σ region 3.2 is disordered and of the template DNA is not traceable, suggesting the compound 17e prevented the formation of a stable open promoter complex. These unique interactions by the large substitutions are likely responsible for the enhanced activity (e.g., smaller $IC_{50}$) against the β-S450L mutant relative to RMP. The structure reported here also provides structural information for guiding the design of advanced analogues with improved activity.

Example 3: In Vivo Studies

Mouse Pharmacokinetics Study (BioDuro)

The solubility of Compound 17e in 11 different vehicles was determined and the vehicle PEG-200/water (80/20) was selected for oral dosing. For i.v. dosing, the vehicle DMSO/PEG-400/PBS (1×) (5/60/35) was used. Female ~20 g BALB/c mice (7-9 weeks old) were used in the study. Three mice were used for each set of conditions. Compound 17e was dosed at 100 mg/kg oral and 2.5 mg/kg i.v. once per day for 1 day and for 5 days. Plasma concentrations were determined over 24 hrs in the single day study and on days 1 and 5 in the 5 day study. Lung exposure was also determined in the 1 day study at 24 hrs post dosing and on day 5 of the 5 day study at 4 hrs and 24 hrs post dosing. Compound concentrations were determined by reverse phase HPLC-MS against a standard curve.

Figure 4:
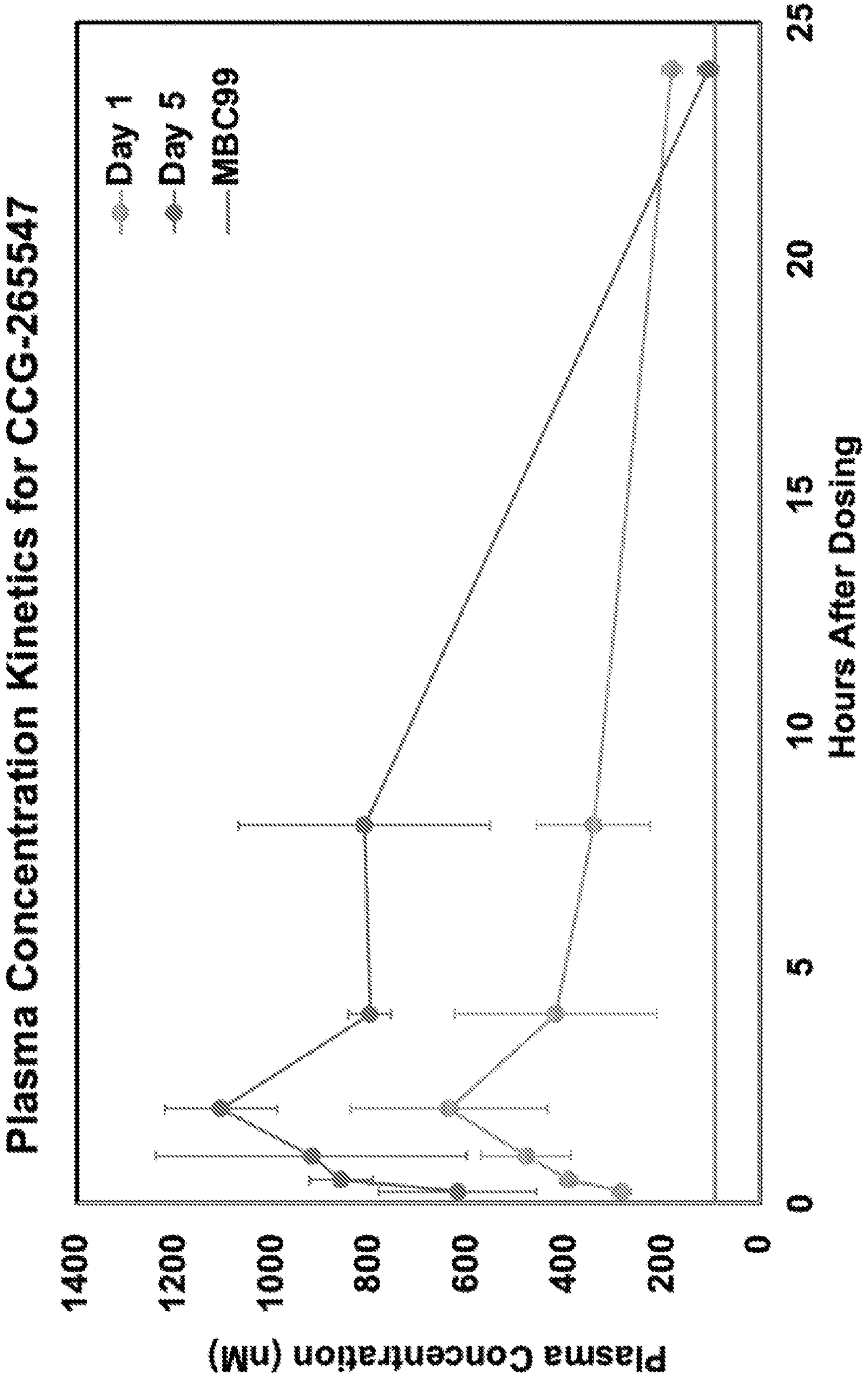
FIG. 4 shows plasma concentration kinetics data for Compound 17e.

Data are shown in FIG. 4 and in Table 7. Compound 17e showed excellent pharmacokinetics in the mouse study. The compound plasma concentration remained well above the $MBC_{99}$ threshold (93 nM) for 24 hrs after a single oral dose of 100 mg/kg. Lung exposure on day 1 and day 5 at 4 hrs post dosing was 2-3 times the $MBC_{99}$. Only at 24 hrs post dosing on day 5, did Compound 17e lung exposure drop below the $MBC_{99}$.

TABLE 7

Plasma and Lung Exposure for Compound 17e

| | ng/mL | | nM | |
|---|---|---|---|---|
| | Avg | SD | Avg | SD |
| Day 1 | One Day Study | | | |
| Plasma, 24 hr | 327 | 73 | 289 | 65 |
| Lung Homogenate, 24 hr | 164 | 54 | 145 | 48 |
| Day 1 | Five Day Study | | | |
| Plasma, 4 hr | 360 | 124 | 319 | 110 |
| Lung Homogenate, 4 hr | 248 | 162 | 219 | 144 |
| Day 5 | Five Day Study | | | |
| Plasma, 4 hr | 688 | 176 | 608 | 155 |
| Lung Homogenate, 4 hr | 323 | 76 | 286 | 67 |
| Plasma, 24 hr | 121 | 23 | 107 | 20 |
| Lung Homogenate, 24 hr | 41 | 4 | 36 | 4 |

Mouse Acute Efficacy Study

Female ~20 g BALB/c mice were infected by aerosol with *M. tuberculosis* Erdman resulting in the deposition of approximately 100 bacilli into the lungs, and the course of infection was then followed by plating homogenates of the lungs on 7H11 agar and determining CFU. Controls consisted of mice treated with the vehicle only. The compounds were prepared weekly in 80% PEG 200 such that the target dosages were obtained by once-daily dosing by oral gavage of 200 μL. Groups of 7 mice were dosed for 5 consecutive days each week for 3 weeks. Mice were sacrificed 3 days after the final dose to minimize carryover from the lung homogenates to the plating medium. Both lungs were homogenized and diluted in Hanks' balanced salt solution (HBSS)-Tween, and aliquots were plated on Middlebrook 7H11 medium. CFU were determined after 3 weeks of incubation at 37° C.

Figure 5:
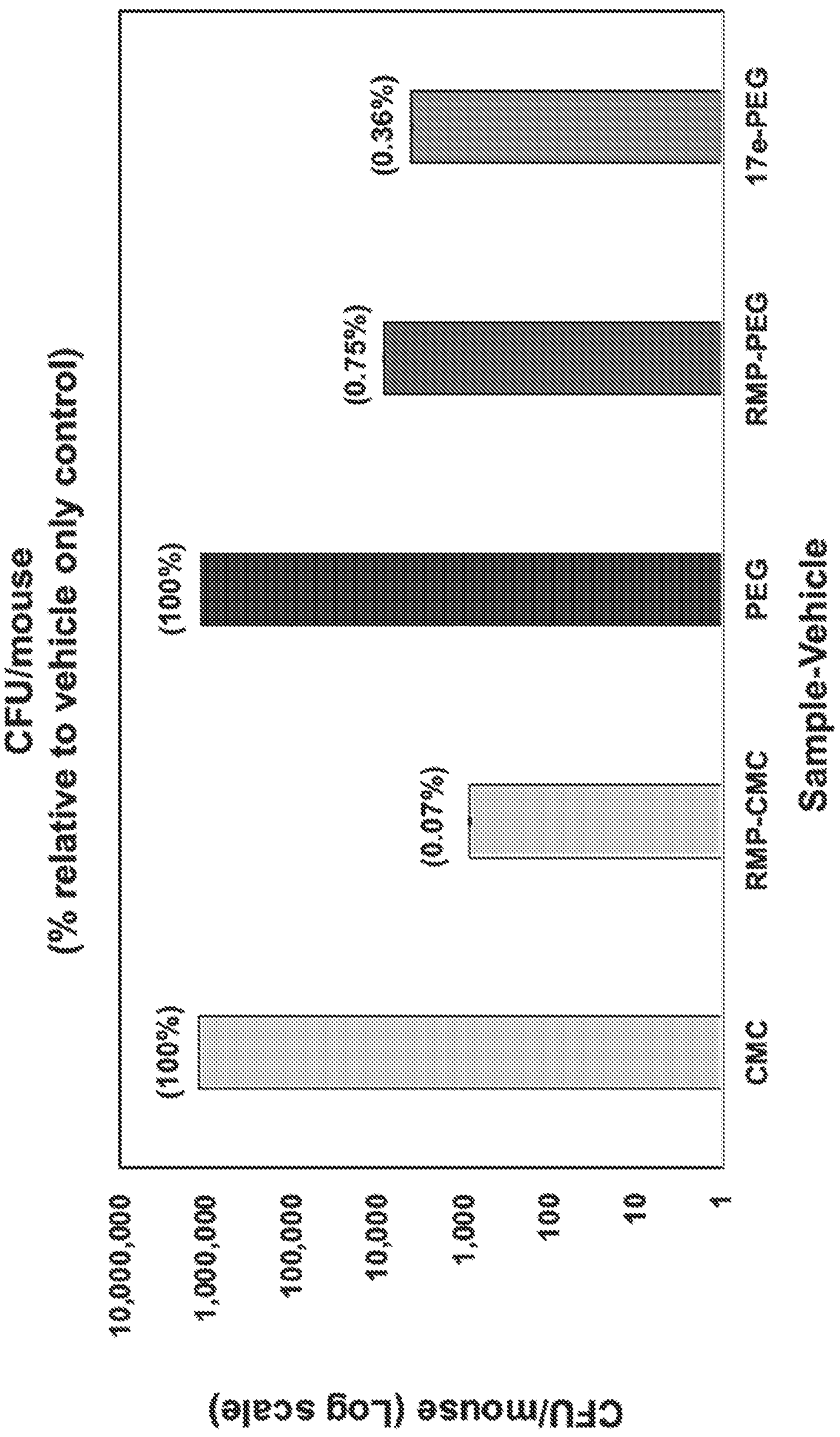
FIG. 5 shows data from an acute efficacy study of Compound 17e and rifampin.

Results are shown in FIG. 5 and Table 8. Compound 17e exhibited excellent efficacy and safety in an acute efficacy study in mice. At 100 mg/kg PO, Compound 17e was at least equal in effectiveness to a rifampin control at 15 mg/kg in the same vehicle. Given the dramatic reduction in CFU relative to the no-treatment control (>99.5% reduction), it is quite possible that Compound 17e would have similar efficacy at lower doses. There were no adverse effects noted in the mice over the 3-week treatment period and the mice actually gained a small amount of weight (0.6-0.7 gm) in both the RMP and Compound 17e treatment arms. This extremely encouraging study demonstrates in vivo efficacy and safety of Compound 17e.

TABLE 8

Acute Efficacy Study Data

| Day | ID | Dosage (mg/kg) | CFU/Mouse | SD | Relative % CFU/Mouse | Relative % SD | Mice Weight (g) Day 0 | Mice Weight (g) Day 31 |
|---|---|---|---|---|---|---|---|---|
| 0 | T3 - initial lung CFU | NA | 280 | 124 | NA | NA | NA | NA |
| 7 | T10 - pre-treatment CFU | NA | 2,880 | 1,518 | NA | NA | NA | NA |

TABLE 8-continued

| Acute Efficacy Study Data | | | | | | | | |
|---|---|---|---|---|---|---|---|---|
| | | Dosage | | | Relative % | Relative | Mice Weight (g) | |
| Day | ID | (mg/kg) | CFU/Mouse | SD | CFU/Mouse | % SD | Day 0 | Day 31 |
| 21 | T31, CMC-Tween* | 0 - QD | 1,210,000 | 567,386 | 100% | 47% | 20.4 | 21.7 |
| 21 | RMP CMC-Tween | 15 - QD | 857 | 933 | 0.071% | 0.084% | 20.3 | 21.6 |
| 21 | PEG-water* | 0-QD | 1,131,429 | 587,810 | 100% | 52% | 18.0 | 21.6 |
| 21 | RMP PEG-water | 15-QD | 8,443 | 6,356 | 0.75% | 0.68% | 20.4 | 21.1 |
| 21 | Compound 17e PEG-water | 100-QD | 4,029 | 2,604 | 0.36% | 0.30% | 20.4 | 21.0 |

*Vehicles: CMC-Tween = 0.5% CMC/0.5% Tween 80, PEG-water = 80% PEG 200, 20% water All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

(I)

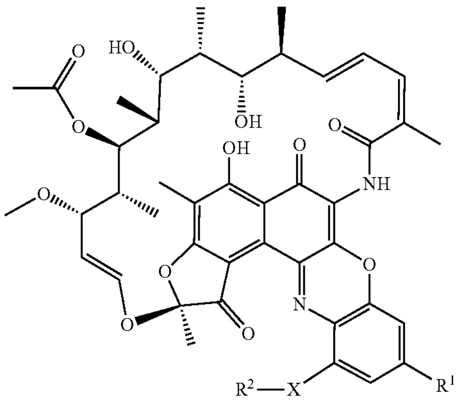

or a pharmaceutically acceptable salt thereof, wherein:

$R^1$ is selected from hydrogen, $C_1$-$C_6$ alkyl, $C_1$-$C_6$ heteroalkyl, —C(O)$R^a$, —N($R^b$)$_2$, —O$R^c$, —$SR_4$, —CH═N—Z, and heterocyclyl, wherein the heterocyclyl is unsubstituted or substituted with one substituent selected from $C_1$-$C_6$ alkyl, $C_1$-$C_6$ alkenyl, —C(O)$R^{a1}$, —C(O)O$R^{b1}$, —C(O)NH$R^{c1}$, —$(CH_2)_{n1}$—$X^{1a}$, —$SO_2$—$X^{1b}$, aryl, heteroaryl, cycloalkyl, and heterocyclyl, wherein when the substituent is aryl, heteroaryl, cycloalkyl, or heterocyclyl, the substituent is optionally further substituted with $C_1$-$C_6$ alkyl or —O—$X^{1c}$;

X is selected from O, S, $SO_2$, $NHSO_2$, $NR^X$, and a bond;

$R^X$ is selected from hydrogen and $C_1$-$C_3$ alkyl;

$R^2$ is selected from hydrogen, $C_1$-$C_6$ alkyl, $C_1$-$C_6$ alkenyl, $C_3$-$C_6$ cycloalkyl, heterocyclyl, aryl, heteroaryl, —$(CH_2)_{m1}$-aryl, —$(CH_2)_{m2}$-heterocyclyl, and —$CH_2$-Ph-$CH_2$-heterocyclyl, wherein each alkyl, alkenyl, cycloalkyl, heterocyclyl, aryl, and heteroaryl is independently unsubstituted or substituted with one or two substituents independently selected from $C_1$-$C_6$ alkyl, hydroxy, amino, —C(O)$R^{a2}$, —C(O)O$R^{b2}$, —C(O)NH$R^{c2}$, —$(CH_2)_{n2}$—$X^{2a}$, —$SO_2$—$X^{2b}$, aryl, heteroaryl, cycloalkyl, and heterocyclyl;

each $R^a$, $R^b$, $R^c$, and $R^d$ is independently selected from hydrogen, $C_1$-$C_6$ alkyl, $C_3$-$C_6$ cycloalkyl, and aryl;

$R^{a1}$ and $R^{a2}$ are each independently selected from hydrogen, $C_1$-$C_6$ alkyl, $C_1$-$C_6$ alkenyl, cycloalkyl, heterocyclyl, aryl, heteroaryl, and —$(CH_2)_p$—Y, wherein each alkyl, alkenyl, cycloalkyl, heterocyclyl, aryl, and heteroaryl is independently unsubstituted or substituted with one substituent selected from aryl, heteroaryl, $C_1$-$C_6$ alkyl, halo, and nitro, and when the substituent is aryl or heteroaryl, it is unsubstituted or substituted with one substituent selected from halo, hydroxy, and —$CONH_2$;

$R^{b1}$ and $R^{b2}$ are each independently selected from hydrogen, $C_1$-$C_6$ alkyl, and heterocyclyl, wherein the heterocyclyl is optionally further substituted with one substituent selected from $C_1$-$C_6$ alkyl, hydroxy, halo, and nitro;

$R^{c1}$ and $R^{c2}$ are each independently selected from hydrogen, $C_1$-$C_6$ alkyl, and aryl, wherein the aryl is unsubstituted or substituted with one substituent selected from $C_1$-$C_6$ alkyl, halo, and nitro;

$X^{1a}$, $X^{1b}$, $X^{1c}$, $X^{2a}$, and $X^{2b}$ are each independently selected from aryl, heteroaryl, cycloalkyl, heterocyclyl, —O-heterocyclyl, —COOH, and —$N(CH_3)_2$, wherein each aryl, heteroaryl, cycloalkyl, or heterocyclyl is independently unsubstituted or substituted with one substituent selected from $C_1$-$C_6$ alkyl, hydroxy, halo, and nitro;

Y is selected from aryl, heteroaryl, cycloalkyl, and heterocyclyl, each of which is independently unsubstituted or substituted with one substituent selected from $C_1$-$C_6$ alkyl, halo, and nitro;

Z is selected from aryl and heteroaryl, each of which is optionally substituted with one substituent selected from heterocyclyl; and m1, m2, n1, n2, and p are each independently 1, 2, 3, 4, 5, or 6;

wherein when $R^1$ is hydrogen, —X—$R^2$ is not:

—$CH_3$,

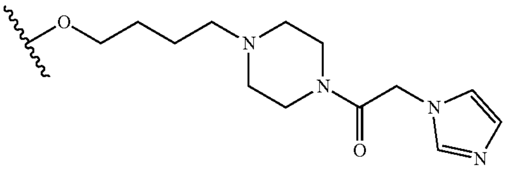

or

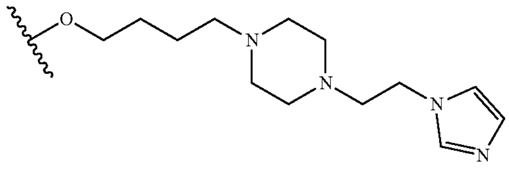

;

and when $R^1$ is

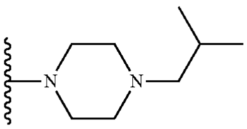

,

—X—$R^2$ is not: —$CH_3$, —SH, or

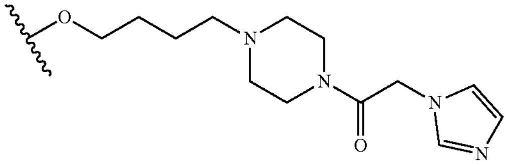

;

and when $R^1$ is

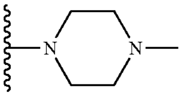

,

—X—$R^2$ is not —$CH_3$;

and when $R^1$ is $CH_3$, —X—$R^2$ is not hydrogen;

and when X is O, $R^2$ is not hydrogen.

2. The compound of claim 1, or a pharmaceutically acceptable salt thereof, wherein $R^1$ is selected from hydrogen and methyl.

3. The compound of claim 1, or a pharmaceutically acceptable salt thereof, wherein $R^1$ is a monocyclic 6-membered heterocyclyl having 1 or 2 heteroatoms independently selected from N, O, and S, wherein the heterocyclyl is unsubstituted or substituted with one substituent selected from $C_1$-$C_6$ alkyl, —$C(O)R^{a1}$, —$C(O)OR^{b1}$, and —$(CH_2)_{n1}$—$X^{1a}$.

4. The compound of claim 3, or a pharmaceutically acceptable salt thereof, wherein the heterocyclyl is unsubstituted or substituted with one substituent selected from $C_1$-$C_4$ alkyl, —$C(O)R^{a1}$, and —$C(O)OR^{b1}$; wherein:

$R^{a1}$ is selected from $C_1$-$C_4$ alkyl, aryl, and heteroaryl, wherein the aryl is unsubstituted or substituted with one heteroaryl substituent; and $R^{b1}$ is selected from hydrogen and $C_1$-$C_4$ alkyl.

5. The compound of claim 1, or a pharmaceutically acceptable salt thereof, wherein $R^1$ is:

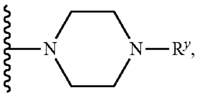

, wherein $R^y$ is selected from $C_1$-$C_4$ alkyl, —$C(O)R^{a1}$, and —$C(O)OR^{b1}$; wherein:

$R^{a1}$ is selected from $C_1$-$C_4$ alkyl, aryl, and heteroaryl, wherein the aryl is unsubstituted or substituted with one heteroaryl substituent; and $R^{b1}$ is selected from hydrogen and $C_1$-$C_4$ alkyl.

6. The compound of claim 1, or a pharmaceutically acceptable salt thereof, wherein $R^1$ is selected from:

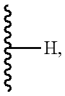

,

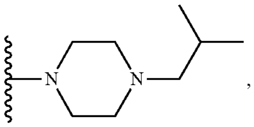

,

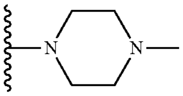

,

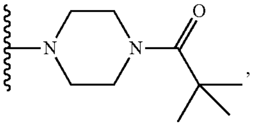

,

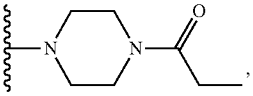

,

-continued

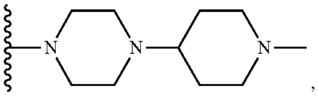,
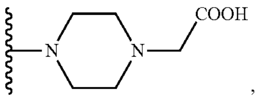,
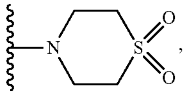,
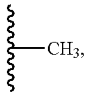
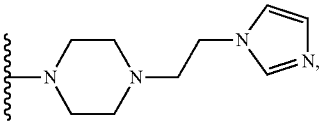
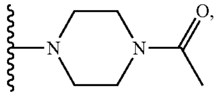
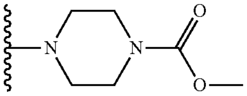,
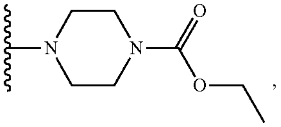,
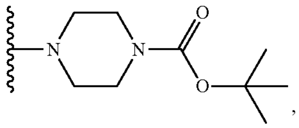,
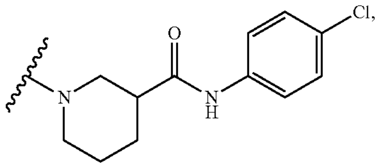
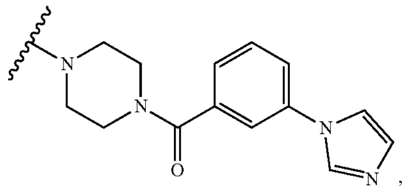,
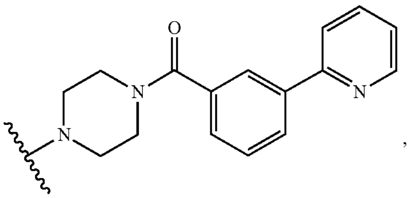,
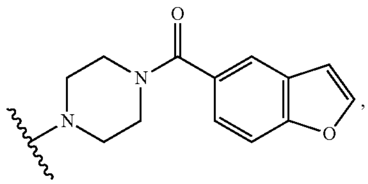,
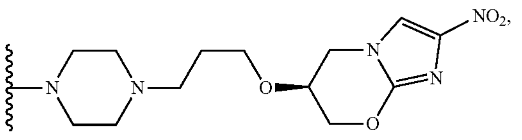
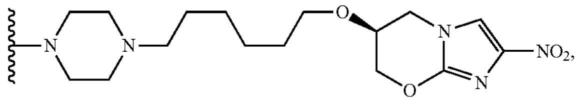
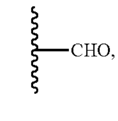
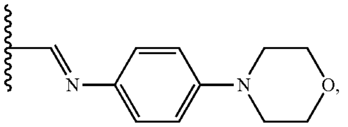

-continued

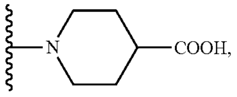
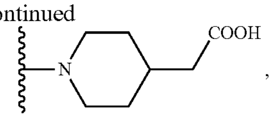,
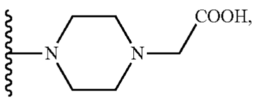
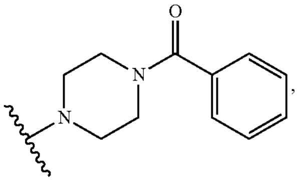,
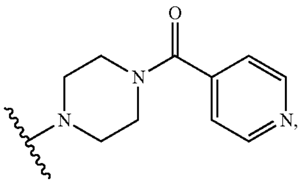
and
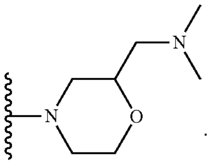.

7. The compound of claim 1, or a pharmaceutically acceptable salt thereof, wherein $R^1$ is:

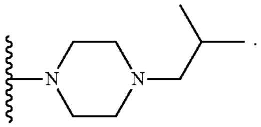 [SMILES: *N1CCN(CC(C)C)CC1].

8. The compound of claim 1, or a pharmaceutically acceptable salt thereof, wherein X is O or a bond.

9. The compound of claim 1, or a pharmaceutically acceptable salt thereof, wherein $R^2$ is selected from hydrogen, $C_1$-$C_6$ alkyl, heterocyclyl, and —$CH_2$-Ph-$CH_2$-heterocyclyl, wherein each heterocyclyl is independently unsubstituted or substituted with one substituent selected from $C_1$-$C_6$ alkyl, —C(O)$R^{a2}$, —C(O)O$R^{b2}$, —C(O)NH$R^{c2}$, —$(CH_2)_{n2}$—$X^{2a}$, and heterocyclyl.

10. The compound of claim 1, or a pharmaceutically acceptable salt thereof, wherein:

X is O;

$R^2$ is —$CH_2$-Ph-$CH_2$-heterocyclyl, wherein the heterocyclyl is a monocyclic 6-membered heterocyclyl having 1 or 2 heteroatoms independently selected from N and O, and is unsubstituted or substituted with one substituent selected from $C_1$-$C_6$ alkyl and —C(O)$R^{a2}$;

$R^{a2}$ is selected from $C_1$-$C_6$ alkyl and —$(CH_2)_p$—Y;

Y is selected from phenyl, monocyclic 5- or 6-membered heteroaryl, and monocyclic 5- or 6-membered heterocyclyl; and p is 1 or 2.

11. The compound of claim 1, or a pharmaceutically acceptable salt thereof, wherein —X—$R^2$ is selected from:

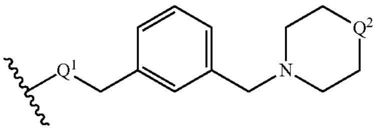
and
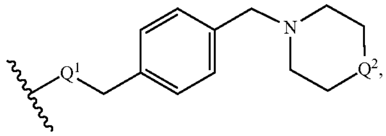

wherein:

each $Q^1$ is independently selected from O, $NR^{q1}$, S, and $SO_2$, each $Q^2$ is independently selected from O, $NR^{q2}$, S, SO, and $SO_2$;

$R^{q1}$ and $R^{q2}$ are each independently selected from hydrogen, $C_1$-$C_4$ alkyl, and —C(O)$R^{a2}$;

$R^{a2}$ is selected from $C_1$-$C_4$ alkyl and —$(CH_2)_p$—Y;

Y is selected from aryl, heteroaryl, cycloalkyl, and heterocyclyl;

p is 1 or 2.

12. The compound of claim 1, or a pharmaceutically acceptable salt thereof, wherein $R^2$ is $C_1$-$C_6$ alkyl.

13. The compound of claim 12, or a pharmaceutically acceptable salt thereof, wherein $R^2$ is methyl.

14. The compound of claim 1, or a pharmaceutically acceptable salt thereof, wherein:

$R^2$ is a 6-membered monocyclic heterocyclyl having 1 or 2 heteroatoms independently selected from N and O, wherein the heterocyclyl is unsubstituted or substituted with one substituent selected from $C_1$-$C_4$ alkyl, —C(O)$R^{a2}$, and —$(CH_2)_{n2}$—$X^{2a}$;

$R^{a2}$ is selected from aryl and heteroaryl, each of which is independently unsubstituted or substituted with one substituent selected from heteroaryl;

$X^{2a}$ is selected from heteroaryl and —COOH; and n2 is 1 or 2.

15. The compound of claim 1, or a pharmaceutically acceptable salt thereof, wherein —X—$R^2$ is selected from:

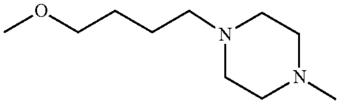,

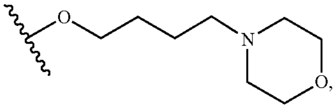,

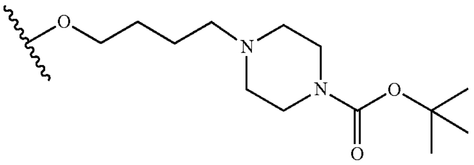,

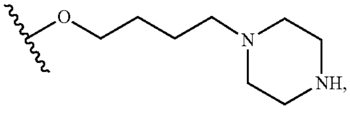,

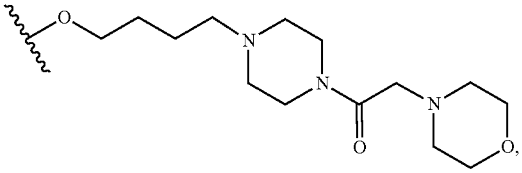,

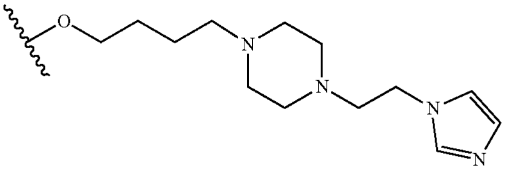,

-continued

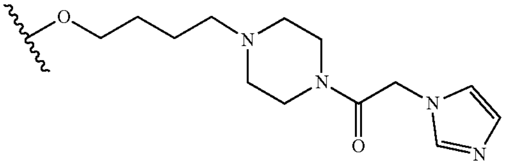,

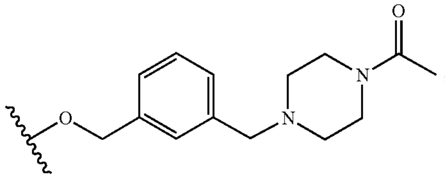,

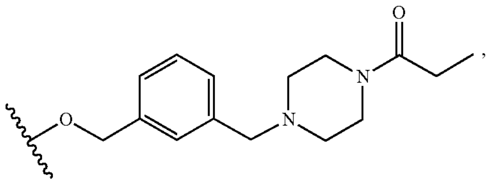,

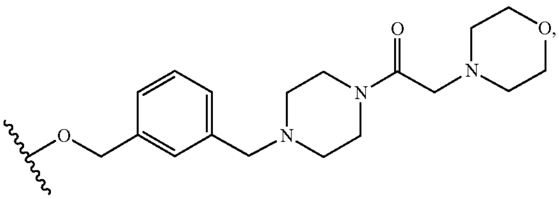,

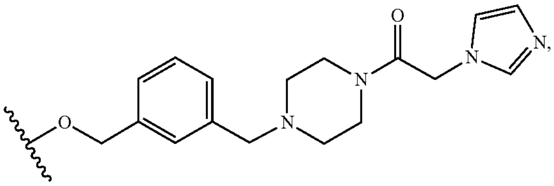,

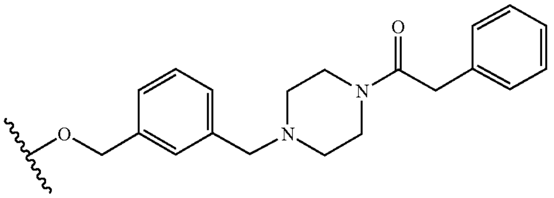,

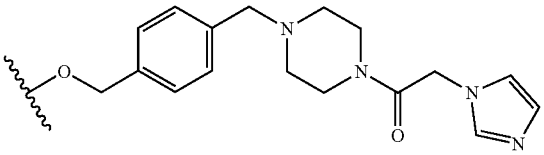,

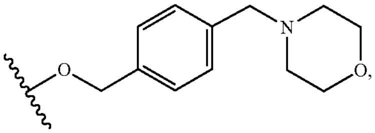,

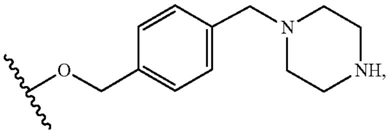,

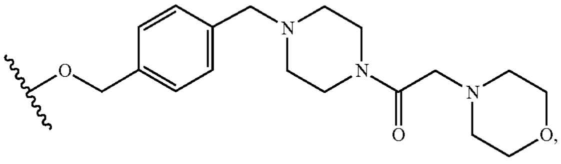,

-continued

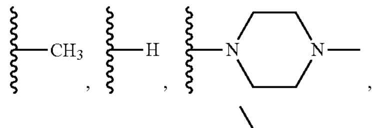

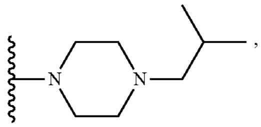

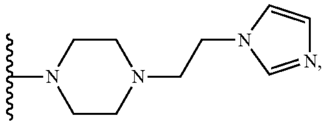

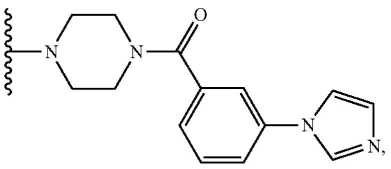

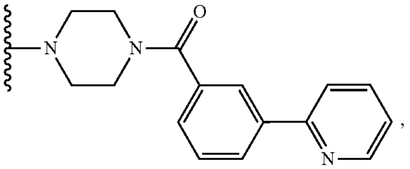

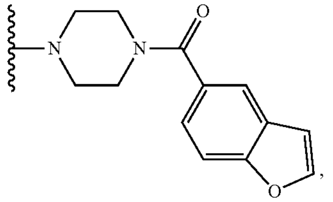

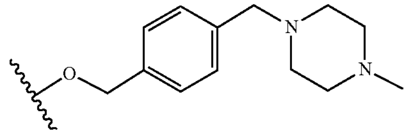

and

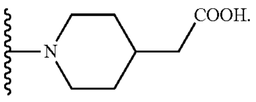

16. The compound of claim 1, or a pharmaceutically acceptable salt thereof, wherein —X—$R^2$ is:

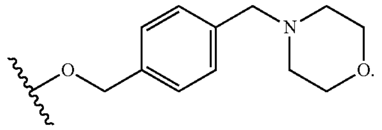 [SMILES: *OCc1ccc(CN2CCOCC2)cc1]

17. A method of manufacturing a compound of claim 1, or a pharmaceutically acceptable salt thereof, comprising:

(a) reacting rifamycin S with a compound of formula (A), followed by treatment with manganese dioxide, to provide a compound of formula (B):

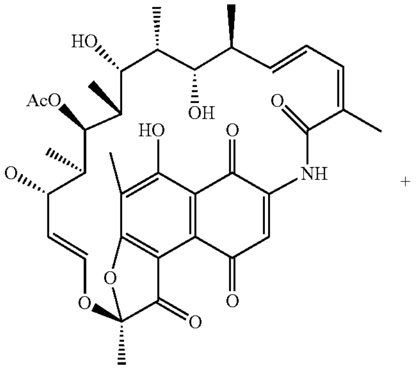

rifamycin S

+

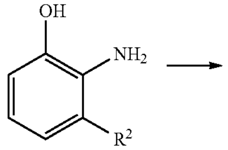

(A)

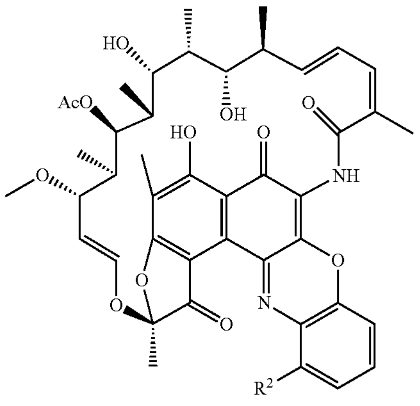

(B)

(b) reacting the compound of formula (B) with a compound of formula $R^1$—H, followed by treatment with manganese dioxide, to provide a compound of claim 1.

18. A pharmaceutical composition comprising a compound of claim 1, or a pharmaceutically acceptable salt thereof, and a pharmaceutically acceptable excipient.

19. A method of treating tuberculosis in a subject in need thereof, comprising administering to the subject a therapeutically effective amount of a compound of claim 1, or a pharmaceutically acceptable salt thereof.

20. A method of killing *Mycobacterium tuberculosis* in a sample, comprising contacting the sample with an effective amount of a compound of claim 1, or a pharmaceutically acceptable salt thereof.

21. The compound of claim 16, or a pharmaceutically acceptable salt thereof, wherein $R^1$ is:

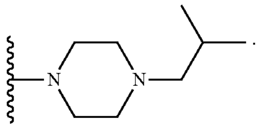 [SMILES: *N1CCN(CC(C)C)CC1]

22. The method of claim 19, wherein $R^1$ is:

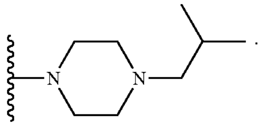 [SMILES: *N1CCN(CC(C)C)CC1]

23. The method of claim 19, wherein -X-$R^2$ is:

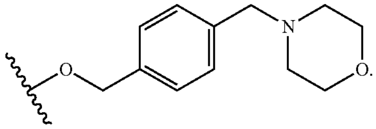 [SMILES: *OCc1ccc(CN2CCOCC2)cc1]

24. The method of claim 19, wherein $R^1$ is

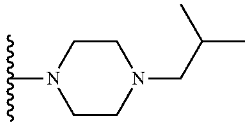 [SMILES: *N1CCN(CC(C)C)CC1]

and-X-$R^2$ is

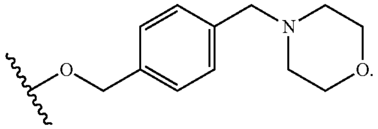 [SMILES: *OCc1ccc(CN2CCOCC2)cc1]

25. The method of claim 19, wherein the subject is infected with human immunodeficiency virus.

26. The method of claim 19, wherein the subject is infected with a drug-resistant strain of *Mycobacterium tuberculosis*.

27. The method of claim 19, wherein the subject is infected with a rifampin-resistant strain of *Mycobacterium tuberculosis*.

28. The method of claim 19, wherein the subject has a persistent tuberculosis infection.

* * * * *